(12) United States Patent
Schou et al.

(10) Patent No.: US 9,233,964 B2
(45) Date of Patent: *Jan. 12, 2016

(54) SULFAMIDE PIPERAZINE DERIVATIVES AS PROTEIN TYROSINE KINASE INHIBITORS AND PHARMACEUTICAL USE THEROF

(75) Inventors: Søren Christian Schou, Ballerup (DK); Daniel Rodriguez Greve, Ballerup (DK); Simon Feldbæk Nielsen, Ballerup (DK); Jens Bjørn Jensen, Ballerup (DK); Kevin Neil Dack, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/977,408

(22) PCT Filed: Jan. 6, 2012

(86) PCT No.: PCT/EP2012/050187
§ 371 (c)(1),
(2), (4) Date: Sep. 10, 2013

(87) PCT Pub. No.: WO2012/093169
PCT Pub. Date: Jul. 12, 2012

(65) Prior Publication Data
US 2013/0345194 A1    Dec. 26, 2013

Related U.S. Application Data

(60) Provisional application No. 61/430,670, filed on Jan. 7, 2011.

(51) Int. Cl.
| A01N 43/90 | (2006.01) |
| A61K 31/519 | (2006.01) |
| C07D 487/00 | (2006.01) |
| C07D 487/04 | (2006.01) |
| A61K 31/5377 | (2006.01) |
| A61K 45/06 | (2006.01) |

(52) U.S. Cl.
CPC ............ *C07D 487/04* (2013.01); *A61K 31/519* (2013.01); *A61K 31/5377* (2013.01); *A61K 45/06* (2013.01)

(58) Field of Classification Search
None
See application file for complete search history.

(56) References Cited

U.S. PATENT DOCUMENTS

| 2004/0058922 A1 | 3/2004 | Blumenkopf et al. |
| 2005/0130954 A1 | 6/2005 | Mitchell et al. |
| 2006/0189638 A1 | 8/2006 | Rawlins et al. |

FOREIGN PATENT DOCUMENTS

| DK | WO2011/003418 | * 1/2011 | ........... C07D 487/04 |
| WO | WO 99/65908 A1 | 12/1999 | |
| WO | WO 99/65909 A1 | 12/1999 | |
| WO | WO 01/42246 A2 | 6/2001 | |
| WO | WO 03/022214 A3 | 3/2003 | |
| WO | WO 2004/035740 A3 | 4/2004 | |
| WO | WO 2004/099205 A1 | 11/2004 | |
| WO | WO 2005/051393 A1 | 6/2005 | |
| WO | WO 2005/060972 A2 | 7/2005 | |
| WO | WO 2005/112938 A3 | 12/2005 | |
| WO | WO 2006/069080 A2 | 6/2006 | |
| WO | WO 2006/096270 A1 | 9/2006 | |
| WO | WO 2006/127587 A1 | 11/2006 | |
| WO | WO 2007/077949 A1 | 7/2007 | |
| WO | WO 2007/104944 A1 | 9/2007 | |

(Continued)

OTHER PUBLICATIONS

O'Shea, "Targeting the Jak/STAT Pathway for Immunosuppression", Ann. Rheum. Dis., 63, 2004, pp. ii67-ii71.

(Continued)

*Primary Examiner* — Jeffrey H Murray
(74) *Attorney, Agent, or Firm* — Birch Stewart Kolasch & Birch, LLP

(57) ABSTRACT

The invention relates to compounds of general Formula (I), Wherein $R_1$, $R_2$, $R_3$, $R_4$, $R_5$, m, n are defined herein, and pharmaceutically acceptable salts, prodrugs, hydrates, or solvates thereof, for use—alone or in combination with one or more other pharmaceutically active compounds—in therapy, as JAK kinase and protein tyrosine kinase inhibitors for preventing, treating or ameliorating diseases and complications thereof, including, for example, psoriasis, atopic dermatitis, rosacea, lupus, multiple sclerosis, rheumatoid arthritis, Type I diabetes, asthma, cancer, autoimmune thyroid disorders, ulcerative colitis, Crohn's disease, Alzheimer's disease, leukaemia, eye diseases such as diabetic retinopathy and macular degeneration as well as other autoimmune diseases and indications where immunosuppression would be desirable for example in organ transplantation.

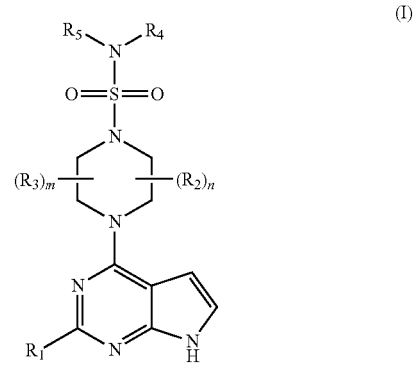

29 Claims, No Drawings

(56) References Cited

FOREIGN PATENT DOCUMENTS

| | | |
|---|---|---|
| WO | WO 2007/117494 A1 | 10/2007 |
| WO | WO 2008/128072 A3 | 10/2008 |
| WO | WO 2009/021169 A2 | 2/2009 |
| WO | WO 2011/003418 A1 | 1/2011 |

OTHER PUBLICATIONS

Schindler et al., "Minireviews: JAK-STAT Signaling: From Interferons to Cytokines", J. Biol. Chem, 282, 2007, pp. 20059-20063.

Schindler et al., "Series Introduction JAK-STAT Signaling in Human Disease", J. Clin. Invest. 109, 2002, pp. 1133-1137.

* cited by examiner

US 9,233,964 B2

SULFAMIDE PIPERAZINE DERIVATIVES AS PROTEIN TYROSINE KINASE INHIBITORS AND PHARMACEUTICAL USE THEROF

CROSS REFERENCE TO RELATED APPLICATIONS

This application is the National Phase of PCT/EP2012/050187 filed on Jan. 6, 2012, which claims priority under 35 U.S.C. 119(e) to U.S. Provisional Application No. 61/430,670 filed on Jan. 7, 2011, all of which are hereby expressly incorporated by reference into the present application.

FIELD OF THE INVENTION

This invention relates to compounds which are inhibitors of protein tyrosine kinases, such as the Janus kinases, and to said compounds for use in therapy, to pharmaceutical compositions comprising said compounds, to methods of treating diseases comprising administering to a patient in need thereof an effective amount of said compound, and to the use of said compounds in the manufacture of medicaments.

BACKGROUND OF THE INVENTION

This invention relates to novel compounds which are inhibitors of protein tyrosine kinases such as the Janus kinases, also referred to as JAK1, JAK2, JAK3 and TYK2. Said compounds are useful in the treatment of diseases related to activity of Janus kinases, including, for example, psoriasis, atopic dermatitis, rosacea, lupus, multiple sclerosis, rheumatoid arthritis, Type I diabetes and complications from diabetes, asthma, cancer, autoimmune thyroid disorders, ulcerative colitis, Crohn's disease, Alzheimer's disease, leukaemia, eye diseases such as diabetic retinopathy and macular degeneration as well as other autoimmune diseases and indications where immunosuppression would be desirable for example in organ transplantation.

Protein tyrosine kinases are a family of enzymes catalysing the transfer of the terminal phosphate of adenosine triphosphate to tyrosine residues in protein substrates. Phosphorylation of tyrosine residues on protein substrates leads to transduction of intracellular signals which regulate a wide variety of intracellular processes such as growth, differentiation and activation of cells of the immune system. As activation of T-cells and B-cells as well as other cells of the immune system such as monocytes and macrophages is implicated in a number of inflammatory conditions and other disorders of the immune system (e.g. autoimmune diseases), modulation of the activity of protein tyrosine kinases appears to be an attractive route to the management of inflammatory diseases. A large number of protein tyrosine kinases have been identified which may be receptor protein tyrosine kinases, e.g. the insulin receptor, or non-receptor protein tyrosine kinases.

The protein tyrosine kinases JAK1, JAK2, JAK3 and TYK2 have essential roles in cytokine-dependent regulation of proliferation and function of cells involved in immune response. They are critical in signal transduction in response to their activation via tyrosine phosphorylation by stimulation of interleukin receptors. (1) Schindler C. et al. JAK-STAT signaling: from interferons to cytokines. J. Biol. Chem. 2007; 282(28):20059; 2) O'Shea J. J. Targeting the Jak/STAT pathway for immunosuppression Ann. Rheum. Dis. 2004; 63 Suppl 2:ii67; 3) Schindler C. Series introduction. JAK-STAT signaling in human disease. J. Clin. Invest. 2002; 109(9):1133).

While JAK1, JAK2 and TYK2 are ubiquitously expressed JAK3 is predominantly expressed in hematopoietic cells.

JAK1 plays a critical role in mediation of biological responses and JAK1 is widely expressed and associated with several major cytokine receptor families. It is involved in signalling by members of the IL-2 receptor family (IL-2, IL-4, IL-7R, IL-9R, IL-15R and IL-21R), the IL-4 receptor family (IL-4R, IL-13R), the gp130 receptor family and class II cytokine receptors.

JAK2 is implicated in signalling by several single chain receptors (including Epo-R, GHR, PRL-R), the IL-3 receptor family, the gp130 receptor family and Class II receptor cytokine family. Thus, JAK2 plays a critical role in transducing signals for Epo, IL-3, GM-CSF, IL-5 and IFNγ. JAK2 knockout mice exhibit an embryonic lethal phenotype.

JAK3 is involved in signal transduction by receptors that employ the common gamma chain of the type I cytokine receptor family (e.g. IL-2, IL-4, IL-7, IL-9, IL-15 and IL-21). XSCID patient populations have been identified with reduced levels of JAK3 protein or with genetic defects to the common gamma chain, suggesting that immune suppression should result from blocking signalling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as immune system diseases, in particular autoimmune diseases.

TYK2 is implicated in type I interferons, IL-6, IL-10, IL-12 and IL-23 signalling. A human patient with a TYK2 deficiency has been described and this patient had a primary immunodeficiency disorder characterized as a hyper-IgE-like syndrome with many opportunistic infections by virus, bacteria and fungi. Because Il-23 has been found to play an important role in many chronic inflammatory conditions, a TYK2 inhibitor could conceivably be very effective in treating diseased influenced by IL-23.

Inhibitors of the Janus kinases are accordingly expected to show utility in the treatment of inflammatory and non-infectious autoimmune diseases wherein these kinases are involved.

It is further envisaged that compounds of the present invention may be useful as inhibitors of other kinases, such as Src family kinases (Src, Yes, Fyn, Lyn, Fgr, Blk, Lck and/or Hck) responsible for receptor mediated signalling in T, B and other immune cells; Raf-1/Ras, MAP kinase signalling pathway; Syk and ZAP70 kinases responsible of activation of immune cells.

WO1999065908A1, WO1999065909A1, and WO2001042246A2 disclose pyrrolo[2,3-d]pyrimidine compounds as inhibitors of the enzyme protein tyrosine kinases such as Janus kinase 3 and as useful therapy as immunosuppressive agents.

WO2003022214A3 discloses piperazine and homopiperazine compounds for use in the treatment of thrombosis.

WO2004035740A3 discloses aromatic bicyclic heterocycles to modulate IL-12 production.

WO2004099205A1 discloses azaindole compounds as kinase inhibitors.

WO 2005112938A3 discloses disalt nitrogen-heteroaryl inhibitors of IL-12 production.

WO2005051393A1 discloses a method of treatment of atherosclerosis by administering a pyrrolo[2,3-d]pyrimidine compound.

WO2005060972A2 discloses a method of treating or preventing chronic, acute or hyperacute organ transplant rejection using pyrrolo[2,3-d]pyrimidine compounds.

WO2006096270A1 discloses pyrrolopyrimidines useful as inhibitors of protein kinase.

WO2006069080A2 discloses pyrrolo[2,3-d]pyridine-4-yl amines and pyrrolo[2,3b]pyrimidine-4-yl amines useful in the treatment of diseases related to activity of Janus kinases.

WO2006127587A1 discloses pyrrolopyrimidines useful as inhibitors of protein kinase.

WO2007077949A1 discloses heterocyclic Janus kinase 3 inhibitors being useful for the treatment or prevention of various immune diseases.

WO2007117494A1 discloses deazapurines useful as inhibitors of Janus kinases.

WO2007104944A1 discloses pyrrolopyrimidine derivatives having HSP90 inhibitory activity and useful in the treatment of inter alia cancer.

WO2008128072A3 discloses heterocyclic compounds as AXL kinase inhibitors useful for the treatment of cancer or hyperproliferative disorders.

WO2009021169A2 discloses heterocyclic compounds useful as kinase inhibitors.

US2004/0058922 A1 discloses pyrrolo[2,3-d]pyrimidine compounds as inhibitors of protein tyrosine kinases, such as the enzyme Janus Kinase 3 and as useful therapy as immunosuppressive agents.

US2005/0130954 A1 discloses AKT protein kinase inhibitors for the treatment of hyperproliferative diseases such as cancer.

US2006/0189638 A1 discloses 4-piperidin-1-yl-7H-pyrrolo[2,3-d]pyrimidine compounds and their use for e.g. treatment of hyperproliferative disorders.

SUMMARY OF THE INVENTION

The present inventors have surprisingly found that a novel class of compounds exhibit a high inhibitory activity on one or more of the Janus kinase receptors JAK1, JAK2, JAK3 and TYK2.

It is further envisaged that compounds of the present invention may be useful as inhibitors of other kinases, such as Src family kinases (Src, Yes, Fyn, Lyn, Fgr, Blk, Lck and/or Hck) responsible for receptor mediated signalling in T, B and other immune cells; Raf-1/Ras, MAP kinase signalling pathway; Syk and ZAP70 kinases responsible of activation of immune cells and as such show utility in the treatment of inflammatory and non-infectious autoimmune diseases wherein these kinases are involved. Compounds of the present invention may have improved pharmacokinetic properties such as improved solubility and absorption, reduced adverse side effects and increased or decreased metabolic stability in comparison to known structurally related compounds.

A particular advantage of some of the compounds of the present invention is that they show high systemic clearance.

An advantage of some of the compounds of the present invention is that they show low systemic clearance.

Some compounds of the present invention show improved JAK kinase inhibitory activity in comparison to known structurally related compounds.

Accordingly, the invention relates to compounds of general formula I:

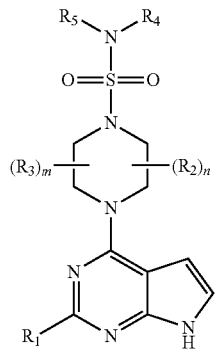

wherein
m is 0, 1 or 2;
n is 2 or 4;
$R_1$ is selected from the group consisting of hydrogen, halogen, cyano, —$NH_2$, —$SO_2NH_2$, —$SONH_2$, and —$CONH_2$;
or $R_1$ is selected from the group consisting of alkyl-, heteroalkyl-, cycloalkyl-, heterocyclyl-, $R_{1a}$O—, $R_{1a}$S—, $(R_{1a})_2$N—, $R_{1b}$—C(=O)N($R_{1c}$)—, $R_{1b}$O—C(=O)N($R_{1c}$)—, $R_{1b}$—C(=O)—, $(R_{1b})_2$N—C(=O)N($R_{1c}$)—, $R_{1b}$—S(=O)$_2$ N($R_{1c}$)— and $(R_{1b})_2$N—S(=O)$_2$N($R_{1c}$)— either of which may be optionally substituted with one or more $R_{1d}$;
$R_{1a}$ is hydrogen;
or $R_{1a}$ independently at each occurrence is selected from the group consisting of alkyl-, heteroalkyl-, cycloalkyl- and heterocyclyl- either of which may be optionally substituted with one or more $R_{1e}$;
or in the case where two $R_{1a}$s are attached to the same N, they may together with the N atom to which they are attached form a heterocycle which may be optionally substituted with one or more $R_{1e}$;
$R_{1b}$ and $R_{1c}$ independently at each occurrence are selected from the group consisting of hydrogen, alkyl-, heteroalkyl-, cycloalkyl- and heterocyclyl- either of which may be optionally substituted with one or more $R_{1e}$;
or in the case where two $R_{1b}$s are attached to the same N, they may together with the N atom to which they are attached form a heterocycle which may be optionally substituted with one or more $R_{1e}$;
$R_{1d}$ and $R_{1e}$ independently at each occurrence are selected from the group consisting of halogen, cyano, hydroxy, oxo, —$NH_2$, —$SO_2NH_2$, —$CONH_2$, alkyl-, heteroalkyl-, cycloalkyl-, heterocyclyl-, $R_{1f}$O—, $R_{1f}$S—, $(R_{1f})_2$N—, $R_{1f}$O—C(=O)—, $(R_{1f})_2$N—C(=O)—, $R_{1f}$—C(=O)N($R_{1f}$)—, $R_{1f}$O—C(=O)N($R_{1f}$)—, $(R_{1f})_2$N—C(=O)N($R_{1f}$)—, $R_{1f}$—C(=O)O—, $(R_{1f})_2$N—C(=O)O—, $(R_{1f})_2$N—S(=O)$_2$— and $R_{1f}$—S(=O)$_2$N($R_{1f}$)—;
$R_{1f}$ independently at each occurrence is selected from the group consisting of hydrogen, alkyl-, heteroalkyl-, cycloalkyl- and heterocyclyl-;
or in the case where two $R_{1f}$s are attached to the same N, they may together with the N atom to which they are attached form a heterocycle;
$R_2$ is independently at each occurrence a covalent bond or alkyl- or heteroalkyl- group, where any two $R_2$s are attached to the same C ring atom, and together with this C ring atom said two $R_2$s form a carbocycle or heterocycle, hence always forming a spirocyclic piperazine;
$R_3$ independently at each occurrence is selected from the group consisting of halogen, cyano, hydroxy, oxo, alkyl-, heteroalkyl-, cycloalkyl-, heterocyclyl-, $R_{3a}$O—, $R_{3a}$S—, $(R_{3a})_2N-$, $R_{3a}-C(=O)-$, $R_{3a}O-C(=O)-$, $(R_{3a})_2N-C(=O)-$, $R_{3a}-C(=O)N(R_{3b})-$, $R_{3a}O-C(=O)N(R_{3b})-$, $R_{3a}-C(=O)O-$, $(R_{3a})_2N-C(=O)O-$, $R_{3a}-S(=O)-$, $R_{3a}-S(=O)_2-$, $(R_{3a})_2N-S(=O)_2-$ and $R_{3a}-S(=O)_2N(R_{3b})-$;

$R_{3a}$ and $R_{3b}$ independently at each occurrence are selected from the group consisting of hydrogen, alkyl-, heteroalkyl-, cycloalkyl- and heterocyclylor in the case where two $R_{1a}$s are attached to the same N, they may together with the N atom to which they are attached form a heterocycle;

$R_4$ and $R_5$ independently at each occurrence is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, aryloxyalkyl-, heteroarylalkyl-, heteroaryloxyalkyl-, $R_6O-L-$, $R_6S-L-$, $(R_6)_2N-L-$, $R_6-C(=O)-L-$, $R_6O-C(=O)-L-$, $(R_6)_2N-C(=O)-L-$, $R_6-C(=O)N(R_6)-L-$, $R_6O-C(=O)N(R_6)-L-$, $(R_6)_2N-C(=O)N(R_6)-L-$, $R_6-C(=O)O-L-$, $(R_6)_2N-C(=O)O-L-$, $R_6-S(=O)_2-L-$, $(R_6)_2N-S(=O)_2-L-$, $R_6-S(=O)_2N(R_6)-L-$ and $(R_6)_2N-S(=O)_2N(R_6)-L$ either of which may be optionally substituted with one or more $R_7$;

or $R_4$ and $R_5$ can together with the N atom to which they are attached form a heterocyclic ring which may be optionally substituted with one or more $R_7$;

or $R_4$ and $R_5$ independently can be hydrogen;

L is independently at each occurrence selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, aryloxyalkyl-, heteroarylalkyl- and heteroaryloxyalkyl-;

or when $R_4$ or $R_5$ is selected from $R_6O-L-$, L can also be a bond;

$R_6$ independently at each occurrence is selected from the group consisting of hydrogen, alkyl-, heteroalkyl-, alkenyl-, alkynyl-, cycloalkyl-, heterocyclyl-, aryl-, arylalkyl- and heteroaryl-, cycloalkylalkyl- either of which may be optionally substituted with one or more substituents selected from the group consisting of halogen, cyano, hydroxy, trifluoromethyl, oxo, $-NH_2$, $-SO_2NH_2$, $-SONH_2$, $-CONH_2$ and $-O(C_1-C_4)$;

or in the case where two $R_6$ are attached to the same N, they may together with the N atom to which they are attached form a heterocycle which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$;

$R_7$ independently at each occurrence is selected from the group consisting of halogen, cyano, hydroxy, trifluoromethyl, oxo, $-NH_2$, $-SO_2NH_2$, $-SONH_2$, $-CONH_2$ and $=CH_2$, or $R_7$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, alkoxy-, aryloxyalkyl-, heteroarylalkyl-, heteroaryloxyalkyl-, $R_8O-L-$, $R_8S-L-$, $(R_8)_2N-L-$, $R_8-C(=O)-L-$, $R_8O-C(=O)-L-$, $(R_8)_2N-C(=O)-L-$, $R_8-C(=O)N(R_8)-L-$, $R_8O-C(=O)N(R_8)-L-$, $(R_8)_2N-C(=O)N(R_8)-L-$, $R_8-C(=O)O-L-$, $(R_8)_2N-C(=O)O-L-$, $R_8-S(=O)_2-L-$, $(R_8)_2N-S(=O)_2-L-$, $R_8-S(=O)_2N(R_8)-L-$ and $(R_8)_2N-S(=O)_2N(R_8)-L$ either of which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$;

$R_8$ independently at each occurrence is selected from the group consisting of hydrogen, alkyl-, heteroalkyl-, alkenyl-, alkynyl-, cycloalkyl-, heterocyclyl-, cycloalkylalkyl-, heterocyclylalkyl-, aryl-, arylalkyl-, heteroaryl-, and heteroarylalkyl- either of which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$;

or in the case where two $R_8$ are attached to the same N, they may together with the N atom to which they are attached form a heterocycle which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$;

and pharmaceutically acceptable salts, prodrugs, hydrates, or solvates thereof;

with the proviso that when $R_1$ is hydrogen, and m is 1, and n is 2, and the two $R_2$'s form a cyclopropyl ring together with the carbon atom to which they are attached, and $R_4$ is methyl, $R_5$ is not selected from the group consisting of cyanoethyl or cyclohexyl; and with the proviso that when $R_1$ is hydrogen, and m is 0, and n is 2, and the two $R_2$'s form a cyclopropyl ring together with the carbon atom to which they are attached, and $R_5$ is methyl, $R_4$ is not selected from the group consisting of cyanoethyl or cyclohexyl;

and with the proviso that when $R_1$ is hydrogen, and m is 0, and n is 2, and the two $R_2$'s form a cyclopropyl ring together with the carbon atom to which they are attached, and $R_4$ is ethyl, $R_5$ is not ethyl.

DETAILED DESCRIPTION OF THE INVENTION

Definitions

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12 or 1-10 e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

In the present context, the term "alkyl" is intended to indicate the radical obtained when one hydrogen atom is removed from a hydrocarbon. Said alkyl may be branched or straight-chained and comprises 1-20, preferably 1-10, such as 2-6, such as 3-4, such as 1-2, such as 1-3, such as 1-4, such as 1-5 such as 2-3, such as 2-4, such as 2-5, such as 3-5, such as 3-6 carbon atoms. The term includes the subclasses normal alkyl (n-alkyl), secondary and tertiary alkyl, such as methyl, ethyl, n-propyl, isopropyl, n-butyl, isobutyl, sec-butyl, tert-butyl, pentyl, isopentyl, hexyl and isohexyl.

In the present context, the term "$(C_a-C_b)$alkyl" wherein a and b are integers refers to a straight or branched chain alkyl radical having from a to b carbon atoms, e.g. 1-5 or 1-4, such as 1-4 or 1-3 carbon atoms. Thus when a is 1 and b is 5, for example, the term includes methyl, ethyl, n-propyl, isopropyl, n-butyl, isobutyl, sec-butyl, tert-butyl, pentyl and isopentyl.

The term "alkylene" is intended to indicate a divalent saturated aliphatic hydrocarbyl group preferably having from 1 to 6 and more preferably 1 to 3 carbon atoms that are either straight-chained or branched. This term is exemplified by groups such as methylene ($-CH_2-$), ethylene (—CH$_2$CH$_2$—), n-propylene (—CH$_2$CH$_2$CH$_2$—), iso-propylene (—CH$_2$CH(CH$_3$)—) or (—CH(CH$_3$)CH$_2$—), and the like.

The term "cycloalkyl" is intended to indicate a saturated cycloalkane radical, including polycyclic radicals, such as bicyclic or tricyclic radicals, comprising 3-20 carbon atoms, preferably 3-10 carbon atoms, in particular 3-8 carbon atoms, such as 3-6 carbon atoms, such as 4-5 carbon atoms, such as 3-5 carbon atoms, e.g. cyclopropyl, cyclobutyl, cyclopentyl, cyclohexyl, cycloheptyl and cyclooctyl and cubanyl.

The term "cycloalkylene" is intended to indicate a divalent cycloalkyl group as defined herein.

The term "alkenyl" is intended to indicate a hydrocarbon radical comprising 2-20 carbon atoms, preferably 2-10, in particular 2-6 carbon atoms, such as 2-4 carbon atoms, and having at least 1 and preferably from 1 to 2 sites of double bond unsaturation, e.g. ethenyl, allyl, propenyl, butenyl, pentenyl, nonenyl, or hexenyl. Included within this term are the cis and trans isomers or mixtures of these isomers.

The term "alkenylene" is intended to indicate a divalent aliphatic hydrocarbyl group preferably having from 2 to 6 and more preferably 2 to 4 carbon atoms that are either straight-chained or branched and having at least 1 and preferably from 1 to 2 sites of double bond unsaturation. This term is exemplified by groups such as ethenylene (—CH=CH—), propenylene (—CH=CHCH$_2$—), 1-butenylene (—CH=CHCH$_2$CH$_2$—) or 2-butenylene (—CH$_2$CH=CHCH$_2$—), and the like.

The term "cycloalkenyl" is intended to indicate mono-, di- tri- or tetraunsaturated non-aromatic cyclic hydrocarbon radicals, including polycyclic radicals, comprising 3-20 carbon atoms, typically comprising 3-10 carbon atoms, such as 3-8 carbon atoms, such as 4-6 carbon atoms, e.g. cyclopropenyl, cyclobutenyl, cyclopentenyl or cyclohexenyl.

The term "cycloalkenylene" is intended to indicate a divalent cycloalkenyl group as defined herein.

The term "alkynyl" is intended to indicate an hydrocarbon radical comprising 1-5 C—C triple bonds and 2-20 carbon atoms, the alkane chain typically comprising 2-10 carbon atoms, in particular 2-6 carbon atoms, such as 2-4 carbon atoms, e.g. ethynyl, propynyl, butynyl, pentynyl or hexynyl.

The term "alkynylene" is intended to indicate a divalent aliphatic hydrocarbyl group preferably having from 2 to 6 and more preferably 2 to 4 carbon atoms that are either straight-chained or branched and having at least 1 and preferably from 1 to 2 sites of triple bond unsaturation. This term is exemplified by groups such as ethynylene (—CC—), propynylene (—CCCH$_2$—), 1-butynylene (—CCCH$_2$CH$_2$—) or 2-butynylene (—CH$_2$CCCH$_2$—), and the like.

The term "cycloalkynyl" is intended to indicate mono-, di-, tri- or tetra-unsaturated non-aromatic cyclic hydrocarbon radicals, including polycyclic radicals, comprising 3-20 carbon atoms, typically comprising 3-10 carbon atoms, such as 3-8 carbon atoms, such as 4-6 carbon atoms, and at least 1 and preferably from 1 to 2 sites of triple bond unsaturation, e.g. cyclopropynyl, cyclobutynyl, cyclopentynyl or cyclohexynyl.

The term "cycloalkynylene" is intended to indicate a divalent cycloalkynyl group as defined herein.

The term "heterocyclic" and "heterocyclyl" is intended to indicate a saturated or unsaturated group having a single ring or multiple condensed rings, including fused bridged and spiro ring systems, and having from 3 to 15 ring atoms, including 1 to 4 hetero atoms, such as 1-5 carbon atoms and 1-3 heteroatoms, such as 1-4 carbon atoms and 1-3 heteroatoms, such as 1-5 carbon atoms and 1-2 heteroatoms, such as 1-5 carbon atoms and 1 heteroatom. These ring atoms are selected from the group consisting of nitrogen, sulphur and oxygen, wherein, in fused ring systems, one or more of the rings can be cycloalkyl, aryl, or heteroaryl, provided that the point of attachment is through the non-aromatic ring. In one embodiment, the nitrogen and/or sulphur atom(s) of the heterocyclic group are optionally oxidized to provide for the N-oxide, —S(O)—, or —SO2- moieties. Examples include tetrahydrofuranyl, pyrrolidinyl, dioxolanyl, morpholinyl, piperidinyl, tetrahydropyranyl, dioxothiolanyl, dioxothianyl, oxetanyl, or azetidinyl.

The term "heterocycloalkenyl" is intended to indicate a cycloalkenyl radical as defined above, including polycyclic radicals, optionally fused with carbocyclic rings, comprising 1-6 heteroatoms, preferably 1-3 heteroatoms, selected from O, N, or S, e.g. tetrahydropyranol.

The term "heterocyclylalkyl" is intended to indicate a heterocyclyl group as defined herein connected via an alkyl group as defined herein.

The term "aryl" is intended to indicate a radical of aromatic carbocyclic rings comprising 6-20 carbon atoms, such as 6-14 carbon atoms, preferably 6-12, such as 6-10 carbon atoms, in particular 5- or 6-membered rings, optionally fused carbocyclic rings with at least one aromatic ring, such as phenyl, naphthyl, biphenyl, anthracenyl, indenyl or indanyl.

The terms "arylalkyl" and "arylcycloalkyl" are intended to indicate an aryl group as defined herein connected via an alkyl or a cycloalkyl group as defined herein, respectively.

The term "heteroaryl" is intended to include radicals of heterocyclic aromatic rings, optionally fused with carbocyclic rings or heterocyclic rings, comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms or 1-2 heteroatoms selected from O, S and N, or optionally fused bicyclic rings with 1-4 heteroatoms, and wherein at least one ring is aromatic. Examples of heteroaryl include, but are not limited to, pyridyl, quinolyl, isoquinolyl, indolyl, tetrazolyl, furyl, thiazolyl, imidazolyl, imidazo[1,2-a]pyrimidinyl, pyrazolyl, oxazolyl, oxadiazolyl, thiophenyl, 1,2,4-triazolyl, isoxazolyl, thienyl, pyrazinyl, pyrimidinyl, [1,2,3]triazolyl, isothiazolyl, imidazo[2,1-b]thiazolyl, benzimidazolyl, benzothiophenyl, benzofuranyl or pyrrolyl.

The term "aryloxy" is intended to indicate groups —O-aryl, wherein aryl is as defined herein, including, by way of example, phenoxy, napthoxy, and the like.

The term "alkyloxy" is intended to indicate the groups —O-alkyl, —O-alkenyl-, and —O-alkynyl-, wherein alkyl, alkenyl and alkynyl are as defined herein.

The term "halogen" is intended to indicate a substituent from the 7$^{th}$ main group of the periodic table, preferably fluoro, chloro and bromo.

The term "amino" refers to the group —NH$_2$.

The term "aminoalkyl" is intended to indicate a radical of the formula -alkyl-NH$_2$, wherein alkyl represents alkylene, cycloalkylene as indicated above, e.g. aminoalkylene, aminocycloethylene etc.

The term "arylamino" is intended to indicate a radical of the formula —NR$_2$, wherein R is aryl as indicated above e.g. phenylamino.

The term "arylaminoalkyl" is intended to indicate an arylamino group as defined herein connected via an alkyl group as defined herein.

The term "alkylthio" is intended to indicate a radical of the formula —S—R, wherein R is alkyl as indicated above.

The term "oxo" is intended to indicate an oxygen atom which is connected via a double bond:

The term "dioxothiolanyl" is intended to indicate radicals of the structures:

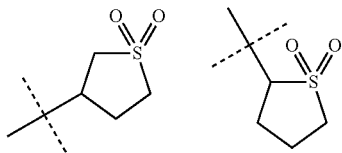

The term "dioxothianyl" is intended to indicate radicals of the structures:

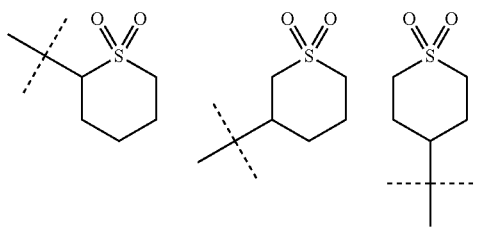

The term "pharmaceutically acceptable salt" is intended to indicate salts prepared by reacting a compound of formula I, which comprises a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, silver hydroxide, ammonia or the like.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Unless indicated otherwise, the nomenclature of substituents that are not explicitly defined herein are arrived at by naming the terminal portion of the functionality followed by the adjacent functionality towards the point of attachment. For example, the group "arylalkyloxycarbonyl" refers to the group (aryl)-(alkyl)-O—C(O)—.

The term "JAK1" is used to indicate a protein tyrosine kinase of the JAK (Janus protein tyrosine kinase) family highly expressed in immune cells where it is essential for signalling by members of the IL-2 receptor family (IL-2, IL-4, IL-7R, IL-9R, IL-15R and IL-21R), the IL-4 receptor family (IL-4R, IL-13R), the gp130 receptor family and class II cytokine receptors.

The term "JAK2" is used to indicate a protein tyrosine kinase of the JAK (Janus protein tyrosine kinase) family highly expressed in immune cells where it is essential for signalling downstream of many cytokines and growth factors including the proinflammatory cytokines Epo, IFN-γ, IL-3, IL-5, and GM-CSF.

The term "JAK3" is used to indicate a protein tyrosine kinase of the JAK (Janus protein tyrosine kinase) family highly expressed in immune cells where it is essential for signalling downstream of many cytokines and growth factors including the proinflammatory cytokines IL-2, IL-4, IL-7, IL-9, IL-15 and IL-21.

The term "TYK2" is used to indicate a protein tyrosine kinase of the JAK (Janus protein tyrosine kinase) family, and TYK2 is implicated in type I interferons, IL-6, IL-10, IL-12 and IL-23 signaling.

Embodiments of Compounds of Formula I

An embodiment of the invention provides a compound of formula I
wherein
m is 0, 1 or 2;
n is 2 or 4;
$R_1$ is selected from the group consisting of hydrogen, halogen, cyano, —$NH_2$, —$SO_2NH_2$, —$SONH_2$, and —$CONH_2$;
or $R_1$ is selected from the group consisting of alkyl-, heteroalkyl-, cycloalkyl-, heterocyclyl-, $R_{1a}$O—, $R_{1a}$S—, $(R_{1a})_2$N—, $R_{1b}$—C(=O)N($R_{1c}$)—, $R_{1b}$O—C(=O)N($R_{1c}$)—, $R_{1b}$O—C(=O)—, $(R_{1b})_2$N—C(=O)N($R_{1c}$)—, $R_{1b}$—S(=O)$_2$N($R_{1c}$)— and $(R_{1b})_2$N—S(=O)$_2$N($R_{1c}$)— either of which may be optionally substituted with one or more $R_{1d}$;
$R_{1a}$ is hydrogen;
or $R_{1a}$ independently at each occurrence is selected from the group consisting of alkyl-, heteroalkyl-, cycloalkyl- and heterocyclyl- either of which may be optionally substituted with one or more $R_{1e}$;
or in the case where two $R_{1a}$s are attached to the same N, they may together with the N atom to which they are attached form a heterocycle which may be optionally substituted with one or more $R_{1e}$;
$R_{1b}$ and $R_{1c}$ independently at each occurrence are selected from the group consisting of hydrogen, alkyl-, heteroalkyl-, cycloalkyl- and heterocyclyl- either of which may be optionally substituted with one or more $R_{1e}$;
or in the case where two $R_{1b}$s are attached to the same N, they may together with the N atom to which they are attached form a heterocycle which may be optionally substituted with one or more $R_{1e}$;
$R_{1d}$ and $R_{1e}$ independently at each occurrence are selected from the group consisting of halogen, cyano, hydroxy, oxo, —$NH_2$, —$SO_2NH_2$, —$CONH_2$, alkyl-, heteroalkyl-, cycloalkyl-, heterocyclyl-, $R_{1f}$O—, $R_{1f}$S—, $(R_{1f})_2$N—, $R_{1f}$O—C(=O)—, $(R_{1f})_2$N—C(=O)—, $R_{1f}$—C(=O)N($R_{1f}$)—, $R_{1f}$O—C(=O)N($R_{1f}$)—, $(R_{1f})_2$N—C(=O)N($R_{1f}$)—, $R_{1f}$—C(=O)O—, $(R_{1f})_2$N—C(=O)O—, $(R_{1f})_2$N—S(=O)$_2$— and $R_{1f}$—S(=O)$_2$N($R_{1f}$)—;
$R_{1f}$ independently at each occurrence is selected from the group consisting of hydrogen, alkyl-, heteroalkyl-, cycloalkyl- and heterocyclyl-;
or in the case where two $R_{1f}$s are attached to the same N, they may together with the N atom to which they are attached form a heterocycle;
$R_2$ is independently at each occurrence a covalent bond or alkyl- or heteroalkyl- group, where any two $R_2$s are attached to the same C ring atom, and together with this C ring atom said two $R_2$s form a carbocycle or heterocycle, hence always forming a spirocyclic piperazine;
$R_3$ independently at each occurrence is selected from the group consisting of halogen, cyano, hydroxy, oxo, alkyl-, heteroalkyl-, cycloalkyl-, heterocyclyl-, $R_{3a}O\text{—}$, $R_{3a}S\text{—}$, $(R_{3a})_2N\text{—}$, $R_{3a}\text{—}C(\text{=}O)\text{—}$, $R_{3a}O\text{—}C(\text{=}O)\text{—}$, $(R_{3a})_2N\text{—}C(\text{=}O)\text{—}$, $R_{3a}\text{—}C(\text{=}O)N(R_{3b})\text{—}$, $R_{3a}O\text{—}C(\text{=}O)N(R_{3b})\text{—}$, $R_{3a}\text{—}C(\text{=}O)O\text{—}$, $(R_{3a})_2N\text{—}C(\text{=}O)O\text{—}$, $R_{3a}\text{—}S(\text{=}O)\text{—}$, $R_{3a}\text{—}S(\text{=}O)_2\text{—}$, $(R_{3a})_2N\text{—}S(\text{=}O)_2\text{—}$ and $R_{3a}\text{—}S(\text{=}O)_2N(R_{3b})\text{—}$;

$R_{3a}$ and $R_{ab}$ independently at each occurrence are selected from the group consisting of hydrogen, alkyl-, heteroalkyl-, cycloalkyl- and heterocyclylor in the case where two $R_{1a}$s are attached to the same N, they may together with the N atom to which they are attached form a heterocycle;

$R_4$ and $R_5$ independently at each occurrence is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, aryloxyalkyl-, heteroarylalkyl-, heteroaryloxyalkyl-, $R_6O\text{-}L\text{-}$, $R_6S\text{-}L\text{-}$, $(R_6)_2N\text{-}L\text{-}$, $R_6\text{—}C(\text{=}O)\text{-}L\text{-}$, $R_6O\text{—}C(\text{=}O)\text{-}L\text{-}$, $(R_6)_2N\text{—}C(\text{=}O)\text{-}L\text{-}$, $R_6\text{—}C(\text{=}O)N(R_6)\text{-}L\text{-}$, $R_6O\text{—}C(\text{=}O)N(R_6)\text{-}L\text{-}$, $(R_6)_2N\text{—}C(\text{=}O)N(R_6)\text{-}L\text{-}$, $R_6\text{—}C(\text{=}O)O\text{-}L\text{-}$, $(R_6)_2N\text{—}C(\text{=}O)O\text{-}L\text{-}$, $R_6\text{—}S(\text{=}O)_2\text{-}L\text{-}$, $(R_6)_2N\text{—}S(\text{=}O)_2\text{-}L\text{-}$, $R_6\text{—}S(\text{=}O)_2N(R_6)\text{-}L\text{-}$ and $(R_6)_2N\text{—}S(\text{=}O)_2N(R_6)\text{-}L$ either of which may be optionally substituted with one or more $R_7$;

or $R_4$ and $R_5$ can together with the N atom to which they are attached form a heterocyclic ring which may be optionally substituted with one or more $R_7$;

or $R_4$ and $R_5$ independently can be hydrogen;

L is independently at each occurrence selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, aryloxyalkyl-, heteroarylalkyl- and heteroaryloxyalkyl-;

$R_6$ independently at each occurrence is selected from the group consisting of hydrogen, alkyl-, heteroalkyl-, alkenyl-, alkynyl-, cycloalkyl-, heterocyclyl-, aryl-, arylalkyl- and heteroaryl-either of which may be optionally substituted with one or more substituents selected from the group consisting of halogen, cyano, hydroxy, trifluoromethyl, oxo, $\text{—}NH_2$, $\text{—}SO_2NH_2$, $\text{—}SONH_2$ and $\text{—}CONH_2$;

or in the case where two $R_6$ are attached to the same N, they may together with the N atom to which they are attached form a heterocycle which may be optionally substituted with one or more substituents selected from the group consisting of halogen, cyano, hydroxy, trifluoromethyl, oxo, $\text{—}NH_2$, $\text{—}SO_2NH_2$, $\text{—}SONH_2$ and $\text{—}CONH_2$;

$R_7$ independently at each occurrence is selected from the group consisting of halogen, cyano, hydroxy, trifluoromethyl, oxo, $\text{—}NH_2$, $\text{—}SO_2NH_2$, $\text{—}SONH_2$ and $\text{—}CONH_2$ or $R_7$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, alkoxy-, aryloxyalkyl-, heteroarylalkyl-, heteroaryloxyalkyl-, $R_8O\text{-}L\text{-}$, $R_8S\text{-}L\text{-}$, $(R_8)_2N\text{-}L\text{-}$, $R_8\text{—}C(\text{=}O)\text{-}L\text{-}$, $R_8O\text{—}C(\text{=}O)\text{-}L\text{-}$, $(R_8)_2N\text{—}C(\text{=}O)\text{-}L\text{-}$, $R_8\text{—}C(\text{=}O)N(R_8)\text{-}L\text{-}$, $R_8O\text{—}C(\text{=}O)N(R_8)\text{-}L\text{-}$, $(R_8)_2N\text{—}C(\text{=}O)N(R_8)\text{-}L\text{-}$, $R_8\text{—}C(\text{=}O)O\text{-}L\text{-}$, $(R_8)_2N\text{—}C(\text{=}O)O\text{-}L\text{-}$, $R_8\text{—}S(\text{=}O)_2\text{-}L\text{-}$, $(R_8)_2N\text{—}S(\text{=}O)_2\text{-}L\text{-}$, $R_8\text{—}S(\text{=}O)_2N(R_8)\text{-}L\text{-}$ and $(R_8)_2N\text{—}S(\text{=}O)_2N(R_8)\text{-}L$ either of which may be optionally substituted with one or more substituents selected from the group consisting of halogen, cyano, hydroxy, trifluoromethyl, oxo, $\text{—}NH_2$, $\text{—}SO_2NH_2$, $\text{—}SONH_2$ and $\text{—}CONH_2$;

$R_8$ independently at each occurrence is selected from the group consisting of hydrogen, alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, and heteroarylalkyl- either of which may be optionally substituted with one or more substituents selected from the group consisting of halogen, cyano, hydroxy, trifluoromethyl, oxo, $\text{—}NH_2$, $\text{—}SO_2NH_2$, $\text{—}SONH_2$ and $\text{—}CONH_2$;

or in the case where two $R_8$ are attached to the same N, they may together with the N atom to which they are attached form a heterocycle which may be optionally substituted with one or more substituents selected from the group consisting of halogen, cyano, hydroxy, trifluoromethyl, oxo, $\text{—}NH_2$, $\text{—}SO_2NH_2$, $\text{—}SONH_2$ and $\text{—}CONH_2$;

and pharmaceutically acceptable salts, prodrugs, hydrates, or solvates thereof.

Another embodiment of the invention provides a compound of formula I wherein m is 0, 1 or 2;

n is 2 or 4;

$R_1$ is selected from the group consisting of hydrogen, halogen, cyano, $\text{—}NH_2$, $\text{—}SO_2NH_2$, $\text{—}SONH_2$, and $\text{—}CONH_2$;

or $R_1$ is selected from the group consisting of $(C_1\text{-}C_4)$alkyl-, heteroalkyl-, $(C_3\text{-}C_6)$cycloalkyl-, heterocyclyl-, $R_{1a}O\text{—}$, $R_{1a}S\text{—}$, $(R_{1a})_2N\text{—}$, $R_{1b}\text{—}C(\text{=}O)N(R_{1c})\text{—}$, $R_{1b}O\text{—}C(\text{=}O)N(R_{1c})\text{—}$, $R_{1b}O\text{—}C(\text{=}O)\text{—}$, $(R_{1b})_2N\text{—}C(\text{=}O)N(R_{1c})\text{—}$, $R_{1b}\text{—}S(\text{=}O)_2N(R_{1c})\text{—}$ and $(R_{1b})_2N\text{—}S(\text{=}O)_2N(R_{1c})\text{—}$ either of which may be optionally substituted with one or more $R_{1d}$;

$R_{1a}$ is hydrogen;

or $R_{1a}$ independently at each occurrence is selected from the group consisting of $(C_1\text{-}C_4)$alkyl-, heteroalkyl-, $(C_3\text{-}C_6)$cycloalkyl- and heterocyclyl- either of which may be optionally substituted with one or more $R_{1e}$;

or in the case where two $R_{1a}$s are attached to the same N, they may together with the N atom to which they are attached form a heterocycle which may be optionally substituted with one or more $R_{1e}$;

$R_{1b}$ and $R_{1c}$ independently at each occurrence are selected from the group consisting of hydrogen, $(C_1\text{-}C_4)$alkyl-, heteroalkyl-, $(C_3\text{-}C_6)$cycloalkyl- and heterocyclyl- either of which may be optionally substituted with one or more $R_{1e}$;

or in the case where two $R_{1b}$s are attached to the same N, they may together with the N atom to which they are attached form a heterocycle which may be optionally substituted with one or more $R_{1e}$;

$R_{1d}$ and $R_{1e}$ independently at each occurrence are selected from the group consisting of halogen, cyano, hydroxy, oxo, $\text{—}NH_2$, $\text{—}SO_2NH_2$, $\text{—}CONH_2$, $(C_1\text{-}C_4)$alkyl-, heteroalkyl-, $(C_3\text{-}C_6)$cycloalkyl-, heterocyclyl-, $R_{1f}O\text{—}$, $R_{1f}S\text{—}$, $(R_{1f})_2N\text{—}$, $R_{1f}O\text{—}C(\text{=}O)\text{—}$, $(R_{1f})_2N\text{—}C(\text{=}O)\text{—}$, $R_{1f}\text{—}C(\text{=}O)N(R_{1f})\text{—}$, $R_{1f}O\text{—}C(\text{=}O)N(R_{1f})\text{—}$, $(R_{1f})_2N\text{—}C(\text{=}O)N(R_{1f})$, $R_{1f}\text{—}C(\text{=}O)O\text{—}$, $(R_{1f})_2N\text{—}C(\text{=}O)O\text{—}$, $(R_{1f})_2N\text{—}S(\text{=}O)_2\text{—}$ and $R_{1f}\text{—}S(\text{=}O)_2N(R_{1f})\text{—}$;

$R_{1f}$ independently at each occurrence is selected from the group consisting of hydrogen, $(C_1\text{-}C_4)$alkyl-, heteroalkyl-, $(C_3\text{-}C_6)$cycloalkyl- and heterocyclyl-;

or in the case where two $R_{1f}$s are attached to the same N, they may together with the N atom to which they are attached form a heterocycle;

$R_2$ is independently at each occurrence a covalent bond or $(C_1\text{-}C_4)$alkyl- or heteroalkyl-group, where any two $R_2$s are attached to the same C ring atom, and together with this C ring atom said two $R_2$s form a carbocycle or heterocycle, hence always forming a spirocyclic piperazine;

$R_3$ independently at each occurrence is selected from the group consisting of halogen, cyano, hydroxy, oxo, $(C_1\text{-}C_4)$alkyl-, heteroalkyl-, $(C_3\text{-}C_6)$cycloalkyl-, heterocyclyl-, $R_{3a}O\text{—}$, $R_{3a}S\text{—}$, $(R_{3a})_2N\text{—}$, $R_{3a}\text{—}C(\text{=}O)\text{—}$, $R_{3a}O\text{—}C$ (=O)—, $(R_{3a})_2N$—C(=O)—, $R_{3a}$—C(=O)N($R_{3b}$)—, $R_{3a}$O—C(=O)N($R_{3b}$)—, $R_{3a}$—C(=O)O—, $(R_{3a})_2N$—C(=O)O—, $R_{3a}$—S(=O)—, $R_{3a}$—S(=O)$_2$—, $(R_{3a})_2N$—S(=O)$_2$— and $R_{3a}$—S(=O)$_2$N($R_{3b}$)—;

$R_{3a}$ and $R_{ab}$ independently at each occurrence are selected from the group consisting of hydrogen, $(C_1$-$C_4)$alkyl-, heteroalkyl-, $(C_3$-$C_6)$cycloalkyl- and heterocyclylor in the case where two $R_{3a}$s are attached to the same N, they may together with the N atom to which they are attached form a heterocycle;

$R_4$ and $R_5$ independently at each occurrence is selected from the group consisting of $(C_1$-$C_5)$alkyl-, heteroalkyl-, $(C_2$-$C_4)$alkenyl-, $(C_2$-$C_4)$alkynyl-, $(C_3$-$C_8)$cycloalkyl-, cycloalkenyl-, cycloalkynyl-, heterocyclyl-, cycloalkyl($C_1$-$C_4$)alkyl-, heterocyclyl($C_1$-$C_4$)alkyl, $(C_1$-$C_4)$alkyl($C_3$-$C_8$)cycloalkyl-, $(C_1$-$C_4)$alkylheterocyclyl-, aryl-, heteroaryl-, aryl($C_1$-$C_4$)alkyl-, aryloxy($C_1$-$C_4$)alkyl-, heteroaryl($C_1$-$C_4$)alkyl-, heteroaryloxy($C_1$-$C_4$)alkyl-, $R_6$O-L-, $R_6$S-L-, $(R_6)_2$N-L-, $R_6$—C(=O)-L-, $R_6$O—C(=O)-L-, $(R_6)_2$N—C(=O)-L-, $R_6$—C(=O)N($R_6$)-L-, $R_6$O—C(=O)N($R_6$)-L-, $(R_6)_2$N—C(=O)N($R_6$)-L-, $R_6$—C(=O)O-L-, $(R_6)_2$N—C(=O)O-L-, $R_6$—S(=O)$_2$-L-, $(R_6)_2$N—S(=O)$_2$-L-, $R_6$—S(=O)$_2$N($R_6$)-L- and $(R_6)_2$N—S(=O)$_2$N($R_6$)-L either of which may be optionally substituted with one or more $R_7$;

or $R_4$ and $R_5$ can together with the N atom to which they are attached form a heterocyclic ring which may be optionally substituted with one or more $R_7$;

or $R_4$ and $R_5$ independently can be hydrogen;

L is independently at each occurrence selected from the group consisting of $(C_1$-$C_4)$alkyl-, heteroalkyl-, $(C_2$-$C_4)$alkenyl-, $(C_2$-$C_4)$alkynyl-, $(C_3$-$C_8)$cycloalkyl-, cycloalkenyl-, cycloalkynyl-, heterocyclyl-, $(C_3$-$C_8)$cycloalkyl($C_1$-$C_4$)alkyl-, heterocyclylalkyl, $(C_1$-$C_4)$alkyl($C_3$-$C_8$)cycloalkyl-, $(C_1$-$C_4)$alkylheterocyclyl-, aryl-, heteroaryl-, aryl($C_1$-$C_4$)alkyl-, aryloxy($C_1$-$C_4$)alkyl-, heteroaryl($C_1$-$C_4$)alkyl- and heteroaryloxy($C_1$-$C_4$)alkyl-;

or when $R_4$ or $R_5$ is selected from $R_6$O-L-, L can also be a bond;

$R_6$ independently at each occurrence is selected from the group consisting of hydrogen, $(C_1$-$C_4)$alkyl-, heteroalkyl-, $(C_2$-$C_4)$alkenyl-, $(C_2$-$C_4)$alkynyl-, $(C_3$-$C_6)$cycloalkyl-, heterocyclyl-, aryl-, aryl($C_1$-$C_4$)alkyl- and heteroaryl-, $(C_3$-$C_6)$cycloalkyl($C_1$-$C_4$)alkyl- either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ and —O($C_1$-$C_4$);

or in the case where two $R_6$ are attached to the same N, they may together with the N atom to which they are attached form a heterocycle which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

$R_7$ independently at each occurrence is selected from the group consisting of halogen, cyano, hydroxy, trifluoromethyl, oxo, —NH$_2$, —SO$_2$NH$_2$, —SONH$_2$, —CONH$_2$ and =CH$_2$, or $R_7$ is selected from the group consisting of $(C_1$-$C_4)$alkyl-, heteroalkyl-, $(C_2$-$C_4)$alkenyl-, $(C_2$-$C_4)$alkynyl-, $(C_3$-$C_8)$cycloalkyl-, cycloalkenyl-, cycloalkynyl-, heterocyclyl-, $(C_3$-$C_8)$cycloalkylalkyl-, heterocyclyl($C_1$-$C_4$)alkyl, $(C_1$-$C_4)$alkyl($C_3$-$C_8$)cycloalkyl-, $(C_1$-$C_4)$alkylheterocyclyl-, aryl-, heteroaryl-, aryl($C_1$-$C_4$)alkyl-, alkoxy-, aryloxy($C_1$-$C_4$)alkyl-, heteroaryl($C_1$-$C_4$)alkyl-, heteroaryloxy($C_1$-$C_4$)alkyl-, $R_8$O-L-, $R_8$S-L-, $(R_8)_2$N-L-, $R_8$—C(=O)-L-, $R_8$O—C(=O)-L-, $(R_8)_2$N—C(=O)-L-, $R_8$—C(=O)N($R_8$)-L-, $R_8$O—C(=O)N($R_8$)-L-, $(R_8)_2$N—C(=O)N($R_8$)-L-, $R_8$—C(=O)O-L-, $(R_8)_2$N—C(=O)O-L-, $R_8$—S(=O)$_2$-L-, $(R_8)_2$N—S(=O)$_2$-L-, $R_8$—S(=O)$_2$N($R_8$)-L- and $(R_8)_2$N—S(=O)$_2$N($R_8$)-L either of which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

$R_8$ independently at each occurrence is selected from the group consisting of hydrogen, $(C_1$-$C_4)$alkyl-, heteroalkyl-, $(C_2$-$C_4)$alkenyl-, $(C_2$-$C_4)$alkynyl-, $(C_3$-$C_6)$cycloalkyl-, heterocyclyl-, $(C_3$-$C_6)$cyclolalkyl($C_1$-$C_4$)alkyl-, heterocyclyl($C_1$-$C_4$)alkyl-, aryl-, aryl($C_1$-$C_4$)alkyl-, heteroaryl-, and heteroaryl($C_1$-$C_4$)alkyl- either of which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

or in the case where two $R_8$ are attached to the same N, they may together with the N atom to which they are attached form a heterocycle which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

and pharmaceutically acceptable salts, prodrugs, hydrates, or solvates thereof;

with the proviso that when $R_1$ is hydrogen, and m is 0, and n is 2, and the two $R_2$'s form a cyclopropyl ring together with the carbon atom to which they are attached, and $R_4$ is methyl, $R_5$ is not selected from the group consisting of cyanoethyl or cyclohexyl;

and with the proviso that when $R_1$ is hydrogen, and m is 0, and n is 2, and the two $R_2$'s form a cyclopropyl ring together with the carbon atom to which they are attached, and $R_5$ is methyl, $R_4$ is not selected from the group consisting of cyanoethyl or cyclohexyl;

and with the proviso that when $R_1$ is hydrogen, and m is 0, and n is 2, and the two $R_2$'s form a cyclopropyl ring together with the carbon atom to which they are attached, and $R_4$ is ethyl, $R_5$ is not ethyl.

An embodiment of the invention provides a compound of formula I wherein m is 0 or 1.

An embodiment of the invention provides a compound of formula I wherein m is 0.

An embodiment of the invention provides a compound of formula I wherein n is 2.

An embodiment of the invention provides a compound of formula I wherein $R_1$ is selected from the group consisting of hydrogen, —NH$_2$, —SO$_2$NH$_2$, —SONH$_2$, and —CONH$_2$.

An embodiment of the invention provides a compound of formula I wherein $R_1$ is hydrogen.

An embodiment of the invention provides a compound of formula I wherein $R_1$ is selected from the group consisting $(R_{1a})_2$N—, $R_{1b}$—C(=O)N($R_{1c}$)—, $R_{1b}$O—C(=O)N($R_{1c}$)—, $R_{1b}$O—C(=O)—, $(R_{1b})_2$N—C(=O)N($R_{1c}$)—, $R_{1b}$—S(=O)$_2$N($R_{1c}$)— and $(R_{1b})_2$N—S(=O)$_2$N($R_{1c}$)— either of which may be optionally substituted with one or more $R_{1d}$.

An embodiment of the invention provides a compound of formula I wherein $R_{1a}$ is hydrogen.

An embodiment of the invention provides a compound of formula I wherein each $R_2$ independently at each occurrence is selected from the group consisting of

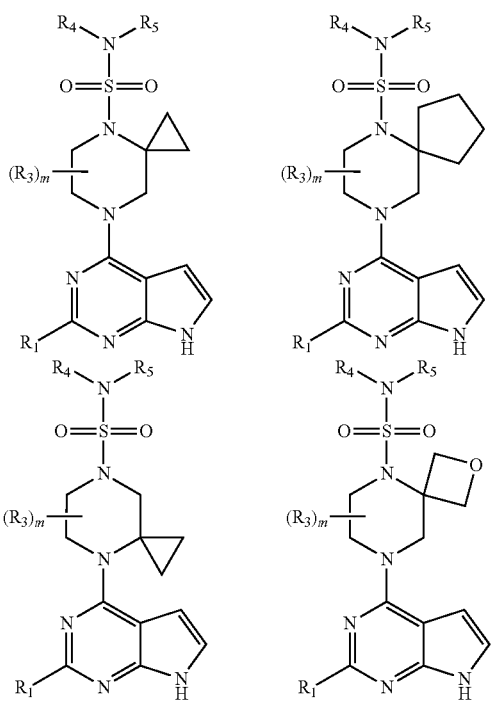

An embodiment of the invention provides a compound of formula I wherein $R_2$ is

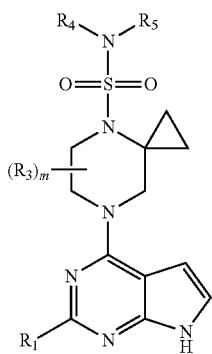

An embodiment of the invention provides a compound of formula I wherein m=0 and wherein $R_1$ is hydrogen.

An embodiment of the invention provides a compound of formula I wherein $R_3$ independently at each occurrence is selected from the group consisting of cyano, hydroxy, oxo, alkyl-, heteroalkyl-, and $R_{3a}O$—.

An embodiment of the invention provides a compound of formula I wherein $R_3$ independently at each occurrence is selected from the group consisting of cyano, hydroxy, oxo, $(C_1-C_4)$alkyl-, heteroalkyl-, and $R_{3a}O$—.

An embodiment of the invention provides a compound of formula I wherein $R_4$ and $R_5$ independently at each occurrence is selected from the group consisting of alkyl-, heteroalkyl-, cycloalkyl-, heterocyclyl-, cycloalkylalkyl-, heterocyclylalkyl, alkylcycloalkyl-, alkylheterocyclyl-, aryl-, heteroaryl-, arylalkyl-, aryloxyalkyl-, heteroarylalkyl-, heteroaryloxyalkyl-, $R_6O$-L-, $R_6S$-L-, $(R_6)_2N$-L-, $R_6O$—C(=O)-L-, $(R_6)_2N$—C(=O)-L-, $R_6$—C(=O)N($R_6$)-L-, $R_6O$—C(=O)N($R_6$)-L-, $(R_6)_2N$—C(=O)N($R_6$)-L-, $R_6$—C(=O)O-L-, $(R_6)_2N$—C(=O)O-L-, $R_6$—S(=O)$_2$-L-, $(R_6)_2$N—S(=O)$_2$-L-, $R_6$—S(=O)$_2$N($R_6$)-L- and $(R_6)_2N$—S(=O)$_2$N($R_6$)-L either of which may be optionally substituted with one or more $R_7$.

An embodiment of the invention provides a compound of formula I wherein $R_4$ and $R_5$ independently at each occurrence is selected from the group consisting of $(C_1-C_5)$alkyl-, heteroalkyl-, $(C_3-C_8)$cycloalkyl-, heterocyclyl-, $(C_3-C_8)$cycloalkyl$(C_1-C_4)$alkyl-, heterocyclyl$(C_1-C_4)$alkyl, $(C_1-C_4)$alkyl$(C_3-C_8)$cycloalkyl-, $(C_1-C_4)$alkylheterocyclyl-, aryl-, heteroaryl-, aryl$(C_1-C_4)$alkyl-, aryloxy$(C_1-C_4)$alkyl-, heteroaryl$(C_1-C_4)$alkyl-, heteroaryloxy$(C_1-C_4)$alkyl-, $R_6O$-L-, $R_6S$-L-, $(R_6)_2N$-L-, $R_6O$—C(=O)-L-, $(R_6)_2N$—C(=O)-L-, $R_6$—C(=O)N($R_6$)-L-, $R_6O$—C(=O)N($R_6$)-L-, $(R_6)_2N$—C(=O)N($R_6$)-L-, $R_6$—C(=O)O-L-, $(R_6)_2N$—C(=O)O-L-, $R_6$—S(=O)$_2$-L-, $(R_6)_2N$—S(=O)$_2$-L-, $R_6$—S(=O)$_2$N($R_6$)-L-, and $(R_6)_2N$—S(=O)$_2$N($R_6$)-L either of which may be optionally substituted with one or more $R_7$.

An embodiment of the invention provides a compound of formula I wherein $R_4$ and $R_5$ together with the N atom to which they are attached form a heterocyclic ring which may be optionally substituted with one or more $R_7$.

An embodiment of the invention provides a compound of formula I wherein $R_4$ is hydrogen.

An embodiment of the invention provides a compound of formula I wherein $R_5$ is hydrogen.

An embodiment of the invention provides a compound of formula I wherein L is independently at each occurrence selected from the group consisting of alkyl-, heteroalkyl-, cycloalkyl-, heterocyclyl-, cycloalkylalkyl-, heterocyclylalkyl, alkylcycloalkyl-, alkylheterocyclyl-.

An embodiment of the invention provides a compound of formula I wherein L is independently at each occurrence selected from the group consisting of $(C_1-C_4)$alkyl-, heteroalkyl-, $(C_3-C_8)$cycloalkyl-, heterocyclyl-, $(C_3-C_8)$cycloalkyl$(C_1-C_4)$alkyl-, heterocyclyl$(C_1-C_4)$alkyl, alkyl$(C_3-C_8)$cycloalkyl-, $(C_1-C_4)$alkylheterocyclyl-, aryl$(C_1-C_4)$alkyl- and heteroaryl$(C_1-C_4)$alkyl-.

An embodiment of the invention provides a compound of formula I wherein $R_4$ and $R_5$ independently are selected from the group consisting of hydrogen, methyl, ethyl, propyl, butyl, isopropyl, isobutyl, isoamyl, pentyl, benzyl, butynyl, cyclopropyl, cyclobutyl, cyclopentyl, oxetanyl, phenyl, phenylpropyl, phenethyl, pyridylmethyl, cyclopropylmethyl, cyclopropylethyl, cyclobutylmethyl, cyclopentylmethyl, cyclopentylethyl, cyclopentylpropyl, cyclohexylmethyl, cyclohexylethyl, cubanylmethyl, tetrahydrofuranylmethyl, tetrahydropyranylmethyl, morpholinylethyl, dioxothiolanylmethyl, dioxothiolanylethyl, dioxothianyl, dioxothianylmethyl, dioxothianylethyl, azetidinyl, pyrrolidinylmethyl, piperidinylmethyl, pyrazolylmethyl, pyrazolylethyl, pyrrolylethyl, isoxazolylmethyl, isoxazolylethyl, imidazolylethyl, $R_6O$—C(=O)-L-, $R_6$—C(=O)N($R_6$)-L-, $R_6O$-L-, $(R_6)_2N$—C(=O)-L-, $(R_6)_2N$-L-, $(R_6)_2N$—S(=O)$_2$-L-, $R_6$—S(=O)$_2$-L-, $R_6$—C(=O)-L-, either of which may be optionally substituted with one or more $R_7$; and wherein L is selected from the group consisting of methyl, ethyl, propyl, furanylmethyl, benzyl, azetidinyl, pyrrolidinylmethyl, piperidinylmethyl; and wherein $R_6$ is independently selected from the group consisting of hydrogen, methyl, ethyl, propyl, isobutyl, tert-butyl, phenyl, benzyl, trifluoromethyl, cyclopropylmethyl, either of which $R_6$ may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$, —O(C$_1$-C$_4$).

An embodiment of the invention provides a compound of formula I wherein $R_4$ and $R_5$ independently are selected from the group consisting of hydrogen, methyl, propyl, butyl, isopropyl, isobutyl, isoamyl, pentyl, benzyl, butynyl, cyclopropyl, cyclobutyl, cyclopentyl, oxetanyl, phenyl, phenylpropyl, phenethyl, pyridylmethyl, cyclopropylmethyl, cyclopropylethyl, cyclobutylmethyl, cyclopentylmethyl, cyclopentylethyl, cyclopentylpropyl, cyclohexylmethyl, cyclohexylethyl, cubanylmethyl, tetrahydrofuranylmethyl, tetrahydropyranylmethyl, morpholinylethyl, dioxothiolanylmethyl, dioxothiolanylethyl, dioxothianyl, dioxothianylmethyl, dioxothianylethyl, azetidinyl, pyrrolidinylmethyl, piperidinylmethyl, pyrazolylmethyl, pyrazolylethyl, pyrrolylethyl, isoxazolylmethyl, isoxazolylethyl, imidazolylethyl, $R_6O-C(=O)-L-$, $R_6-C(=O)N(R_6)-L-$, $R_6O-L-$, $(R_6)_2N-C(=O)-L-$, $(R_6)_2N-L-$, $(R_6)_2N-S(=O)_2-L-$, $R_6-S(=O)_2-L-$, $R_6-C(=O)-L-$, either of which may be optionally substituted with one or more $R_7$; and wherein L is selected from the group consisting of methyl, ethyl, propyl, furanylmethyl, benzyl, azetidinyl, pyrrolidinylmethyl, piperidinylmethyl; and wherein $R_6$ is independently selected from the group consisting of hydrogen, methyl, ethyl, propyl, isobutyl, tert-butyl, phenyl, benzyl, trifluoromethyl, cyclopropylmethyl, either of which $R_6$ may be optionally substituted with one or more substituents selected from the group consisting of halogen, cyano, hydroxy, trifluoromethyl, oxo, $-NH_2$, $-SO_2NH_2$, $-SONH_2$ and $-CONH_2$, $-O(C_1-C_4)$.

An embodiment of the invention provides a compound of formula I wherein $R_7$ independently at each occurrence is selected from the group consisting of fluoro, chloro, cyano, hydroxy, trifluoromethyl, oxo, $-NH_2$, $-SO_2NH_2$, $-SONH_2$, $-CONH_2$, and $=CH_2$.

An embodiment of the invention provides a compound of formula I wherein $R_7$ is selected from the group consisting of alkyl-, heteroalkyl-, alkynyl-, cycloalkyl-, heterocyclyl-, cycloalkylalkyl-, heterocyclylalkyl, alkylcycloalkyl-, alkylheterocyclyl-, arylalkyl-, $R_8O-$, $R_8S-$, $(R_8)_2N-$, $R_8O-C(=O)-$, $(R_8)_2N-C(=O)-$, $R_8-C(=O)N(R_8)-$, $R_8O-C(=O)N(R_8)-$, $(R_8)_2N-C(=O)N(R_8)-$, $R_8-C(=O)O-$, $(R_8)_2N-C(=O)O-$, $R_8-S(=O)_2-$, $(R_8)_2N-S(=O)_2-$, $R_8-S(=O)_2N(R_8)-$ and $(R_8)_2N-S(=O)_2N(R_8)-$ either of which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$.

An embodiment of the invention provides a compound of formula I wherein $R_7$ is selected from the group consisting of methyl, tert-butyl, phenyl, cyclopropyl, cyclobutyl, cyclopentyl, cyclohexyl, tetrahydrofuranyl, tetrahydropyranyl, morpholinyl, dioxothiolanyl, dioxothianyl, pyrrolidinyl, piperidinyl, pyrazolyl, pyrrolyl, pyridyl, imidazolyl, benzyl, $R_8O-C(=O)-$, $R_8O-$, $(R_8)_2N-C(=O)-$ and $(R_8)_2N-$, either of which may be optionally substituted with one or more substituents selected from the group consisting of fluoro, chloro, cyano, hydroxy, trifluoromethyl and oxo; and wherein $R_8$ is selected from the group consisting of methyl, ethyl and phenyl.

An embodiment of the invention provides a compound of formula I wherein $R_7$ independently at each occurrence is selected from the group consisting of halogen, cyano, hydroxy, trifluoromethyl, oxo, $-NH_2$, $-SO_2NH_2$, $-SONH_2$ and $-CONH_2$.

An embodiment of the invention provides a compound of formula I wherein $R_7$ is selected from the group consisting of alkyl-, heteroalkyl-, alkynyl-, cycloalkyl-, heterocyclyl-, cycloalkylalkyl-, heterocyclylalkyl, alkylcycloalkyl-, alkylheterocyclyl-, $R_8O-$, $R_8S-$, $(R_8)_2N-$, $R_8O-C(=O)-$, $(R_8)_2N-C(O)-$, $R_8-C(O)N(R_8)-$, $R_8O-C(=O)N(R_8)-$, $(R_8)_2N-C(=O)N(R_8)-$, $R_8-C(=O)O-$, $(R_8)_2N-C(=O)O-$, $R_8-S(=O)_2-$, $(R_8)_2N-S(=O)_2-$, $R_8-S(=O)_2N(R_8)-$ and $(R_8)_2N-S(=O)_2N(R_8)-$ either of which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$;

An embodiment of the invention provides a compound of formula I wherein $R_7$ is selected from the group consisting of $(C_1-C_4)$alkyl-, heteroalkyl-, $(C_2-C_4)$alkynyl-, $(C_3-C_8)$cycloalkyl-, heterocyclyl-, $(C_3-C_8)$cycloalkyl$(C_1-C_4)$alkyl-, heterocyclyl$(C_1-C_4)$alkyl, $(C_1-C_4)$alkyl$(C_3-C_8)$cycloalkyl-, $(C_1-C_4)$alkylheterocyclyl-, aryl$(C_1-C_4)$alkyl-, $R_8O-$, $R_8S-$, $(R_8)_2N-$, $R_8O-C(=O)-$, $(R_8)_2N-C(=O)-$, $R_8-C(=O)N(R_8)-$, $R_8O-(=O)N(R_8)-$, $(R_8)_2N-C(=O)N(R_8)-$, $R_8-C(=O)O-$, $(R_8)_2N-C(=O)O-$, $R_8-S(=O)_2-$, $(R_8)_2N-S(=O)_2-$, $R_8-S(=O)_2N(R_8)-$ and $(R_8)_2N-S(=O)_2N(R_8)-$ either of which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$.

An embodiment of the invention provides a compound of formula I wherein $R_8$ independently at each occurrence is selected from the group consisting of hydrogen, alkyl-, heteroalkyl-, cycloalkyl-, heterocyclyl-, cyclolalkylalkyl-, heterocyclylalkyl-, aryl-, arylalkyl-, heteroaryl-, and heteroarylalkyl- either of which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$.

An embodiment of the invention provides a compound of formula I wherein $R_8$ independently at each occurrence is selected from the group consisting of hydrogen, $(C_1-C_4)$alkyl-, heteroalkyl-, $(C_3-C_6)$cycloalkyl-, heterocyclyl-, $(C_3-C_6)$cyclolalkyl$(C_1-C_4)$alkyl-, heterocyclyl$(C_1-C_4)$alkyl-, aryl-, aryl$(C_1-C_4)$alkyl-, heteroaryl-, and heteroaryl$(C_1-C_4)$alkyl- either of which may be optionally substituted with one or more substituents selected from the group consisting of halogen, cyano, hydroxy, trifluoromethyl, oxo, $-NH_2$, $-SO_2NH_2$, $-SONH_2$ and $-CONH_2$.

An embodiment of the invention provides a compound of formula wherein one of $R_4$ and $R_5$ is selected from the group consisting of $(C_1-C_2)$alkyl-, heteroalkyl-, $(C_2-C_4)$alkenyl-, $(C_2-C_4)$alkynyl-, $(C_3-C_8)$cycloalkyl-, cycloalkenyl-, cycloalkynyl-, heterocyclyl-, cycloalkyl$(C_1-C_4)$alkyl-, heterocyclyl$(C_1-C_4)$alkyl, $(C_1-C_4)$alkyl$(C_3-C_8)$cycloalkyl-, $(C_1-C_4)$alkylheterocyclyl-, aryl-, heteroaryl-, aryl$(C_1-C_4)$alkyl-, aryloxy$(C_1-C_4)$alkyl-, heteroaryl$(C_1-C_4)$alkyl-, heteroaryloxy$(C_1-C_4)$alkyl-, $R_6O-L-$, $R_6S-L-$, $(R_6)_2N-L-$, $R_6-C(=O)-L-$, $R_6O-C(=O)-L-$, $(R^6)_2N-C(=O)-L-$, $R_6-C(=O)N(R_6)-L-$, $R_6O-C(=O)N(R_6)-L-$, $(R_6)_2N-C(=O)N(R_6)-L-$, $R_6-C(=O)O-L-$, $(R^6)_2N-C(=O)O-L-$, $R_6-S(=O)_2-L-$, $(R_6)_2N-S(=O)_2-L-$, $R_6-S(=O)_2N(R_6)-L-$ and $(R_6)_2N-S(=O)_2N(R_6)-L$ either of which may be optionally substituted with one or more $R_7$;

and wherein the other $R_4$ or $R_5$ is selected from the group consisting of $(C_3-C_8)$alkyl-, heteroalkyl-, $(C_2-C_4)$alkenyl-, $(C_2-C_4)$alkynyl-, $(C_3-C_5)$cycloalkyl-, cycloalkenyl-, cycloalkynyl-, heterocyclyl-, cycloalkyl$(C_1-C_4)$alkyl-, heterocyclyl$(C_1-C_4)$alkyl, $(C_1-C_4)$alkyl$(C_3-C_8)$cycloalkyl-, $(C_1-C_4)$alkylheterocyclyl-, aryl-, heteroaryl-, aryl$(C_1-C_4)$alkyl-, aryloxy$(C_1-C_4)$alkyl-, heteroaryl$(C_1-C_4)$alkyl-, heteroaryloxy$(C_1-C_4)$alkyl-, $R_6S-L-$, $(R_6)_2N-L-$, $R_6-C(=O)-L-$, $R_6O-C(=O)-L-$, $(R^6)_2N-C(=O)-L-$, $R_6-C(=O)N(R_6)-L-$, $R_6O-C(=O)N(R_6)-L-$, $(R_6)_2N-C(=O)N(R_6)-L-$, $R_6-C(=O)O-L-$, $(R^6)_2N-C(=O)O-L-$, $R_6-S(=O)_2-L-$, $(R_6)_2N—S(=O)_2$-L-, $R_6—S(=O)_2N(R_6)$-L- and $(R_6)_2N—S(=O)_2N(R_6)$-L either of which may be optionally substituted with one or more $R_7$;

or $R_4$ and $R_5$ can together with the N atom to which they are attached form a heterocyclic ring which may be optionally substituted with one or more $R_7$;

or $R_4$ and $R_5$ independently can be hydrogen;

An embodiment of the invention provides a compound of formula wherein at least one of $R_4$ and $R_5$ is selected from the group consisting of heteroalkyl-, heterocyclyl($C_1$-$C_4$)alkyl, aryl($C_1$-$C_4$)alkyl-, and heteroaryl($C_1$-$C_4$)alkyl-, wherein said heteroalkyl-, heterocyclyl($C_1$-$C_4$)alkyl, aryl($C_1$-$C_4$)alkyl- and heteroaryl($C_1$-$C_4$)alkyl- is substituted with one or more $R_7$;

An embodiment of the invention provides a compound of formula I wherein at least one of $R_4$ and $R_5$ is benzyl which is substituted with one or more $R_7$.

An embodiment of the invention provides a compound of formula I wherein at least one of $R_4$ and $R_5$ is selected from the group consisting of $R_6$O-L-, $(R_6)_2$N-L-, $R_6$—C(=O)-L-, $R_6$O—C(=O)-L-, $(R_6)_2$N—C(=O)-L-, $R_6$—C(=O)N($R_6$)-L-, $R_6$O—C(=O)N($R_6$)-L-, $(R_6)_2$N—C(=O)N($R_6$)-L-, $R_6$—C(=O)O-L-, $(R_6)_2$N—C(=O)O-L-, $R_6$—S(=O)_2-L-, $(R_6)_2$N—S(=O)_2-L-, $R_6$—S(=O)_2N($R_6$)-L- and $(R_6)_2$N—S(=O)_2N($R_6$)-L-, either of which may be optionally substituted with one or more $R_7$; wherein L independently at each occurrence is selected from the group consisting of heterocyclyl-, heterocyclyl($C_1$-$C_4$)alkyl, ($C_1$-$C_4$)alkylheterocyclyl-, aryl($C_1$-$C_4$)alkyl- and heteroaryl($C_1$-$C_4$)alkyl-.

An embodiment of the invention provides a compound of formula I wherein one of $R_4$ and $R_5$ is selected from the group consisting of dioxothiolanylmethyl, dioxothiolanylethyl, dioxothianylmethyl and dioxothianylethyl.

An embodiment of the invention provides a compound of formula I wherein one of $R_4$ and $R_5$ is dioxothiolanylmethyl.

An embodiment of the invention provides a compound of formula I wherein one of $R_4$ and $R_5$ is dioxothianylmethyl.

An embodiment of the invention provides a compound of formula I wherein at least one of $R_4$ and $R_5$ is selected from $R_6$—C(=O)-L-, $R_6$—S(=O)_2-L- or $(R_6)_2$N—S(=O)_2-L-, which may be optionally substituted with one or more $R_7$; wherein L is selected from the group consisting of heterocyclyl-, heterocyclyl($C_1$-$C_4$)alkyl, ($C_1$-$C_4$)alkylheterocyclyl-, aryl($C_1$-$C_4$)alkyl- and heteroaryl($C_1$-$C_4$)alkyl-.

An embodiment of the invention provides a compound of formula I wherein at least one of $R_4$ and $R_5$ is selected from $R_6$—C(=O)-L-, $R_6$—S(=O)_2-L- or $(R_6)_2$N—S(=O)_2-L-, which may be optionally substituted with one or more $R_7$; wherein L is selected from the group consisting of piperidinylmethyl, pyrrolidinylmethyl, benzyl and azetidinyl; and wherein R6 is selected from the group consisting of hydrogen, methyl, ethyl, propyl, cyclopropylmethyl, hydroxymethyl, hydroxyethyl, cyanoethyl, cyanopropyl.

An embodiment of the invention provides a compound of formula I wherein $R_6$—C(=O)-L-, $R_6$—S(=O)_2-L- or $(R_6)_2$N—S(=O)_2-L- is substituted by at least two fluoro; and wherein L is selected from the group consisting of piperidinylmethyl, pyrrolidinylmethyl, benzyl and azetidinyl; and wherein R6 is selected from the group consisting of hydrogen, methyl, ethyl, propyl, cyclopropylmethyl, hydroxymethyl, hydroxyethyl, cyanoethyl, cyanopropyl.

An embodiment of the invention provides a compound of formula I wherein one of $R_4$ and $R_5$ is selected from the group consisting of heterocyclyl($C_1$-$C_4$)alkyl and ($C_3$-$C_6$)cycloalkyl($C_1$-$C_4$)alkyl and wherein said heterocyclyl($C_1$-$C_4$)alkyl and ($C_3$-$C_6$)cycloalkyl($C_1$-$C_4$)alkyl is substituted with two or more $R_7$; wherein at least two $R_7$ are fluoro.

An embodiment of the invention provides a compound of formula I wherein one of $R_4$ and $R_5$ is selected from the group consisting of cyclopropylmethyl, cyclobutylmethyl, cyclohexylmethyl and pyrrolidinylmethyl and wherein said cyclopropylmethyl, cyclobutylmethyl, cyclohexylmethyl and pyrrolidinylmethyl is substituted with two or more $R_7$; wherein at least two $R_7$ are fluoro.

An embodiment of the invention provides a compound of formula I wherein $R_4$ is methyl.

An embodiment of the invention provides a compound of formula I wherein $R_5$ is methyl.

An embodiment of the invention provides a compound of formula I which is selected from 7-(7H-Pyrrolo[2,3-d]pyrimidin-4-yl)-4,7-diaza-spiro[2.5] octane-4-sulfonic acid amide, 7-(7H-Pyrrolo[2,3-d]pyrimidin-4-yl)-4,7-diaza-spiro[2.5] octane-4-sulfonic acid methylamide, 7-(7H-Pyrrolo[2,3-d]pyrimidin-4-yl)-4,7-diaza-spiro[2.5] octane-4-sulfonic acid phenethyl-amide, 4-[4-(Imidazole-1-sulfonyl)-4,7-diaza-spiro[2.5]oct-7-yl]-7H-pyrrolo[2,3-d]pyrimidine, N-methyl-N-(pyrrolidin-3-ylmethyl)-5-(7H-pyrrolo[2,3-d] pyrimidin-4-yl)-5,8-diazaspiro[2.5]octane-8-sulfonamide, N-methyl-N-(4-piperidylmethyl)-5-(7H-pyrrolo[2,3-d]pyrimidin-4-yl)-5,8-diazaspiro[2.5]octane-8-sulfonamide as formic acid salt, N-methyl-N-(3-piperidylmethyl)-5-(7H-pyrrolo[2,3-d]pyrimidin-4-yl)-5,8-diazaspiro[2.5]octane-8-sulfonamide as formic acid salt, N-[[(2S)-4,4-difluoropyrrolidin-2-yl]methyl]-N-methyl-5-(7H-pyrrolo[2,3-d]pyrimidin-4-yl)-5,8-diazaspiro[2.5]octane-8-sulfonamide as formic acid salt, N-cyclobutyl-5-(7H-pyrrolo[2,3-d]pyrimidin-4-yl)-5,8-diazaspiro[2.5]octane-8-sulfonamide, N-[(1,1-dioxothiolan-3-yl)methyl]-5-(7H-pyrrolo[2,3-d]pyrimidin-4-yl)-5,8-diazaspiro[2.5]octane-8-sulfonamide, N-[(1,1-dioxothian-4-yl)methyl]-5-(7H-pyrrolo[2,3-d]pyrimidin-4-yl)-5,8-diazaspiro[2.5]octane-8-sulfonamide, N-(2-cyanoethyl)-5-(7H-pyrrolo[2,3-d]pyrimidin-4-yl)-5,8-diazaspiro[2.5]octane-8-sulfonamide, N-(oxetan-3-yl)-5-(7H-pyrrolo[2,3-d]pyrimidin-4-yl)-5,8-diazaspiro[2.5]octane-8-sulfonamide, N-benzyloxy-5-(7H-pyrrolo[2,3-d]pyrimidin-4-yl)-5,8-diazaspiro[2.5]octane-8-sulfonamide, (NZ)—N-[(4-methoxyphenyl)methylene]-5-(7H-pyrrolo[2,3-d]pyrimidin-4-yl)-5,8-diazaspiro[2.5]octane-8-sulfonamide, N-(azetidin-3-yl)-N-methyl-5-(7H-pyrrolo[2,3-d]pyrimidin-4-yl)-5,8-diazaspiro[2.5]octane-8-sulfonamide, N-methyl-N-[[(2R)-pyrrolidin-2-yl]methyl]-5-(7H-pyrrolo [2,3-d]pyrimidin-4-yl)-5,8-diazaspiro[2.5]octane-8-sulfonamide, N-methyl-N-[[(2S)-pyrrolidin-2-yl]methyl]-5-(7H-pyrrolo [2,3-d]pyrimidin-4-yl)-5,8-diazaspiro[2.5]octane-8-sulfonamide as formic acid salt, tert-butyl N-[[5-(7H-pyrrolo[2,3-d]pyrimidin-4-yl)-5,8-diazaspiro[2.5]octan-8-yl]sulfonyl]carbamate, 4-{4-[Phenethyl-(3-phenyl-propyl)-sulfamoyl]-4,7-diazaspiro[2.5]oct-7-yl}-pyrrolo[2,3-d]pyrimidine-7-carboxylic acid tert-butyl ester, 7-(7H-Pyrrolo[2,3-d]pyrimidin-4-yl)-4,7-diaza-spiro[2.5] octane-4-sulfonic acid cyclopropylmethyl-phenethyl-amide, 7-(7H-Pyrrolo[2,3-d]pyrimidin-4-yl)-4,7-diaza-spiro[2.5] octane-4-sulfonic acid cyclobutylmethyl-phenethyl-amide, 7-(7H-Pyrrolo[2,3-d]pyrimidin-4-yl)-4,7-diaza-spiro[2.5]
octane-4-sulfonic acid (2-oxo-butyl)-phenethyl-amide,
7-(7H-Pyrrolo[2,3-d]pyrimidin-4-yl)-4,7-diaza-spiro[2.5]
octane-4-sulfonic acid (3-hydroxy-propyl)-phenethyl-amide,
7-(7H-Pyrrolo[2,3-d]pyrimidin-4-yl)-4,7-diaza-spiro[2.5]
octane-4-sulfonic acid isobutyl-phenethyl-amide,
7-(7H-Pyrrolo[2,3-d]pyrimidin-4-yl)-4,7-diaza-spiro[2.5]
octane-4-sulfonic acid phenethyl-propyl-amide,
7-(7H-Pyrrolo[2,3-d]pyrimidin-4-yl)-4,7-diaza-spiro[2.5]
octane-4-sulfonic acid cyclohexylmethyl-phenethyl-amide,
7-(7H-Pyrrolo[2,3-d]pyrimidin-4-yl)-4,7-diaza-spiro[2.5]
octane-4-sulfonic acid diphenethylamide,
7-(7H-Pyrrolo[2,3-d]pyrimidin-4-yl)-4,7-diaza-spiro[2.5]
octane-4-sulfonic acid cyanomethyl-phenethyl-amide,
7-(7H-Pyrrolo[2,3-d]pyrimidin-4-yl)-4,7-diaza-spiro[2.5]
octane-4-sulfonic acid (4-cyano-butyl)-phenethyl-amide,
7-(7H-Pyrrolo[2,3-d]pyrimidin-4-yl)-4,7-diaza-spiro[2.5]
octane-4-sulfonic acid phenethyl-(tetrahydro-pyran-2-ylmethyl)-amide,
7-(7H-Pyrrolo[2,3-d]pyrimidin-4-yl)-4,7-diaza-spiro[2.5]
octane-4-sulfonic acid (2-methoxy-ethyl)-phenethyl-amide,
7-(7H-Pyrrolo[2,3-d]pyrimidin-4-yl)-4,7-diaza-spiro[2.5]
octane-4-sulfonic acid but-2-ynyl-phenethyl-amide,
7-(7H-Pyrrolo[2,3-d]pyrimidin-4-yl)-4,7-diaza-spiro[2.5]
octane-4-sulfonic acid phenethyl-(2-pyrazol-1-yl-ethyl)-amide,
7-(7H-Pyrrolo[2,3-d]pyrimidin-4-yl)-4,7-diaza-spiro[2.5]
octane-4-sulfonic acid (2-hydroxy-ethyl)-phenethyl-amide,
{Phenethyl-[7-(7H-pyrrolo[2,3-d]pyrimidin-4-yl)-4,7-diaza-spiro[2.5]octane-4-sulfonyl]-amino}-acetic acid ethyl ester,
7-(7H-Pyrrolo[2,3-d]pyrimidin-4-yl)-4,7-diaza-spiro[2.5]
octane-4-sulfonic acid [2-(4-fluoro-phenyl)-ethyl]-phenethyl-amide,
7-(7H-Pyrrolo[2,3-d]pyrimidin-4-yl)-4,7-diaza-spiro[2.5]
octane-4-sulfonic acid [2-(3-fluoro-phenyl)-ethyl]-phenethyl-amide,
N-Benzyl-2-{phenethyl-[7-(7H-pyrrolo[2,3-d]pyrimidin-4-yl)-4,7-diaza-spiro[2.5]octane-4-sulfonyl]-amino}-acetamide,
7-(7H-Pyrrolo[2,3-d]pyrimidin-4-yl)-4,7-diaza-spiro[2.5]
octane-4-sulfonic acid methyl-(3-phenyl-propyl)-amide,
7-(7H-Pyrrolo[2,3-d]pyrimidin-4-yl)-4,7-diaza-spiro[2.5]
octane-4-sulfonic acid (2-cyclohexyl-ethyl)-methyl-amide,
7-(7H-Pyrrolo[2,3-d]pyrimidin-4-yl)-4,7-diaza-spiro[2.5]
octane-4-sulfonic acid methyl-(2-oxo-2-phenyl-ethyl)-amide,
7-(7H-Pyrrolo[2,3-d]pyrimidin-4-yl)-4,7-diaza-spiro[2.5]
octane-4-sulfonic acid (3-cyano-benzyl)-methyl-amide,
7-(7H-Pyrrolo[2,3-d]pyrimidin-4-yl)-4,7-diaza-spiro[2.5]
octane-4-sulfonic acid (2-cyano-benzyl)-methyl-amide,
7-(7H-Pyrrolo[2,3-d]pyrimidin-4-yl)-4,7-diaza-spiro[2.5]
octane-4-sulfonic acid cyclohexyl methyl-methyl-amide,
7-(7H-Pyrrolo[2,3-d]pyrimidin-4-yl)-4,7-diaza-spiro[2.5]
octane-4-sulfonic acid [2-(4-fluoro-phenyl)-ethyl]-methyl-amide,
7-(7H-Pyrrolo[2,3-d]pyrimidin-4-yl)-4,7-diaza-spiro[2.5]
octane-4-sulfonic acid [2-(3-fluoro-phenyl)-ethyl]-methyl-amide,
7-(7H-Pyrrolo[2,3-d]pyrimidin-4-yl)-4,7-diaza-spiro[2.5]
octane-4-sulfonic acid methyl-(2-pyrrol-1-yl-ethyl)-amide,
7-(7H-Pyrrolo[2,3-d]pyrimidin-4-yl)-4,7-diaza-spiro[2.5]
octane-4-sulfonic acid methyl-(3-methyl-butyl)-amide,
7-(7H-Pyrrolo[2,3-d]pyrimidin-4-yl)-4,7-diaza-spiro[2.5]
octane-4-sulfonic acid methyl-pyridin-2-ylmethyl-amide,
7-(7H-Pyrrolo[2,3-d]pyrimidin-4-yl)-4,7-diaza-spiro[2.5]
octane-4-sulfonic acid [3-(4-cyano-phenyl)-propyl]-methyl-amide,
7-(7H-Pyrrolo[2,3-d]pyrimidin-4-yl)-4,7-diaza-spiro[2.5]
octane-4-sulfonic acid [3-(3-cyano-phenyl)-propyl]-methyl-amide,
7-(7H-Pyrrolo[2,3-d]pyrimidin-4-yl)-4,7-diaza-spiro[2.5]
octane-4-sulfonic acid methyl-(2-phenoxy-ethyl)-amide,
7-(7H-Pyrrolo[2,3-d]pyrimidin-4-yl)-4,7-diaza-spiro[2.5]
octane-4-sulfonic acid [2-(3,5-dimethyl-isoxazol-4-yl)-ethyl]-methyl-amide,
7-(7H-Pyrrolo[2,3-d]pyrimidin-4-yl)-4,7-diaza-spiro[2.5]
octane-4-sulfonic acid (3-cyano-propyl)-phenethyl-amide,
{Methyl-[7-(7H-pyrrolo[2,3-d]pyrimidin-4-yl)-4,7-diaza-spiro[2.5]octane-4-sulfonyl]-amino}-acetic acid methyl ester,
7-(7H-Pyrrolo[2,3-d]pyrimidin-4-yl)-4,7-diaza-spiro[2.5]
octane-4-sulfonic acid (3-cyano-propyl)-methyl-amide,
N,N-Dimethyl-2-{methyl-[7-(7H-pyrrolo[2,3-d]pyrimidin-4-yl)-4,7-diaza-spiro[2.5]octane-4-sulfonyl]-amino}-acetamide,
N-(cyclopropylmethyl)-N-methyl-5-(7H-pyrrolo[2,3-d]pyrimidin-4-yl)-5,8-diazaspiro[2.5]octane-8-sulfonamide,
N-(cyclobutylmethyl)-N-methyl-5-(7H-pyrrolo[2,3-d]pyrimidin-4-yl)-5,8-diazaspiro[2.5]octane-8-sulfonamide,
N-cyclopentyl-N-methyl-5-(7H-pyrrolo[2,3-d]pyrimidin-4-yl)-5,8-diazaspiro[2.5]octane-8-sulfonamide,
N-[(4,4-difluorocyclohexyl)methyl]-N-methyl-5-(7H-pyrrolo[2,3-d]pyrimidin-4-yl)-5,8-diazaspiro[2.5]octane-8-sulfonamide,
N-methyl-N-(2-phenylpropyl)-5-(7H-pyrrolo[2,3-d]pyrimidin-4-yl)-5,8-diazaspiro[2.5]octane-8-sulfonamide,
N-methyl-5-(7H-pyrrolo[2,3-d]pyrimidin-4-yl)-N-(tetrahydropyran-2-ylmethyl)-5,8-diazaspiro[2.5]octane-8-sulfonamide,
N-[[5-(dimethylsulfamoyl)-2-furyl]methyl]-N-methyl-5-(7H-pyrrolo[2,3-d]pyrimidin-4-yl)-5,8-diazaspiro[2.5]octane-8-sulfonamide,
N-methyl-N-(2-pyrazol-1-ylethyl)-5-(7H-pyrrolo[2,3-d]pyrimidin-4-yl)-5,8-diazaspiro[2.5]octane-8-sulfonamide,
N-methyl-N-[(3-methylisoxazol-5-yl)methyl]-5-(7H-pyrrolo[2,3-d]pyrimidin-4-yl)-5,8-diazaspiro[2.5]octane-8-sulfonamide,
N-(isoxazol-5-ylmethyl)-N-methyl-5-(7H-pyrrolo[2,3-d]pyrimidin-4-yl)-5,8-diazaspiro[2.5]octane-8-sulfonamide,
N-[2-(4-chlorophenoxy)ethyl]-N-methyl-5-(7H-pyrrolo[2,3-d]pyrimidin-4-yl)-5,8-diazaspiro[2.5]octane-8-sulfonamide,
N-[2-(2-cyanophenoxy)ethyl]-N-methyl-5-(7H-pyrrolo[2,3-d]pyrimidin-4-yl)-5,8-diazaspiro[2.5]octane-8-sulfonamide,
N-[2-(3-cyanophenoxy)ethyl]-N-methyl-5-(7H-pyrrolo[2,3-d]pyrimidin-4-yl)-5,8-diazaspiro[2.5]octane-8-sulfonamide,
N-[2-(4-cyanophenoxy)ethyl]-N-methyl-5-(7H-pyrrolo[2,3-d]pyrimidin-4-yl)-5,8-diazaspiro[2.5]octane-8-sulfonamide,
N-(cyclopentylmethyl)-N-methyl-5-(7H-pyrrolo[2,3-d]pyrimidin-4-yl)-5,8-diazaspiro[2.5]octane-8-sulfonamide,
N-(2-cyclopentylethyl)-N-methyl-5-(7H-pyrrolo[2,3-d]pyrimidin-4-yl)-5,8-diazaspiro[2.5]octane-8-sulfonamide, N-[2-(1,1-dioxothiolan-3-yl)ethyl]-N-methyl-5-(7H-pyrrolo[2,3-d]pyrimidin-4-yl)-5,8-diazaspiro[2.5]octane-8-sulfonamide, N-[(1,1-dioxothian-3-yl)methyl]-N-methyl-5-(7H-pyrrolo[2,3-d]pyrimidin-4-yl)-5,8-diazaspiro[2.5]octane-8-sulfonamide, N-[(2-fluorophenyl)methyl]-N-methyl-5-(7H-pyrrolo[2,3-d]pyrimidin-4-yl)-5,8-diazaspiro[2.5]octane-8-sulfonamide, N-[(3-fluorophenyl)methyl]-N-methyl-5-(7H-pyrrolo[2,3-d]pyrimidin-4-yl)-5,8-diazaspiro[2.5]octane-8-sulfonamide, N-[(4-fluorophenyl)methyl]-N-methyl-5-(7H-pyrrolo[2,3-d]pyrimidin-4-yl)-5,8-diazaspiro[2.5]octane-8-sulfonamide, N-methyl-5-(7H-pyrrolo[2,3-d]pyrimidin-4-yl)-N-[[4-(trifluoromethoxy)phenyl]methyl]-5,8-diazaspiro[2.5]octane-8-sulfonamide, N-methyl-5-(7H-pyrrolo[2,3-d]pyrimidin-4-yl)-N-[[4-(trifluoromethyl)phenyl]methyl]-5,8-diazaspiro[2.5]octane-8-sulfonamide, N-(2-cyclopropylethyl)-N-methyl-5-(7H-pyrrolo[2,3-d]pyrimidin-4-yl)-5,8-diazaspiro[2.5]octane-8-sulfonamide, N-methyl-N-[(4-methylsulfonylphenyl)methyl]-5-(7H-pyrrolo[2,3-d]pyrimidin-4-yl)-5,8-diazaspiro[2.5]octane-8-sulfonamide, N-[(4-tert-butylcyclohexyl)methyl]-N-methyl-5-(7H-pyrrolo[2,3-d]pyrimidin-4-yl)-5,8-diazaspiro[2.5]octane-8-sulfonamide, N-[(3,3-difluorocyclobutyl)methyl]-N-methyl-5-(7H-pyrrolo[2,3-d]pyrimidin-4-yl)-5,8-diazaspiro[2.5]octane-8-sulfonamide, N-[(2,2-difluorocyclopropyl)methyl]-N-methyl-5-(7H-pyrrolo[2,3-d]pyrimidin-4-yl)-5,8-diazaspiro[2.5]octane-8-sulfonamide, N-methyl-N-[(4-methylenecyclohexyl)methyl]-5-(7H-pyrrolo[2,3-d]pyrimidin-4-yl)-5,8-diazaspiro[2.5]octane-8-sulfonamide, N-methyl-N-[(3-oxocyclobutyl)methyl]-5-(7H-pyrrolo[2,3-d]pyrimidin-4-yl)-5,8-diazaspiro[2.5]octane-8-sulfonamide, N-methyl-5-(7H-pyrrolo[2,3-d]pyrimidin-4-yl)-N-(tetrahydropyran-4-ylmethyl)-5,8-diazaspiro[2.5]octane-8-sulfonamide, N-methyl-5-(7H-pyrrolo[2,3-d]pyrimidin-4-yl)-N-[(3-sulfamoylphenyl)methyl]-5,8-diazaspiro[2.5]octane-8-sulfonamide, N-methyl-5-(7H-pyrrolo[2,3-d]pyrimidin-4-yl)-N-[(4-sulfamoylphenyl)methyl]-5,8-diazaspiro[2.5]octane-8-sulfonamide, N-[[1-(difluoromethyl)-3H-pyrazol-3-yl]methyl]-N-methyl-5-(7H-pyrrolo[2,3-d]pyrimidin-4-yl)-5,8-diazaspiro[2.5]octane-8-sulfonamide, N-[[1-(2,2-difluoroethyl)-3H-pyrazol-3-yl]-methyl]-N-methyl-5-(7H-pyrrolo[2,3-d]pyrimidin-4-yl)-5,8-diazaspiro[2.5]octane-8-sulfonamide, 7-(7H-Pyrrolo[2,3-d]pyrimidin-4-yl)-4,7-diaza-spiro[2.5]octane-4-sulfonic acid (4-cyano-benzyl)-methyl-amide, 4-[4-(Piperidine-1-sulfonyl)-4,7-diaza-spiro[2.5]oct-7-yl]-7H-pyrrolo[2,3-d]pyrimidine, 1-[7-(7H-Pyrrolo[2,3-d]pyrimidin-4-yl)-4,7-diaza-spiro[2.5]octane-4-sulfonyl]-piperidine-4-carbonitrile, 7-(7H-Pyrrolo[2,3-d]pyrimidin-4-yl)-4,7-diaza-spiro[2.5]octane-4-sulfonic acid methyl-phenyl-amide, 7-(7H-Pyrrolo[2,3-d]pyrimidin-4-yl)-4,7-diaza-spiro[2.5]octane-4-sulfonic acid (2-cyano-ethyl)-cyclopropyl-amide, 1-[7-(7H-Pyrrolo[2,3-d]pyrimidin-4-yl)-4,7-diaza-spiro[2.5]octane-4-sulfonyl]-piperidine-3-carbonitrile, 7-(7H-Pyrrolo[2,3-d]pyrimidin-4-yl)-4,7-diaza-spiro[2.5]octane-4-sulfonic acid [2-(3,4-dimethoxy-phenyl)-ethyl]-methyl-amide, 7-(7H-Pyrrolo[2,3-d]pyrimidin-4-yl)-4,7-diaza-spiro[2.5]octane-4-sulfonic acid benzyl-methyl-amide, 7-(7H-Pyrrolo[2,3-d]pyrimidin-4-yl)-4,7-diaza-spiro[2.5]octane-4-sulfonic acid dimethylamide, 7-(7H-Pyrrolo[2,3-d]pyrimidin-4-yl)-4,7-diaza-spiro[2.5]octane-4-sulfonic acid isopropylamide, 7-(7H-Pyrrolo[2,3-d]pyrimidin-4-yl)-4,7-diaza-spiro[2.5]octane-4-sulfonic acid phenethyl-(3-phenyl-propyl)-amide, 7-(7H-Pyrrolo[2,3-d]pyrimidin-4-yl)-4,7-diaza-spiro[2.5]octane-4-sulfonic acid (2-hydroxy-ethyl)-amide, 7-(7H-Pyrrolo[2,3-d]pyrimidin-4-yl)-4,7-diaza-spiro[2.5]octane-4-sulfonic acid bis-(2-hydroxy-ethyl)-amide, 7-(7H-Pyrrolo[2,3-d]pyrimidin-4-yl)-4,7-diaza-spiro[2.5]octane-4-sulfonic acid (3-cyano-propyl)-amide, 7-(7H-Pyrrolo[2,3-d]pyrimidin-4-yl)-4,7-diaza-spiro[2.5]octane-4-sulfonic acid bis-(3-cyano-propyl)-amide, 7-(7H-Pyrrolo[2,3-d]pyrimidin-4-yl)-4,7-diaza-spiro[2.5]octane-4-sulfonic acid (3-cyano-propyl)-(3-phenyl-propyl)-amide, 7-(7H-Pyrrolo[2,3-d]pyrimidin-4-yl)-4,7-diaza-spiro[2.5]octane-4-sulfonic acid methyl-phenethyl-amide, N-isopropyl-N-methyl-5-(7H-pyrrolo[2,3-d]pyrimidin-4-yl)-5,8-diazaspiro[2.5]octane-8-sulfonamide, N-ethyl-N-isopropyl-5-(7H-pyrrolo[2,3-d]pyrimidin-4-yl)-5,8-diazaspiro[2.5]octane-8-sulfonamide, N-(cyanomethyl)-N-isopropyl-5-(7H-pyrrolo[2,3-d]pyrimidin-4-yl)-5,8-diazaspiro[2.5]octane-8-sulfonamide, N-(2-hydroxyethyl)-N-isopropyl-5-(7H-pyrrolo[2,3-d]pyrimidin-4-yl)-5,8-diazaspiro[2.5]octane-8-sulfonamide, N-cyclobutyl-N-methyl-5-(7H-pyrrolo[2,3-d]pyrimidin-4-yl)-5,8-diazaspiro[2.5]octane-8-sulfonamide, N-cyclobutyl-N-ethyl-5-(7H-pyrrolo[2,3-d]pyrimidin-4-yl)-5,8-diazaspiro[2.5]octane-8-sulfonamide, N-(cyanomethyl)-N-cyclobutyl-5-(7H-pyrrolo[2,3-d]pyrimidin-4-yl)-5,8-diazaspiro[2.5]octane-8-sulfonamide, N-cyclobutyl-N-(2-hydroxyethyl)-5-(7H-pyrrolo[2,3-d]pyrimidin-4-yl)-5,8-diazaspiro[2.5]octane-8-sulfonamide, N-(3-cyanopropyl)-N-cyclobutyl-5-(7H-pyrrolo[2,3-d]pyrimidin-4-yl)-5,8-diazaspiro[2.5]octane-8-sulfonamide, N-cyclobutyl-N-(2-methoxyethyl)-5-(7H-pyrrolo[2,3-d]pyrimidin-4-yl)-5,8-diazaspiro[2.5]octane-8-sulfonamide, N-cyclobutyl-N-(2-imidazol-1-ylethyl)-5-(7H-pyrrolo[2,3-d]pyrimidin-4-yl)-5,8-diazaspiro[2.5]octane-8-sulfonamide, N-cyclobutyl-N-[3-(dimethylamino)propyl]-5-(7H-pyrrolo[2,3-d]pyrimidin-4-yl)-5,8-diazaspiro[2.5]octane-8-sulfonamide, N-cyclobutyl-N-(2-morpholinoethyl)-5-(7H-pyrrolo[2,3-d]pyrimidin-4-yl)-5,8-diazaspiro[2.5]octane-8-sulfonamide, N-(1-cyanoethyl)-N-cyclobutyl-5-(7H-pyrrolo[2,3-d]pyrimidin-4-yl)-5,8-diazaspiro[2.5]octane-8-sulfonamide, N-(cyanomethyl)-N-(2-hydroxyethyl)-5-(7H-pyrrolo[2,3-d]pyrimidin-4-yl)-5,8-diazaspiro[2.5]octane-8-sulfonamide, N-(2-hydroxyethyl)-N-methyl-5-(7H-pyrrolo[2,3-d]pyrimidin-4-yl)-5,8-diazaspiro[2.5]octane-8-sulfonamide, N-(3-cyanopropyl)-N-(2-hydroxyethyl)-5-(7H-pyrrolo[2,3-d]pyrimidin-4-yl)-5,8-diazaspiro[2.5]octane-8-sulfonamide, N-(2-hydroxyethyl)-N-(2-phenoxyethyl)-5-(7H-pyrrolo[2,3-d]pyrimidin-4-yl)-5,8-diazaspiro[2.5]octane-8-sulfonamide,
N-methyl-N-(oxetan-3-yl)-5-(7H-pyrrolo[2,3-d]pyrimidin-4-yl)-5,8-diazaspiro[2.5]octane-8-sulfonamide,
N-(cyanomethyl)-N-(oxetan-3-yl)-5-(7H-pyrrolo[2,3-d]pyrimidin-4-yl)-5,8-diazaspiro[2.5]octane-8-sulfonamide,
N-(3-cyanopropyl)-N-(oxetan-3-yl)-5-(7H-pyrrolo[2,3-d]pyrimidin-4-yl)-5,8-diazaspiro[2.5]octane-8-sulfonamide,
N-(oxetan-3-yl)-N-(2-phenoxyethyl)-5-(7H-pyrrolo[2,3-d]pyrimidin-4-yl)-5,8-diazaspiro[2.5]octane-8-sulfonamide,
N-(2-hydroxyethyl)-N-(oxetan-3-yl)-5-(7H-pyrrolo[2,3-d]pyrimidin-4-yl)-5,8-diazaspiro[2.5]octane-8-sulfonamide,
N-(1-cyanoethyl)-N-(oxetan-3-yl)-5-(7H-pyrrolo[2,3-d]pyrimidin-4-yl)-5,8-diazaspiro[2.5]octane-8-sulfonamide,
N-methyl-N-[(1-propylsulfonylpyrrolidin-3-yl)ethyl]-5-(7H-pyrrolo[2,3-d]pyrimidin-4-yl)-5,8-diazaspiro[2.5]octane-8-sulfonamide,
N-methyl-N-[(1-methylsulfonyl)pyrrolidin-3-yl)methyl]-5-(7H-pyrrolo[2,3-d]pyrimidin-4-yl)-5,8-diazaspiro[2.5]octane-8-sulfonamide,
N-[[1-(2-methoxyethylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide,
N-[[1-(3-cyanopropylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide,
N-[[1-(cyclopropylmethylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide,
N-[[1-(3-hydroxypropanoyl)pyrrolidin-3-yl]methyl]-N-methyl-5-(7H-pyrrolo[2,3-d]pyrimidin-4-yl)-5,8-diazaspiro[2.5]octane-8-sulfonamide,
N-[[1-(3-hydroxybutanoyl)pyrrolidin-3-yl]methyl]-N-methyl-5-(7H-pyrrolo[2,3-d]pyrimidin-4-yl)-5,8-diazaspiro[2.5]octane-8-sulfonamide,
N-methyl-N-[(1-propanoylpyrrolidin-3-yl)methyl]-5-(7H-pyrrolo[2,3-d]pyrimidin-4-yl)-5,8-diazaspiro[2.5]octane-8-sulfonamide,
N-[[1-(3-cyanopropanoyl)pyrrolidin-3-yl]methyl]-N-methyl-5-(7H-pyrrolo[2,3-d]pyrimidin-4-yl)-5,8-diazaspiro[2.5]octane-8-sulfonamide,
N-[[1-(2,3-dihydroxypropanoyl)pyrrolidin-3-yl]methyl]-N-methyl-5-(7H-pyrrolo[2,3-d]pyrimidin-4-yl)-5,8-diazaspiro[2.5]octane-8-sulfonamide,
N-[(1-formylpyrrolidin-3-yl)methyl]-N-methyl-5-(7H-pyrrolo[2,3-d]pyrimidin-4-yl)-5,8-diazaspiro[2.5]octane-8-sulfonamide,
3,3,3-trifluoro-N-methyl-N-[[5-(7H-pyrrolo[2,3-d]pyrimidin-4-yl)-5,8-diazaspiro[2.5]octan-8-yl]sulfonyl]propanamide,
4,4-difluoro-N-methyl-N-[[5-(7H-pyrrolo[2,3-d]pyrimidin-4-yl)-5,8-diazaspiro[2.5]octan-8-yl]sulfonyl]cyclohexanecarboxamide,
4,4,4-trifluoro-N-methyl-N-[[5-(7H-pyrrolo[2,3-d]pyrimidin-4-yl)-5,8-diazaspiro[2.5]octan-8-yl]sulfonyl]butanamide,
N-methyl-1,1-dioxo-N-[[5-(7H-pyrrolo[2,3-d]pyrimidin-4-yl)-5,8-diazaspiro[2.5]octan-8-yl]sulfonyl]thiane-3-carboxamide,
2-(1,1-dioxothian-4-yl)-N-methyl-N-[[5-(7H-pyrrolo[2,3-d]pyrimidin-4-yl)-5,8-diazaspiro[2.5]octan-8-yl]sulfonyl]acetamide,
3-(1,1-dioxothiolan-3-yl)-N-methyl-N-[[5-(7H-pyrrolo[2,3-d]pyrimidin-4-yl)-5,8-diazaspiro[2.5]octan-8-yl]sulfonyl]propanamide,
2-(1,1-dioxothiolan-3-yl)-N-methyl-N-[[5-(7H-pyrrolo[2,3-d]pyrimidin-4-yl)-5,8-diazaspiro[2.5]octan-8-yl]sulfonyl]acetamide,
N-methyl-1,1-dioxo-N-[[5-(7H-pyrrolo[2,3-d]pyrimidin-4-yl)-5,8-diazaspiro[2.5]octan-8-yl]sulfonyl]thiane-4-carboxamide,
N-methyl-1,1-dioxo-N-[[5-(7H-pyrrolo[2,3-d]pyrimidin-4-yl)-5,8-diazaspiro[2.5]octan-8-yl]sulfonyl]thiane-3-carboxamide,
N-methyl-N-[[5-(7H-pyrrolo[2,3-d]pyrimidin-4-yl)-5,8-diazaspiro[2.5]octan-8-yl]sulfonyl]cyclopentanecarboxamide,
2-cyclopentyl-N-methyl-N-[[5-(7H-pyrrolo[2,3-d]pyrimidin-4-yl)-5,8-diazaspiro[2.5]octan-8-yl]sulfonyl]acetamide,
3-cyclopentyl-N-methyl-N-[[5-(7H-pyrrolo[2,3-d]pyrimidin-4-yl)-5,8-diazaspiro[2.5]octan-8-yl]sulfonyl]propanamide,
N-cyclopropyl-N-methyl-5-(7H-pyrrolo[2,3-d]pyrimidin-4-yl)-5,8-diazaspiro[2.5]octane-8-sulfonamide,
N-(2-cyanoethyl)-5-(7H-pyrrolo[2,3-d]pyrimidin-4-yl)-N-(tetrahydrofuran-2-ylmethyl)-5,8-diazaspiro[2.5]octane-8-sulfonamide,
N-(1-methylbutyl)-5-(7H-pyrrolo[2,3-d]pyrimidin-4-yl)-5,8-diazaspiro[2.5]octane-8-sulfonamide,
N-cyclopentyl-5-(7H-pyrrolo[2,3-d]pyrimidin-4-yl)-5,8-diazaspiro[2.5]octane-8-sulfonamide,
N,N-bis(cyanomethyl)-5-(7H-pyrrolo[2,3-d]pyrimidin-4-yl)-5,8-diazaspiro[2.5]octane-8-sulfonamide,
N,N-dibenzyl-5-(7H-pyrrolo[2,3-d]pyrimidin-4-yl)-5,8-diazaspiro[2.5]octane-8-sulfonamide,
N-benzyl-5-(7H-pyrrolo[2,3-d]pyrimidin-4-yl)-5,8-diazaspiro[2.5]octane-8-sulfonamide,
N-[(4,4-difluorocyclohexyl)methyl]-5-(7H-pyrrolo[2,3-d]pyrimidin-4-yl)-5,8-diazaspiro[2.5]octane-8-sulfonamide,
N-[(4,4-difluorocyclohexyl)methyl]-N-ethyl-5-(7H-pyrrolo[2,3-d]pyrimidin-4-yl)-5,8-diazaspiro[2.5]octane-8-sulfonamide,
N,N-bis[(4,4-difluorocyclohexyl)methyl]-5-(7H-pyrrolo[2,3-d]pyrimidin-4-yl)-5,8-diazaspiro[2.5]octane-8-sulfonamide,
N-[[1-(3-hydroxypropanoyl)-4-piperidyl]methyl]-N-methyl-5-(7H-pyrrolo[2,3-d]pyrimidin-4-yl)-5,8-diazaspiro[2.5]octane-8-sulfonamide,
N-[[1-(3-cyanopropanoyl)-4-piperidyl]methyl]-N-methyl-5-(7H-pyrrolo[2,3-d]pyrimidin-4-yl)-5,8-diazaspiro[2.5]octane-8-sulfonamide,
N-[[1-(3-cyanopropanoyl)-3-piperidyl]methyl]-N-methyl-5-(7H-pyrrolo[2,3-d]pyrimidin-4-yl)-5,8-diazaspiro[2.5]octane-8-sulfonamide,
N-[[1-(3-hydroxypropanoyl)-3-piperidyl]methyl]-N-methyl-5-(7H-pyrrolo[2,3-d]pyrimidin-4-yl)-5,8-diazaspiro[2.5]octane-8-sulfonamide,
N-[[(2S)-4,4-difluoro-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2S)-1-(3-cyanopropanoyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2S)-4,4-difluoro-1-formyl-pyrrolidin-2-yl]methyl]-N-methyl-5-(7H-pyrrolo[2,3-d]pyrimidin-4-yl)-5,8-diazaspiro[2.5]octane-8-sulfonamide, N-methyl-N-[(1-methylsulfonyl-4-piperidyl)methyl]-5-(7H-pyrrolo[2,3-d]pyrimidin-4-yl)-5,8-diazaspiro[2.5]octane-8-sulfonamide,
N-[[1-(3-cyanopropylsulfonyl)-4-piperidyl]methyl]-N-methyl-5-(7H-pyrrolo[2,3-d]pyrimidin-4-yl)-5,8-diazaspiro[2.5]octane-8-sulfonamide,
N-methyl-N-[(1-methylsulfonyl-3-piperidyl)methyl]-5-(7H-pyrrolo[2,3-d]pyrimidin-4-yl)-5,8-diazaspiro[2.5]octane-8-sulfonamide,
N-[[1-(3-cyanopropylsulfonyl)-3-piperidyl]methyl]-N-methyl-5-(7H-pyrrolo[2,3-d]pyrimidin-4-yl)-5,8-diazaspiro[2.5]octane-8-sulfonamide,
N-[[(2S)-4,4-difluoro-1-methylsulfonyl-pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2S)-1-(3-cyanopropylsulfonyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2S)-1-(cyclopropylmethylsulfonyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide,
N-[(1,1-dioxothiolan-3-yl)methyl]-N-methyl-5-(7H-pyrrolo[2,3-d]pyrimidin-4-yl)-5,8-diazaspiro[2.5]octane-8-sulfonamide,
N-(cyanomethyl)-N-[(1,1-dioxothiolan-3-yl)methyl]-5-(7H-pyrrolo[2,3-d]pyrimidin-4-yl)-5,8-diazaspiro[2.5]octane-8-sulfonamide,
N-[(1,1-dioxothiolan-3-yl)methyl]-N-(2-hydroxyethyl)-5-(7H-pyrrolo[2,3-d]pyrimidin-4-yl)-5,8-diazaspiro[2.5]octane-8-sulfonamide,
N-[(1,1-dioxothian-4-yl)methyl]-N-methyl-5-(7H-pyrrolo[2,3-d]pyrimidin-4-yl)-5,8-diazaspiro[2.5]octane-8-sulfonamide,
N-(cyanomethyl)-N-[(1,1-dioxothian-4-yl)methyl]-5-(7H-pyrrolo[2,3-d]pyrimidin-4-yl)-5,8-diazaspiro[2.5]octane-8-sulfonamide,
N-[(1,1-dioxothian-4-yl)methyl]-N-(2-hydroxyethyl)-5-(7H-pyrrolo[2,3-d]pyrimidin-4-yl)-5,8-diazaspiro[2.5]octane-8-sulfonamide,
N-(2-cyanoethyl)-N-(cyanomethyl)-5-(7H-pyrrolo[2,3-d]pyrimidin-4-yl)-5,8-diazaspiro[2.5]octane-8-sulfonamide,
N-[(1,1-dioxothiolan-3-yl)methyl]-N-[[5-(7H-pyrrolo[2,3-d]pyrimidin-4-yl)-5,8-diazaspiro[2.5]octan-8-yl]sulfonyl]acetamide,
N-[(1,1-dioxothian-4-yl)methyl]-N-[[5-(7H-pyrrolo[2,3-d]pyrimidin-4-yl)-5,8-diazaspiro[2.5]octan-8-yl]sulfonyl]acetamide,
N-benzyloxy-N-methyl-5-(7H-pyrrolo[2,3-d]pyrimidin-4-yl)-5,8-diazaspiro[2.5]octane-8-sulfonamide,
N-[[(2S)-1-benzylpyrrolidin-2-yl]methyl]-5-(7H-pyrrolo[2,3-d]pyrimidin-4-yl)-5,8-diazaspiro[2.5]octane-8-sulfonamide,
N-[[5-(7H-pyrrolo[2,3-d]pyrimidin-4-yl)-5,8-diazaspiro[2.5]octan-8-yl]sulfonyl]formamide,
N-[(4-cyanocuban-1-yl)methyl]-N-methyl-5-(7H-pyrrolo[2,3-d]pyrimidin-4-yl)-5,8-diazaspiro[2.5]octane-8-sulfonamide,
N-[1-(2-hydroxyacetyl)azetidin-3-yl]-N-methyl-5-(7H-pyrrolo[2,3-d]pyrimidin-4-yl)-5,8-diazaspiro[2.5]octane-8-sulfonamide,
N-[1-(3-hydroxypropanoyl)azetidin-3-yl]-N-methyl-5-(7H-pyrrolo[2,3-d]pyrimidin-4-yl)-5,8-diazaspiro[2.5]octane-8-sulfonamide,
N-methyl-N-(1-methylsulfonylazetidin-3-yl)-5-(7H-pyrrolo[2,3-d]pyrimidin-4-yl)-5,8-diazaspiro[2.5]octane-8-sulfonamide,
N-methyl-N-[[(2R)-1-methylsulfonylpyrrolidin-2-yl]methyl]-5-(7H-pyrrolo[2,3-d]pyrimidin-4-yl)-5,8-diazaspiro[2.5]octane-8-sulfonamide,
N-[[(2R)-1-(3-cyanopropylsulfonyl)pyrrolidin-2-yl]methyl]-N-methyl-5-(7H-pyrrolo[2,3-d]pyrimidin-4-yl)-5,8-diazaspiro[2.5]octane-8-sulfonamide,
N-methyl-N-[[(2S)-5-oxopyrrolidin-2-yl]methyl]-5-(7H-pyrrolo[2,3-d]pyrimidin-4-yl)-5,8-diazaspiro[2.5]octane-8-sulfonamide,
N-methyl-N-[[(2R)-5-oxopyrrolidin-2-yl]methyl]-5-(7H-pyrrolo[2,3-d]pyrimidin-4-yl)-5,8-diazaspiro[2.5]octane-8-sulfonamide,
N-[[(2R)-1-(2-hydroxyacetyl)pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2R)-1-(2,3-dihydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2R)-1-(3-cyanopropanoyl)pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2R)-1-formylpyrrolidin-2-yl]methyl]-N-methyl-5-(7H-pyrrolo[2,3-d]pyrimidin-4-yl)-5,8-diazaspiro[2.5]octane-8-sulfonamide,
N-[[(2R)-1-(2-cyanoacetyl)pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2R)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2S)-1-formylpyrrolidin-2-yl]methyl]-N-methyl-5-(7H-pyrrolo[2,3-d]pyrimidin-4-yl)-5,8-diazaspiro[2.5]octane-8-sulfonamide,
N-[[(2S)-1-(2-hydroxyacetyl)pyrrolidin-2-yl]methyl]-N-methyl-5-(7H-pyrrolo[2,3-d]pyrimidin-4-yl)-5,8-diazaspiro[2.5]octane-8-sulfonamide,
N-[[(2S)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide,
N-methyl-N-[[(2S)-1-methylsulfonylpyrrolidin-2-yl]methyl]-5-(7H-pyrrolo[2,3-d]pyrimidin-4-yl)-5,8-diazaspiro[2.5]octane-8-sulfonamide,
N-[(4-methoxyphenyl)methyl]-5-(7H-pyrrolo[2,3-d]pyrimidin-4-yl)-5,8-diazaspiro[2.5]octane-8-sulfonamide or tert-butyl N-(3-methylsulfonylpropyl)-N-[[5-(7H-pyrrolo[2,3-d]pyrimidin-4-yl)-5,8-diazaspiro[2.5]octan-8-yl]sulfonyl]carbamate An embodiment of the invention provides a compound of formula I, wherein the compound is 7-(7H-Pyrrolo[2,3-d]pyrimidin-4-yl)-4,7-diaza-spiro[2.5]octane-4-sulfonic acid cyanomethyl-phenethyl-amide.

An embodiment of the invention provides a compound of formula I, wherein the compound is 7-(7H-Pyrrolo[2,3-d]pyrimidin-4-yl)-4,7-diaza-spiro[2.5]octane-4-sulfonic acid methyl-phenethyl-amide.

An embodiment of the invention provides a compound of formula I, wherein the compound is N-(cyanomethyl)-N-phenethyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-methyl-5-(7H-pyrrolo[2,3-d]pyrimidin-4-yl)-N-[(4-sulfamoylphenyl)methyl]-5,8-diazaspiro[2.5]octane-8-sulfonamide.

An embodiment of the invention provides a compound of formula I, wherein the compound is N-[(4,4-difluorocyclohexyl)methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[[(2S)-1-(cyclopropylmethylsulfonyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-methyl-N-phenethyl-5-(7H-pyrrolo[2,3-d]pyrimidin-4-yl)-5,8-diazaspiro[2.5]octane-8-sulfonamide.

An embodiment of the invention provides a compound of formula I, wherein the compound is 4,4-difluoro-N-methyl-N-[[5-(7H-pyrrolo[2,3-d]pyrimidin-4-yl)-5,8-diazaspiro[2.5]octan-8-yl]sulfonyl]cyclohexanecarboxamide.

An embodiment of the invention provides a compound of formula I, wherein the compound is N-[[(2S)-1-(2-hydroxyacetyl)pyrrolidin-2-yl]methyl]-N-methyl-5-(7Hpyrrolo[2,3-d]pyrimidin-4-yl)-5,8-diazaspiro[2.5]octane-8-Sulfonamide.

An embodiment of the invention provides a compound of formula I, wherein the compound is N-[[(2S)-4,4-difluoropyrrolidin-2-yl]methyl]-N-methyl-5-(7H-pyrrolo[2,3-d]pyrimidin-4-yl)-5,8-diazaspiro[2.5]octane-8-sulfonamide;formic acid.

An embodiment of the invention provides a compound of formula I, wherein the compound is N-[[(2S)-4,4-difluoro-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[(1,1-dioxothiolan-3-yl)methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-methyl-N-(1-methylsulfonylazetidin-3-yl)-5-(7H-pyrrolo[2,3-d]pyrimidin-4-yl)-5,8-diazaspiro[2.5]octane-8-sulfonamide.

An embodiment of the invention provides a compound of formula I, wherein the compound is N-methyl-N-[[(2R)-1-methylsulfonylpyrrolidin-2-yl]methyl]-5-(7Hpyrrolo[2,3-d]pyrimidin-4-yl)-5,8-diazaspiro[2.5]octane-8-Sulfonamide.

An embodiment of the invention provides a compound of formula I, wherein the compound is N-methyl-N-[[(2R)-5-oxopyrrolidin-2-yl]methyl]-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[[(2S)-4,4-difluoro-1-methylsulfonyl-pyrrolidin-2-yl]methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[(1,1-dioxothian-4-yl)methyl]-N-methyl-5-(7H-pyrrolo[2,3-d]pyrimidin-4-yl)-5,8-diazaspiro[2.5]octane-8-sulfonamide An embodiment of the invention provides a compound of formula I, wherein the compound is N-(2-hydroxyethyl)-N-phenethyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-(cyclobutylmethyl)-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-methyl-N-[[(2S)-5-oxopyrrolidin-2-yl]methyl]-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[[(2R)-1-(3-cyanopropanoyl)pyrrolidin-2-yl]methyl]-N-methyl-5-(7H-pyrrolo[2,3-d]pyrimidin-4-yl)-5,8-diazaspiro[2.5]octane-8-Sulfonamide.

An embodiment of the invention provides a compound of formula I, wherein the compound is N-[[(2S)-1-(3-cyanopropylsulfonyl)-4,4-difluoro-pyrrolidin-2-yl]methyl]-N-methyl-5-(7H-pyrrolo[2,3-d]pyrimidin-4-yl)-5,8-diaza-spiro[2.5]octane-8-sulfonamide.

An embodiment of the invention provides a compound of formula I, wherein the compound is N-(cyanomethyl)-N-[(1,1-dioxothiolan-3-yl)methyl]-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[2-(4-fluorophenyl)ethyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-(cyclopentylmethyl)-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[[(2R)-1-(2-hydroxyacetyl)pyrrolidin-2-yl]methyl]-N-methyl-5-(7Hpyrrolo[2,3-d]pyrimidin-4-yl)-5,8-diazaspiro[2.5]octane-8-Sulfonamide.

An embodiment of the invention provides a compound of formula I, wherein the compound is N-methyl-N-[[(2S)-1-methylsulfonylpyrrolidin-2-yl]methyl]-5-(7Hpyrrolo[2,3-d]pyrimidin-4-yl)-5,8-diazaspiro[2.5]octane-8-Sulfonamide.

An embodiment of the invention provides a compound of formula I, wherein the compound is N-[[(2R)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-Sulfonamide.

An embodiment of the invention provides a compound of formula I, wherein the compound is N-[[(2S)-4,4-difluoro-1-formyl-pyrrolidin-2-yl]methyl]-N-methyl-5-(7Hpyrrolo[2,3-d]pyrimidin-4-yl)-5,8-diazaspiro[2.5]octane-8-Sulfonamide.

An embodiment of the invention provides a compound of formula I, wherein the compound is N-[[(2R)-1-formylpyrrolidin-2-yl]methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[[(2R)-1-(2,3-dihydroxypropanoyl)pyrrolidin-2-yl]methyl]-N-methyl-5-(7H-pyrrolo[2,3-d]pyrimidin-4-yl)-5,8-diazaspiro[2.5]octane-8-Sulfonamide.

An embodiment of the invention provides a compound of formula I, wherein the compound is N-[[(2S)-1-formylpyrrolidin-2-yl]methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[[(2S)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-Sulfonamide.

An embodiment of the invention provides a compound of formula I, wherein the compound is N-(cyanomethyl)-N-[(1,1-dioxothian-4-yl)methyl]-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[(3,3-difluorocyclobutyl)methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[(4-cyanocuban-1-yl)

methyl]-N-methyl-5-(7H-pyrrolo[2,3-d]pyrimidin-4-yl)-5,8-diazaspiro[2.5]octane-8-sulfonamide.

An embodiment of the invention provides a compound of formula I, wherein the compound is N-[[(2R)-1-(2-cyanoacetyl)pyrrolidin-2-yl]methyl]-N-methyl-5-(7Hpyrrolo[2,3-d]pyrimidin-4-yl)-5,8-diazaspiro[2.5]octane-8-Sulfonamide.

An embodiment of the invention provides a compound of formula I, wherein the compound is N-[[(2S)-1-(3-cyanopropanoyl)-4,4-difluoro-pyrrolidin-2-yl]methyl]-Nmethyl-5-(7H-pyrrolo[2,3-d]pyrimidin-4-yl)-5,8-diazaspiro[2.5]octane-8-sulfonamide.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention relates to all such isomers, either in pure form or as mixtures thereof. The invention also relates to all possible tautomers of the compounds of formula I.

An embodiment of the invention a pharmaceutical composition comprising a compound of formula I or a pharmaceutically acceptable salt, hydrate, or solvate thereof together with a pharmaceutically acceptable vehicle or excipient.

An embodiment of the invention a pharmaceutical composition comprising a compound of formula I or a pharmaceutically acceptable salt, hydrate, or solvate thereof together with a pharmaceutically acceptable vehicle or excipient, and further comprising another therapeutically active compound.

In an embodiment of the invention the compounds of formula I according to the invention may be used in therapy.

In an embodiment of the invention the compounds of formula I according to the invention may be useful in therapy, such as for the use in the treatment of dermal diseases or conditions or acute or chronic cutaneous wound disorders.

In an embodiment of the invention the dermal disease or condition is selected from the group consisting of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

In an embodiment of the invention the compounds of formula I according to the invention may be used in the prophylaxis, treatment and/or amelioration of diseases of the immune system, in particular autoimmune diseases.

In an embodiment of the invention the compounds of formula I according to the invention may be used in the prophylaxis, treatment and/or amelioration of diseases, such as psoriasis, rosacea, lupus, multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases.

In an embodiment of the invention the compounds of formula I according to the invention may be used for the manufacture of a medicament for the prophylaxis, treatment and/or amelioration of diseases of the immune system, such as autoimmune diseases.

In an embodiment of the invention the compounds of formula I according to the invention may be used for the manufacture of a medicament for the prophylaxis, treatment and/or amelioration of skin diseases, such as psoriasis, rosacea, lupus, multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases.

In an embodiment of the invention the compounds of formula I according to the invention may be used for the manufacture of a medicament for the prophylaxis, treatment and/or amelioration of diseases of the immune system, such as autoimmune diseases wherein the medicament further comprises another therapeutically active compound.

In an embodiment of the invention the compounds of formula I according to the invention may be used for the manufacture of a medicament for the prophylaxis, treatment and/or amelioration of skin diseases, such as psoriasis, rosacea, lupus, multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases wherein the medicament further comprises another therapeutically active compound.

In an embodiment of the invention the compounds of formula I according to the invention may be used as an anti-inflammatory agent capable of modulating the activity of a protein tyrosin kinase of the JAK family of protein tyrosine kinases.

In an embodiment of the invention the compounds of formula I according to the invention may be used as an anti-inflammatory agent capable of modulating the activity of JAK1, JAK2, JAK3 or TYK2 protein tyrosine kinases.

In an embodiment of the invention the compounds of formula I according to the invention may be used in the treatment, amelioration or prophylaxis of non-infectious anti-inflammatory or autoimmune diseases or conditions wherein the non-infectious inflammatory diseases or conditions are selected from the group consisting of acute inflammatory diseases such as acute lung injury, acute respiratory distress syndrome, allergy, anaphylaxis, sepsis or graft-versus-host disease, or chronic inflammatory diseases such as osteoarthritis, gout, psoriatic arthritis, hepatic cirrhosis, multiple sclerosis, or ocular diseases or conditions such as non-infectious (e.g. allergic) conjunctivitis, uveitis, iritis, keratitis, scleritis, episcleritis, sympathitic ophthalmitis, blepharitis, keratoconjunctivitis sicca, or immunological cornea graft rejection, and the autoimmune diseases or conditions are selected from the group consisting of autoimmune gastritis, Addison's disease, autoimmune hemolytic anemia, autoimmune thyroiditis, chronic idiopathic urticaria, chronic immune polynephropathy, diabetes, diabetic nephropathy, myasthenia gravis, pemphigus vulgaris, pernicious anemia, primary biliary cirrhosis, systemic lupus erythematosus and thyroid eye disease.

An embodiment of the invention provides a method of preventing, treating or ameliorating diseases of the immune system, such as autoimmune diseases, the method comprising administering to a patient in need thereof an effective amount of a compound of formula I.

An embodiment of the invention provides a method of preventing, treating or ameliorating skin diseases, such as psoriasis, rosacea, lupus, multiple sclerosis, rheumatoid arthritis, Type I diabetes and complications from diabetes, asthma, atopic dermatitis, cancer, autoimmune thyroid disorders, ulcerative colitis, Crohn's disease, Alzheimer's disease, leukaemia, eye diseases such as diabetic retinopathy and macular degeneration as well as other autoimmune diseases, the method comprising administering to a patient in need thereof an effective amount of a compound of formula I.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition or pharmaceutical formulation. The invention therefore relates to a pharmaceutical composition comprising a compound of formula I, optionally together with one or more other therapeutically active compounds, such as differentiating agents such as vitamin D derivatives and all-trans retinoid acid; corticosteroids, such as dexamethasone and prednisone, chemotherapeutic agents, anticancer agents, cytotoxic agents, together with a pharmaceutically acceptable excipient or vehicle. The excipient must be "acceptable" in the sense of being compatible with the other ingredients of the composition and not deleterious to the recipient thereof.

If the treatment involves administration of another therapeutically active compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said compounds.

Conveniently, the active ingredient comprises from 0.1-99.9% by weight of the composition.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or car-riers. In the form of a dosage unit, the compound may be administered one or more times a day at appropriate intervals, always depending, however, on the condition of the patient, and in accordance with the prescription made by the medical practitioner. It is also envisaged that in certain treatment regimes, administration with longer intervals e.g. every other day, every week, or even with longer intervals may be beneficial.

Conveniently, dosage unit of a formulation contains between 0.01 mg and 1000 mg, preferably between 1 mg and 500 mg, such as between 5 mg and 100 mg of a compound of formula I.

The formulations include e.g. those in a form suitable for ophthalmic (including sustained or time-released), oral (including sustained or timed release), rectal, parenteral (including subcutaneous, intraperitoneal, intramuscular, intraarticular and intravenous), transdermal, topical, nasal or buccal administration.

The formulations may conveniently be presented in dosage unit form and may be prepared by any of the methods well known in the art of pharmacy, e.g. as disclosed in Remington, The Science and Practice of Pharmacy, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Tehcnology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops, intravitreal injection and time-released drug systems.

For topical administration, the compound of formula I may typically be present in an amount of from 0.01 to 20% by weight of the composition, such as 0.1% to about 10%, but may also be present in an amount of up to about 50% of the composition.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for nasal or buccal administration include powder, self-propelling and spray formulations, such as aerosols and atomisers. Such formulations are disclosed in greater detail in e.g. *Modern Pharmaceutics*, 2$^{nd}$ ed., G. S. Banker and C. T. Rhodes (Eds.), page 427-432, Marcel Dekker, New York; *Modern Pharmaceutics*, 3th ed., G. S. Banker and C. T. Rhodes (Eds.), page 618-619 and 718-721, Marcel Dekker, New York and *Encyclopedia of Pharmaceutical Technology vol.* 10, J Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

EXAMPLES

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

General Procedures, Preparations and Examples $^1$H nuclear magnetic resonance (NMR) spectra were recorded at 300 MHz or 600 MHz. Chemical shift values (δ, in ppm) are quoted in the specified solvent relative to internal tetramethylsilane (δ=0.00) or chloroform (δ=7.25) standards. DMSO-d$_6$ is simply referred to as DMSO in the lists containing the NMR data. The value of a multiplet, either defined (doublet (d), double doublet (dd), triplet (t), quartet (q)) or not (m) at the approximate mid point is given unless a range is quoted. (br) indicates a broad peak. The organic solvents used were usually anhydrous. Chromatography was performed on Merck silica gel 60 (0.040-0.063 mm). The solvent ratios indicated refer to v:v unless otherwise noted.

The following abbreviations have been used throughout:
BOC tert-butoxycarbonyl
DCM dichloromethane
DMF N,N'-Dimethylformamide
DMSO dimethyl sulfoxide
Et ethyl
EtOAc ethylacetate
EtOH ethanole
L liter
LG leaving group
m milli
Me methyl
NMR nuclear magnetic resonance
Ms mesylate
PG protecting group
Ph phenyl
Pybrop bromotripyrrolidinophosphonium hexafluorophosphate
THF tetrahydrofuran v volume
Preparative HPLC/MS Preparative HPLC/MS was performed on a Dionex APS-system with two Shimadzu PP150 prep. pumps and a Thermo MSQ Plus mass spectrometer. Column: Waters) (Terra C-18, 150 mm×19 mm, 5 µm; solventsystem: A=water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).

Analytical HPLC/MS Analytical HPLC/MS was performed on a system consisting of a Waters Acquity UPLC, Waters Micromass LCT Premier XE mass spectrometer, Waters Acquity PDA. Column: Acquity UPLC HSS T3 1.8 µm; 2.1× 50 mm; solventsystem: A=10 mM Ammonium acetate+0.1% HCOOH and B=CH$_3$CN+0.1% HCOOH; flow rate=0.7 mL/min; method (4.8 min): Linear gradient method going from 1% B to 95% B in 2.6 minutes and staying at 95% B for 1.2 minute.

General Procedure of Preparation:

The compounds of the invention can for example be prepared by the general methods outlined in Schemes 1a and 1b, wherein R$_1$, R$_2$, R$_3$, R$_4$, R$_5$, m and n are defined as described herein.

PG represents a suitable protecting group ("Protective Groups in Organic Synthesis", 3rd ed., Greene T. W. and Wuts P. G. M., John Wiley & Sons Inc.), such as, but not restricted to BOC, SEM and Ts.

LG represents a suitable leaving group, such as, but not restricted to: fluorine, chlorine, bromide, iodide, methoxy, N-imidazolyl-, —OMs or —OTs.

Scheme 1a
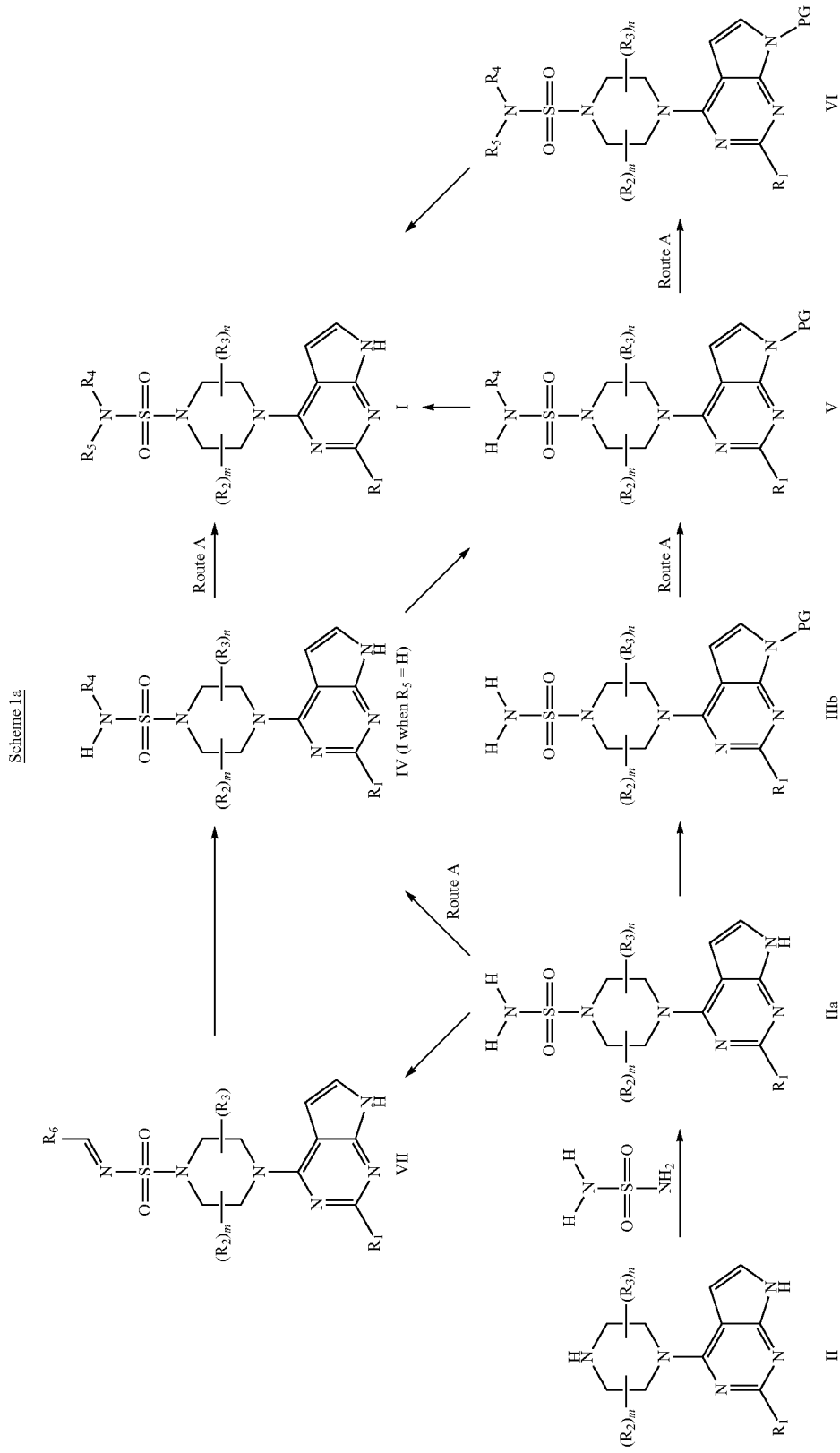

-continued
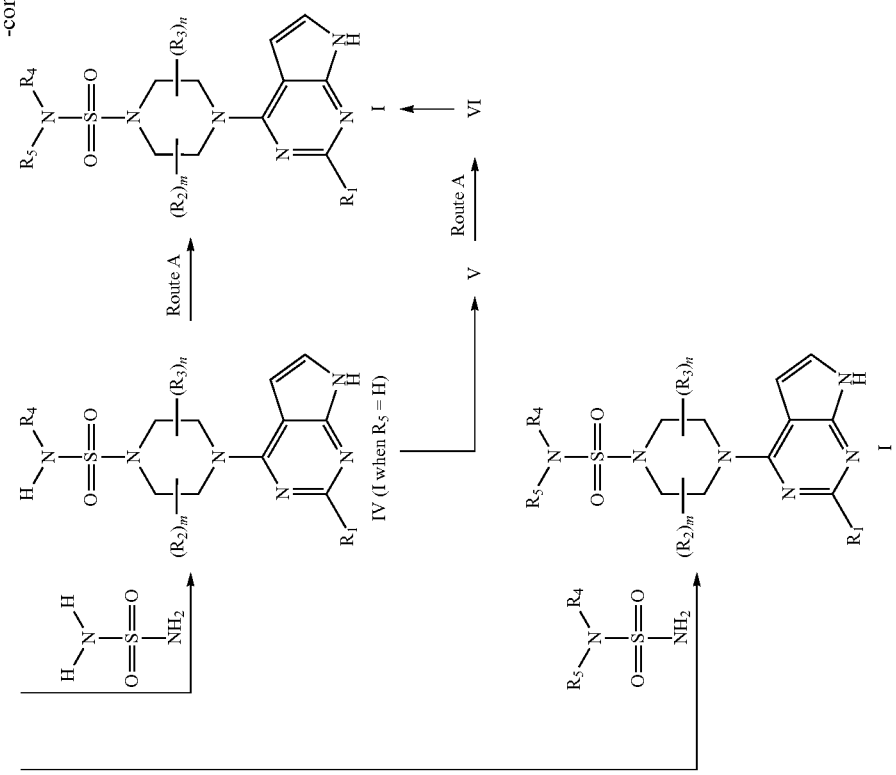

Compounds of general formula II can be reacted with sulfamide or a substituted sulfamide to give compounds of general formula I, IIIa and IV. Such substitutions with sulfamide and sulfamide derivatives are known in the literature (Synthesis, 1983, 192-194; Organic preparations and procedures international, 1984, 16, 49-77).

Compounds of general formula IIIa and IV can optionally be protected with a suitable protecting group, such as the BOC group, to give compounds of general formula IIIb and V, respectively.

Compounds of general formula IIIa and IIIb can be derivatized to compounds of general formula IV and V, respectively, using general route A. Compounds of general formula IIIa can furthermore be reacted with a suitable aldehyde to give compounds of general structure VII.

Compounds of general formula IV and V can be derivatized to compounds of general formula I and VI, respectively, using general route A.

General route A is a route where a sulfamide derivative of e.g. general formula I, IIIa, IIIb, IV and V is derivatized at the NH or the $NH_2$ nitrogen of the sulfamide moiety by reacting said sulfamide with an appropriate derivative of $R_4$ or $R_5$ incorporating a suitable leaving group, like halide, mesylate or tosylate. The reaction is performed in a suitable solvent such as dioxane at an appropriate temperature such as from 0° C. to 180° C.

Compounds of general formula V and VI can be deprotected to compounds of general formula I, using standard procedures known to a chemist skilled in the art of organic synthesis (e.g "*Protective Groups in Organic Synthesis*", $3^{rd}$ ed., Greene T. W. and Wuts P. G. M., John Wiley & Sons Inc.).

Compounds of general formula VII can be reduced to compounds of general formula IV, using standard procedures known to a chemist skilled in the art of organic synthesis.

Scheme 1b

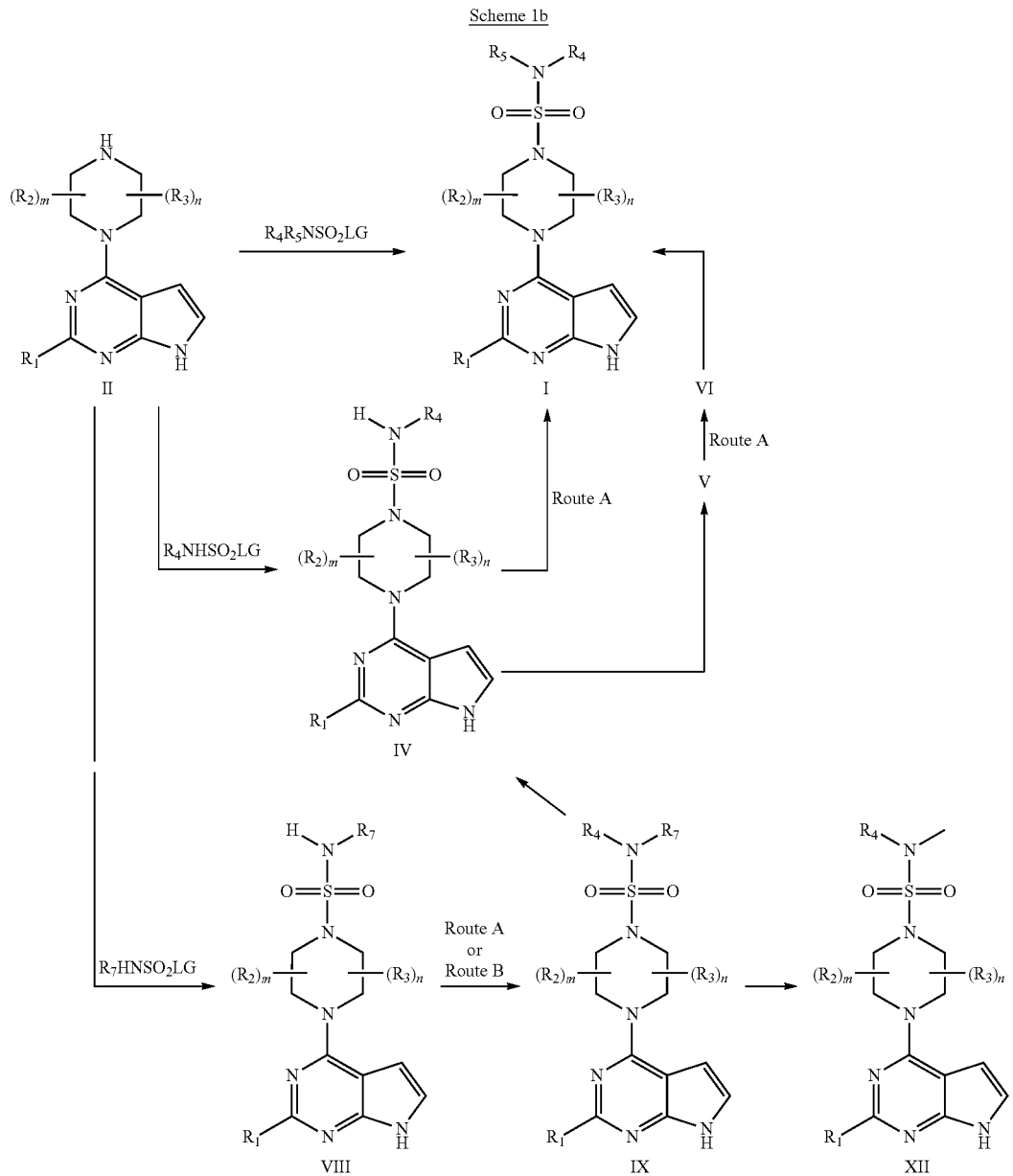

Compounds of general formula II can furthermore be reacted with substituted sulfamoyl derivatives, i.e. $R_4R_5NSO_2LG$ in Scheme 1b where LG for example could be Cl, to give compounds of general formula I and IV. Such reactions between e.g. substituted sulfamoyl chlorides and amines are known in the literature (Organic preparations and procedures international, 1984, 16, 49-77; J. Med. Chem. 1999, 42, 1178-1192; Bio. Org. Med. Chem. Lett. 2008, 18, 1312-1317).

Compounds of general formula II can furthermore be reacted with substituted sulfamoyl imidazole derivatives, i.e. $R_4R_5NSO_2LG$ in Scheme 1b where LG is imidazol-N-yl, to give compounds of general formula I and IV. Such reactions between substituted sulfamoyl imidazoles derivatives and amines are known in the literature (Organic preparations and procedures international, 1984, 16, 49-77; J. Org. Chem. 2003, 68, 115-119).

Alternatively, compounds of general structure II can be reacted with $R_7HNSO_2LG$ in Scheme 1b where $R_7$ is an alkoxy-carbonyl, such as BOC or methyloxy-carbonyl and where LG for example could be Cl, to give compounds of general formula VIII.

Compounds of general structure VIII can either be further derivatised using general route A or alternatively be transformed into compounds of general structure 1× using Route B being standard Mitsunobu procedures known to a chemist skilled in the art of organic synthesis (O. Mitsunobu et al., Bull. Chem. Soc. Japan 40, 935 (1967); David L. Hughes, Progress in the Mitsunobu reaction. A review, Organic Preparations and Procedures International, Vol. 28, Iss. 2, 1996).

Compounds of general structure IX can be reduced using standard procedures known to a chemist skilled in the art of organic synthesis, to give compounds of general formula XII (US2007/191293 A1, 2007).

Compounds of the general formula II can be prepared by the general method outlined in Scheme 2.

Scheme 2

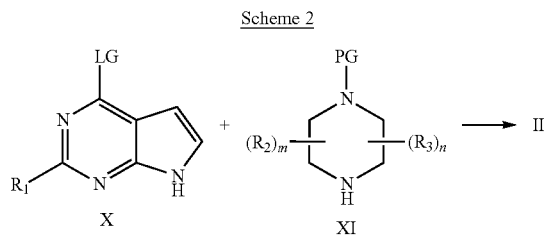

The reaction between X and XI to form II can be performed in the presence or absence of an acid (such as HCl) or a base (such as $Et_3N$ or $K_2CO_3$), in a suitable solvent (such as DMF, EtOH or water) at a suitable temperature such as from room temperature to 200° C. by conventional heating or microwave induced heating.

Alternatively, the reaction between X and XI to form II can be performed in the presence of a transition metal based catalysis with a suitable ligand a suitable base and in a suitable solvent, at a suitable temperature such as from room temperature to 200° C. by conventional heating or microwave induced heating. Typical transition metals includes Pd and Cu, suitable ligands includes P-based ligands like 2,2'-bis(diphenylphosphino)1,1'-binaphthyl and 4,5-bis-diphenylphosphanyl-9,9-dimethyl-9H-xanthene, and N-based ligands like N,N'-dimethylcyclohexane-1,2-diamine, suitable bases includes $Cs_2CO_3$, sodium tert-butoxide and $K_3PO_4$, and suitable solvents include dioxane and toluene.

Any protecting group represented by PG, such as but not limited to BOC and benzyl, can in general be introduced and removed by standard procedures known to a chemist skilled in the art of organic synthesis (e.g "Protective Groups in Organic Synthesis", $3^{rd}$ ed., Greene T. W. and Wuts P. G. M., John Wiley & Sons Inc.).

Compounds of the general formula X and XI are either commercially available or are prepared from commercially available molecules by synthetic transformations according to standard procedures known to a chemist skilled in the art of organic synthesis.

Compounds of the general formula XI can for example be prepared by reduction of monoketopiperazines, either commercially available or prepared by methods known to a chemist skilled in the art of organic synthesis.

Compounds of the general formula XI can for example be prepared by derivatisation of monoketopiperazines, either commercially available or prepared by methods known to a chemist skilled in the art of organic synthesis, for example by cyclopropanation of appropriately substituted monoketopiperazines.

INTERMEDIATES

Intermediate 1

7-(7H-Pyrrolo[2,3-d]pyrimidin-4-yl)-4,7-diaza-spiro[2.5]octane-4-sulfonic acid amide

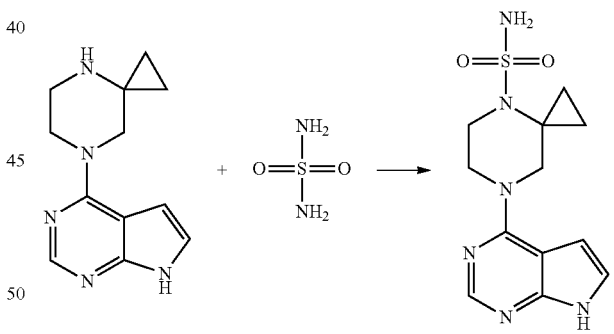

To 4-(4,7-diaza-spiro[2.5]oct-7-yl)-7H-pyrrolo[2,3-d]pyrimidine (1 g, 4.4 mmol) (intermediate 21) in dry dioxane (20 mL) was added sulfamide (419 mg, 4.4 mmol). The reaction mixture was heated to reflux for 6 hours. After evaporation of the solvent in vacuo the crude mixture was purified by flash chromatography on silica using heptane→EtOAc:MeOH (9:1) as eluent.

1H NMR (600 MHz, DMSO) δ 11.71 (s, 1H), 8.13 (s, 1H), 7.18 (dd, J=3.3, 1.9 Hz, 1H), 7.10 (s, 2H), 6.59 (d, J=2.9 Hz, 1H), 4.12-4.02 (m, 2H), 3.88 (s, 2H), 3.65-3.57 (m, 2H), 1.07 (s, 2H), 0.82 (d, J=1.6 Hz, 2H).

13C NMR (151 MHz, DMSO) δ 156.47, 151.83, 150.36, 121.30, 101.92, 100.78, 49.04, 47.14, 42.12, 38.51, 13.13.

Intermediate 2

4-(4-Sulfamoyl-4,7-diaza-spiro[2.5]oct-7-yl)-pyrrolo[2,3-d]pyrimidine-7-carboxylic acid tert-butyl ester

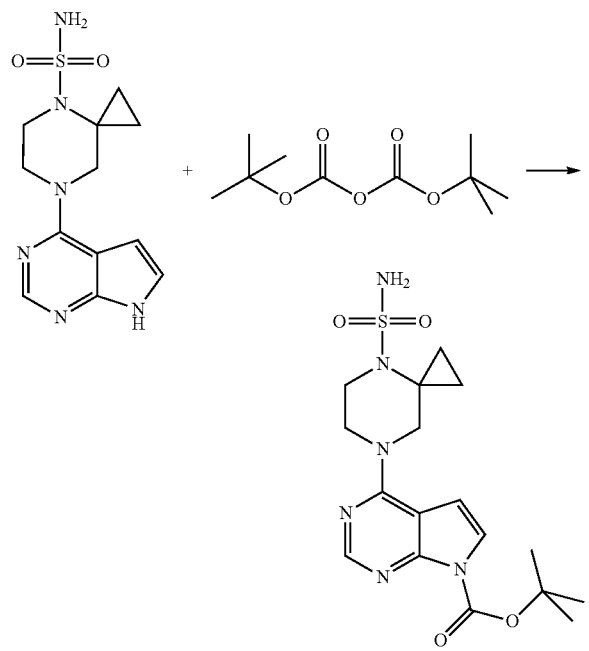

7-(7H-Pyrrolo[2,3-d]pyrimidin-4-yl)-4,7-diaza-spiro[2.5]octane-4-sulfonic acid amide (intermediate 1) (1.5 g, 4.86 mmol) was dissolved in dry DMF (20 ml), added $Cs_2CO_3$ (1.59 g, 4.86 mmol) and cooled to 0° C. A solution of $BOC_2O$ (1.06 g, 4.86 mmol) in dry DMF (10 mL) was added and the reaction mixture was allowed to warm up to rt and stirred at rt for 16 h. The crude mixture was treated with water (150 mL) and extracted with EtOAc (3×100 mL). The combined organic phases were washed with $H_2O$ (2×50 mL), brine (2×50 mL), dried over $Na_2SO_4$, filtered and concentrated in vacuo. The product was purified by flash chromatography on silica using EtOAc in heptane as eluent.

1H NMR (300 MHz, $CDCl_3$) δ 8.47 (s, 1H), 7.37 (d, J=4.2 Hz, 1H), 6.42 (d, J=4.2 Hz, 1H), 5.30 (s, 2H), 4.19-4.05 (m, 2H), 3.94 (s, 2H), 3.82-3.67 (m, 2H), 1.64 (s, 9H), 1.31-1.17 (m, 2H), 0.87 (q, J=5.6 Hz, 2H).

13C NMR (75 MHz, $CDCl_3$) δ 157.27, 153.15, 153.08, 147.33, 122.38, 104.97, 103.92, 84.75, 50.59, 47.87, 43.41, 39.16, 28.01, 13.76.

Intermediate 3

7-(7H-Pyrrolo[2,3-d]pyrimidin-4-yl)-4,7-diaza-spiro[2.5]octane-4-sulfonic acid methylamide

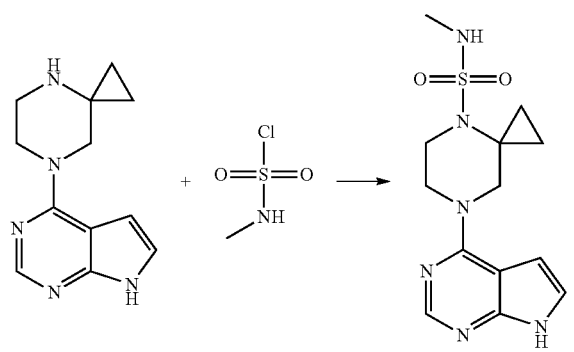

To 4-(4,7-Diaza-spiro[2.5]oct-7-yl)-7H-pyrrolo[2,3-d]pyrimidine (2 g, 8.7 mmol) (intermediate 21) in dry pyridine (100 mL) was cooled to 0° C. and dropwise added a solution of commercial available methylsulfamoyl chloride (419 mg, 8.7 mmol) in dry $Et_2O$ (5 mL). After complete addition, the reaction mixture was allowed to warm up to rt and was afterwards stirred at rt for 1 h. An additional equivalent of methylsulfamoyl chloride (419 mg, 8.7 mmol) in dry $Et_2O$ (5 mL) was added and after additional 1 h at rt a third equivalent of methylsulfamoyl chloride (419 mg, 8.7 mmol) in dry $Et_2O$ (5 mL) was added. The crude mixture was treated with water (150 mL) and extracted with EtOAc (3×100 mL). The combined organic phases were washed with $H_2O$ (2×50 mL), brine (2×50 mL), dried over $Na_2SO_4$, filtered and concentrated in vacuo. Recrystallised in EtOH:$CH_2Cl_2$ affording the title compound as white crystals.

1H NMR (300 MHz, DMSO) δ 11.71 (s, 1H), 8.14 (s, 1H), 7.19 (d, J=2.9 Hz, 2H), 6.60 (d, J=3.5 Hz, 1H), 4.13-3.98 (m, 2H), 3.85 (s, 2H), 3.63-3.47 (m, 2H), 2.41 (d, J=2.5 Hz, 3H), 1.12-0.96 (m, 2H), 0.84 (dd, J=7.0, 5.1 Hz, 2H).

Intermediate 4

4-(4-Methylsulfamoyl-4,7-diaza-spiro[2.5]oct-7-yl)-pyrrolo[2,3-d]pyrimidine-7-carboxylic acid tert-butyl ester

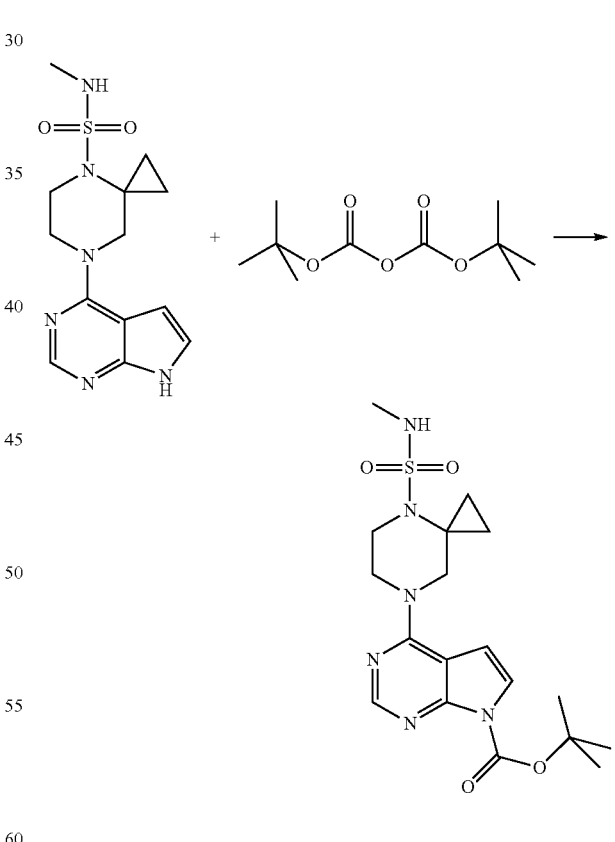

Prepared in a way similar to intermediate 2, using intermediate 3, instead of intermediate 1.

1H NMR (600 MHz, DMSO) δ 8.31 (s, 1H), 7.53 (d, J=4.2 Hz, 1H), 7.24 (q, J=4.9 Hz, 1H), 6.87 (d, J=4.2 Hz, 1H), 4.08-3.97 (m, 2H), 3.83 (s, 2H), 3.63-3.47 (m, 2H), 2.40 (d, J=4.9 Hz, 3H), 1.60 (s, 9H), 1.01 (t, J=5.9 Hz, 2H), 0.84 (dd, J=4.4, 2.2 Hz, 2H).

Intermediate 5

7-(7H-Pyrrolo[2,3-d]pyrimidin-4-yl)-4,7-diaza-spiro[2.5]octane-4-sulfonic acid phenethyl-amide

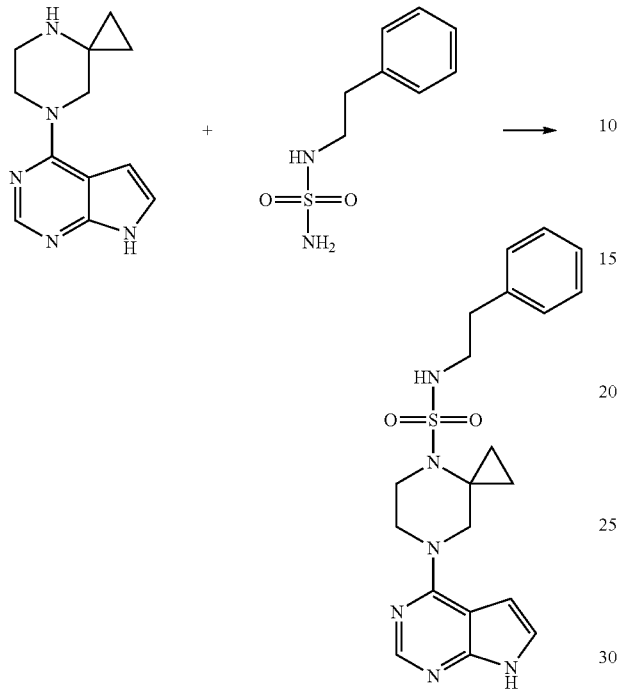

Prepared in a way similar to intermediate 1, using 2-(sulfamoylamino)-ethylbenzene instead of sulfamide.

1H NMR (300 MHz, DMSO) δ 11.71 (s, 1H), 8.14 (s, 1H), 7.46 (s, 1H), 7.37-7.23 (m, 2H), 7.21 (d, J=7.2 Hz, 4H), 6.58 (d, J=3.3 Hz, 1H), 4.03 (dd, J=6.2, 2.8 Hz, 2H), 3.82 (s, 2H), 3.59-3.42 (m, 2H), 3.00 (dd, J=12.0, 7.2 Hz, 2H), 2.74 (t, J=7.4 Hz, 2H), 0.98 (t, J=5.9 Hz, 2H), 0.87-0.74 (m, 2H).

Intermediate 6

4-(4-Phenethylsulfamoyl-4,7-diaza-spiro[2.5]oct-7-yl)-pyrrolo[2,3-d]pyrimidine-7-carboxylic acid tert-butyl ester

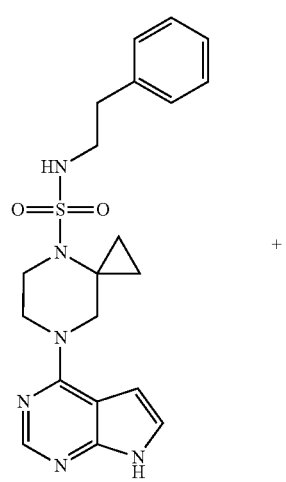

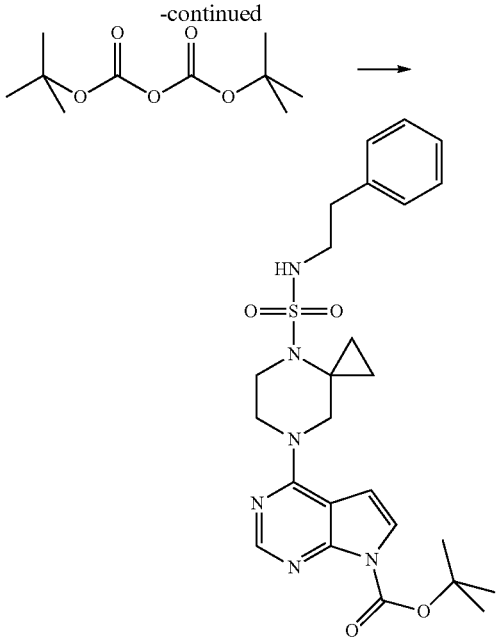

Prepared in a way similar to intermediate 4, using intermediate 5, instead of intermediate 3.

1H NMR (300 MHz, DMSO) δ 8.31 (s, 1H), 7.52 (d, J=4.2 Hz, 1H), 7.48 (t, J=5.6 Hz, 1H), 7.36-7.25 (m, 2H), 7.25-7.13 (m, 3H), 6.85 (d, J=4.2 Hz, 1H), 4.18-3.90 (m, 2H), 3.80 (s, 2H), 3.62-3.40 (m, 2H), 3.13-2.90 (m, 2H), 2.73 (t, J=7.4 Hz, 2H), 1.60 (s, 9H), 0.98 (t, J=5.9 Hz, 2H), 0.81 (q, J=5.3 Hz, 2H).

Intermediate 7

1-(2H-Imidazole-1-sulfonyl)-piperidine-3-carbonitrile

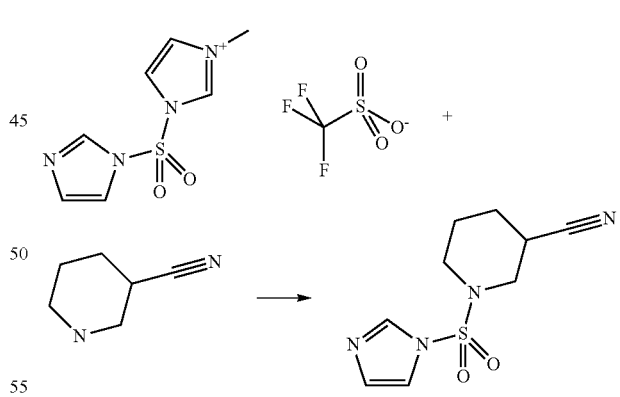

To commercial available trifluoro-methanesulfonate3-(2H-imidazole-1-sulfonyl)-1-methyl-3H-imidazol-1-ium (0.28 mmol) in dry CH$_3$CN (1.5 mL) was added piperidine-3-carbonitrile. The reaction mixture was stirred at rt for 2 h. T The pure compound were obtained by standard preparative HPLC purification of the reaction mixture.

1H NMR (300 MHz, CDCl3) δ 7.95 (s, 1H), 7.26 (s, 1H), 7.19 (s, 1H), 3.56 (dd, J=12.1, 3.5 Hz, 1H), 3.32 (ddd, J=19.8, 9.4, 5.9 Hz, 2H), 3.12 (dd, J=11.4, 8.4 Hz, 1H), 2.88 (td, J=7.6, 3.7 Hz, 1H), 2.05-1.87 (m, 2H), 1.75 (ddt, J=12.2, 8.8, 5.7 Hz, 2H).

Using this procedure the following compounds were obtained:

Intermediate 8

1-(Imidazole-1-sulfonyl)-piperidine-4-carbonitrile

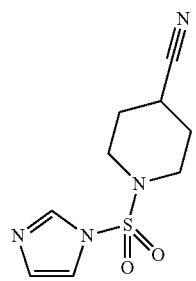 [SMILES: N#CC1CCN(S(=O)(=O)n2ccnc2)CC1]

1H NMR (300 MHz, CDCl3) δ 7.91 (s, 1H), 7.24 (t, J=1.3 Hz, 1H), 7.18 (s, 1H), 3.58-3.17 (m, 4H), 2.80 (tt, J=6.6, 4.6 Hz, 1H), 2.20-1.79 (m, 4H).

Intermediate 9

Imidazole-1-sulfonic acid cyanomethyl-cyclopropyl-amide

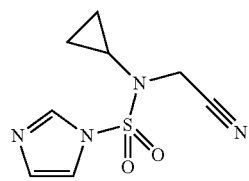 [SMILES: N#CCN(C1CC1)S(=O)(=O)n1ccnc1]

1H NMR (300 MHz, CDCl$_3$) δ 8.20 (s, 1H), 7.41 (s, 1H), 7.27 (s, 1H), 4.31 (s, 2H), 2.40 (ddd, J=10.2, 6.6, 4.0 Hz, 1H), 1.00 (dt, J=4.2, 2.9 Hz, 4H).

Intermediate 10

Imidazole-1-sulfonic acid (2-cyano-ethyl)-cyclopropyl-amide

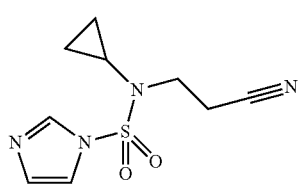 [SMILES: N#CCCN(C1CC1)S(=O)(=O)n1ccnc1]

1H NMR (300 MHz, CDCl$_3$) δ 8.00 (s, 1H), 7.31 (t, J=1.3 Hz, 1H), 7.19 (s, 1H), 3.58 (t, J=6.7 Hz, 2H), 2.74 (t, J=6.7 Hz, 2H), 2.31 (ddd, J=12.3, 6.8, 3.8 Hz, 1H), 1.08-0.76 (m, 4H).

Intermediate 11

Imidazole-1-sulfonic acid [2-(3,4-dimethoxy-phenyl)-ethyl]-methyl-amide

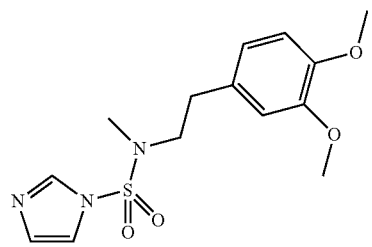 [SMILES: COc1ccc(CCN(C)S(=O)(=O)n2ccnc2)cc1OC]

1H NMR (300 MHz, DMSO) δ 8.20 (s, 1H), 7.65 (t, J=1.4 Hz, 1H), 7.15 (d, J=0.9 Hz, 1H), 6.85 (dd, J=9.0, 5.0 Hz, 2H), 6.74 (dd, J=8.1, 1.9 Hz, 1H), 3.73 (d, J=6.6 Hz, 6H), 3.43-3.34 (m, 2H), 2.85 (s, 3H), 2.76-2.64 (m, 2H).

Intermediate 12

Imidazole-1-sulfonic acid benzyl-(2-cyano-ethyl)-amide

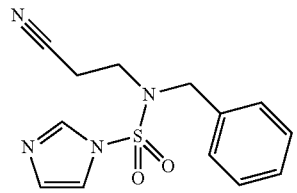 [SMILES: N#CCCN(Cc1ccccc1)S(=O)(=O)n1ccnc1]

1H NMR (300 MHz, CDCl3) δ 7.99 (s, 1H), 7.42-7.34 (m, 3H), 7.28 (d, J=1.6 Hz, 1H), 7.24-7.15 (m, 3H), 4.50 (s, 2H), 3.49 (t, J=7.1 Hz, 2H), 2.42 (t, J=7.1 Hz, 2H).

Intermediate 13

1-(Imidazole-1-sulfonyl)-piperidine

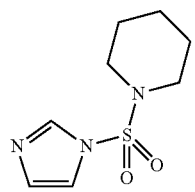 [SMILES: O=S(=O)(N1CCCCC1)n1ccnc1]

1H NMR (300 MHz, CDCl3) δ 7.99 (s, 1H), 7.26 (s, 1H), 7.18 (s, 1H), 3.23-3.11 (m, 4H), 1.67 (dt, J=11.2, 5.7 Hz, 4H), 1.58-1.44 (m, 2H).

Intermediate 14

Imidazole-1-sulfonic acid methyl-phenethyl-amide

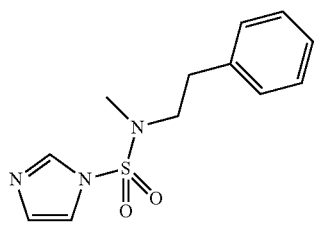 [SMILES: CN(CCc1ccccc1)S(=O)(=O)n1ccnc1]

1H NMR (300 MHz, DMSO) δ 8.19 (s, 1H), 7.64 (t, J=1.4 Hz, 1H), 7.38-7.17 (m, 5H), 7.14 (d, J=1.0 Hz, 1H), 3.40 (dd, J=8.3, 6.8 Hz, 2H), 2.85 (s, 3H), 2.82-2.71 (m, 2H).

Intermediate 15

4-[4-(Imidazole-1-sulfonyl)-4,7-diaza-spiro[2.5]oct-7-yl]-7H-pyrrolo[2,3-d]pyrimidine 1H NMR (300 MHz, DMSO) δ 11.76 (s, 1H), 8.30 (t, J=0.9 Hz, 1H), 8.13 (s, 1H), 7.74 (t, J=1.4 Hz, 1H), 7.21 (d, J=3.6 Hz, 1H), 7.15 (dd, J=1.5, 0.8 Hz, 1H), 6.53 (d, J=3.7 Hz, 1H), 3.85 (dd, J=13.4, 5.9 Hz, 4H), 3.36 (s, 2H), 1.19 (q, J=5.4 Hz, 2H), 0.98 (q, J=5.5 Hz, 2H).

Intermediate 16

4-{4-[2-(Tetrahydro-pyran-2-yloxy)-ethylsulfamoyl]-4,7-diaza-spiro[2.5]oct-7-yl}-pyrrolo[2,3-d]pyrimidine-7-carboxylic acid tert-butyl ester and Intermediate 17

4-(4-{Bis-[2-(tetrahydro-pyran-2-yloxy)-ethyl]-sulfamoyl}-4,7-diaza-spiro[2.5]oct-7-yl)-pyrrolo[2,3-d]pyrimidine-7-carboxylic acid tert-butyl ester

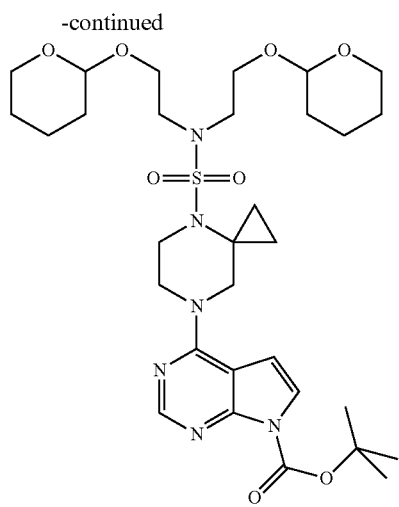

4-(4-Sulfamoyl-4,7-diaza-spiro[2.5]oct-7-yl)-pyrrolo[2,3-d]pyrimidine-7-carboxylic acid tert-butyl ester (intermediate 2) (1 g, 2.45 mmol) was dissolved in dry DMF (20 ml), added K₂CO₃ (1.59 g, 4.86 mmol) and heated to 50° C. A solution of 2-(2-bromoethoxy)-tetrahydro-pyran (260 mg, 1.22 mmol) in dry DMF (5 mL) was added and the reaction mixture was stirred at 50° C. for 1 h. Additional 0.5 equivalent (260 mg, 1.22 mmol) 2-(2-bromo-ethoxy)-tetrahydro-pyran was added and after another hour at 50° C. one additional equivalent was added. After being stirred at 50° C. for a total of 3 h additional 2-(2-bromo-ethoxy)-tetrahydro-pyran (2 eq, 1.04 g, 4.9 mmol) was added and the reaction mixture was stirred at 50° C. for 65 h. The crude mixture was treated with water (100 mL) and extracted with EtOAc (3×100 mL). The combined organic phases were washed with H₂O (2×50 mL), brine (2×50 mL), dried over Na₂SO₄, filtered and concentrated in vacuo. The products were purified by flash chromatography on silica using EtOAc in heptane as eluent.

Intermediate 16

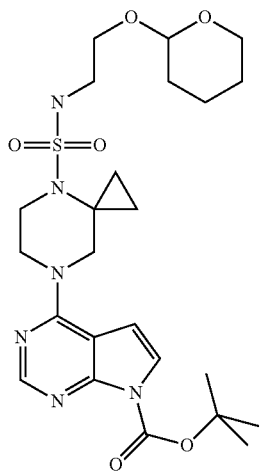 [SMILES: CC(C)(C)OC(=O)n1ccc2c(N3CCN(S(=O)(=O)NCCOC4CCCCO4)C4(CC4)C3)ncnc21]

1H NMR (300 MHz, CDCl3) δ 8.49 (s, 1H), 7.64 (s, 1H), 7.45-7.35 (m, 1H), 6.48-6.39 (m, 1H), 4.52 (s, 2H), 4.19-4.09 (m, 2H), 3.89 (s, 2H), 3.84 (m, 2H), 3.57 (m, 4H), 1.66 (s, 9H), 1.48 (d, J=2.9 Hz, 3H), 1.26 (m, 4H), 0.90 (m, 4H).

Intermediate 17

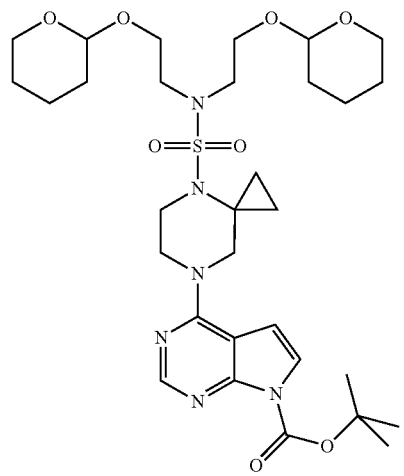 [SMILES: CC(C)(C)OC(=O)n1ccc2c(N3CCN(S(=O)(=O)N(CCOC4CCCCO4)CCOC4CCCCO4)C4(CC4)C3)ncnc21]

1H NMR (300 MHz, DMSO) δ 8.32 (s, 1H), 7.53 (d, J=4.2 Hz, 1H), 6.85 (d, J=4.2 Hz, 1H), 4.58 (s, 2H), 4.03 (d, J=4.9 Hz, 2H), 3.84 (s, 2H), 3.75 (dt, J=8.6, 4.4 Hz, 4H), 3.62-3.29 (m, 12H), 1.79-1.63 (m, 2H), 1.60 (s, 9H), 1.49 (m, 8H), 1.06 (t, J=5.7 Hz, 2H), 0.86 (t, J=6.0 Hz, 2H).

Intermediate 18

4-[4-(3-Cyano-propylsulfamoyl)-4,7-diaza-spiro[2.5]oct-7-yl]-pyrrolo[2,3-d]pyrimidine-7-carboxylic acid tert-butyl ester and Intermediate 19

4-{4-[Bis-(3-cyano-propyl)-sulfamoyl]-4,7-diaza-spiro[2.5]oct-7-yl}-pyrrolo[2,3-d]pyrimidine-7-carboxylic acid tert-butyl ester

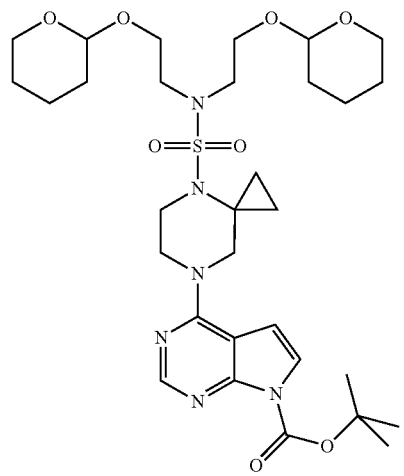 [SMILES: CC(C)(C)OC(=O)n1ccc2c(N3CCN(S(=O)(=O)N(CCOC4CCCCO4)CCOC4CCCCO4)C4(CC4)C3)ncnc21] 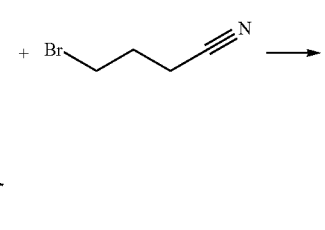

Intermediate 18

4-[4-(3-Cyano-propylsulfamoyl)-4,7-diaza-spiro[2.5]oct-7-yl]-pyrrolo[2,3-d]pyrimidine-7-carboxylic acid tert-butyl ester 1H NMR (300 MHz, CDCl3) δ 8.49 (s, 1H), 7.40 (dd, J=4.2, 2.0 Hz, 1H), 6.43 (d, J=4.2 Hz, 1H), 4.97 (t, J=6.3 Hz, 1H), 4.17-4.08 (m, 2H), 3.94 (d, J=5.2 Hz, 2H), 3.71-3.63 (m, 2H), 3.33-3.23 (m, 2H), 2.53-2.37 (m, 2H), 2.02-1.86 (m, 2H), 1.66 (s, 9H), 1.14-1.02 (m, 2H), 0.92 (td, J=6.9, 3.9 Hz, 2H).

Intermediate 19

4-{4-[Bis-(3-cyano-propyl)-sulfamoyl]-4,7-diaza-spiro[2.5]oct-7-yl}-pyrrolo[2,3-d]pyrimidine-7-carboxylic acid tert-butyl ester 1H NMR (300 MHz, CDCl3) δ 8.50 (s, 1H), 7.40 (dd, J=4.2, 1.9 Hz, 1H), 6.43 (d, J=4.2 Hz, 1H), 4.20-4.08 (m, 2H), 3.94 (s, 2H), 3.65-3.57 (m, 2H), 3.34-3.22 (m, 4H), 2.43 (t, J=6.9 Hz, 4H), 2.02-1.90 (m, 4H), 1.66 (s, 9H), 1.06 (t, J=6.3 Hz, 2H), 0.93 (t, J=6.4 Hz, 2H).

Intermediate 20

7-(7H-pyrrolo[2,3-d]pyrimidin-4-yl)-4,7-diazaspiro[2.5]octane-4-carboxylic acid tert-butyl ester To commercially available 4-chloro-7H-pyrrolo[2,3-d]pyrimidine (1.0 g, 6.5 mmol) dissolved in DMF (5 ml) was added Et3N (1.3 ml, 9.8 mmol) followed by commercially available 4,7-diaza-spiro[2.5]octane-4-carboxylic acid tert-butyl ester (1.5 g, 7.2 mmol). The reaction mixture was heated for 16 hours at 110° C. After evaporation of the solvent in vacuo the crude mixture was treated with water (25 mL) and extracted with EtOAc (4×30 mL) the combined organic phases were washed with brine (2×20 mL), dried over Na2SO4, filtered and concentrated in vacuo to provide 1.5 g crude. The product was purified by flash chromatography on silica using EtOAc in heptane as eluent.

---

4-(4-Sulfamoyl-4,7-diaza-spiro[2.5]oct-7-yl)-pyrrolo[2,3-d]pyrimidine-7-carboxylic acid tert-butyl ester (intermediate 2) (112 mg, 0.27 mmol) was dissolved in dry DMF (2 ml), added K2CO3 (38 mg, 0.27 mmol) and cooled to 0° C. A solution of 4-bromobutyronitrile (40 mg, 0.27 mmol) in dry DMF (0.5 mL) was added and the reaction mixture was stirred at rt for 16 h. The crude mixture was treated with water (10 mL) and extracted with EtOAc (3×10 mL). The combined organic phases were washed with H2O (2×10 mL), brine (2×10 mL), dried over Na2SO4, filtered and concentrated in vacuo. The products were purified by flash chromatography on silica using EtOAc in heptane as eluent.

$^1$H NMR (300 MHz, DMSO) δ=11.70 (s, 1H), 8.15 (s, 1H), 7.18 (m, 1H), 6.59 (m, 1H), 3.90 (m, 2H), 3.73 (m, 2H), 3.62-3.53 (m, 2H), 1.68-1.11 (m, 9H), 1.01-0.57 (m, 5H).

Intermediate 21

4-(4,7-Diaza-spiro[2.5]oct-7-yl)-7H-pyrrolo[2,3-d]pyrimidine

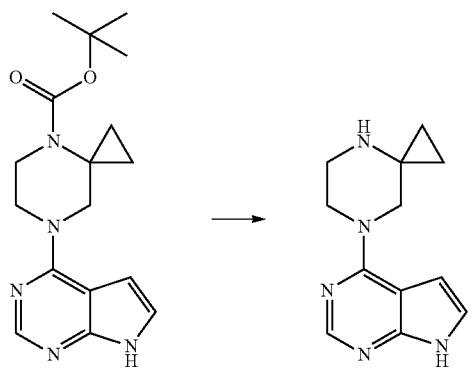 [SMILES: CC(C)(C)OC(=O)N1CCN(c2ncnc3[nH]ccc23)CC12CC2 ; c1nc(N2CCNC3(CC3)C2)c2cc[nH]c2n1]

To 7-(7H-pyrrolo[2,3-d]pyrimidin-4-yl)-4,7-diazaspiro[2.5]octane-4-carboxylic acid tert-butyl ester (intermediate 20) (0.5 g, mmol) dissolved in diethyl ether (20 ml) was added HCl in dioxane (ml, M) and the reaction mixture was stirred for 5 hours at room temperature. The precipitate was isolated by filtration, and washed with diethyl ether (2×5 ml). The precipitate was suspended in THF (50 ml) and stirred vigorously with K$_2$CO$_3$ (5 gram) for 3 hours. After filtration and evaporation of the solvent in vacuo, the product was obtained as an off-white compound.

$^1$H NMR (300 MHz, DMSO) δ=11.64 (s, 1H), 8.09 (s, 1H), 7.21-7.08 (m, 1H), 6.53 (m, 1H), 3.92-3.79 (m, 2H), 3.71 (s, 2H), 2.94-2.81 (m, 2H), 1.29 (br s, 1H), 0.59-0.37 (m, 4H).

Alternatively Synthesis of Intermediate 21

4-(4,7-Diaza-spiro[2.5]oct-7-yl)-7H-pyrrolo[2,3-d]pyrimidine

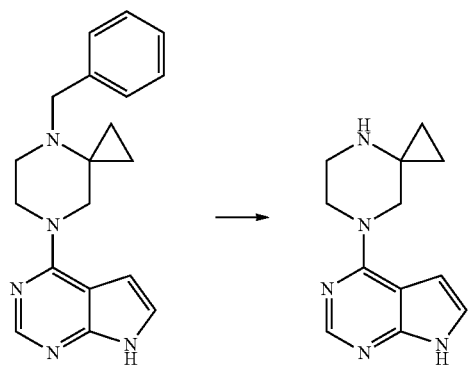 [SMILES: c1ccc(CN2CCN(c3ncnc4[nH]ccc34)CC23CC3)cc1 ; c1nc(N2CCNC3(CC3)C2)c2cc[nH]c2n1]

To 4-(4-benzyl-4,7-diaza-spiro[2.5]oct-7-yl)-7H-pyrrolo[2,3-d]pyrimidine (intermediate 22) (50 g, 78.36 mmol) in MeOH, was added 10% Pd/C (20 g) and HCOONH$_4$ (98 g, 783.69 mmol) and the reaction mixture was heated to reflux for 30 min. The reaction mixture was filtered through celite bed and washed with MeOH and concentrated under reduced pressure. The crude compound was treated with 50% NaOH solution (200 ml) and stirred for 15 min and solid was obtained by filtration. And the solid was wash with 50 ml of water and dried under vacuum. The crude compound (33 g) in acetone (10 times) was heated to reflux for 30 min. The reaction mixture was cooled and filtered and the solid was washed with acetone to afford the title compound as a solid (29.78 g, 83%).

Intermediate 22

4-(4-Benzyl-4,7-diaza-spiro[2.5]oct-7-yl)-7H-pyrrolo[2,3-d]pyrimidine

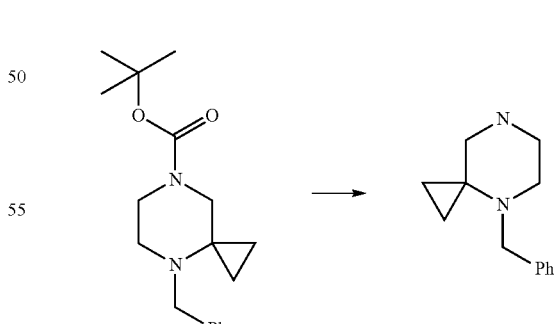

To a stirred solution of 4-chloro-7H-pyrrolo[2,3-d]pyrimidine (29.2 g, 190.98 mmol) in water, was added intermediate 23 (50 g, 210 mmol) and K$_2$CO$_3$ (79 g, 572.9 mmol) and the resultant reaction mixture was heated to 100° C. for 16 h. The reaction mixture was cooled to RT and filtered. The obtained solid was washed with diethyl ether to afford the title compound. (50 g, 80%).

$^1$H NMR (300 MHz, DMSO) δ=11.70 (br, 1H), 8.10 (s, 1H), 7.32 (m, 5H), 7.14 (d, 1H), 6.58 (d, 1H), 3.95 (br, 4H), 3.80 (br, 2H), 2.82 (m, 2H), 0.64 (m, 4H)

Intermediate 23

4-benzyl-4,7-diaza-spiro[2.5]octane

To a stirred solution of intermediate 24 (96 g) in THF (500 mL) was added 4N HCl in dioxane (200 mL) and the resultant reaction mixture was stirred at RT for 16 h. The reaction mixture was concentrated under reduced pressure. The crude was washed with n-pentane to afford title compound as a solid (75 g, 100%).

¹H NMR (300 MHz, DMSO) δ=7.4 (br, 5H), 4.00-4.40 (br, 2H), 3.00-3.80 (br, 6H), 0.81 (br, 4H)

Intermediate 24

4-benzyl-4,7-diaza-spiro[2.5]octane-7-carboxylic acid tert-butyl ester

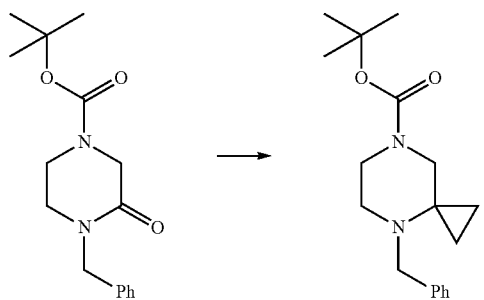 [SMILES: CC(C)(C)OC(=O)N1CCN(Cc2ccccc2)C(=O)C1 ; CC(C)(C)OC(=O)N1CCN(Cc2ccccc2)C2(CC2)C1]

To EtMgBr (344 mL) in THF cooled to −78° C. was added Ti(O^iPr)₄ (39 g, 137.93 mmol), followed by commercially available 4-benzyl-3-oxo-piperazine-1-carboxylic acid tert-butyl ester (40 g, 137.93 mmol) and the resultant reaction mixture was heated to reflux for 1 h. After cooling the reaction mixture to 5° C., another portion of EtMgBr (344 ml) and Ti(O^iPr)₄ (39 g, 137.93 mmol) was added. The mixture was stirred for 16 h at RT. The reaction mixture was quenched with NH₄Cl solution and stirred for 15 min and filtered through a celite bed and washed with EtOAc. The aqueous layer was again extracted with EtOAc (3×). The combined EtOAc layers were washed with water and dried over Na₂SO₄ and concentrated under reduced pressure. Purification by column chromatography to afforded the title compound as a solid (24 g, 58%).

¹H NMR (300 MHz, DMSO) δ=7.20 (m, 5H), 3.80 (s, 2H), 3.40 (m, 2H), 3.22 (m, 2H), 2.63 (m, 2H), 1.38 (s, 9H), 0.58 (br, 4H)

Intermediate 25

N-methyl-N-(pyrrolidin-3-ylmethyl)-5-(7H-pyrrolo[2,3-d]pyrimidin-4-yl)-5,8-diazaspiro[2.5]octane-8-sulfonamide

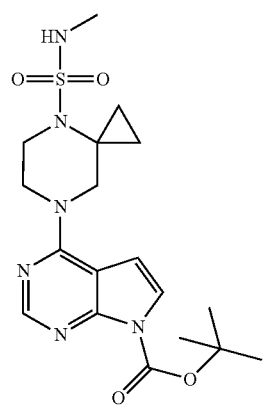

+

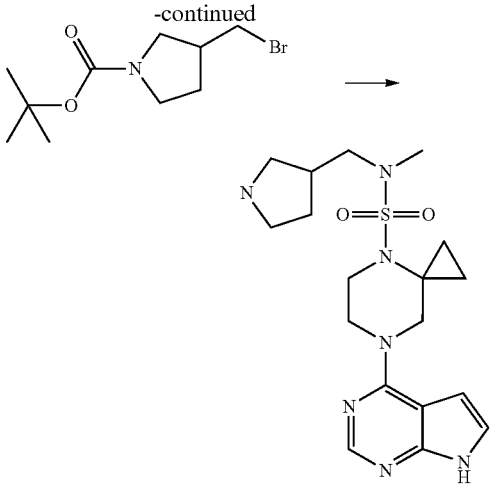

4-(4-Methylsulfamoyl-4,7-diaza-spiro[2.5]oct-7-yl)-pyrrolo[2,3-d]pyrimidine-7-carboxylic acid tert-butyl ester (intermediate 4) (0.71 mmol) was dissolved in dry DMF (0.5 mL) and added Cs₂CO₃ (1.42 mmol) and tert-butyl 3-(bromomethyl)pyrrolidine-1-carboxylate (0.85 mmol). Stirred at 45° C. for 16 h and then added H₂O (2 mL). Extracted with EtOAc (3×2 mL) and the combined organic phases were concentrated in vacuo. The residual oil was treated with a mixture of 1,1,1,3,3,3-hexafluoro-2-propanol: 2,2,2-trifluoroethanol (3:1, 4 mL) at 150° C. for 2 h. The crude reaction mixture was concentrated on celite in vacuo and purified by standard column chromatography using methanol in DCM as eluent. The obtained compound was recrystallized in methanol:EtOAc affording the title compound as solid.

LC-MS: 1.59 min, ES (+), m/z: 406.202

Using this procedure the following compounds were obtained:

Intermediate 26

N-methyl-N-(4-piperidylmethyl)-5-(7H-pyrrolo[2,3-d]pyrimidin-4-yl)-5,8-diazaspiro[2.5]octane-8-sulfonamide as formoc acid salt

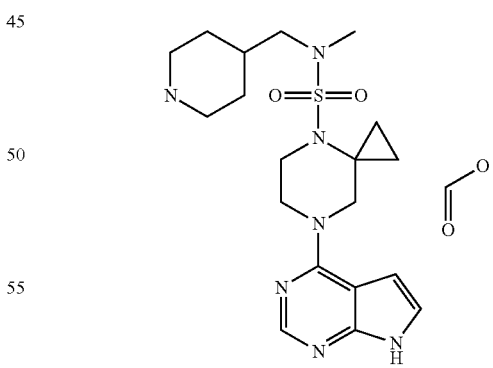

1H NMR (600 MHz, DMSO) δ 11.77 (s, 1H), 8.41 (s, 1H), 8.14 (s, 1H), 7.20 (d, J=3.5 Hz, 1H), 6.60 (d, J=3.5 Hz, 1H), 4.05 (t, J=5.2 Hz, 2H), 3.84 (s, 4H), 3.52 (t, J=5.1 Hz, 2H), 3.15 (dt, J=12.4, 3.4 Hz, 2H), 2.96 (d, J=7.3 Hz, 2H), 2.76-2.60 (m, 5H), 1.80 (dqd, J=11.0, 7.3, 3.8 Hz, 1H), 1.71 (dd, J=13.9, 3.8 Hz, 2H), 1.20 (qd, J=12.8, 3.9 Hz, 2H), 1.03-0.77 (m, 4H).

LC-MS: 1.61 min, ES (+), m/z: 420.211

Intermediate 27

N-methyl-N-(3-piperidylmethyl)-5-(7H-pyrrolo[2,3-d]pyrimidin-4-yl)-5,8-diazaspiro[2.5]octane-8-sulfonamide as formic acid salt

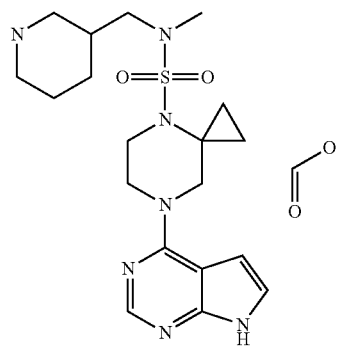

1H NMR (600 MHz, DMSO) δ 11.78 (s, 1H), 8.40 (s, 1H), 8.14 (s, 1H), 7.20 (d, J=3.7 Hz, 1H), 6.60 (d, J=3.7 Hz, 1H), 4.05 (t, J=5.3 Hz, 2H), 3.83 (d, J=1.7 Hz, 2H), 3.53 (t, J=5.1 Hz, 2H), 3.16-3.04 (m, 2H), 2.98 (qd, J=13.8, 7.4 Hz, 2H), 2.69 (s, 3H), 2.63 (d, J=2.9 Hz, 1H), 2.42 (t, J=11.6 Hz, 1H), 1.94 (d, J=7.7 Hz, 1H), 1.77-1.66 (m, 2H), 1.60-1.49 (m, 1H), 1.12 (td, J=12.0, 8.5 Hz, 1H), 1.04-0.79 (m, 4H).

LC-MS: 1.60 min, ES (+), m/z: 420.218

Intermediate 28

N-[[(2S)-4,4-difluoropyrrolidin-2-yl]methyl]-N-methyl-5-(7H-pyrrolo[2,3-d]pyrimidin-4-yl)-5,8-diazaspiro[2.5]octane-8-sulfonamide as formic acid salt

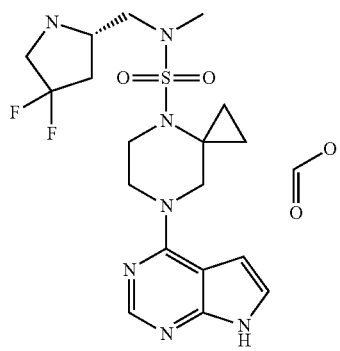

1H NMR (600 MHz, DMSO) δ 11.73 (s, 1H), 8.18 (s, 1H), 8.14 (s, 1H), 7.19 (dd, J=3.6, 2.3 Hz, 1H), 6.60 (dd, J=3.6, 1.9 Hz, 1H), 4.09-4.00 (m, 2H), 3.84 (s, 2H), 3.54 (td, J=4.9, 2.3 Hz, 2H), 3.45 (p, J=7.2 Hz, 2H), 3.21-3.01 (m, 4H), 2.75 (s, 3H), 2.38-2.26 (m, 1H), 1.92 (m, 2H), 1.04-0.94 (m, 2H), 0.91-0.83 (m, 2H).

LC-MS: 1.63 min, ES (+), m/z: 442.174

Intermediate 50

N-(azetidin-3-yl)-N-methyl-5-(7H-pyrrolo[2,3-d]pyrimidin-4-yl)-5,8-diazaspiro[2.5]octane-8-sulfonamide

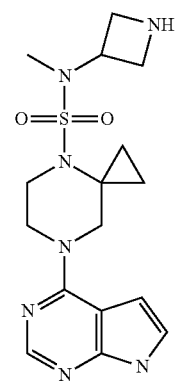 [SMILES: CN(C1CNC1)S(=O)(=O)N1CCN(c2ncnc3[nH]ccc23)CC12CC2]

1H NMR (300 MHz, DMSO) δ 11.73 (s, 1H), 8.13 (s, 1H), 7.19 (d, J=3.5 Hz, 1H), 6.59 (d, J=3.6 Hz, 1H), 4.37 (p, J=7.5 Hz, 1H), 4.10-3.92 (m, 2H), 3.81 (s, 2H), 3.61 (m, 2H), 3.50 (dd, J=6.3, 4.0 Hz, 2H), 2.74 (s, 3H), 1.05-0.77 (m, 4H).

LC-MS: 1.56 min, ES (+), m/z: 378.172

Intermediate 51

N-methyl-N-[[(2R)-pyrrolidin-2-yl]methyl]-5-(7H-pyrrolo[2,3-d]pyrimidin-4-yl)-5,8-diazaspiro[2.5]octane-8-sulfonamide

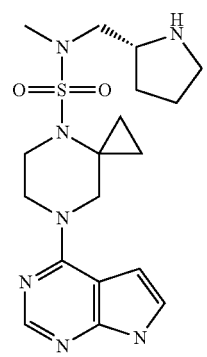 [SMILES: CN(C[C@H]1CCCN1)S(=O)(=O)N1CCN(c2ncnc3[nH]ccc23)CC12CC2]

1H NMR (300 MHz, DMSO) δ 11.71 (s, 1H), 8.13 (s, 1H), 7.18 (d, J=3.4 Hz, 1H), 6.59 (d, J=3.5 Hz, 1H), 4.04 (t, J=5.1 Hz, 2H), 3.84 (s, 2H), 3.54 (dd, J=6.3, 4.0 Hz, 2H), 3.26-3.16 (m, 2H), 3.12-2.84 (m, 2H), 2.84-2.67 (m, 5H), 1.91-1.52 (m, 3H), 1.43-1.17 (m, 1H), 1.09-0.73 (m, 4H).

LC-MS: 1.58 min, ES (+), m/z: 406.204

Intermediate 52

N-methyl-N-[[(2S)-pyrrolidin-2-yl]methyl]-5-(7H-pyrrolo[2,3-d]pyrimidin-4-yl)-5,8-diazaspiro[2.5]octane-8-sulfonamide as formic acid salt

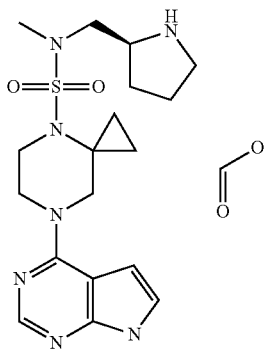 [SMILES: CN(C[C@@H]1CCCN1)S(=O)(=O)N1CCN(c2ncnc3[nH]ccc23)CC12CC2 ; O=CO]

1H NMR (300 MHz, DMSO) δ 11.73 (s, 1H), 8.29 (s, 1H), 8.14 (s, 1H), 7.19 (d, J=3.5 Hz, 1H), 6.59 (d, J=3.6 Hz, 1H), 4.05 (t, J=5.2 Hz, 2H), 3.84 (s, 2H), 3.54 (t, J=5.0 Hz, 2H), 3.22-3.01 (m, 2H), 2.96-2.85 (m, 1H), 2.75 (s, 3H), 1.94-1.61 (m, 3H), 1.50-1.36 (m, 1H), 1.09-0.83 (m, 4H).

LC-MS: 1.57 min, ES (+), m/z: 406.201

Intermediate 29

N-cyclobutylsulfamoyl chloride

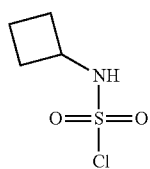

Sulfuryl chloride (104 mmol) was dissolved in dry CH3CN (25 mL), added cyclobutylamine hydrochloride (31 mmol) and stirred at reflux for 16 h. The obtained reaction mixture was cooled to rt and concentrated in vacuo. The obtained residue was trituated with Et$_2$O (2×25 mL). The combined Et$_2$O-phases were concentrated in vacuo affording the title compound as oil.

1H NMR (300 MHz, CDCl3) δ 5.75 (s, 1H), 4.27-4.04 (m, 1H), 2.64-2.37 (m, 2H), 2.26-1.96 (m, 2H), 1.93-1.68 (m, 2H).

Intermediate 30

N-cyclobutyl-5-(7H-pyrrolo[2,3-d]pyrimidin-4-yl)-5,8-diazaspiro[2.5]octane-8-sulfonamide

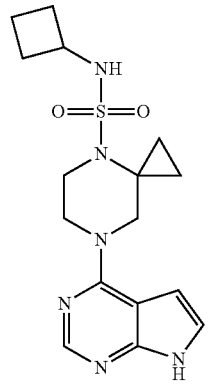

To 4-(4,7-diaza-spiro[2.5]oct-7-yl)-7H-pyrrolo[2,3-d]pyrimidine (6.55 mmol) (intermediate 21) in dry pyridine (25 mL) was added N-cyclobutylsulfamoyl chloride (7.86 mmol) (Intermediate 29). The reaction mixture was stirred at rt for 16 h. After evaporation of the solvent in vacuo the crude mixture was purified by flash chromatography on silica using heptane→MeOH:EtOAc affording the title compound as white crystals.

1H NMR (300 MHz, DMSO) δ 11.76 (s, 1H), 8.15 (s, 1H), 7.73 (d, J=8.4 Hz, 1H), 7.20 (dd, J=3.5, 1.9 Hz, 1H), 6.61 (dd, J=3.4, 1.5 Hz, 1H), 4.05 (t, J=5.1 Hz, 2H), 3.83 (s, 2H), 3.53 (dd, J=6.7, 4.1 Hz, 3H), 2.23-2.03 (m, 2H), 2.00-1.76 (m, 2H), 1.55 (ddt, J=15.9, 6.8, 3.2 Hz, 2H), 1.09-0.75 (m, 4H).

LC-MS: 1.96 min, ES (+), m/z: 363.159

Intermediate 31 tert-butyl 4-[8-(cyclobutylsulfamoyl)-5,8-diazaspiro[2.5]octan-5-yl]pyrrolo[2,3-d]pyrimidine-7-carboxylate

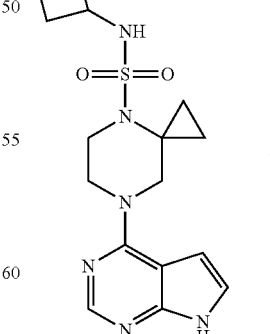

+

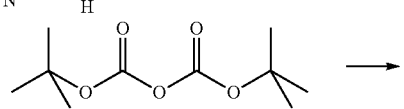

-continued

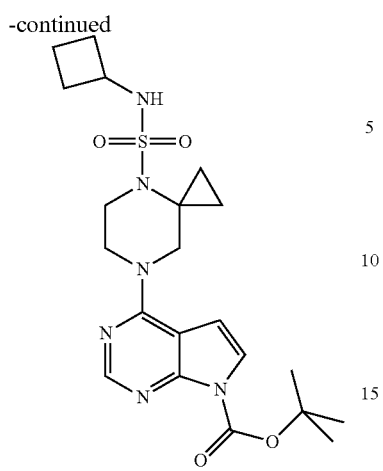

N-cyclobutyl-5-(7H-pyrrolo[2,3-d]pyrimidin-4-yl)-5,8-diazaspiro[2.5]octane-8-sulfonamide (intermediate 30) (4.4 mmol) was dissolved in dry DMF (15 ml), added $K_2CO_3$ (5.28 mmol) and cooled to 0° C. A solution of $BOC_2O$ (1.06 g, 4.86 mmol) in dry DMF (5 mL) was added and the reaction mixture was allowed to warm up freely to rt and stirred at rt for 16 h. The crude mixture was treated with water (150 mL) and extracted with EtOAc (3×100 mL). The combined organic phases were washed with $H_2O$ (2×50 mL), brine (2×50 mL), dried over $Na_2SO_4$, filtered and concentrated in vacuo. The product was purified by flash chromatography on silica using EtOAc in heptane as eluent.

1H NMR (300 MHz, DMSO) δ 8.31 (s, 1H), 7.75 (d, J=8.4 Hz, 1H), 7.53 (d, J=4.1 Hz, 1H), 6.86 (d, J=4.2 Hz, 1H), 4.10-3.96 (m, 2H), 3.81 (s, 2H), 3.53 (dd, J=6.7, 4.0 Hz, 3H), 2.18-2.02 (m, 2H), 1.95-1.83 (m, 2H), 1.60 (s, 11H), 1.06-0.74 (m, 4H).

Using this procedure the following compounds were obtained:

Intermediate 32

Tert-butyl 4-[8-(isopropylsulfamoyl)-5,8-diazaspiro[2.5]octan-5-yl]pyrrolo[2,3-d]pyrimidine-7-carboxylate

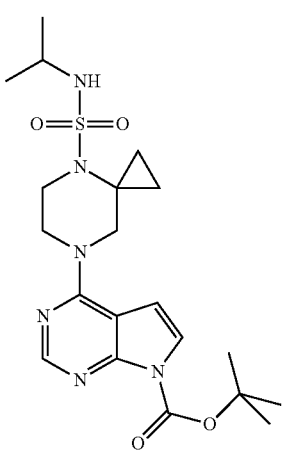 [SMILES: CC(C)NS(=O)(=O)N1CCN(c2ncnc3c2ccn3C(=O)OC(C)(C)C)CC12CC2]

1H NMR (300 MHz, DMSO) δ 8.31 (s, 1H), 7.52 (d, J=4.2 Hz, 1H), 7.29 (d, J=7.4 Hz, 1H), 6.86 (d, J=4.2 Hz, 1H), 4.09-3.99 (m, 2H), 3.82 (s, 2H), 3.55 (dd, J=6.4, 3.9 Hz, 2H), 3.27-3.07 (m, 1H), 1.60 (s, 9H), 1.06 (d, J=6.7 Hz, 8H), 0.92-0.77 (m, 2H).

Intermediate 42 tert-butyl 4-[8-[(1,1-dioxothiolan-3-yl)methylsulfamoyl]-5,8-diazaspiro[2.5]octan-5-yl]pyrrolo[2,3-d]pyrimidine-7-carboxylate

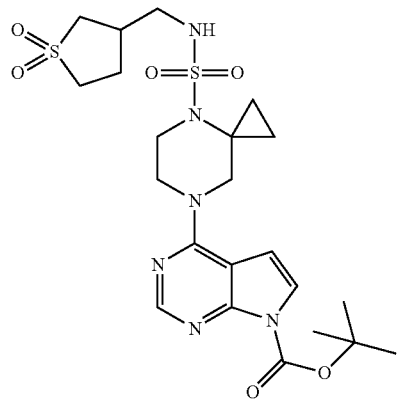 [SMILES: CC(C)(C)OC(=O)n1ccc2c(N3CCN(S(=O)(=O)NCC4CCS(=O)(=O)C4)C4(CC4)C3)ncnc21]

1H NMR (300 MHz, DMSO) δ 8.31 (s, 1H), 7.60 (t, J=6.0 Hz, 1H), 7.53 (d, J=4.2 Hz, 1H), 6.87 (d, J=4.2 Hz, 1H), 4.04 (t, J=5.0 Hz, 2H), 3.83 (s, 2H), 3.56 (d, J=5.0 Hz, 2H), 3.31 (s, 1H), 3.25-2.97 (m, 3H), 2.89 (t, J=6.4 Hz, 2H), 2.79 (dd, J=13.2, 9.6 Hz, 1H), 2.27-2.13 (m, 1H), 1.88-1.72 (m, 1H), 1.60 (s, 9H), 1.08-0.78 (m, 4H).

Intermediate 43 tert-butyl 4-[8-(oxetan-3-ylsulfamoyl)-5,8-diazaspiro[2.5]octan-5-yl]pyrrolo[2,3-d]pyrimidine-7-carboxylate

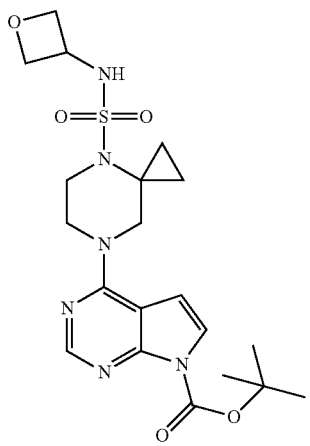 [SMILES: CC(C)(C)OC(=O)n1ccc2c(N3CCN(S(=O)(=O)NC4COC4)C4(CC4)C3)ncnc21]

1H NMR (300 MHz, DMSO) δ 8.31 (s, 2H), 7.53 (d, J=4.1 Hz, 1H), 6.86 (d, J=4.2 Hz, 1H), 4.63 (dd, J=7.4, 6.4 Hz, 2H), 4.44 (t, J=6.4 Hz, 2H), 4.28 (p, J=7.1 Hz, 1H), 4.04 (td, J=4.4, 3.7, 2.0 Hz, 2H), 3.80 (s, 2H), 3.59-3.45 (m, 2H), 1.60 (s, 9H), 1.07-0.95 (m, 2H), 0.90-0.79 (m, 2H).

Intermediate 44 tert-butyl 4-[8-[(1,1-dioxothian-4-yl)methylsulfamoyl]-5,8-diazaspiro[2.5]octan-5-yl]pyrrolo[2,3-d]pyrimidine-7-carboxylate

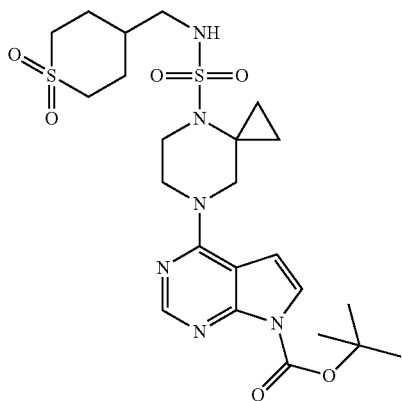 [SMILES: CC(C)(C)OC(=O)n1ccc2c(N3CCN(S(=O)(=O)NCC4CCS(=O)(=O)CC4)C4(CC4)C3)ncnc21]

1H NMR (300 MHz, DMSO) δ 8.31 (s, 1H), 7.59-7.47 (m, 2H), 6.86 (d, J=4.2 Hz, 1H), 4.04 (m, 2H), 3.83 (s, 2H), 3.55 (t, J=5.0 Hz, 2H), 3.05 (dt, J=16.2, 11.3 Hz, 4H), 2.70 (t, J=6.3 Hz, 2H), 2.09-1.92 (m, 2H), 1.81-1.65 (m, 1H), 1.60 (s, 9H), 1.08-0.76 (m, 4H).

Intermediate 45 tert-butyl 4-[8-(2-cyanoethylsulfamoyl)-5,8-diazaspiro[2.5]octan-5-yl]pyrrolo[2,3-d]pyrimidine-7-carboxylate

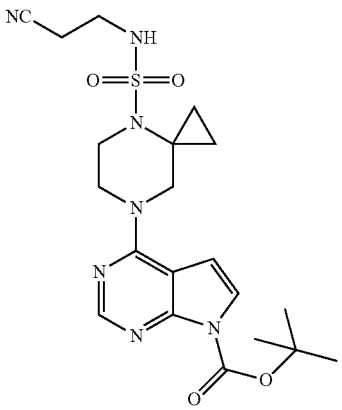 [SMILES: CC(C)(C)OC(=O)n1ccc2c(N3CCN(S(=O)(=O)NCCC#N)C4(CC4)C3)ncnc21]

1H NMR (300 MHz, DMSO) δ 8.31 (s, 1H), 7.79 (t, J=5.9 Hz, 1H), 7.53 (d, J=4.2 Hz, 1H), 6.87 (d, J=4.2 Hz, 1H), 4.04 (dd, J=6.3, 3.9 Hz, 2H), 3.83 (s, 2H), 3.59-3.52 (m, 2H), 3.03 (q, J=6.2 Hz, 2H), 2.63 (t, J=6.4 Hz, 2H), 1.60 (s, 9H), 1.13-0.76 (m, 4H).

Intermediate 33

3-(Sulfamoylamino)oxetane

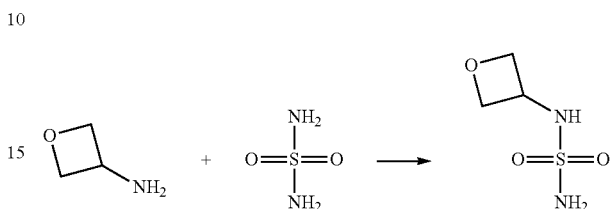

Sulfamide (15.6 mmol) was dissolved in H$_2$O (8 mL), added oxetan-3-amine (6.85 mmol) and stirred at 70° C. for 16 h and then at 100° C. for another 16 h. The obtained reaction mixture was cooled to rt and freezedried affording the title compound as white solid. Used without further purification.

1H NMR (300 MHz, DMSO) δ 7.44 (d, J=8.0 Hz, 1H), 6.64 (s, 2H), 4.77-4.58 (m, 2H), 4.49 (t, J=6.2 Hz, 2H), 4.45-4.33 (m, 1H).

Using this procedure the following compounds were obtained:

Intermediate 39

1-cyano-2-(sulfamoylamino)ethane

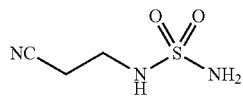

Obtained as white solid. Used without further purification.

Intermediate 34

1,1-Dioxo-3-[(sulfamoylamino)methyl]thiolane

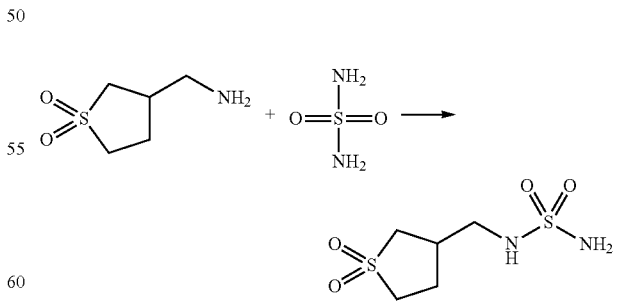

Sulfamide (2.4 mmol) was dissolved in H$_2$O (10 mL), added (1,1-dioxothiolan-3-yl)methanamine (2 mmol) and stirred at reflux for 16 h. The obtained reaction mixture was cooled to rt and freezedried affording the title compound as an oil. Used without further purification.

Using this procedure the following compounds were obtained:

Intermediate 35

1,1-Dioxo-3-[(sulfamoylamino)methyl]thiolane

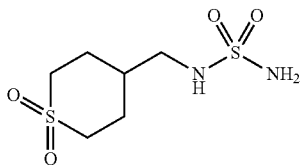 [SMILES: NS(=O)(=O)NCC1CCS(=O)(=O)CC1]

Obtained as an oil and used without further purification

Intermediate 36

Cyano-(sulfamoylamino)methane

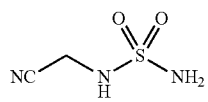

Obtained as a solid and used without further purification

Intermediate 37

N-[(1,1-dioxothiolan-3-yl)methyl]-5-(7H-pyrrolo[2,3-d]pyrimidin-4-yl)-5,8-diazaspiro[2.5]octane-8-sulfonamide

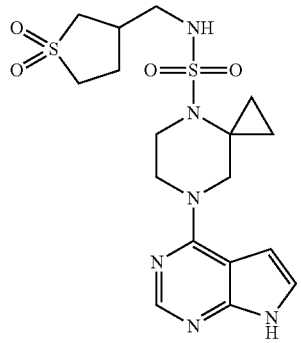 [SMILES: O=S1(=O)CCC(CNS(=O)(=O)N2CCN(c3ncnc4[nH]ccc34)CC23CC3)C1]

Prepared in a way similar to intermediate 1, using intermediate 34 instead of sulfamide.

1H NMR (300 MHz, DMSO) δ 11.72 (s, 1H), 8.13 (s, 1H), 7.59 (t, J=5.9 Hz, 1H), 7.19 (dd, J=3.6, 2.3 Hz, 1H), 6.60 (dd, J=3.7, 1.8 Hz, 1H), 4.05 (t, J=5.2 Hz, 2H), 3.84 (s, 2H), 3.55 (t, J=5.3 Hz, 2H), 3.26-2.98 (m, 4H), 2.89 (t, J=6.3 Hz, 2H), 2.85-2.68 (m, 1H), 2.31-2.13 (m, 1H), 1.87-1.70 (m, 1H), 1.12-0.76 (m, 4H).

LC-MS: 1.71 min, ES (+), m/z: 441.123

Intermediate 38

N-[(1,1-dioxothian-4-yl)methyl]-5-(7H-pyrrolo[2,3-d]pyrimidin-4-yl)-5,8-diazaspiro[2.5]octane-8-sulfonamide

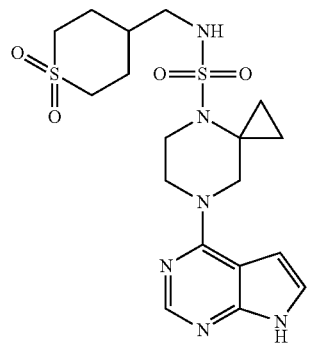 [SMILES: O=S1(=O)CCC(CNS(=O)(=O)N2CCN(c3ncnc4[nH]ccc34)CC23CC3)CC1]

Prepared in a way similar to intermediate 1, using intermediate 35 instead of sulfamide.

1H NMR (300 MHz, DMSO) δ 11.70 (s, 1H), 8.13 (s, 1H), 7.49 (t, J=6.1 Hz, 1H), 7.18 (dd, J=3.6, 2.4 Hz, 1H), 6.59 (dd, J=3.7, 1.8 Hz, 1H), 4.05 (t, J=5.1 Hz, 2H), 3.84 (s, 2H), 3.54 (t, J=5.1 Hz, 2H), 3.18-2.92 (m, 4H), 2.70 (t, J=6.3 Hz, 2H), 2.02 (d, J=13.0 Hz, 2H), 1.79-1.47 (m, 3H), 1.09-0.72 (m, 4H).

LC-MS: 1.73 min, ES (+), m/z: 455.151

Intermediate 40

N-(2-cyanoethyl)-5-(7H-pyrrolo[2,3-d]pyrimidin-4-yl)-5,8-diazaspiro[2.5]octane-8-sulfonamide

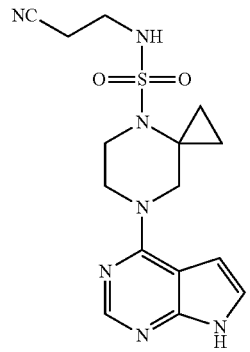

Prepared in a way similar to intermediate 1, using intermediate 39 instead of sulfamide.

1H NMR (300 MHz, DMSO) δ 11.71 (s, 1H), 8.14 (s, 1H), 7.76 (s, 1H), 7.19 (dd, J=3.5, 2.1 Hz, 1H), 6.60 (dd, J=3.6, 1.5 Hz, 1H), 4.04 (q, J=5.1 Hz, 2H), 3.84 (s, 2H), 3.57 (dd, J=6.3, 3.9 Hz, 2H), 3.03 (t, J=6.4 Hz, 2H), 2.63 (t, J=6.4 Hz, 2H), 1.09-0.80 (m, 4H).

LC-MS: 1.72 min, ES (+), m/z: 362.129

Intermediate 41

N-(oxetan-3-yl)-5-(7H-pyrrolo[2,3-d]pyrimidin-4-yl)-5,8-diazaspiro[2.5]octane-8-sulfonamide

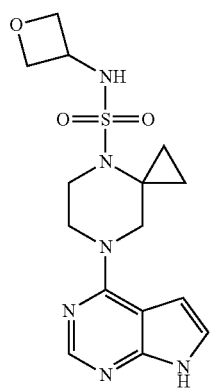 [SMILES: O=S(=O)(NC1COC1)N1CCN(c2ncnc3[nH]ccc23)CC12CC2]

Prepared in a way similar to intermediate 1, using intermediate 33 instead of sulfamide.

1H NMR (300 MHz, DMSO) δ 11.71 (s, 1H), 8.29 (br, 1H), 8.14 (s, 1H), 7.19 (d, J=3.6 Hz, 1H), 6.60 (d, J=3.6 Hz, 1H), 4.63 (dd, J=7.5, 6.4 Hz, 2H), 4.44 (t, J=6.5 Hz, 2H), 4.29 (p, J=7.0 Hz, 1H), 4.05 (dd, J=6.5, 3.8 Hz, 2H), 3.81 (s, 2H), 3.52 (tt, J=7.8, 3.4 Hz, 2H), 1.07-0.79 (m, 4H).

LC-MS: 1.69 min, ES (+), m/z: 365.116

Intermediate 46

N-benzyloxy-5-(7H-pyrrolo[2,3-d]pyrimidin-4-yl)-5,8-diazaspiro[2.5]octane-8-sulfonamide

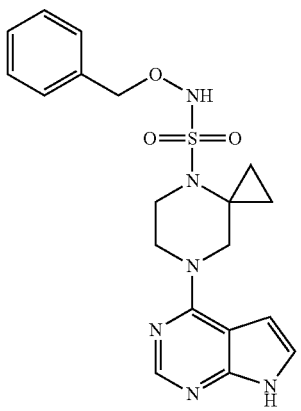 [SMILES: O=S(=O)(NOCc1ccccc1)N1CCN(c2ncnc3[nH]ccc23)CC12CC2]

O-benzylhydroxylamine hydrochloride (5.13 mmol) was dissolved in DCM (20 mL) and treated with 1N NaOH (6 mL). The phases were separated and the organic phase was washed with H$_2$O, dried for 30 min using Na$_2$SO$_4$ and filtered. The obtained solution was cooled to 0° C. and slowly added a solution of HOSO$_2$Cl (1.71 mmol) in dry DCM (5 mL). After 1 h at 0° C. a white precipitate was filtered off. The precipitate was washed with DCM and thereafter Et$_2$O before being dried (freezedryer). The obtained dry compound was suspended in dry toluene (15 mL), added PCl$_5$ (2.05 mmol) and stirred at reflux for 1 h. After being cooled to rt, the reaction mixture was filtered and the filtrate was concentrated in vacuo. The obtained oil was added neat to a solution of 4-(4,7-Diaza-spiro[2.5]oct-7-yl)-7H-pyrrolo[2,3-d]pyrimidine (Intermediate 21) (1.71 mmol) in pyridine (7 mL) and stirred at 40° C. for 16 h. The pure compound was obtained by standard preparative HPLC purification.

1H NMR (300 MHz, DMSO) δ 11.71 (s, 1H), 10.11 (s, 1H), 8.12 (s, 1H), 7.43-7.27 (m, 5H), 7.22-7.15 (m, 1H), 6.54 (dd, J=3.7, 1.8 Hz, 1H), 4.86 (s, 2H), 4.03 (t, J=4.9 Hz, 2H), 3.81 (s, 2H), 3.66-3.55 (m, 2H), 1.17-1.05 (m, 2H), 0.93-0.74 (m, 2H).

LC-MS: 2.11 min, ES (+), m/z: 415.151

Intermediate 47 tert-butyl 4-[8-(tert-butoxycarbonylsulfamoyl)-5,8-diazaspiro[2.5]octan-5-yl]pyrrolo[2,3-d]pyrimidine-7-carboxylate

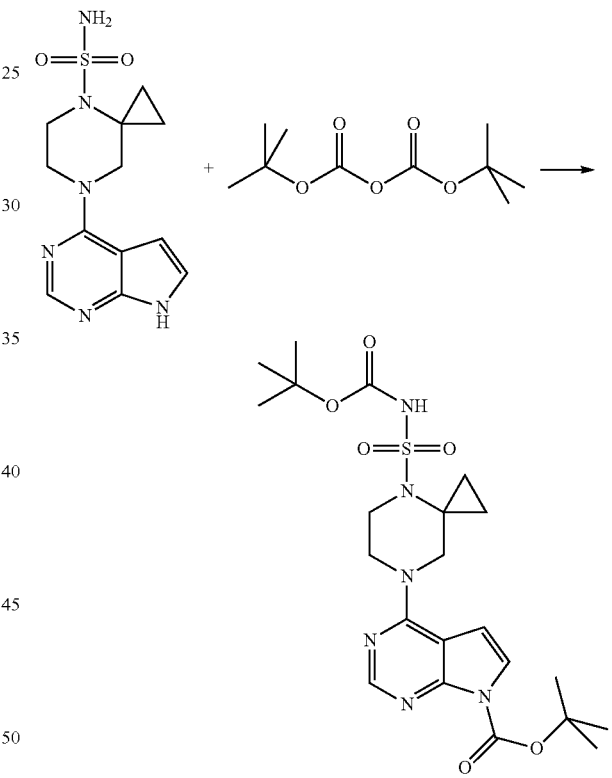

7-(7H-Pyrrolo[2,3-d]pyrimidin-4-yl)-4,7-diaza-spiro[2.5]octane-4-sulfonic acid amide (intermediate 1) (1.95 mmol) was dissolved in dry DMF (15 ml), added Cs$_2$CO$_3$ (4.29 mmol), BOC$_2$O (4.29 mmol) and stirred at rt for 16 h. The crude mixture was treated with water (150 mL) and extracted with EtOAc (3×100 mL). The combined organic phases were washed with H$_2$O (2×50 mL), brine (2×50 mL), dried over Na$_2$SO$_4$, filtered and concentrated in vacuo. The product was purified by flash chromatography on silica using EtOAc in heptane as eluent.

1H NMR (300 MHz, DMSO) δ 11.24 (s, 1H), 8.32 (s, 1H), 7.54 (d, J=4.2 Hz, 1H), 6.87 (d, J=4.3 Hz, 1H), 4.04 (dd, J=6.8, 3.8 Hz, 2H), 3.78 (s, 2H), 3.68 (dd, J=6.5, 3.8 Hz, 2H), 1.60 (s, 9H), 1.38 (s, 9H), 0.87 (dt, J=11.3, 4.4 Hz, 4H).

Intermediate 48 tert-butyl 4-[8-[[(2S)-1-benzylpyrrolidin-2-yl]methyl-tert-butoxycarbonyl-sulfamoyl]-5,8-diazaspiro[2.5]octan-5-yl]pyrrolo[2,3-d]pyrimidine-7-carboxylate

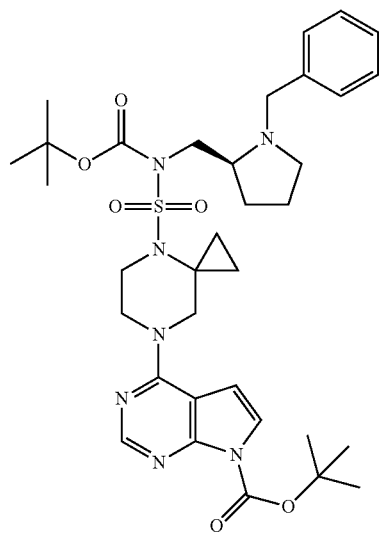 [SMILES: CC(C)(C)OC(=O)N(C[C@@H]1CCCN1Cc1ccccc1)S(=O)(=O)N1CCN(c2ncnc3c2ccn3C(=O)OC(C)(C)C)CC12CC2]

Tert-butyl 4-[8-(tert-butoxycarbonylsulfamoyl)-5,8-diazaspiro[2.5]octan-5-yl]pyrrolo[2,3-d]pyrimidine-7-carboxylate (intermediate 47) (0.55 mmol) was dissolved in dry THF (3 mL) and added [(2S)-1-benzylpyrrolidin-2-yl]methanol (0.61 mmol) and triphenylphosphine (0.66 mmol). The reaction mixture was cooled to 0° C. and slowly added isopropyl (NZ)—N-isopropoxycarbonyliminocarbamate (0.66 mmol). The reaction mixture was allowed to warm up freely to rt and stirred at rt for 16 h. The crude mixture was treated with water (50 mL) and extracted with EtOAc (3×50 mL). The combined organic phases were washed with H₂O (2×50 mL), brine (2×50 mL), dried over Na₂SO₄, filtered and concentrated in vacuo. The product was purified by flash chromatography on silica using EtOAc in heptane as eluent.

1H NMR (300 MHz, DMSO) δ 8.32 (s, 1H), 7.54 (d, J=4.2 Hz, 1H), 7.37-7.18 (m, 5H), 6.88 (d, J=4.2 Hz, 1H), 4.77 (hept, J=6.2 Hz, 4H), 4.14-3.93 (m, 4H), 3.87-3.56 (m, 6H), 2.91-2.81 (m, 1H), 2.81-2.70 (m, 1H), 1.91-1.78 (m, 1H), 1.60 (s, 9H), 1.41 (s, 9H), 0.97-0.81 (m, 4H).

Intermediate 49

(NZ)—N-[(4-methoxyphenyl)methylene]-5-(7H-pyrrolo[2,3-d]pyrimidin-4-yl)-5,8-diazaspiro[2.5]octane-8-sulfonamide

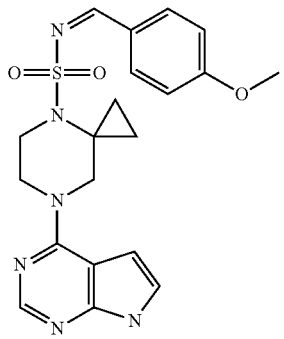 [SMILES: COc1ccc(/C=N\S(=O)(=O)N2CCN(c3ncnc4[nH]ccc34)CC23CC3)cc1]

7-(7H-Pyrrolo[2,3-d]pyrimidin-4-yl)-4,7-diaza-spiro[2.5]octane-4-sulfonic acid amide (intermediate 1) (0.46 mmol) was suspended en dry toluene (5 ml), added 4-methoxybenzaldehyde (0.46 mmol) and stirred at reflux for 48 h. The obtained reaction mixture was concentrated in vacuo on silica. The product was purified by flash chromatography on silica using EtOAc in heptane as eluent.

1H NMR (300 MHz, DMSO) δ 11.70 (s, 1H), 8.93 (s, 1H), 8.09 (s, 1H), 8.00-7.89 (m, 2H), 7.17 (dd, J=3.6, 2.2 Hz, 1H), 7.13-7.00 (m, 2H), 6.56 (dd, J=3.4, 1.6 Hz, 1H), 4.07 (t, J=5.1 Hz, 2H), 3.85 (s, 3H), 3.82 (s, 2H), 3.72 (dd, J=6.5, 4.0 Hz, 2H), 1.30-1.13 (m, 2H), 0.95-0.82 (m, 2H).

LC-MS: 2.23 min, ES (+), m/z: 427.135

Intermediate 53 tert-butyl N-[[5-(7H-pyrrolo[2,3-d]pyrimidin-4-yl)-5,8-diazaspiro[2.5]octan-8-yl]sulfonyl]carbamate

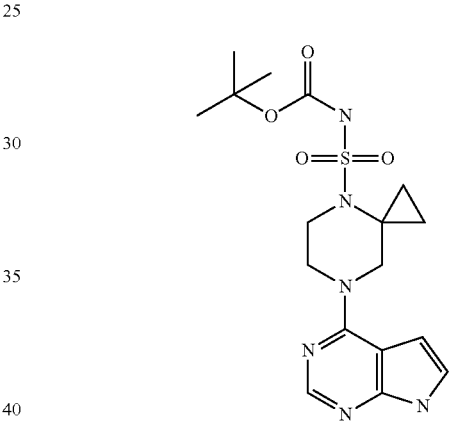

N-(oxomethylene)sulfamoyl chloride (13.4 mmol) was dissolved in dry benzene (5 mL) and dropwise added t-BuOH (13.4 mmol) while the temperature was kept below 25° C. The reaction mixture was stirred at 25° C. for 2 h, added hexane (5 mL) and cooled to 0° C. Precipitate was collected by filtration, washed with hexane affording tert-butyl N-chlorosulfonylcarbamate as white crystals. 4-(4,7-diaza-spiro[2.5]oct-7-yl)-7H-pyrrolo[2,3-d]pyrimidine (4.6 mmol) (intermediate 21) was suspended in dry DCM (25 mL) and added triethylamine (6.9 mmol). To this suspension was slowly added tert-butyl N-chlorosulfonylcarbamate (4.6 mmol) at rt. After 15 min all starting material has been consumed. The obtained reaction mixture was concentrated in vacuo on celite. The product was purified by flash chromatography on silica using EtOAc:MeOH in heptane as eluent.

1H NMR (300 MHz, DMSO) δ 11.72 (s, 1H), 11.22 (s, 1H), 8.14 (s, 1H), 7.19 (dd, J=3.5, 2.3 Hz, 1H), 6.61 (dd, J=3.7, 1.7 Hz, 1H), 4.09-3.99 (m, 2H), 3.80 (s, 2H), 3.67 (dd, J=6.5, 3.7 Hz, 2H), 1.38 (s, 9H), 1.17-1.06 (m, 2H), 0.96-0.81 (m, 2H).

LC-MS: 1.98 min, ES (+), m/z: 409.166

Examples

Example 1

4-{4-[Phenethyl-(3-phenyl-propyl)-sulfamoyl]-4,7-diaza-spiro[2.5]oct-7-yl}-pyrrolo[2,3-d]pyrimidine-7-carboxylic acid tert-butyl ester

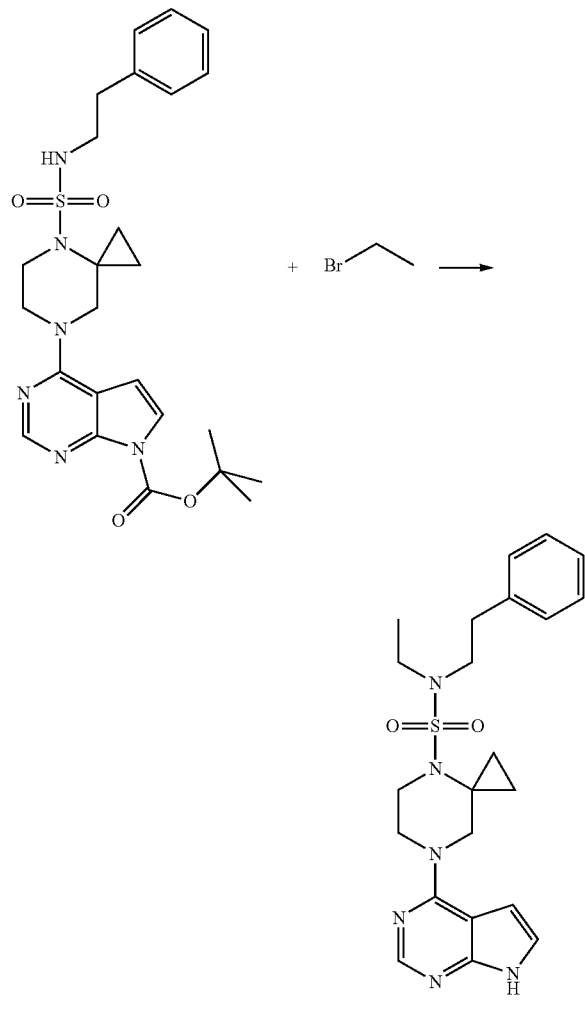

4-(4-Phenethylsulfamoyl-4,7-diaza-spiro[2.5]oct-7-yl)-pyrrolo[2,3-d]pyrimidine-7-carboxylic acid tert-butyl ester (intermediate 6) (0.1 mmol) was dissolved in dry DMF (0.5 mL) and added $Cs_2CO_3$ (0.12 mmol) and bromo-ethane (0.12 mmol). Stirred at rt for 16 h and then added $H_2O$ (2 mL). Extracted with EtOAc (3×2 mL) and the combined organic phases were concentrated in vacuo. The residual oil was treated with TFA (1 mL) at rt for 3 h. The pure compound was obtained by standard preparative HPLC purification of the reaction mixture.

1H NMR (300 MHz, DMSO) δ 12.71 (s, 1H), 8.41 (s, 1H), 7.44 (dd, J=3.2, 1.7 Hz, 1H), 7.38-7.12 (m, 5H), 6.91 (d, J=3.1 Hz, 1H), 4.26-4.07 (m, 2H), 3.94 (s, 2H), 3.60-3.43 (m, 2H), 3.42-3.27 (m, 2H), 3.23 (q, J=7.1 Hz, 2H), 2.92-2.77 (m, 2H), 1.11 (t, J=7.1 Hz, 3H), 1.02 (t, J=5.9 Hz, 2H), 0.93 (t, J=6.1 Hz, 2H).

Using this procedure the following compounds were obtained:

Example 2

7-(7H-Pyrrolo[2,3-d]pyrimidin-4-yl)-4,7-diaza-spiro[2.5]octane-4-sulfonic acid cyclopropylmethyl-phenethyl-amide

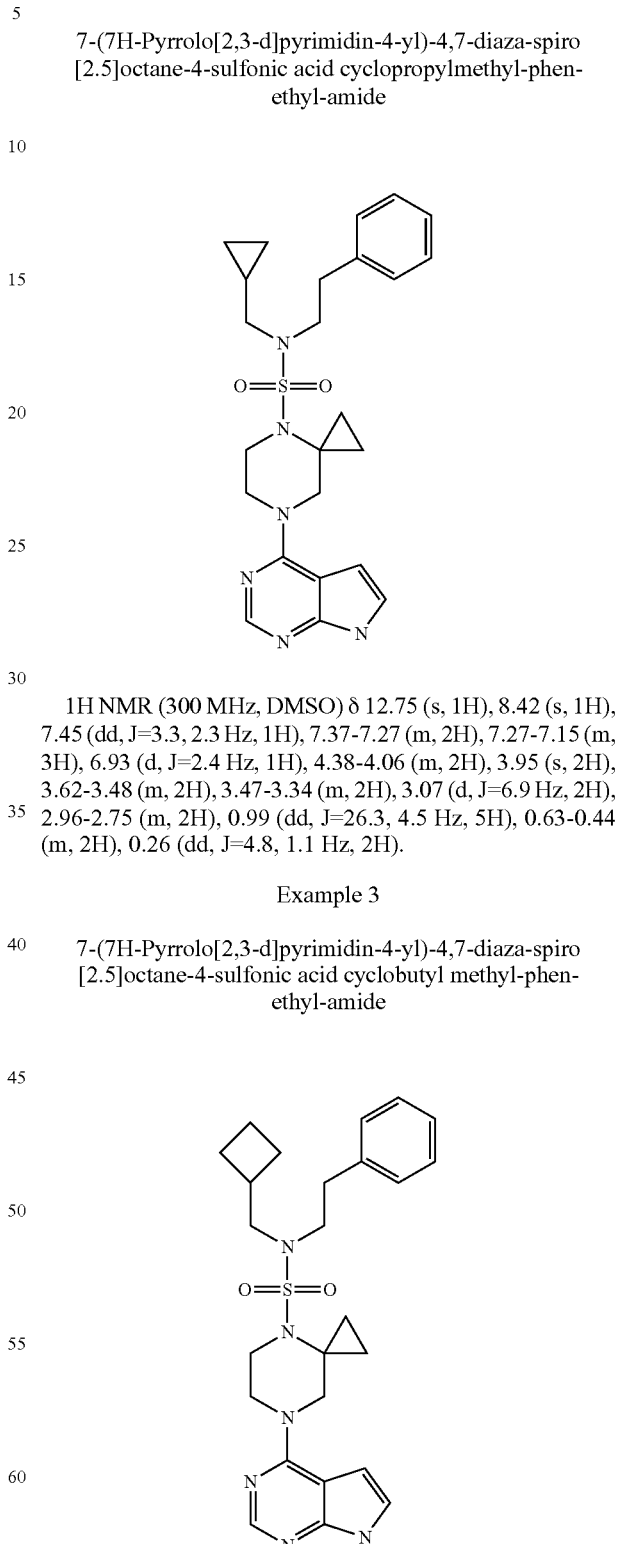

1H NMR (300 MHz, DMSO) δ 12.75 (s, 1H), 8.42 (s, 1H), 7.45 (dd, J=3.3, 2.3 Hz, 1H), 7.37-7.27 (m, 2H), 7.27-7.15 (m, 3H), 6.93 (d, J=2.4 Hz, 1H), 4.38-4.06 (m, 2H), 3.95 (s, 2H), 3.62-3.48 (m, 2H), 3.47-3.34 (m, 2H), 3.07 (d, J=6.9 Hz, 2H), 2.96-2.75 (m, 2H), 0.99 (dd, J=26.3, 4.5 Hz, 5H), 0.63-0.44 (m, 2H), 0.26 (dd, J=4.8, 1.1 Hz, 2H).

Example 3

7-(7H-Pyrrolo[2,3-d]pyrimidin-4-yl)-4,7-diaza-spiro[2.5]octane-4-sulfonic acid cyclobutyl methyl-phenethyl-amide

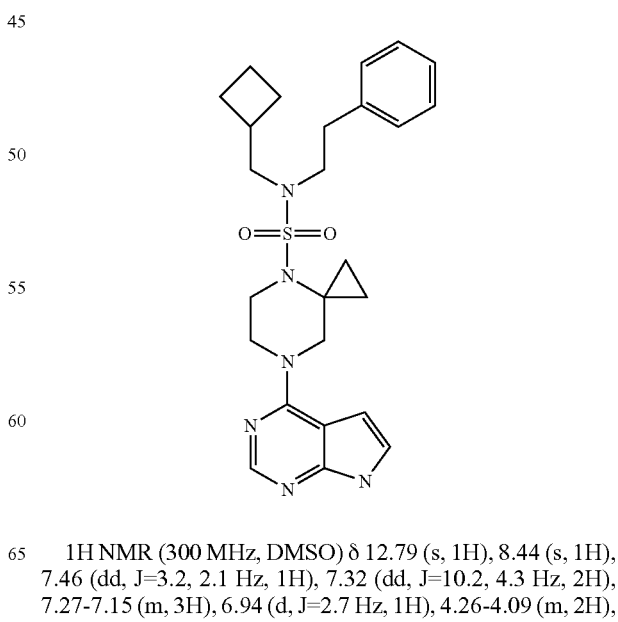

1H NMR (300 MHz, DMSO) δ 12.79 (s, 1H), 8.44 (s, 1H), 7.46 (dd, J=3.2, 2.1 Hz, 1H), 7.32 (dd, J=10.2, 4.3 Hz, 2H), 7.27-7.15 (m, 3H), 6.94 (d, J=2.7 Hz, 1H), 4.26-4.09 (m, 2H), 3.96 (s, 2H), 3.66-3.44 (m, 2H), 3.37-3.23 (m, 2H), 3.23-3.14 (m, 2H), 2.88-2.75 (m, 2H), 2.58 (dt, J=15.1, 7.6 Hz, 1H), 2.01 (dt, J=8.4, 5.9 Hz, 2H), 1.79 (ddt, J=23.8, 17.9, 8.4 Hz, 4H), 1.04 (t, J=5.9 Hz, 2H), 0.95 (t, J=6.1 Hz, 2H).

Example 4

7-(7H-Pyrrolo[2,3-d]pyrimidin-4-yl)-4,7-diaza-spiro[2.5]octane-4-sulfonic acid (2-oxo-butyl)-phenethyl-amide

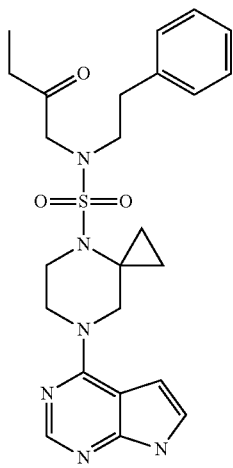 [SMILES: CCC(=O)CN(CCc1ccccc1)S(=O)(=O)N1CCN(c2ncnc3[nH]ccc23)CC12CC2]

1H NMR (300 MHz, DMSO) δ 12.42 (s, 1H), 8.33 (s, 1H), 7.37 (dd, J=3.3, 1.6 Hz, 1H), 7.34-7.25 (m, 2H), 7.21 (dd, J=6.8, 4.5 Hz, 3H), 6.82 (d, J=3.2 Hz, 1H), 4.16 (s, 2H), 4.15-4.02 (m, 2H), 3.89 (s, 2H), 3.54-3.44 (m, 2H), 3.37-3.24 (m, 2H), 2.88-2.73 (m, 2H), 2.43 (q, J=7.3 Hz, 2H), 1.08-0.85 (m, 7H).

Example 5

7-(7H-Pyrrolo[2,3-d]pyrimidin-4-yl)-4,7-diaza-spiro[2.5]octane-4-sulfonic acid (3-hydroxy-propyl)-phenethyl-amide

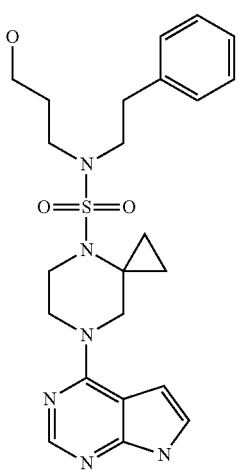 [SMILES: O=S(=O)(N(CCCO)CCc1ccccc1)N1CCN(c2ncnc3[nH]ccc23)CC12CC2]

1H NMR (300 MHz, DMSO) δ 12.23 (s, 1H), 8.28 (s, 1H), 7.36-7.27 (m, 3H), 7.27-7.17 (m, 3H), 6.78 (s, 1H), 4.09 (s, 2H), 3.88 (s, 2H), 3.45 (m, 2H), 3.41 (t, J=6.1 Hz, 2H), 3.35-3.27 (m, 2H), 3.20 (dd, J=13.1, 5.3 Hz, 2H), 3.02-2.69 (m, 2H), 1.82-1.53 (m, 2H), 1.00 (m, 2H), 0.90 (m, 2H).

Example 6

7-(7H-Pyrrolo[2,3-d]pyrimidin-4-yl)-4,7-diaza-spiro[2.5]octane-4-sulfonic acid isobutyl-phenethyl-amide

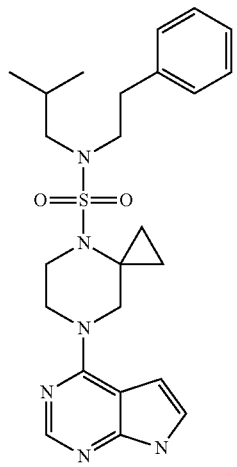 [SMILES: CC(C)CN(CCc1ccccc1)S(=O)(=O)N1CCN(c2ncnc3[nH]ccc23)CC12CC2]

1H NMR (300 MHz, DMSO) δ 12.76 (s, 1H), 8.43 (s, 1H), 7.46 (dd, J=3.3, 2.3 Hz, 1H), 7.36-7.27 (m, 2H), 7.21 (dd, J=9.9, 4.4 Hz, 3H), 6.94 (d, J=2.5 Hz, 1H), 4.24-4.10 (m, 2H), 3.96 (d, J=5.5 Hz, 2H), 3.58-3.43 (m, 2H), 3.36-3.21 (m, 2H), 2.99 (d, J=7.5 Hz, 2H), 2.91-2.74 (m, 2H), 1.90 (dq, J=13.7, 6.8 Hz, 1H), 1.03 (d, J=3.9 Hz, 2H), 0.96 (t, J=6.1 Hz, 2H), 0.88 (d, J=6.6 Hz, 6H).

Example 7

7-(7H-Pyrrolo[2,3-d]pyrimidin-4-yl)-4,7-diaza-spiro[2.5]octane-4-sulfonic acid phenethyl-propyl-amide

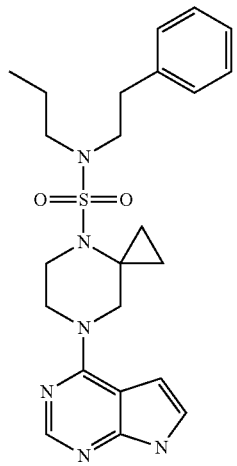 [SMILES: CCCN(CCc1ccccc1)S(=O)(=O)N1CCN(c2ncnc3[nH]ccc23)CC12CC2]

1H NMR (300 MHz, DMSO) δ 12.65 (s, 1H), 8.40 (s, 1H), 7.42 (dd, J=3.2, 1.5 Hz, 1H), 7.37-7.27 (m, 2H), 7.27-7.17 (m, 3H), 6.89 (d, J=3.2 Hz, 1H), 4.27-4.05 (m, 2H), 3.94 (s, 2H), 3.58-3.40 (m, 2H), 3.40-3.20 (m, 2H), 3.19-3.03 (m, 2H), 2.89-2.68 (m, 2H), 1.67-1.42 (m, 2H), 1.02 (t, J=6.0 Hz, 2H), 0.93 (t, J=6.1 Hz, 2H), 0.84 (t, J=7.4 Hz, 3H).

Example 8

7-(7H-Pyrrolo[2,3-d]pyrimidin-4-yl)-4,7-diaza-spiro[2.5]octane-4-sulfonic acid cyclohexylmethyl-phenethyl-amide

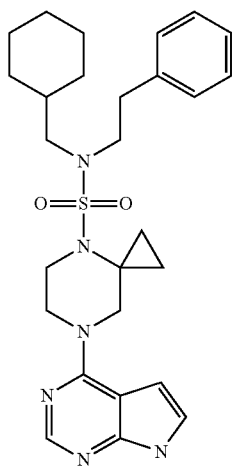 [SMILES: O=S(=O)(N(CCc1ccccc1)CC1CCCCC1)N1CCN(c2ncnc3[nH]ccc23)CC12CC2]

1H NMR (300 MHz, DMSO) δ 11.90 (s, 1H), 8.19 (s, 1H), 7.61-7.26 (m, 2H), 7.26-7.17 (m, 4H), 6.66 (d, J=2.8 Hz, 1H), 4.22-3.94 (m, 2H), 3.86 (s, 2H), 3.50-3.37 (m, 2H), 3.34-3.20 (m, 2H), 2.98 (d, J=7.2 Hz, 2H), 2.91-2.76 (m, 2H), 1.62 (dd, J=29.9, 11.2 Hz, 6H), 1.39-1.05 (m, 3H), 1.05-0.74 (m, 6H).

Example 18

7-(7H-Pyrrolo[2,3-d]pyrimidin-4-yl)-4,7-diaza-spiro[2.5]octane-4-sulfonic acid diphenethylamide

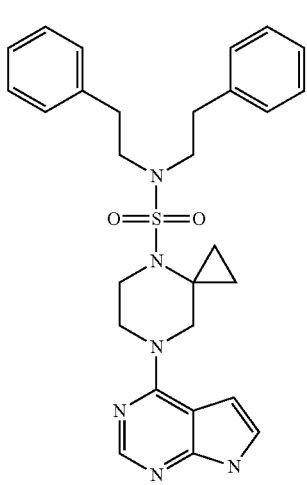 [SMILES: O=S(=O)(N(CCc1ccccc1)CCc1ccccc1)N1CCN(c2ncnc3[nH]ccc23)CC12CC2]

1H NMR (300 MHz, DMSO) δ 11.71 (s, 1H), 8.13 (s, 1H), 7.36-7.27 (m, 4H), 7.26-7.14 (m, 7H), 6.58 (dd, J=3.5, 1.7 Hz, 1H), 4.02 (s, 2H), 3.83 (s, 2H), 3.44-3.26 (m, 6H), 2.87-2.76 (m, 4H), 1.07-0.72 (m, 4H).

Example 19

7-(7H-Pyrrolo[2,3-d]pyrimidin-4-yl)-4,7-diaza-spiro[2.5]octane-4-sulfonic acid cyanomethyl-phenethyl-amide

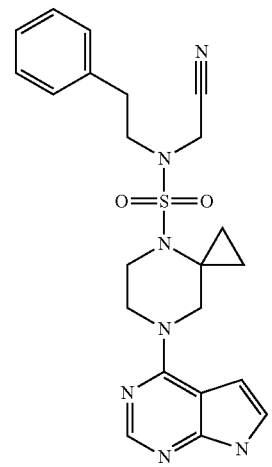 [SMILES: N#CCN(CCc1ccccc1)S(=O)(=O)N1CCN(c2ncnc3[nH]ccc23)CC12CC2]

1H NMR (300 MHz, DMSO) δ 11.73 (s, 1H), 8.13 (s, 1H), 7.39-7.07 (m, 6H), 6.57 (s, 1H), 4.40 (s, 2H), 4.15-3.90 (m, 2H), 3.80 (s, 2H), 3.48-3.30 (m, 4H), 2.89 (t, J=7.5 Hz, 2H), 1.04-0.77 (m, 4H).

Example 20

7-(7H-Pyrrolo[2,3-d]pyrimidin-4-yl)-4,7-diaza-spiro[2.5]octane-4-sulfonic acid (4-cyano-butyl)-phenethyl-amide 1H NMR (300 MHz, DMSO) δ 11.82 (s, 1H), 8.16 (s, 1H), 7.36-7.18 (m, 6H), 6.62 (dd, J=3.5, 1.7 Hz, 1H), 4.09-3.97 (m, 2H), 3.84 (s, 2H), 3.43 (dd, J=5.2, 4.6 Hz, 4H), 3.33-3.25 (m, 2H), 3.17 (t, J=7.0 Hz, 2H), 2.87-2.78 (m, 2H), 1.76-1.44 (m, 4H), 1.08-0.81 (m, 4H).

Example 21

7-(7H-Pyrrolo[2,3-d]pyrimidin-4-yl)-4,7-diaza-spiro[2.5]octane-4-sulfonic acid phenethyl-(tetrahydro-pyran-2-ylmethyl)-amide

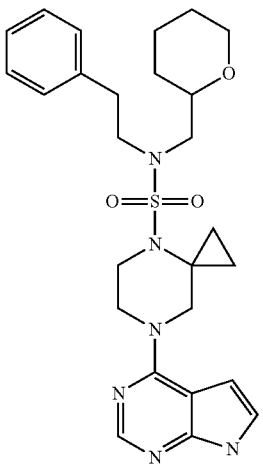 [SMILES: O=S(=O)(N(CCc1ccccc1)CC1CCCCO1)N1CCN(c2ncnc3[nH]ccc23)CC12CC2]

1H NMR (300 MHz, DMSO) δ 11.74 (s, 1H), 8.14 (s, 1H), 7.37-7.26 (m, 2H), 7.26-7.17 (m, 4H), 6.59 (dd, J=3.6, 1.7 Hz, 1H), 4.07-3.99 (m, 2H), 3.83 (s, 2H), 3.46-3.39 (m, 2H), 3.32-3.26 (m, 5H), 3.11 (t, J=7.1 Hz, 2H), 2.88-2.76 (m, 2H), 2.44 (t, J=6.8 Hz, 2H), 1.56-1.33 (m, 4H), 0.99-0.80 (m, 4H).

Example 22

7-(7H-Pyrrolo[2,3-d]pyrimidin-4-yl)-4,7-diaza-spiro[2.5]octane-4-sulfonic acid (2-methoxy-ethyl)-phenethyl-amide

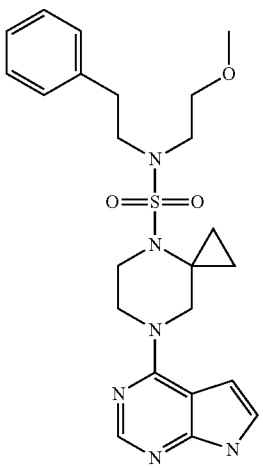 [SMILES: COCCN(CCc1ccccc1)S(=O)(=O)N1CCN(c2ncnc3[nH]ccc23)CC12CC2]

1H NMR (300 MHz, DMSO) δ 11.85 (s, 1H), 8.17 (s, 1H), 7.58-7.08 (m, 6H), 6.64 (dd, J=3.5, 1.6 Hz, 1H), 4.14-3.96 (m, 2H), 3.85 (s, 2H), 3.46 (dd, J=10.3, 4.6 Hz, 4H), 3.41-3.28 (m, 4H), 3.27 (s, 3H), 2.94-2.75 (m, 2H), 1.14-0.80 (m, 4H).

Example 23

7-(7H-Pyrrolo[2,3-d]pyrimidin-4-yl)-4,7-diaza-spiro[2.5]octane-4-sulfonic acid but-2-ynyl-phenethyl-amide

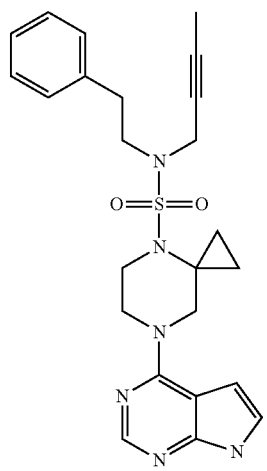 [SMILES: CC#CCN(CCc1ccccc1)S(=O)(=O)N1CCN(c2ncnc3[nH]ccc23)CC12CC2]

1H NMR (300 MHz, DMSO) δ 11.80 (s, 1H), 8.16 (s, 1H), 7.42-7.26 (m, 2H), 7.26-7.17 (m, 4H), 6.61 (dd, J=3.6, 1.7 Hz, 1H), 4.08-3.99 (m, 2H), 3.96 (d, J=2.4 Hz, 2H), 3.82 (s, 2H), 3.39 (m, 4H), 2.94-2.76 (m, 2H), 1.81 (t, J=2.3 Hz, 3H), 0.98 (t, J=5.9 Hz, 2H), 0.84 (t, J=6.1 Hz, 2H).

Example 24

7-(7H-Pyrrolo[2,3-d]pyrimidin-4-yl)-4,7-diaza-spiro[2.5]octane-4-sulfonic acid phenethyl-(2-pyrazol-1-yl-ethyl)-amide

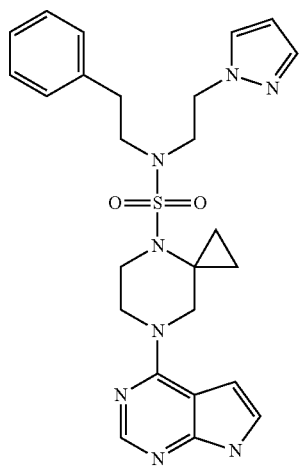 [SMILES: O=S(=O)(N(CCc1ccccc1)CCn1cccn1)N1CCN(c2ncnc3[nH]ccc23)CC12CC2]

1H NMR (300 MHz, DMSO) δ 11.71 (s, 1H), 8.13 (s, 1H), 7.75 (d, J=2.2 Hz, 1H), 7.49 (d, J=1.6 Hz, 1H), 7.30 (t, J=7.2 Hz, 2H), 7.24-7.09 (m, 4H), 6.58 (dd, J=3.5, 1.8 Hz, 1H), 6.26 (t, J=2.0 Hz, 1H), 4.27 (t, J=6.2 Hz, 2H), 4.09-3.93 (m, 2H), 3.82 (s, 2H), 3.58 (t, J=6.3 Hz, 2H), 3.34 (m, 2H), 3.21-3.09 (m, 2H), 2.73-2.63 (m, 2H), 1.07-0.73 (m, 4H).

Example 25

7-(7H-Pyrrolo[2,3-d]pyrimidin-4-yl)-4,7-diaza-spiro[2.5]octane-4-sulfonic acid (2-hydroxy-ethyl)-phenethyl-amide

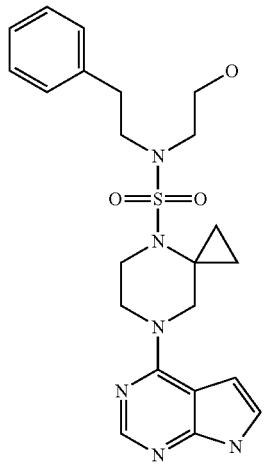 [SMILES: O=S(=O)(N(CCO)CCc1ccccc1)N1CCN(c2ncnc3[nH]ccc23)CC12CC2]

1H NMR (600 MHz, DMSO) δ 11.73 (s, 1H), 8.13 (s, 1H), 7.38-7.28 (m, 2H), 7.25-7.17 (m, 4H), 6.59 (d, J=3.6 Hz, 1H), 4.80 (t, J=5.3 Hz, 1H), 4.04 (s, 2H), 3.84 (s, 2H), 3.54 (q, J=6.1 Hz, 2H), 3.46 (t, J=5.1 Hz, 2H), 3.40-3.34 (m, 2H), 3.21 (t, J=6.3 Hz, 2H), 2.87-2.82 (m, 2H), 1.00 (t, J=5.6 Hz, 2H), 0.90-0.80 (m, 2H).

Example 46

{Phenethyl-[7-(7H-pyrrolo[2,3-d]pyrimidin-4-yl)-4,7-diaza-spiro[2.5]octane-4-sulfonyl]-amino}-acetic acid ethyl ester

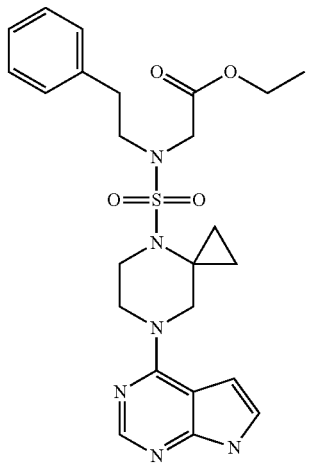 [SMILES: CCOC(=O)CN(CCc1ccccc1)S(=O)(=O)N1CCN(c2ncnc3[nH]ccc23)CC12CC2]

1H NMR (300 MHz, DMSO) δ 11.70 (s, 1H), 8.13 (s, 1H), 7.35-7.13 (m, 6H), 6.58 (s, 1H), 4.13 (q, J=7.1 Hz, 2H), 4.03 (m, 4H), 3.81 (s, 2H), 3.48-3.34 (m, 4H), 2.89-2.73 (m, 2H), 1.21 (t, J=7.1 Hz, 3H), 0.99-0.80 (m, 4H).

Example 47

7-(7H-Pyrrolo[2,3-d]pyrimidin-4-yl)-4,7-diaza-spiro[2.5]octane-4-sulfonic acid [2-(4-fluoro-phenyl)-ethyl]-phenethyl-amide

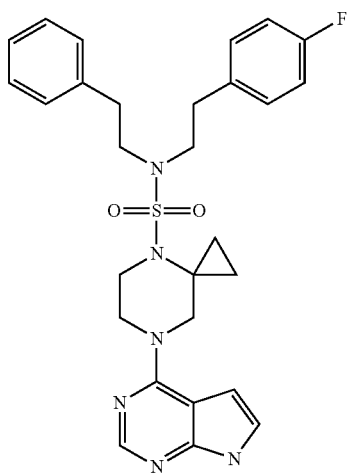 [SMILES: O=S(=O)(N(CCc1ccccc1)CCc1ccc(F)cc1)N1CCN(c2ncnc3[nH]ccc23)CC12CC2]

1H NMR (300 MHz, DMSO) δ 11.70 (s, 1H), 8.13 (s, 1H), 7.44-6.96 (m, 10H), 6.57 (dd, J=3.6, 1.8 Hz, 1H), 4.11-3.96 (m, 2H), 3.82 (s, 2H), 3.41-3.33 (m, 6H), 2.84 (dd, J=15.5, 8.0 Hz, 4H), 0.95 (t, J=5.9 Hz, 2H), 0.85 (t, J=6.0 Hz, 2H).

LC-MS (MSX13330): 2.61 min, ES (+), m/z: 535.215

Example 48

7-(7H-Pyrrolo[2,3-d]pyrimidin-4-yl)-4,7-diaza-spiro[2.5]octane-4-sulfonic acid [2-(3-fluoro-phenyl)-ethyl]-phenethyl-amide

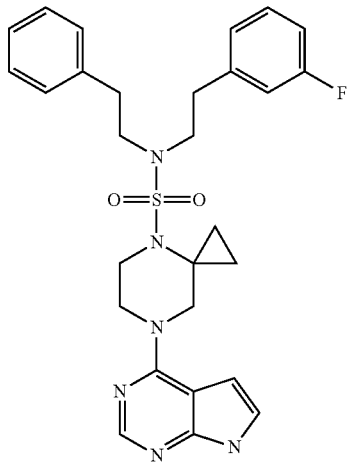 [SMILES: O=S(=O)(N(CCc1ccccc1)CCc1cccc(F)c1)N1CCN(c2ncnc3[nH]ccc23)CC12CC2]

1H NMR (300 MHz, DMSO) δ 11.70 (s, 1H), 8.13 (s, 1H), 7.36-7.05 (m, 10H), 6.57 (dd, J=3.6, 1.8 Hz, 1H), 4.02 (s, 2H), 3.83 (s, 2H), 3.41-3.32 (m, 4H), 2.95-2.72 (m, 4H), 0.95 (t, J=5.4 Hz, 2H), 0.85 (t, J=6.1 Hz, 2H).

Example 49

N-Benzyl-2-{phenethyl-[7-(7H-pyrrolo[2,3-d]pyrimidin-4-yl)-4,7-diaza-spiro[2.5]octane-4-sulfonyl]-amino}-acetamide

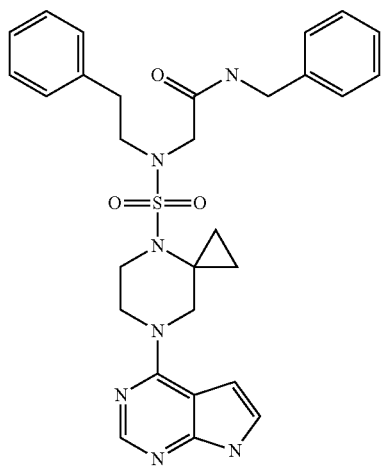 [SMILES: O=C(CN(CCc1ccccc1)S(=O)(=O)N1CCN(c2ncnc3[nH]ccc23)CC12CC2)NCc1ccccc1]

1H NMR (300 MHz, DMSO) δ 11.70 (s, 1H), 8.45 (t, J=5.9 Hz, 1H), 7.40-7.06 (m, 12H), 6.57 (dd, J=3.6, 1.8 Hz, 1H), 4.30 (d, J=5.9 Hz, 2H), 4.02 (m, 2H), 3.87 (s, 2H), 3.81 (s, 2H), 3.55-3.37 (m, 4H), 2.90-2.79 (m, 2H), 0.99 (t, J=5.8 Hz, 2H), 0.81 (t, J=5.9 Hz, 2H).

Example 10

7-(7H-Pyrrolo[2,3-d]pyrimidin-4-yl)-4,7-diaza-spiro[2.5]octane-4-sulfonic acid methyl-(3-phenyl-propyl)-amide

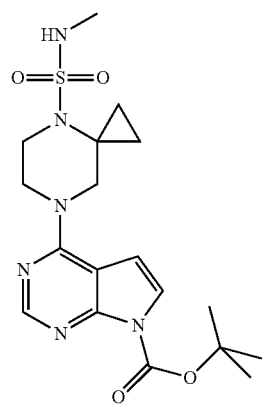

+

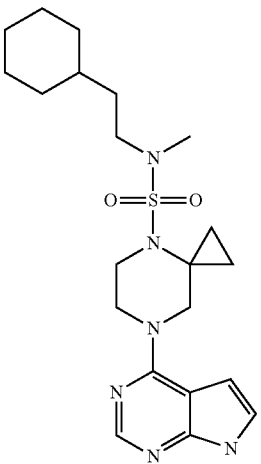 [SMILES: CN(CCC1CCCCC1)S(=O)(=O)N1CCN(c2ncnc3[nH]ccc23)CC12CC2]

4-(4-Methylsulfamoyl-4,7-diaza-spiro[2.5]oct-7-yl)-pyrrolo[2,3-d]pyrimidine-7-carboxylic acid tert-butyl ester (intermediate 4) (0.71 mmol) was dissolved in dry DMF (0.5 mL) and added Cs$_2$CO$_3$ (0.85 mmol) and (3-bromo-propyl)-benzene (0.085 mmol). Stirred at 35° C. for 1.5 h and then added H$_2$O (2 mL). Extracted with EtOAc (3×2 mL) and the combined organic phases were concentrated in vacuo. The residual oil was treated with TFA (2 mL) at rt→45° C. for 1.5 h. The crude reaction mixture was concentrated in vacuo and redissolved in DMSO (0.5 mL). The pure compounds were obtained by standard preparative HPLC purification of the reaction mixture.

1H NMR (300 MHz, DMSO) δ 12.28 (s, 1H), 8.30 (s, 1H), 7.56-7.07 (m, 6H), 6.79 (d, J=2.0 Hz, 1H), 4.22-3.94 (m, 2H), 3.88 (s, 2H), 3.62-3.40 (m, 2H), 3.20-2.95 (m, 2H), 2.71 (s, 3H), 2.63-2.52 (m, 2H), 1.89-1.70 (m, 2H), 0.94 (dd, J=21.9, 4.3 Hz, 4H).

Using this procedure the following compounds were obtained:

Example 11

7-(7H-Pyrrolo[2,3-d]pyrimidin-4-yl)-4,7-diaza-spiro[2.5]octane-4-sulfonic acid (2-cyclohexyl-ethyl)-methyl-amide 1H NMR (300 MHz, DMSO) δ 12.07 (s, 1H), 8.24 (s, 1H), 7.29 (dd, J=3.4, 2.4 Hz, 1H), 6.72 (dd, J=3.5, 1.6 Hz, 1H), 4.23-3.99 (m, 2H), 3.87 (s, 2H), 3.59-3.46 (m, 2H), 3.16-2.96 (m, 2H), 2.67 (s, 3H), 1.77-1.53 (m, 5H), 1.40 (dd, J=14.7, 6.9 Hz, 2H), 1.30-1.10 (m, 4H), 1.07-0.76 (m, 6H).

Example 12

7-(7H-Pyrrolo[2,3-d]pyrimidin-4-yl)-4,7-diaza-spiro[2.5]octane-4-sulfonic acid methyl-(2-oxo-2-phenyl-ethyl)-amide

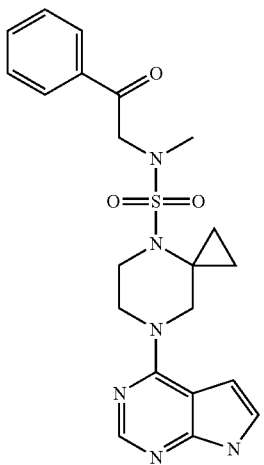 [SMILES: CN(CC(=O)c1ccccc1)S(=O)(=O)N1CCN(c2ncnc3[nH]ccc23)CC12CC2]

1H NMR (300 MHz, DMSO) δ 11.71 (s, 1H), 8.14 (s, 1H), 8.03-7.93 (m, 2H), 7.68 (t, J=7.3 Hz, 1H), 7.56 (t, J=7.6 Hz, 2H), 7.31-7.11 (m, 1H), 6.74-6.53 (m, 1H), 4.77 (s, 2H), 4.25-3.93 (m, 2H), 3.85 (s, 2H), 3.65-3.45 (m, 2H), 2.81 (s, 3H), 1.06 (t, J=5.8 Hz, 2H), 0.87 (t, J=6.0 Hz, 2H).

Example 13

7-(7H-Pyrrolo[2,3-d]pyrimidin-4-yl)-4,7-diaza-spiro[2.5]octane-4-sulfonic acid (3-cyano-benzyl)-methyl-amide

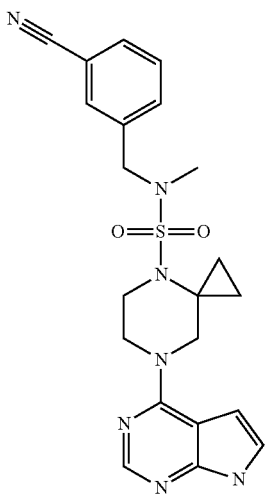 [SMILES: CN(Cc1cccc(C#N)c1)S(=O)(=O)N1CCN(c2ncnc3[nH]ccc23)CC12CC2]

1H NMR (300 MHz, DMSO) δ 11.72 (s, 1H), 8.14 (s, 1H), 7.85-7.3 (m, 2H), 7.71-7.51 (m, 2H), 7.20 (dd, J=3.5, 2.5 Hz, 1H), 6.60 (dd, J=3.6, 1.8 Hz, 1H), 4.35 (s, 2H), 4.15-3.96 (m, 2H), 3.87 (s, 2H), 3.73-3.50 (m, 2H), 2.64 (s, 3H), 1.03 (t, J=5.9 Hz, 2H), 0.91 (s, 2H).

Example 14

7-(7H-Pyrrolo[2,3-d]pyrimidin-4-yl)-4,7-diaza-spiro[2.5]octane-4-sulfonic acid (2-cyano-benzyl)-methyl-amide

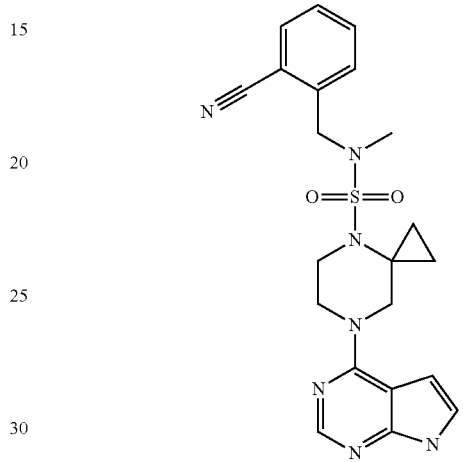

1H NMR (300 MHz, DMSO) δ 11.83 (s, 1H), 8.17 (s, 1H), 7.87 (d, J=7.7 Hz, 1H), 7.77 (t, J=7.6 Hz, 1H), 7.66-7.46 (m, 2H), 7.22 (s, 1H), 6.64 (s, 1H), 4.49 (s, 2H), 4.08 (s, 2H), 3.87 (s, 2H), 3.72-3.53 (m, 2H), 2.71 (s, 3H), 1.05-0.96 (m, 2H), 0.96-0.85 (m, 2H).

Example 15

7-(7H-Pyrrolo[2,3-d]pyrimidin-4-yl)-4,7-diaza-spiro[2.5]octane-4-sulfonic acid cyclohexylmethyl-methyl-amide

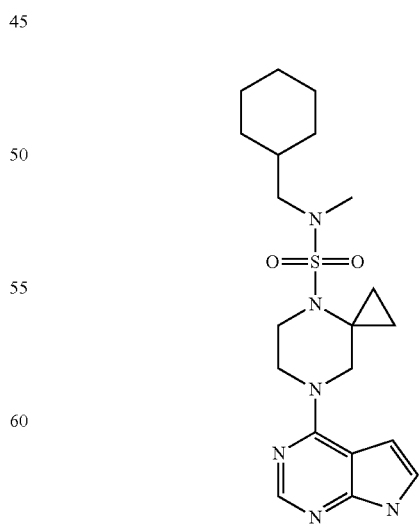

1H NMR (300 MHz, DMSO) δ 11.71 (s, 1H), 8.13 (s, 1H), 7.23-7.11 (m, 1H), 6.59 (dd, J=3.5, 1.7 Hz, 1H), 4.12-3.94 (m,

2H), 3.83 (s, 2H), 3.58-3.40 (m, 2H), 2.89 (d, J=7.2 Hz, 2H), 2.65 (s, 3H), 1.60 (ddd, J=13.7, 11.1, 7.8 Hz, 5H), 1.32-1.06 (m, 4H), 1.08-0.74 (m, 6H).

Example 16

7-(7H-Pyrrolo[2,3-d]pyrimidin-4-yl)-4,7-diaza-spiro[2.5]octane-4-sulfonic acid [2-(4-fluoro-phenyl)-ethyl]-methyl-amide

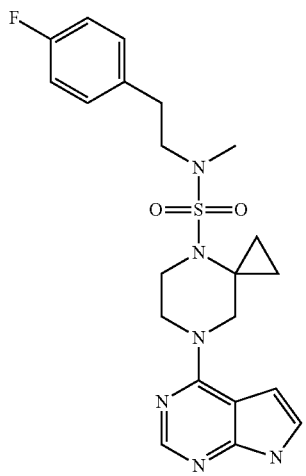 [SMILES: CN(CCc1ccc(F)cc1)S(=O)(=O)N1CCN(c2ncnc3[nH]ccc23)CC12CC2]

1H NMR (300 MHz, DMSO) δ 11.88 (s, 1H), 8.17 (s, 1H), 7.34-7.19 (m, 3H), 7.18-7.03 (m, 2H), 6.63 (dd, J=3.5, 1.7 Hz, 1H), 4.18-3.88 (m, 2H), 3.82 (s, 2H), 3.48-3.38 (m, 2H), 3.35-3.21 (m, 2H), 2.87-2.77 (m, 2H), 2.71 (s, 3H), 1.02-0.89 (m, 2H), 0.89-0.79 (m, 2H).

Example 17

7-(7H-Pyrrolo[2,3-d]pyrimidin-4-yl)-4,7-diaza-spiro[2.5]octane-4-sulfonic acid [2-(3-fluoro-phenyl)-ethyl]-methyl-amide

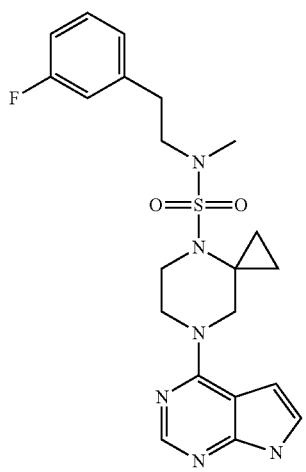 [SMILES: CN(CCc1cccc(F)c1)S(=O)(=O)N1CCN(c2ncnc3[nH]ccc23)CC12CC2]

1H NMR (300 MHz, DMSO) δ 11.72 (s, 1H), 8.13 (s, 1H), 7.35 (td, J=8.0, 6.3 Hz, 1H), 7.18 (dd, J=3.5, 2.5 Hz, 1H), 7.14-7.00 (m, 3H), 6.57 (dd, J=3.6, 1.8 Hz, 1H), 4.06-3.93 (m, 2H), 3.81 (s, 2H), 3.50-3.36 (m, 2H), 3.37-3.17 (m, 2H), 2.85 (t, J=7.4 Hz, 2H), 2.71 (s, 3H), 0.97-0.88 (m, 2H), 0.88-0.79 (m, 2H).

Example 26

7-(7H-Pyrrolo[2,3-d]pyrimidin-4-yl)-4,7-diaza-spiro[2.5]octane-4-sulfonic acid methyl-(2-pyrrol-1-yl-ethyl)-amide

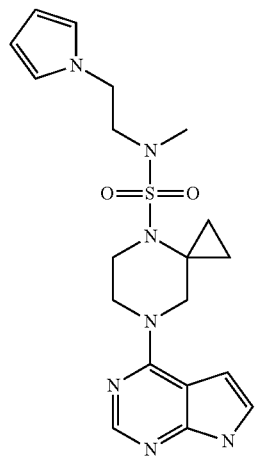 [SMILES: CN(CCn1cccc1)S(=O)(=O)N1CCN(c2ncnc3[nH]ccc23)CC12CC2]

1H NMR (300 MHz, DMSO) δ 11.82 (s, 1H), 8.16 (s, 1), 7.22 (dd, J=3.4, 2.5 Hz, 1H), 6.77 (t, J=2.1 Hz, 2H), 6.61 (dd, J=3.5, 1.6 Hz, 1H), 6.01 (t, J=2.1 Hz, 2H), 4.17-3.94 (m, 4H), 3.82 (s, 2H), 3.46-3.31 (m, 4H), 2.55 (s, 3H), 1.01-0.78 (m, 4H).

Example 27

7-(7H-Pyrrolo[2,3-d]pyrimidin-4-yl)-4,7-diaza-spiro[2.5]octane-4-sulfonic acid methyl-(3-methyl-butyl)-amide

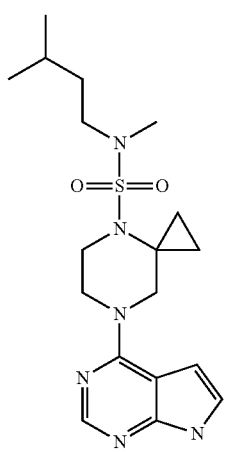 [SMILES: CC(C)CCN(C)S(=O)(=O)N1CCN(c2ncnc3[nH]ccc23)CC12CC2]

1H NMR (300 MHz, DMSO) δ 11.71 (s, 1H), 8.13 (s, 1H), 7.19 (dd, J=3.5, 2.6 Hz, 1H), 6.59 (dd, J=3.6, 1.8 Hz, 1H), 4.10-3.97 (m, 2H), 3.83 (s, 2H), 3.58-3.47 (m, 2H), 3.12-3.00 (m, 2H), 2.67 (s, 3H), 1.64-1.47 (m, 1H), 1.39 (dd, J=14.6, 7.1 Hz, 2H), 0.99 (t, J=6.0 Hz, 2H), 0.88 (d, J=6.6 Hz, 8H).

Example 28

7-(7H-Pyrrolo[2,3-d]pyrimidin-4-yl)-4,7-diaza-spiro[2.5]octane-4-sulfonic acid methyl-pyridin-2-ylm-ethyl-amide

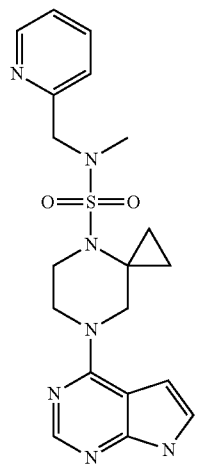 [SMILES: CN(Cc1ccccn1)S(=O)(=O)N1CCN(c2ncnc3[nH]ccc23)CC12CC2]

1H NMR (300 MHz, DMSO) δ 11.72 (s, 1H), 8.54 (d, J=4.9 Hz, 1H), 8.26 (s, 1H), 7.83 (td, J=7.7, 1.8 Hz, 1H), 7.39 (d, J=7.8 Hz, 1H), 7.36-7.27 (m, 1H), 7.24-7.15 (m, 1H), 6.60 (dd, J=3.6, 1.8 Hz, 1H), 4.37 (s, 2H), 4.14-4.00 (m, 2H), 3.86 (s, 2H), 3.63-3.54 (m, 2H), 2.73 (s, 3H), 1.05-1.00 (m, 2H), 0.94-0.82 (m, 2H).

Example 29

7-(7H-Pyrrolo[2,3-d]pyrimidin-4-yl)-4,7-diaza-spiro[2.5]octane-4-sulfonic acid [3-(4-cyano-phenyl)-propyl]-methyl-amide

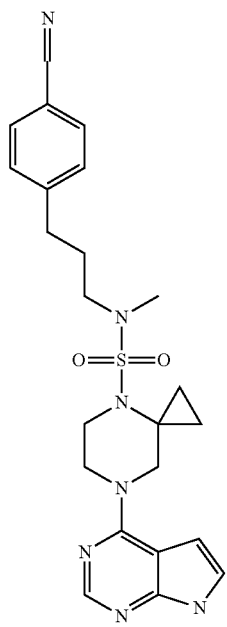 [SMILES: CN(CCCc1ccc(C=N)cc1)S(=O)(=O)N1CCN(c2ncnc3[nH]ccc23)CC12CC2]

1H NMR (300 MHz, DMSO) δ 11.93 (s, 1H), 8.20 (s, 1H), 7.83-7.67 (m, 2H), 7.45 (d, J=8.3 Hz, 2H), 7.32-7.16 (m, 1H), 6.67 (d, J=1.9 Hz, 1H), 4.21-3.97 (m, 2H), 3.84 (s, 2H), 3.59-3.45 (m, 2H), 3.15-3.00 (m, 2H), 2.76-2.61 (m, 5H), 1.91-1.74 (m, 2H), 0.92 (dt, J=11.8, 7.6 Hz, 4H).

Example 30

7-(7H-Pyrrolo[2,3-d]pyrimidin-4-yl)-4,7-diaza-spiro[2.5]octane-4-sulfonic acid [3-(3-cyano-phenyl)-propyl]-methyl-amide

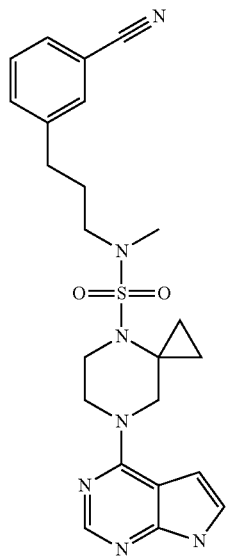 [SMILES: CN(CCCc1cccc(C#N)c1)S(=O)(=O)N1CCN(c2ncnc3[nH]ccc23)CC12CC2]

1H NMR (300 MHz, DMSO) δ 11.96 (s, 1H), 8.21 (s, 1H), 7.73 (s, 1H), 7.65 (ddd, J=19.4, 10.4, 4.6 Hz, 2H), 7.50 (t, J=7.7 Hz, 1H), 7.26 (dd, J=3.4, 2.5 Hz, 1H), 6.68 (dd, J=3.5, 1.6 Hz, 1H), 4.20-3.99 (m, 2H), 3.85 (s, 2H), 3.60-3.41 (m, 2H), 3.21-2.97 (m, 2H), 2.71 (s, 3H), 2.69-2.57 (m, 2H), 1.97-1.73 (m, 2H), 0.92 (dt, J=12.1, 7.7 Hz, 4H).

Example 31

7-(7H-Pyrrolo[2,3-d]pyrimidin-4-yl)-4,7-diaza-spiro[2.5]octane-4-sulfonic acid methyl-(2-phenoxy-ethyl)-amide

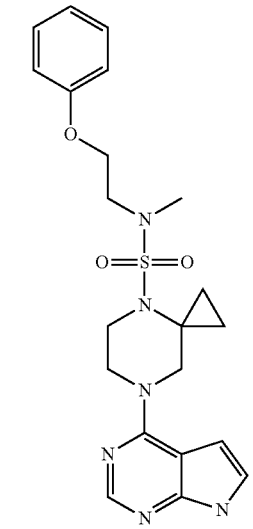 [SMILES: CN(CCOc1ccccc1)S(=O)(=O)N1CCN(c2ncnc3[nH]ccc23)CC12CC2]

1H NMR (300 MHz, DMSO) δ 11.73 (s, 1H), 8.14 (s, 1H), 7.36-7.24 (m, 2H), 7.19 (dd, J=3.5, 2.5 Hz, 1H), 7.02-6.89 (m, 3H), 6.59 (dd, J=3.6, 1.8 Hz, 1H), 4.12 (t, J=5.5 Hz, 2H), 4.09-4.00 (m, 2H), 3.85 (s, 2H), 3.61-3.52 (m, 2H), 3.46 (t, J=5.5 Hz, 2H), 2.82 (s, 3H), 1.03 (t, J=5.9 Hz, 2H), 0.86 (q, J=5.2 Hz, 2H).

Example 32

7-(7H-Pyrrolo[2,3-d]pyrimidin-4-yl)-4,7-diaza-spiro[2.5]octane-4-sulfonic acid [2-(3,5-dimethyl-isoxazol-4-yl)-ethyl]-methyl-amide

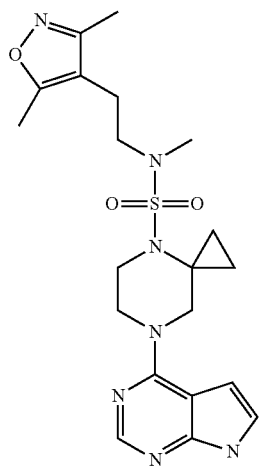 [SMILES: Cc1noc(C)c1CCN(C)S(=O)(=O)N1CCN(c2ncnc3[nH]ccc23)CC12CC2]

1H NMR (300 MHz, DMSO) δ 11.91 (s, 1H), 8.19 (s, 1H), 7.30-7.22 (m, 1H), 6.73-6.61 (m, 1H), 4.12-3.97 (m, 2H), 3.84 (s, 2H), 3.53-3.43 (m, 2H), 3.16 (t, J=7.3 Hz, 2H), 2.74 (s, 3H), 2.57 (t, J=7.3 Hz, 2H), 2.31 (s, 3H), 2.16 (s, 3H), 1.08-0.76 (m, 4H).

Example 33

7-(7H-Pyrrolo[2,3-d]pyrimidin-4-yl)-4,7-diaza-spiro[2.5]octane-4-sulfonic acid (3-cyano-propyl)-phenethyl-amide

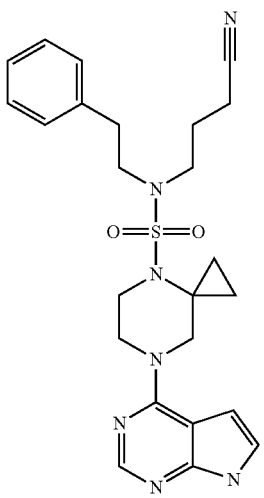 [SMILES: N#CCCCN(CCc1ccccc1)S(=O)(=O)N1CCN(c2ncnc3[nH]ccc23)CC12CC2]

1H NMR (600 MHz, DMSO) δ 11.73 (s, 1H), 8.13 (s, 1H), 7.31 (dd, J=10.4, 4.6 Hz, 2H), 7.23 (dd, J=16.0, 7.4 Hz, 3H), 7.19 (dd, J=3.4, 2.6 Hz, 1H), 6.59 (dd, J=3.6, 1.9 Hz, 1H), 4.04 (dd, J=8.4, 5.7 Hz, 2H), 3.83 (s, 2H), 3.42 (t, J=5.1 Hz, 2H), 3.36-3.30 (m, 2H), 3.26-3.15 (m, 2H), 2.86-2.79 (m, 2H), 2.47 (t, J=7.1 Hz, 2H), 1.86-1.76 (m, 2H), 0.98 (t, J=5.5 Hz, 2H), 0.85 (d, J=15.3 Hz, 2H).

Example 34

{Methyl-[7-(7H-pyrrolo[2,3-d]pyrimidin-4-yl)-4,7-diaza-spiro[2.5]octane-4-sulfonyl]-amino}-acetic acid methyl ester

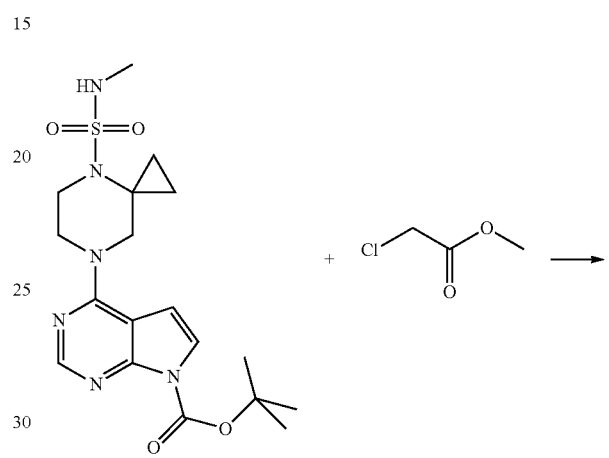

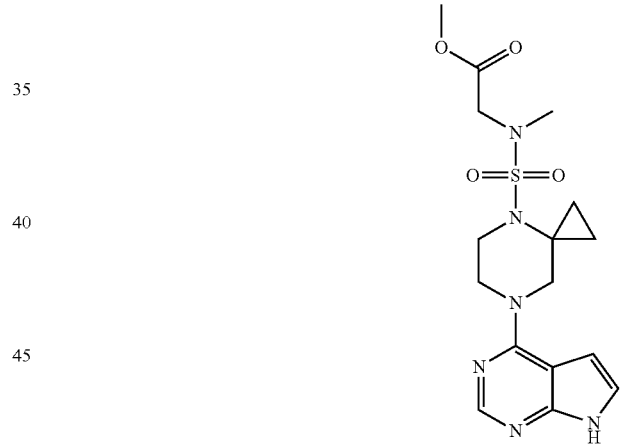

4-(4-Methylsulfamoyl-4,7-diaza-spiro[2.5]oct-7-yl)-pyrrolo[2,3-d]pyrimidine-7-carboxylic acid tert-butyl ester (intermediate 4) (0.047 mmol) was dissolved in dry DMF (0.5 mL) and added $Cs_2CO_3$ (0.071 mmol) and chloro-acetic acid methyl ester (0.071 mmol). Stirred at 40° C. for 2 h and then added $H_2O$ (1.5 mL). Extracted with EtOAc (3×1 mL) and the combined organic phases were washed with brine (1 mL) and concentrated in vacuo. The residual oil was treated with TFA (1 mL) at rt for 1 h. The crude reaction mixture was concentrated in vacuo and redissolved in DMSO (0.5 mL). The pure compound was obtained by standard preparative HPLC purification of the reaction mixture.

1H NMR (300 MHz, DMSO) δ 12.24 (s, 1H), 8.29 (s, 1H), 7.41-7.28 (m, 1H), 6.83-6.74 (m, 1H), 4.13-4.05 (m, 2H), 4.01 (s, 2H), 3.88 (s, 2H), 3.68 (s, 3H), 3.62-3.54 (m, 2H), 2.81 (s, 3H), 1.07 (dd, J=8.9, 2.9 Hz, 2H), 0.96-0.82 (m, 2H).

Using this procedure the following compounds were obtained:

Example 35

7-(7H-Pyrrolo[2,3-d]pyrimidin-4-yl)-4,7-diaza-spiro[2.5]octane-4-sulfonic acid (3-cyano-propyl)-methyl-amide

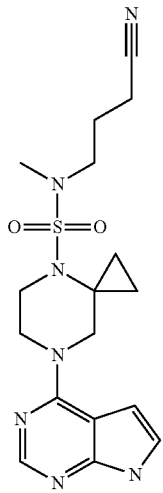 [SMILES: CN(CCCC#N)S(=O)(=O)N1CCN(c2ncnc3[nH]ccc23)CC12CC2]

1H NMR (300 MHz, DMSO) δ 12.06 (s, 1H), 8.24 (s, 1H), 7.47-7.14 (m, 1H), 6.72 (dd, J=3.4, 1.6 Hz, 1H), 4.17-4.03 (m, 2H), 3.87 (s, 2H), 3.60-3.50 (m, 2H), 3.21-3.08 (m, 2H), 2.71 (s, 3H), 2.55-2.40 (m, 2H), 1.82 (p, J=7.2 Hz, 2H), 1.13-0.77 (m, 4H).

Example 36

N,N-Dimethyl-2-{methyl-[7-(7H-pyrrolo[2,3-d]pyrimidin-4-yl)-4,7-diaza-spiro[2.5]octane-4-sulfonyl]-amino}-acetamide

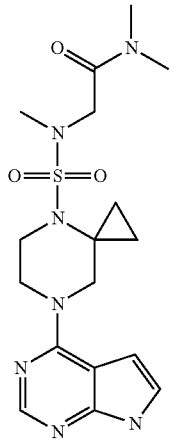 [SMILES: CN(C)C(=O)CN(C)S(=O)(=O)N1CCN(c2ncnc3[nH]ccc23)CC12CC2]

1H NMR (300 MHz, DMSO) δ 11.98 (s, 1H), 8.21 (s, 1H), 7.38-7.10 (m, 1H), 6.80-6.57 (m, 1H), 4.07 (m, 2H), 4.02 (s, 2H), 3.86 (s, 2H), 2.93 (s, 3H), 2.89 (s, 2H), 2.83 (s, 3H), 2.73 (s, 3H), 1.13-1.05 (m, 2H), 0.90-0.80 (m, 2H).
LC-MS (MSX13351): 1.74 min, ES (+), m/z: 408.177

Example 59

N-(cyclopropylmethyl)-N-methyl-5-(7H-pyrrolo[2,3-d]pyrimidin-4-yl)-5,8-diazaspiro[2.5]octane-8-sulfonamide

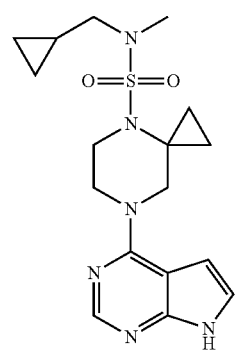 [SMILES: CN(CC1CC1)S(=O)(=O)N1CCN(c2ncnc3[nH]ccc23)CC12CC2]

1H NMR (300 MHz, DMSO) δ 11.72 (s, 1H), 8.13 (s, 1H), 7.19 (dd, J=3.6, 2.2 Hz, 1H), 6.59 (dd, J=3.7, 1.6 Hz, 1H), 4.04 (dd, J=6.1, 4.2 Hz, 2H), 3.84 (s, 2H), 3.54 (dd, J=6.5, 3.8 Hz, 2H), 2.95 (d, J=6.9 Hz, 2H), 2.77 (s, 3H), 1.10-0.78 (m, 5H), 0.55-0.43 (m, 2H), 0.26-0.12 (m, 2H).
LC-MS: 2.10 min, ES (+), m/z: 377.170

Example 60

N-(cyclobutylmethyl)-N-methyl-5-(7H-pyrrolo[2,3-d]pyrimidin-4-yl)-5,8-diazaspiro[2.5]octane-8-sulfonamide

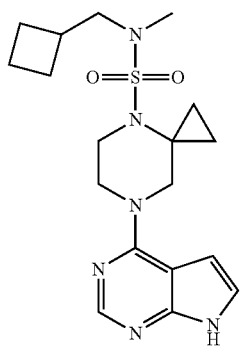 [SMILES: CN(CC1CCC1)S(=O)(=O)N1CCN(c2ncnc3[nH]ccc23)CC12CC2]

1H NMR (300 MHz, DMSO) δ 11.72 (s, 1H), 8.14 (s, 1H), 7.19 (dd, J=3.6, 2.2 Hz, 1H), 6.59 (dd, J=3.7, 1.7 Hz, 1H), 4.15-3.96 (m, 2H), 3.84 (s, 2H), 3.53 (dd, J=6.4, 4.0 Hz, 2H), 3.08 (d, J=7.4 Hz, 2H), 2.64 (s, 3H), 2.12-1.93 (m, 2H), 1.77 (m, 4H), 1.05-0.76 (m, 4H).
LC-MS: 2.24 min, ES (+), m/z: 391.193

Example 61

N-cyclopentyl-N-methyl-5-(7H-pyrrolo[2,3-d]pyrimidin-4-yl)-5,8-diazaspiro[2.5]octane-8-sulfonamide

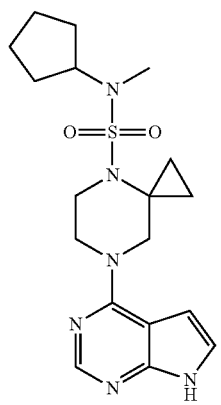

1H NMR (300 MHz, DMSO) δ 11.71 (s, 1H), 8.13 (s, 1H), 7.39-7.03 (m, 1H), 6.59 (dd, J=3.7, 1.8 Hz, 1H), 4.04 (t, J=5.2 Hz, 2H), 3.83 (s, 2H), 3.51 (dd, J=6.3, 4.0 Hz, 2H), 2.61 (s, 3H), 1.86-1.42 (m, 8H), 1.07-0.75 (m, 4H).

LC-MS: 2.21 min, ES (+), m/z: 391.190

Example 62

N-[(4,4-difluorocyclohexyl)methyl]-N-methyl-5-(7H-pyrrolo[2,3-d]pyrimidin-4-yl)-5,8-diazaspiro[2.5]octane-8-sulfonamide

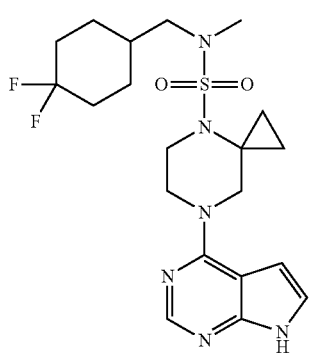

1H NMR (300 MHz, DMSO) δ 11.71 (s, 1H), 8.14 (s, 1H), 7.19 (dd, J=3.6, 2.3 Hz, 1H), 6.59 (dd, J=3.5, 1.7 Hz, 1H), 4.05 (dd, J=6.5, 3.8 Hz, 2H), 3.84 (s, 2H), 3.53 (dd, J=6.3, 3.9 Hz, 2H), 2.98 (d, J=6.9 Hz, 2H), 2.68 (s, 3H), 2.16-1.64 (m, 7H), 1.29-1.06 (m, 2H), 1.04-0.81 (m, 4H).

LC-MS: 2.24 min, ES (+), m/z: 455.199

Example 63

N-methyl-N-(2-phenylpropyl)-5-(7H-pyrrolo[2,3-d]pyrimidin-4-yl)-5,8-diazaspiro[2.5]octane-8-sulfonamide

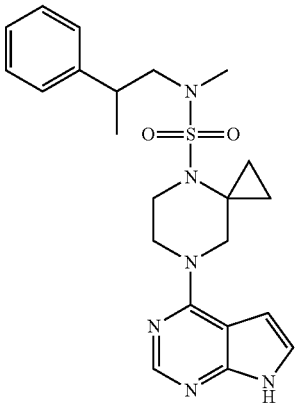 [SMILES: CC(CN(C)S(=O)(=O)N1CCN(c2ncnc3[nH]ccc23)CC12CC2)c1ccccc1]

LC-MS: 2.33 min, ES (+), m/z: 441.206

Example 64

N-methyl-5-(7H-pyrrolo[2,3-d]pyrimidin-4-yl)-N-(tetrahydropyran-2-ylmethyl)-5,8-diazaspiro[2.5]octane-8-sulfonamide

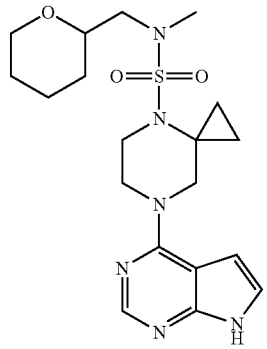 [SMILES: CN(CC1CCCCO1)S(=O)(=O)N1CCN(c2ncnc3[nH]ccc23)CC12CC2]

LC-MS: 2.11 min, ES (+), m/z: 421.194

Example 65

N-[[5-(dimethylsulfamoyl)-2-furyl]methyl]-N-methyl-5-(7H-pyrrolo[2,3-d]pyrimidin-4-yl)-5,8-diazaspiro[2.5]octane-8-sulfonamide

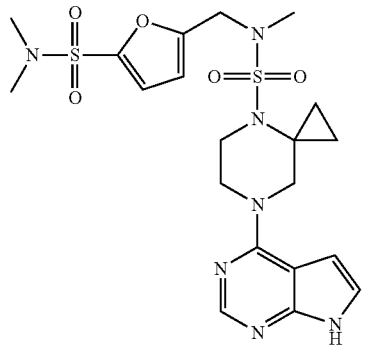 [SMILES: CN(C)S(=O)(=O)c1ccc(CN(C)S(=O)(=O)N2CCN(c3ncnc4[nH]ccc34)CC23CC3)o1]

1H NMR (300 MHz, DMSO) δ 11.72 (s, 1H), 8.14 (s, 1H), 7.19 (dd, J=3.6, 2.4 Hz, 1H), 7.16 (d, J=3.5 Hz, 1H), 6.66 (d, J=3.5 Hz, 1H), 6.59 (dd, J=3.5, 1.8 Hz, 1H), 4.38 (s, 2H), 4.09-3.99 (m, 2H), 3.85 (s, 2H), 3.57 (d, J=5.1 Hz, 2H), 2.73 (s, 6H), 2.70 (s, 3H), 1.14-0.77 (m, 4H).
LC-MS: 2.08 min, ES (+), m/z: 510.156

Example 66

N-methyl-N-(2-pyrazol-1-ylethyl)-5-(7H-pyrrolo[2,3-d]pyrimidin-4-yl)-5,8-diazaspiro[2.5]octane-8-sulfonamide

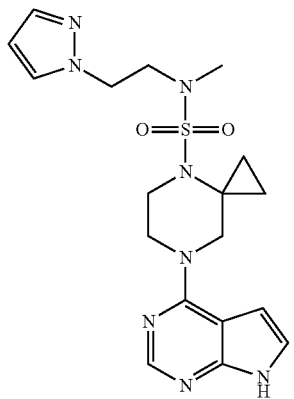 [SMILES: CN(CCn1cccn1)S(=O)(=O)N1CCN(c2ncnc3[nH]ccc23)CC12CC2]

1H NMR (300 MHz, DMSO) δ 11.72 (s, 1H), 8.13 (s, 1H), 7.74 (d, J=2.3 Hz, 1H), 7.47 (d, J=1.6 Hz, 1H), 7.19 (dd, J=3.7, 2.3 Hz, 1H), 6.57 (dd, J=3.7, 1.7 Hz, 1H), 6.25 (t, J=2.1 Hz, 1H), 4.29 (t, J=6.1 Hz, 2H), 4.07-3.94 (m, 2H), 3.81 (s, 2H), 3.47 (t, J=6.1 Hz, 3H), 3.41 (s, 3H), 2.58 (s, 3H), 1.10-0.75 (m, 4H).
LC-MS: 1.86 min, ES (+), m/z: 417.184

Example 67

N-methyl-N-[(3-methylisoxazol-5-yl)methyl]-5-(7H-pyrrolo[2,3-d]pyrimidin-4-yl)-5,8-diazaspiro[2.5]octane-8-sulfonamide

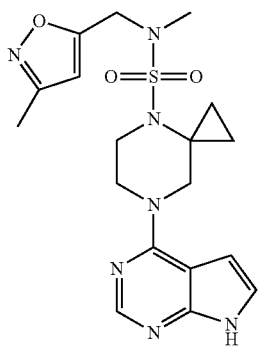 [SMILES: Cc1cc(CN(C)S(=O)(=O)N2CCN(c3ncnc4[nH]ccc34)CC23CC3)on1]

1H NMR (300 MHz, DMSO) δ 11.73 (s, 1H), 8.14 (s, 1H), 7.20 (dd, J=3.6, 2.3 Hz, 1H), 6.60 (dd, J=3.6, 1.7 Hz, 1H), 6.33 (s, 1H), 4.41 (s, 2H), 4.12-3.99 (m, 2H), 3.84 (s, 2H), 3.61-3.47 (m, 2H), 2.73 (s, 3H), 2.23 (s, 3H), 1.08-0.81 (m, 4H).
LC-MS: 1.96 min, ES (+), m/z: 418.145

Example 68

N-(isoxazol-5-ylmethyl)-N-methyl-5-(7H-pyrrolo[2,3-d]pyrimidin-4-yl)-5,8-diazaspiro[2.5]octane-8-sulfonamide

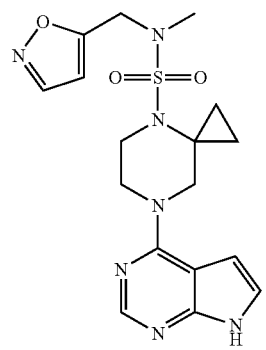

1H NMR (300 MHz, DMSO) δ 11.72 (s, 1H), 8.55 (d, J=1.9 Hz, 1H), 8.14 (s, 1H), 7.19 (dd, J=3.6, 2.4 Hz, 1H), 6.60 (dd, J=3.7, 1.8 Hz, 1H), 6.48 (d, J=1.8 Hz, 1H), 4.49 (s, 2H), 4.04 (d, J=5.2 Hz, 2H), 3.84 (s, 2H), 3.58-3.51 (m, 2H), 2.74 (s, 3H), 1.10-0.77 (m, 4H).
LC-MS: 1.91 min, ES (+), m/z: 404.146

Example 69

N-[2-(4-chlorophenoxy)ethyl]-N-methyl-5-(7H-pyrrolo[2,3-d]pyrimidin-4-yl)-5,8-diazaspiro[2.5]octane-8-sulfonamide

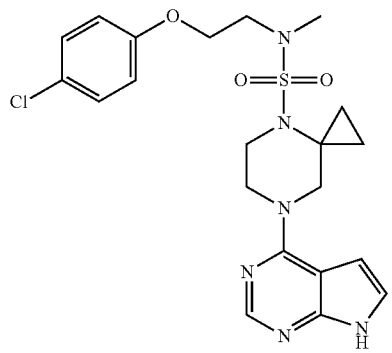 [SMILES: CN(CCOc1ccc(Cl)cc1)S(=O)(=O)N1CCN(c2ncnc3[nH]ccc23)CC12CC2]

1H NMR (300 MHz, DMSO) δ 11.73 (s, 1H), 8.14 (s, 1H), 7.49-7.27 (m, 2H), 7.19 (dd, J=3.6, 2.3 Hz, 1H), 7.08-6.86 (m, 2H), 6.59 (dd, J=3.5, 1.8 Hz, 1H), 4.12 (t, J=5.4 Hz, 2H), 4.03 (d, J=5.1 Hz, 2H), 3.84 (s, 2H), 3.57 (d, J=5.5 Hz, 2H), 3.45 (d, J=5.7 Hz, 2H), 2.80 (s, 3H), 1.12-0.77 (m, 4H).
LC-MS: 2.36 min, ES (+), m/z: 477.142

Example 70

N-[2-(2-cyanophenoxy)ethyl]-N-methyl-5-(7H-pyrrolo[2,3-d]pyrimidin-4-yl)-5,8-diazaspiro[2.5]octane-8-sulfonamide

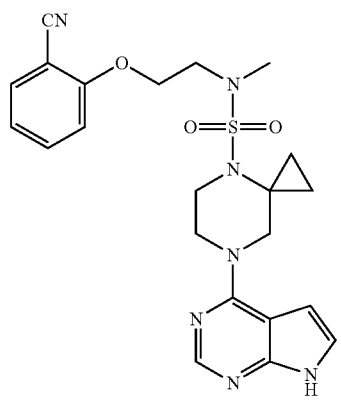 [SMILES: CN(CCOc1ccccc1C#N)S(=O)(=O)N1CCN(c2ncnc3[nH]ccc23)CC12CC2]

1H NMR (300 MHz, DMSO) δ 11.73 (s, 1H), 8.14 (s, 1H), 7.75 (dd, J=7.6, 1.7 Hz, 1H), 7.73-7.63 (m, 1H), 7.29 (d, J=8.5 Hz, 1H), 7.19 (dd, J=3.6, 2.2 Hz, 1H), 7.17-7.08 (m, 1H), 6.58 (dd, J=3.4, 1.9 Hz, 1H), 4.30 (t, J=5.1 Hz, 2H), 4.05 (t, J=5.1 Hz, 2H), 3.85 (s, 2H), 3.56 (d, J=5.0 Hz, 4H), 2.89 (s, 3H), 1.19-0.77 (m, 4H).

LC-MS: 2.15 min, ES (+), m/z: 468.179

Example 71

N-[2-(3-cyanophenoxy)ethyl]-N-methyl-5-(7H-pyrrolo[2,3-d]pyrimidin-4-yl)-5,8-diazaspiro[2.5]octane-8-sulfonamide

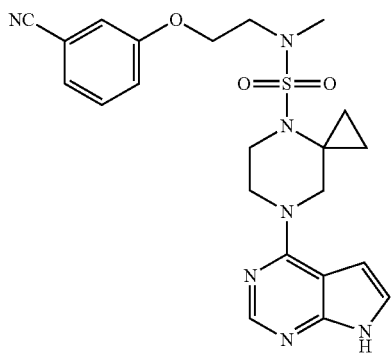 [SMILES: CN(CCOc1cccc(C#N)c1)S(=O)(=O)N1CCN(c2ncnc3[nH]ccc23)CC12CC2]

1H NMR (300 MHz, DMSO) δ 11.72 (s, 1H), 8.14 (s, 1H), 7.56-7.45 (m, 2H), 7.42 (dt, J=7.3, 1.2 Hz, 1H), 7.32 (ddd, J=8.4, 2.6, 1.2 Hz, 1H), 7.19 (dd, J=3.5, 2.1 Hz, 1H), 6.59 (dd, J=3.6, 1.6 Hz, 1H), 4.20 (t, J=5.4 Hz, 2H), 4.05 (t, J=5.1 Hz, 2H), 3.85 (s, 2H), 3.56 (dd, J=6.2, 3.8 Hz, 2H), 3.48 (t, J=5.4 Hz, 2H), 2.81 (s, 3H), 1.10-0.81 (m, 4H).

LC-MS: 2.18 min, ES (+), m/z: 468.186

Example 72

N-[2-(4-cyanophenoxy)ethyl]-N-methyl-5-(7H-pyrrolo[2,3-d]pyrimidin-4-yl)-5,8-diazaspiro[2.5]octane-8-sulfonamide

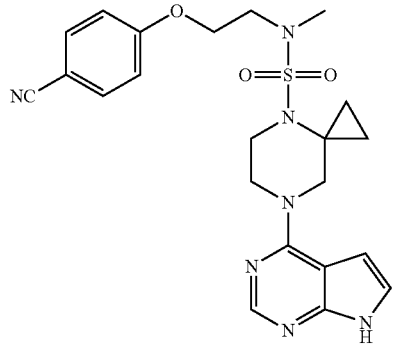

1H NMR (300 MHz, DMSO) δ 11.73 (s, 1H), 8.15 (s, 1H), 7.90-7.63 (m, 2H), 7.20 (dd, J=3.6, 2.2 Hz, 1H), 7.18-7.11 (m, 2H), 6.59 (dd, J=3.7, 1.7 Hz, 1H), 4.23 (t, J=5.2 Hz, 2H), 4.05 (dd, J=6.3, 3.8 Hz, 2H), 3.85 (s, 2H), 3.56 (dd, J=6.2, 3.9 Hz, 2H), 3.50 (t, J=5.4 Hz, 2H), 2.81 (s, 3H), 1.15-0.78 (m, 4H).

LC-MS: 2.15 min, ES (+), m/z: 468.172

Example 73

N-(cyclopentylmethyl)-N-methyl-5-(7H-pyrrolo[2,3-d]pyrimidin-4-yl)-5,8-diazaspiro[2.5]octane-8-sulfonamide

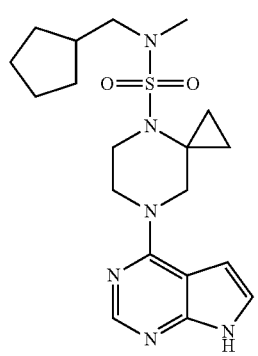 [SMILES: CN(CC1CCCC1)S(=O)(=O)N1CCN(c2ncnc3[nH]ccc23)CC12CC2]

1H NMR (300 MHz, DMSO) δ 11.72 (s, 1H), 8.13 (s, 1H), 7.19 (dd, J=3.6, 2.3 Hz, 1H), 6.59 (dd, J=3.7, 1.8 Hz, 1H), 4.04 (dd, J=6.3, 3.9 Hz, 2H), 3.83 (s, 2H), 3.52 (dd, J=6.3, 3.9 Hz, 2H), 2.96 (d, J=7.6 Hz, 2H), 2.68 (s, 3H), 2.13 (h, J=7.5 Hz, 1H), 1.75-1.40 (m, 6H), 1.29-1.11 (m, 2H), 1.06-0.80 (m, 4H).

LC-MS: 2.33 min, ES (+), m/z: 405.184

Example 74

N-(2-cyclopentylethyl)-N-methyl-5-(7H-pyrrolo[2,3-d]pyrimidin-4-yl)-5,8-diazaspiro[2.5]octane-8-sulfonamide

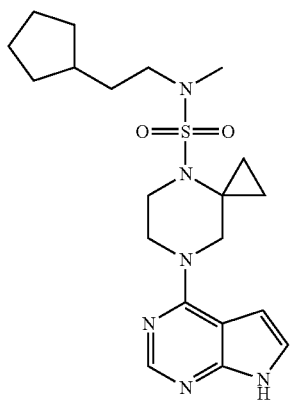 [SMILES: CN(CCC1CCCC1)S(=O)(=O)N1CCN(c2ncnc3[nH]ccc23)CC12CC2]

1H NMR (300 MHz, DMSO) δ 11.73 (s, 1H), 8.14 (s, 1H), 7.19 (dd, J=3.7, 2.1 Hz, 1H), 6.60 (dd, J=3.7, 1.5 Hz, 1H), 4.05 (dd, J=6.1, 3.8 Hz, 2H), 3.84 (s, 2H), 3.53 (dd, J=6.4, 3.9 Hz, 2H), 3.11-2.97 (m, 2H), 2.68 (s, 3H), 1.82-1.62 (m, 3H), 1.63-1.41 (m, 6H), 1.07 (m, 2H), 1.02-0.83 (m, 4H).

LC-MS: 2.45 min, ES (+), m/z: 419.191

Example 75

N-[2-(1,1-dioxothiolan-3-yl)ethyl]-N-methyl-5-(7H-pyrrolo[2,3-d]pyrimidin-4-yl)-5,8-diazaspiro[2.5]octane-8-sulfonamide

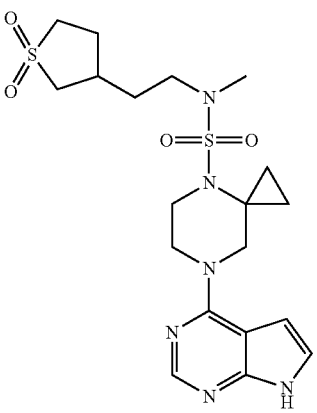 [SMILES: CN(CCC1CCS(=O)(=O)C1)S(=O)(=O)N1CCN(c2ncnc3[nH]ccc23)CC12CC2]

1H NMR (300 MHz, DMSO) δ 11.72 (s, 1H), 8.14 (s, 1H), 7.19 (dd, J=3.6, 2.2 Hz, 1H), 6.59 (dd, J=3.7, 1.7 Hz, 1H), 4.05 (t, J=5.1 Hz, 2H), 3.84 (s, 2H), 3.54 (dd, J=6.4, 3.9 Hz, 2H), 3.40-2.94 (m, 6H), 2.69 (s, 3H), 2.30 (dq, J=9.0, 5.5, 4.4 Hz, 2H), 1.82-1.58 (m, 3H), 1.10-0.76 (m, 4H).

LC-MS: 1.85 min, ES (+), m/z: 469.169

Example 76

N-[(1,1-dioxothian-3-yl)methyl]-N-methyl-5-(7H-pyrrolo[2,3-d]pyrimidin-4-yl)-5,8-diazaspiro[2.5]octane-8-sulfonamide

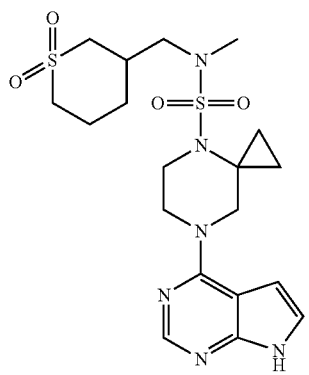 [SMILES: CN(CC1CCCS(=O)(=O)C1)S(=O)(=O)N1CCN(c2ncnc3[nH]ccc23)CC12CC2]

1H NMR (300 MHz, DMSO) δ 11.72 (s, 1H), 8.14 (s, 1H), 7.19 (dd, J=3.7, 2.3 Hz, 1H), 6.60 (dd, J=3.6, 1.7 Hz, 1H), 4.05 (t, J=5.1 Hz, 2H), 3.84 (s, 2H), 3.53 (t, J=5.1 Hz, 2H), 3.17-2.86 (m, 6H), 2.69 (s, 3H), 2.22 (m, 1H), 2.12-1.99 (m, 1H), 1.89-1.68 (m, 2H), 1.22 (qd, J=13.3, 3.5 Hz, 1H), 1.07-0.82 (m, 4H).

LC-MS: 1.83 min, ES (+), m/z: 469.138

Example 77

N-[(2-fluorophenyl)methyl]-N-methyl-5-(7H-pyrrolo[2,3-d]pyrimidin-4-yl)-5,8-diazaspiro[2.5]octane-8-sulfonamide

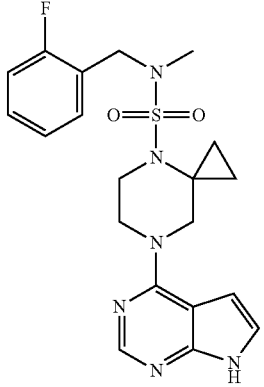 [SMILES: CN(Cc1ccccc1F)S(=O)(=O)N1CCN(c2ncnc3[nH]ccc23)CC12CC2]

1H NMR (300 MHz, DMSO) δ 11.73 (s, 1H), 8.14 (s, 1H), 7.50-7.31 (m, 2H), 7.31-7.13 (m, 3H), 6.60 (dd, J=3.7, 1.7 Hz, 1H), 4.33 (s, 2H), 4.06 (dd, J=6.4, 3.9 Hz, 2H), 3.86 (s, 2H), 3.56 (dd, J=6.2, 3.9 Hz, 2H), 2.64 (s, 3H), 1.06-0.81 (m, 4H).

LC-MS: 2.24 min, ES (+), m/z: 431.166

Example 78

N-[(3-fluorophenyl)methyl]-N-methyl-5-(7H-pyrrolo[2,3-d]pyrimidin-4-yl)-5,8-diazaspiro[2.5]octane-8-sulfonamide

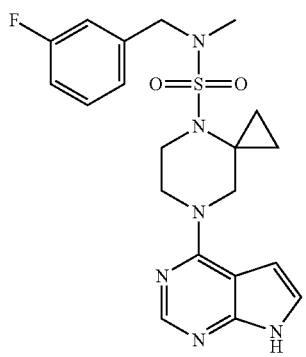 [SMILES: CN(Cc1cccc(F)c1)S(=O)(=O)N1CCN(c2ncnc3[nH]ccc23)CC12CC2]

1H NMR (300 MHz, DMSO) δ 11.73 (s, 1H), 8.15 (s, 1H), 7.44 (ddd, J=9.0, 7.5, 6.0 Hz, 1H), 7.31-7.01 (m, 4H), 6.61 (dd, J=3.8, 1.8 Hz, 1H), 4.30 (s, 2H), 4.08 (t, J=5.1 Hz, 2H), 3.87 (s, 2H), 3.59 (dd, J=6.5, 4.0 Hz, 2H), 2.63 (s, 3H), 1.11-0.82 (m, 4H).

LC-MS: 2.25 min, ES (+), m/z: 431.162

Example 79

N-[(4-fluorophenyl)methyl]-N-methyl-5-(7H-pyrrolo[2,3-d]pyrimidin-4-yl)-5,8-diazaspiro[2.5]octane-8-sulfonamide

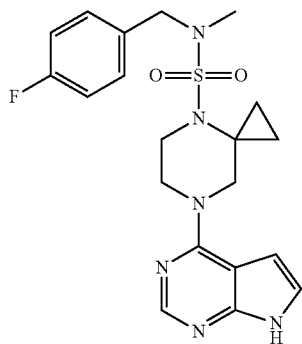 [SMILES: CN(Cc1ccc(F)cc1)S(=O)(=O)N1CCN(c2ncnc3[nH]ccc23)CC12CC2]

1H NMR (300 MHz, DMSO) δ 11.73 (s, 1H), 8.15 (s, 1H), 7.37 (dd, J=8.6, 5.6 Hz, 2H), 7.28-7.11 (m, 3H), 6.61 (dd, J=3.7, 1.7 Hz, 1H), 4.26 (s, 2H), 4.07 (dd, J=6.5, 3.8 Hz, 2H), 3.87 (s, 2H), 3.59 (dd, J=6.3, 3.9 Hz, 2H), 2.59 (s, 3H), 1.09-0.85 (m, 4H).

LC-MS: 2.24 min, ES (+), m/z: 431.163

Example 80

N-methyl-5-(7H-pyrrolo[2,3-d]pyrimidin-4-yl)-N-[[4-(trifluoromethoxy)phenyl]methyl]-5,8-diazaspiro[2.5]octane-8-sulfonamide

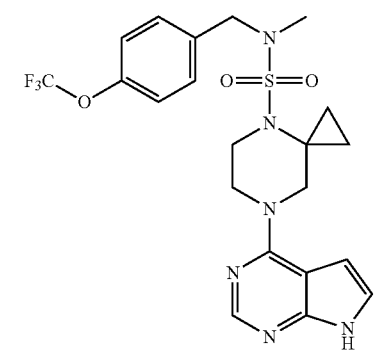

1H NMR (300 MHz, DMSO) δ 11.73 (s, 1H), 8.15 (s, 1H), 7.46 (d, J=8.7 Hz, 2H), 7.38 (d, J=8.3 Hz, 2H), 7.20 (dd, J=3.6, 2.3 Hz, 1H), 6.60 (dd, J=3.7, 1.8 Hz, 1H), 4.31 (s, 2H), 4.08 (t, J=5.1 Hz, 2H), 3.87 (s, 2H), 3.59 (dd, J=6.3, 3.9 Hz, 2H), 2.62 (s, 3H), 1.11-0.83 (m, 4H).

LC-MS: 2.42 min, ES (+), m/z: 497.153

Example 81

N-methyl-5-(7H-pyrrolo[2,3-d]pyrimidin-4-yl)-N-[[4-(trifluoromethyl)phenyl]methyl]-5,8-diazaspiro[2.5]octane-8-sulfonamide

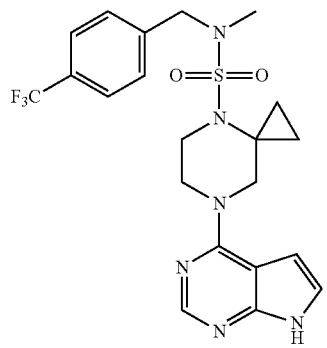 [SMILES: CN(Cc1ccc(C(F)(F)F)cc1)S(=O)(=O)N1CCN(c2ncnc3[nH]ccc23)CC12CC2]

1H NMR (300 MHz, DMSO) δ 11.73 (s, 1H), 8.15 (s, 1H), 7.76 (d, J=8.0 Hz, 2H), 7.56 (d, J=8.0 Hz, 2H), 7.20 (dd, J=3.6, 2.3 Hz, 1H), 6.61 (dd, J=3.5, 1.7 Hz, 1H), 4.39 (s, 2H), 4.08 (dd, J=6.4, 3.8 Hz, 2H), 3.88 (s, 2H), 3.60 (dd, J=6.2, 3.9 Hz, 2H), 2.64 (s, 3H), 1.10-0.86 (m, 4H).

LC-MS: 2.38 min, ES (+), m/z: 481.159

Example 82

N-(2-cyclopropylethyl)-N-methyl-5-(7H-pyrrolo[2,3-d]pyrimidin-4-yl)-5,8-diazaspiro[2.5]octane-8-sulfonamide

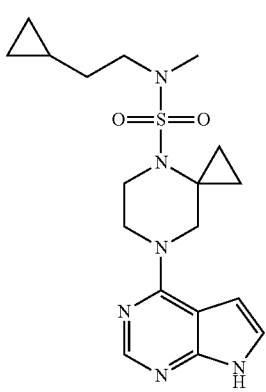 [SMILES: CN(CCC1CC1)S(=O)(=O)N1CCN(c2ncnc3[nH]ccc23)CC12CC2]

1H NMR (300 MHz, DMSO) δ 11.71 (s, 1H), 8.13 (s, 1H), 7.19 (dd, J=3.5, 2.3 Hz, 1H), 6.59 (dd, J=3.7, 1.8 Hz, 1H), 4.04 (t, J=5.3 Hz, 2H), 3.84 (s, 2H), 3.58-3.41 (m, 2H), 3.18-3.06 (m, 2H), 2.69 (s, 3H), 1.48-1.34 (m, 2H), 1.05-0.81 (m, 4H), 0.70-0.56 (m, 1H), 0.47-0.35 (m, 2H), 0.09-0.02 (m, 2H).

LC-MS: 2.21 min, ES (+), m/z: 391.185

Example 83

N-methyl-N-[(4-methylsulfonylphenyl)methyl]-5-(7H-pyrrolo[2,3-d]pyrimidin-4-yl)-5,8-diazaspiro[2.5]octane-8-sulfonamide

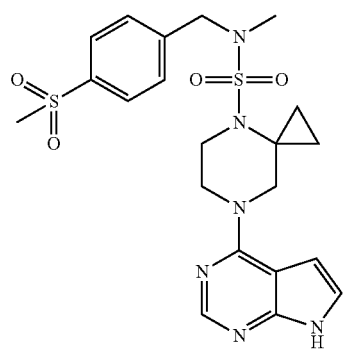 [SMILES: CN(Cc1ccc(S(C)(=O)=O)cc1)S(=O)(=O)N1CCN(c2ncnc3[nH]ccc23)CC12CC2]

1H NMR (300 MHz, DMSO) δ 11.73 (s, 1H), 8.15 (s, 1H), 7.99-7.89 (m, 2H), 7.60 (d, J=8.1 Hz, 2H), 7.20 (d, J=3.6 Hz, 1H), 6.61 (d, J=3.7 Hz, 1H), 4.41 (s, 2H), 4.09 (d, J=5.5 Hz, 2H), 3.87 (s, 2H), 3.60 (t, J=5.1 Hz, 2H), 3.22 (s, 3H), 2.66 (s, 3H), 1.10-0.88 (m, 4H).

LC-MS: 1.98 min, ES (+), m/z: 491.153

Example 84

N-[(4-tert-butylcyclohexyl)methyl]-N-methyl-5-(7H-pyrrolo[2,3-d]pyrimidin-4-yl)-5,8-diazaspiro[2.5]octane-8-sulfonamide

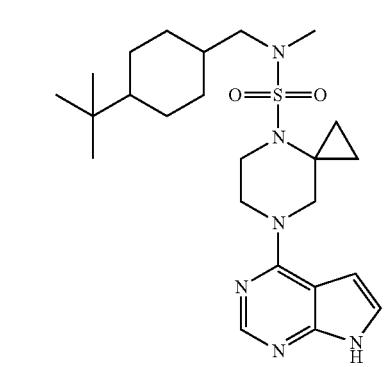

1H NMR (300 MHz, DMSO) δ 11.71 (s, 1H), 8.13 (s, 1H), 7.18 (dd, J=3.6, 2.4 Hz, 1H), 6.59 (dd, J=3.6, 1.7 Hz, 1H), 4.04 (t, J=5.2 Hz, 2H), 3.83 (s, 2H), 3.61-3.44 (m, 2H), 2.87 (d, J=7.2 Hz, 2H), 2.65 (s, 3H), 1.76 (d, J=9.4 Hz, 4H), 1.54-1.40 (m, 1H), 1.14-0.68 (m, 18H).

LC-MS: 2.83 min, ES (+), m/z: 475.286

Example 85

N-[(3,3-difluorocyclobutyl)methyl]-N-methyl-5-(7H-pyrrolo[2,3-d]pyrimidin-4-yl)-5,8-diazaspiro[2.5]octane-8-sulfonamide

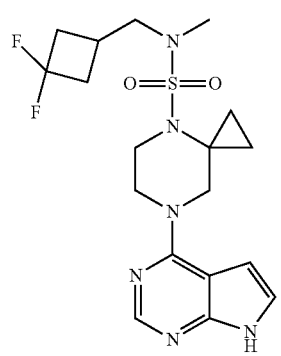 [SMILES: CN(CC1CC(F)(F)C1)S(=O)(=O)N1CCN(c2ncnc3[nH]ccc23)CC12CC2]

1H NMR (300 MHz, DMSO) δ 11.75-11.69 (m, 1H), 8.14 (s, 1H), 7.19 (dd, J=3.6, 2.3 Hz, 1H), 6.59 (dd, J=3.5, 1.7 Hz, 1H), 4.05 (dd, J=6.5, 3.9 Hz, 2H), 3.84 (s, 2H), 3.53 (dd, J=6.3, 3.9 Hz, 2H), 3.20 (d, J=6.7 Hz, 2H), 2.69 (m, 5H), 2.50-2.21 (m, 3H), 1.04-0.82 (m, 4H).

LC-MS: 2.14 min, ES (+), m/z: 427.168

Example 86

N-[(2,2-difluorocyclopropyl)methyl]-N-methyl-5-(7H-pyrrolo[2,3-d]pyrimidin-4-yl)-5,8-diazaspiro[2.5]octane-8-sulfonamide

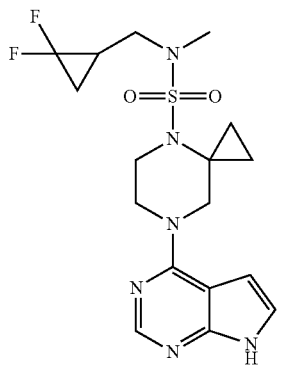 [SMILES: CN(CC1CC1(F)F)S(=O)(=O)N1CCN(c2ncnc3[nH]ccc23)CC12CC2]

1H NMR (300 MHz, DMSO) δ 11.72 (s, 1H), 8.14 (s, 1H), 7.19 (dd, J=3.4, 1.5 Hz, 1H), 6.59 (d, J=3.5 Hz, 1H), 4.04 (dd, J=6.7, 3.7 Hz, 2H), 3.84 (s, 2H), 3.55 (dd, J=6.3, 4.1 Hz, 2H), 3.09 (ddd, J=14.5, 7.7, 1.4 Hz, 1H), 2.74 (s, 3H), 2.08-1.86 (m, 1H), 1.66 (tdd, J=12.2, 7.8, 4.8 Hz, 1H), 1.30 (dtd, J=13.7, 7.7, 3.9 Hz, 1H), 1.07-0.82 (m, 4H).

LC-MS: 2.10 min, ES (+), m/z: 413.151

Example 87

N-methyl-N-[(4-methylenecyclohexyl)methyl]-5-(7H-pyrrolo[2,3-d]pyrimidin-4-yl)-5,8-diazaspiro[2.5]octane-8-sulfonamide

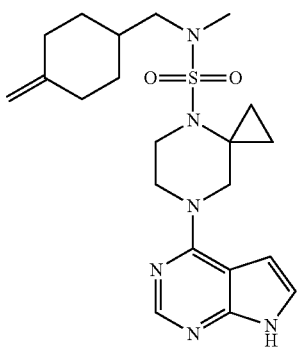 [SMILES: C=C1CCC(CN(C)S(=O)(=O)N2CCN(c3ncnc4[nH]ccc34)CC23CC3)CC1]

1H NMR (300 MHz, DMSO) δ 11.73 (s, 1H), 8.13 (s, 1H), 7.19 (dd, J=3.7, 2.1 Hz, 1H), 6.59 (dd, J=3.7, 1.5 Hz, 1H), 4.61 (t, J=1.6 Hz, 2H), 4.04 (dd, J=6.3, 3.8 Hz, 2H), 3.83 (s, 2H), 3.52 (dd, J=6.2, 3.9 Hz, 2H), 2.93 (d, J=6.8 Hz, 2H), 2.68 (s, 3H), 2.26 (dt, J=13.4, 3.6 Hz, 2H), 1.99 (td, J=13.3, 12.7, 3.8 Hz, 2H), 1.76 (ddq, J=13.4, 10.2, 3.5 Hz, 3H), 1.05-0.80 (m, 6H).

LC-MS: 2.42 min, ES (+), m/z: 431.226

Example 88

N-methyl-N-[(3-oxocyclobutyl)methyl]-5-(7H-pyrrolo[2,3-d]pyrimidin-4-yl)-5,8-diazaspiro[2.5]octane-8-sulfonamide

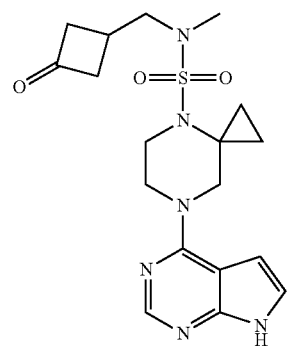 [SMILES: CN(CC1CC(=O)C1)S(=O)(=O)N1CCN(c2ncnc3[nH]ccc23)CC12CC2]

LC-MS: 2.13 min, ES (+), m/z: 405.169

Example 89

N-methyl-5-(7H-pyrrolo[2,3-d]pyrimidin-4-yl)-N-(tetrahydropyran-4-ylmethyl)-5,8-diazaspiro[2.5]octane-8-sulfonamide

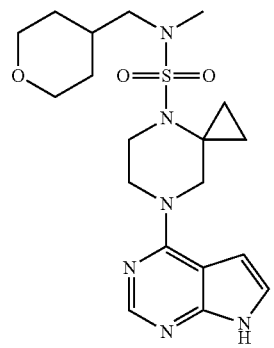 [SMILES: CN(CC1CCOCC1)S(=O)(=O)N1CCN(c2ncnc3[nH]ccc23)CC12CC2]

1H NMR (300 MHz, DMSO) δ 11.72 (s, 1H), 8.14 (s, 1H), 7.19 (dd, J=3.7, 2.2 Hz, 1H), 6.59 (dd, J=3.6, 1.6 Hz, 1H), 4.05 (dd, J=6.2, 3.8 Hz, 2H), 3.91-3.75 (m, 4H), 3.53 (dd, J=6.1, 3.9 Hz, 2H), 3.31-3.19 (m, 2H), 2.95 (d, J=7.2 Hz, 2H), 2.68 (s, 3H), 1.81 (ddh, J=15.1, 7.6, 3.7 Hz, 1H), 1.55 (ddd, J=12.6, 3.7, 1.9 Hz, 2H), 1.24-1.04 (m, 2H), 1.03-0.79 (m, 4H).

LC-MS: 1.94 min, ES (+), m/z: 421.195

Example 90

N-methyl-5-(7H-pyrrolo[2,3-d]pyrimidin-4-yl)-N-[(3-sulfamoylphenyl)methyl]-5,8-diazaspiro[2.5]octane-8-sulfonamide

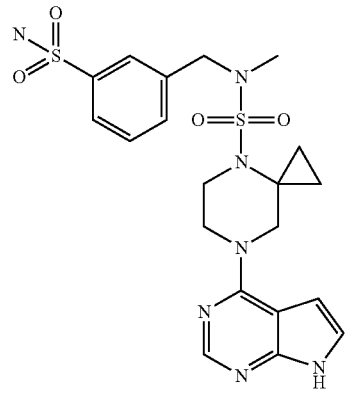 [SMILES: CN(Cc1cccc(S(N)(=O)=O)c1)S(=O)(=O)N1CCN(c2ncnc3[nH]ccc23)CC12CC2]

1H NMR (300 MHz, DMSO) δ 11.72 (s, 1H), 8.14 (s, 1H), 7.85-7.72 (m, 2H), 7.66-7.49 (m, 2H), 7.20 (d, J=3.5 Hz, 1H), 6.60 (d, J=3.6 Hz, 1H), 4.36 (s, 2H), 4.08 (t, J=5.1 Hz, 2H), 3.87 (s, 2H), 3.59 (t, J=5.1 Hz, 2H), 2.65 (s, 3H), 1.18-0.79 (m, 4H).

LC-MS: 1.91 min, ES (+), m/z: 492.142

Example 91

N-methyl-5-(7H-pyrrolo[2,3-d]pyrimidin-4-yl)-N-[(4-sulfamoylphenyl)methyl]-5,8-diazaspiro[2.5]octane-8-sulfonamide

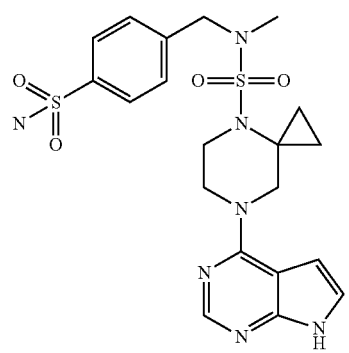 [SMILES: CN(Cc1ccc(S(N)(=O)=O)cc1)S(=O)(=O)N1CCN(c2ncnc3[nH]ccc23)CC12CC2]

1H NMR (300 MHz, DMSO) δ 11.73 (s, 1H), 8.14 (s, 1H), 7.88-7.78 (m, 2H), 7.51 (d, J=8.1 Hz, 2H), 7.35 (s, 2H), 7.24-7.15 (m, 1H), 6.65-6.56 (m, 1H), 4.36 (s, 2H), 4.08 (t, J=5.2 Hz, 2H), 3.87 (s, 2H), 3.60 (t, J=5.1 Hz, 2H), 2.63 (s, 3H), 1.09-0.82 (m, 4H).

LC-MS: 1.89 min, ES (+), m/z: 492.153

Example 92

N-[[1-(difluoromethyl)-3H-pyrazol-3-yl]methyl]-N-methyl-5-(7H-pyrrolo[2,3-d]pyrimidin-4-yl)-5,8-diazaspiro[2.5]octane-8-sulfonamide

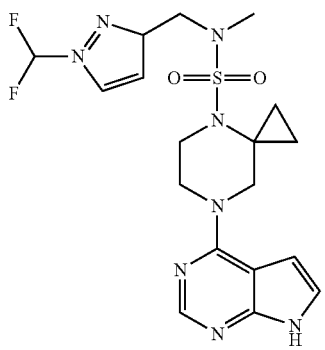

1H NMR (300 MHz, DMSO) δ 11.73 (s, 1H), 8.21 (d, J=2.7 Hz, 1H), 8.14 (s, 1H), 7.78 (t, J=59.1 Hz, 1H), 7.19 (dd, J=3.7, 2.3 Hz, 1H), 6.60 (dd, J=3.6, 1.7 Hz, 1H), 6.48 (d, J=2.7 Hz, 1H), 4.28 (s, 2H), 4.06 (dd, J=6.4, 3.8 Hz, 2H), 3.86 (s, 2H), 3.57 (m, 2H), 2.68 (s, 3H), 1.08-0.80 (m, 4H).

LC-MS: 2.02 min, ES (+), m/z: 453.159

Example 93

N-[[1-(2,2-difluoroethyl)-3H-pyrazol-3-yl]methyl]-N-methyl-5-(7H-pyrrolo[2,3-d]pyrimidin-4-yl)-5,8-diazaspiro[2.5]octane-8-sulfonamide

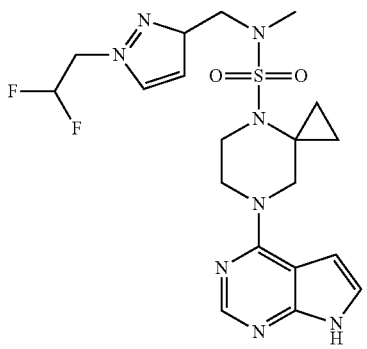

1H NMR (300 MHz, DMSO) δ 11.72 (s, 1H), 8.14 (s, 1H), 7.75 (d, J=2.2 Hz, 1H), 7.19 (dd, J=3.6, 2.4 Hz, 1H), 6.59 (dd, J=3.7, 1.8 Hz, 1H), 6.32 (tt, J=55.0, 3.8 Hz, 1H), 6.27 (d, J=2.3 Hz, 1H), 4.59 (td, J=15.1, 3.8 Hz, 2H), 4.19 (s, 2H), 4.05 (t, J=5.1 Hz, 2H), 3.85 (s, 2H), 3.61-3.48 (m, 2H), 2.64 (s, 3H), 1.12-0.78 (m, 4H).

LC-MS: 1.97 min, ES (+), m/z: 467.165

Example 177

N-[(4-cyanocuban-1-yl)methyl]-N-methyl-5-(7H-pyrrolo[2,3-d]pyrimidin-4-yl)-5,8-diazaspiro[2.5]octane-8-sulfonamide

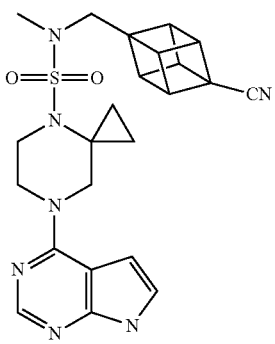 [SMILES: CN(CC12C3C4C1C1C2C3C41C#N)S(=O)(=O)N1CCN(c2ncnc3[nH]ccc23)CC12CC2]

1H NMR (300 MHz, DMSO) δ 11.72 (s, 1H), 8.14 (s, 1H), 7.19 (dd, J=3.6, 2.3 Hz, 1H), 6.59 (dd, J=3.7, 1.7 Hz, 1H), 4.31-4.17 (m, 3H), 4.04 (t, J=5.2 Hz, 2H), 3.98 (dd, J=5.8, 4.0 Hz, 3H), 3.84 (s, 2H), 3.53 (dd, J=6.4, 3.9 Hz, 2H), 3.34 (s, 2H), 2.69 (s, 3H), 1.07-0.76 (m, 4H).

LC-MS: 2.12 min, ES (+), m/z: 464.180

Example 183

N-methyl-N-[[(2S)-5-oxopyrrolidin-2-yl]methyl]-5-(7H-pyrrolo[2,3-d]pyrimidin-4-yl)-5,8-diazaspiro[2.5]octane-8-sulfonamide

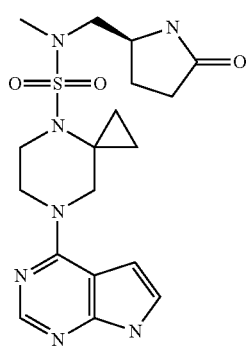

1H NMR (300 MHz, DMSO) δ 11.71 (s, 1H), 8.13 (s, 1H), 7.66 (s, 1H), 7.19 (dd, J=3.7, 2.2 Hz, 1H), 6.59 (dd, J=3.6, 1.7 Hz, 1H), 4.05 (t, J=5.1 Hz, 2H), 3.84 (s, 2H), 3.77-3.67 (m, 1H), 3.54 (t, J=5.1 Hz, 2H), 3.16-2.96 (m, 2H), 2.74 (s, 3H), 2.18-2.03 (m, 3H), 1.82-1.67 (m, 1H), 1.01-0.85 (m, 4H).

LC-MS: 1.70 min, ES (+), m/z: 420.181

Example 184

N-methyl-N-[[(2R)-5-oxopyrrolidin-2-yl]methyl]-5-(7H-pyrrolo[2,3-d]pyrimidin-4-yl)-5,8-diazaspiro[2.5]octane-8-sulfonamide 1H NMR (300 MHz, DMSO) δ 11.71 (s, 1H), 8.13 (s, 1H), 7.66 (s, 1H), 7.19 (dd, J=3.7, 2.3 Hz, 1H), 6.59 (dd, J=3.7, 1.8 Hz, 1H), 4.05 (t, J=5.2 Hz, 2H), 3.84 (s, 2H), 3.77-3.68 (m, 1H), 3.54 (t, J=5.0 Hz, 2H), 3.15-2.97 (m, 2H), 2.74 (s, 3H), 2.22-2.04 (m, 3H), 1.80-1.70 (m, 1H), 1.04-0.82 (m, 4H).

LC-MS: 1.70 min, ES (+), m/z: 420.182

Example 37

7-(7H-Pyrrolo[2,3-d]pyrimidin-4-yl)-4,7-diaza-spiro[2.5]octane-4-sulfonic acid (4-cyano-benzyl)-methyl-amide

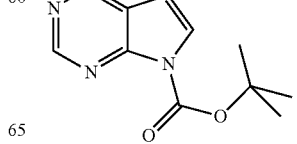

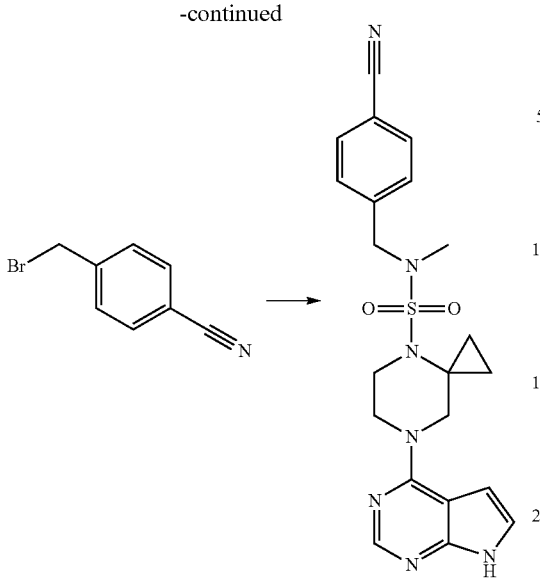

4-(4-Methylsulfamoyl-4,7-diaza-spiro[2.5]oct-7-yl)-pyrrolo[2,3-d]pyrimidine-7-carboxylic acid tert-butyl ester (intermediate 4) (0.237 mmol) was dissolved in dry DMF (2 mL) and added Cs₂CO₃ (0.35 mmol) and 4-bromomethyl-benzonitrile (0.35 mmol). Stirred at rt for 16 h and then added H₂O (10 mL). Extracted with EtOAc (3×10 mL) and the combined organic phases were concentrated in vacuo. Purified by flash chromatography on silica using a gradient of heptane to EtOAc as eluent. The obtained compound was treated with TFA (2 mL) at rt for 2 h. The crude reaction mixture was added sat. Na₂CO₃ to pH=7 and the extracted with EtOAc (3×10 mL). the combined organic phases was washes with brine (10 mL), dried (Na₂SO₄), filtered and concentrated in vacuo. The pure compound was obtained by trituation using CH₂Cl₂.

1H NMR (600 MHz, DMSO) δ 11.75 (s, 1H), 8.14 (s, 1H), 7.87 (d, J=8.3 Hz, 2H), 7.53 (d, J=8.3 Hz, 2H), 7.20 (dd, J=3.4, 2.6 Hz, 1H), 6.61 (dd, J=3.6, 1.9 Hz, 1H), 4.39 (s, 2H), 4.07 (s, 2H), 3.87 (s, 2H), 3.64-3.53 (m, 2H), 2.64 (s, 3H), 1.03 (t, J=5.7 Hz, 2H), 0.91 (q, J=5.4 Hz, 2H).

Example 38

4-[4-(Piperidine-1-sulfonyl)-4,7-diaza-spiro[2.5]oct-7-yl]-7H-pyrrolo[2,3-d]pyrimidine

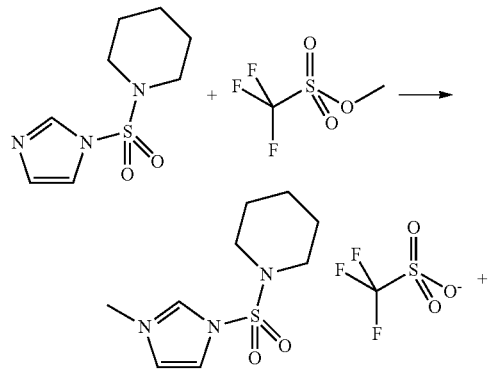

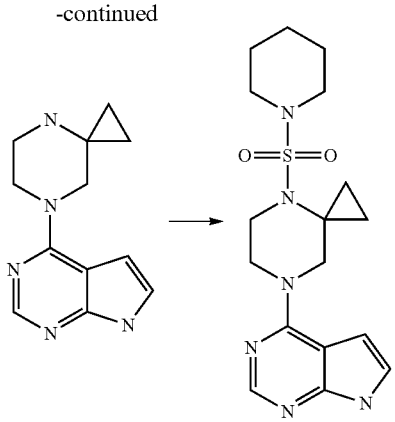

A solution of 1-(imidazole-1-sulfonyl)-piperidine (intermediate 13) (0.047 mmol) in dry CH₂Cl₂ (1 mL) was cooled to 0° C. and added trifluoro-methanesulfonic acid methyl ester (0.047 mmol). The reaction mixture was allowed to warm up freely to rt over a period of 4 h and then concentrated in vacuo. The residual oil was redissolved in dry CH₃CN (1.5 mL), added a solution of 4-(4,7-diaza-spiro[2.5]oct-7-yl)-7H-pyrrolo[2,3-d]pyrimidine (intermediate 21) (0.047 mmol) in DMSO (1 mL) and then stirred at 50° C. for 3 h. The pure compound was obtained by standard preparative HPLC purification of the reaction mixture.

1H NMR (300 MHz, DMSO) δ 11.71 (s, 1H), 8.13 (d, J=1.4 Hz, 1H), 7.28-7.13 (m, 1H), 6.59 (dd, J=3.7, 1.9 Hz, 1H), 4.09-3.97 (m, 2H), 3.82 (s, 2H), 3.59-3.50 (m, 2H), 3.01 (d, J=5.2 Hz, 4H), 1.65-1.41 (m, 6H), 1.03 (t, J=5.9 Hz, 2H), 0.86 (t, J=6.1 Hz, 2H).

Using this procedure the following compounds were obtained:

Example 39

1-[7-(7H-Pyrrolo[2,3-d]pyrimidin-4-yl)-4,7-diaza-spiro[2.5]octane-4-sulfonyl]-piperidine-4-carbonitrile

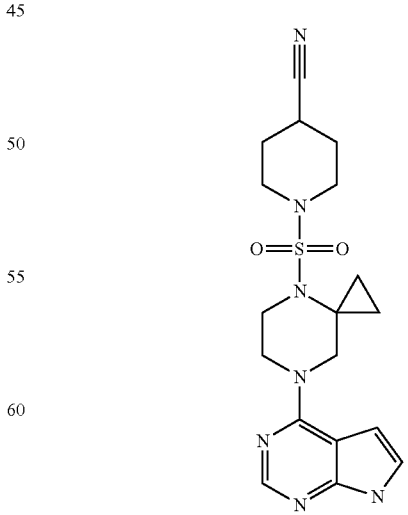

1H NMR (300 MHz, DMSO) δ 11.75 (s, 1H), 8.14 (s, 1H), 7.20 (dd, J=3.5, 2.6 Hz, 1H), 6.60 (dd, J=3.6, 1.8 Hz, 1H), 4.20-3.92 (m, 2H), 3.82 (s, 2H), 3.62-3.48 (m, 2H), 3.23 (m, 3H), 2.99 (m, 2H), 1.93 (m, 2H), 1.82-1.64 (m, 2H), 1.04 (t, J=6.0 Hz, 2H), 0.88 (t, J=6.2 Hz, 2H).

Example 40

7-(7H-Pyrrolo[2,3-d]pyrimidin-4-yl)-4,7-diaza-spiro[2.5]octane-4-sulfonic acid methyl-phenyl-amide

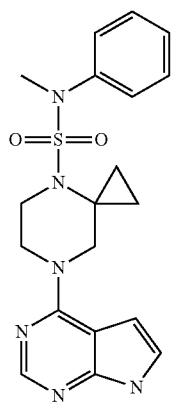 [SMILES: CN(c1ccccc1)S(=O)(=O)N1CCN(c2ncnc3[nH]ccc23)CC12CC2]

1H NMR (300 MHz, DMSO) δ 8.12 (s, 1H), 7.50-7.24 (m, 5H), 7.18 (d, J=3.6 Hz, 1H), 6.57 (d, J=3.6 Hz, 1H), 4.07-3.98 (m, 2H), 3.79 (s, 2H), 3.59-3.53 (m, 2H), 3.14 (s, 3H), 0.82-0.73 (m, 4H). No indole-H observed.

LC-MS (MSX12592): 2.17 min, ES (+), m/z: 399.146

Example 41

7-(7H-Pyrrolo[2,3-d]pyrimidin-4-yl)-4,7-diaza-spiro[2.5]octane-4-sulfonic acid (2-cyano-ethyl)-cyclopropyl-amide

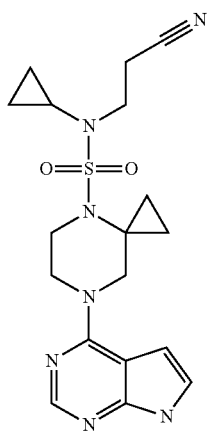 [SMILES: N#CCCN(C1CC1)S(=O)(=O)N1CCN(c2ncnc3[nH]ccc23)CC12CC2]

LC-MS (MSX12244): 1.97 min, ES (+), m/z: 402.175

Example 42

1-[7-(7H-Pyrrolo[2,3-d]pyrimidin-4-yl)-4,7-diaza-spiro[2.5]octane-4-sulfonyl]-piperidine-3-carbonitrile

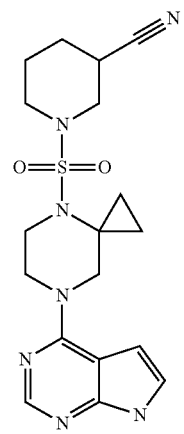 [SMILES: N#CC1CCCN(S(=O)(=O)N2CCN(c3ncnc4[nH]ccc34)CC23CC3)C1]

LC-MS (MSX12245): 1.94 min, ES (+), m/z: 402.171

Example 51

7-(7H-Pyrrolo[2,3-d]pyrimidin-4-yl)-4,7-diaza-spiro[2.5]octane-4-sulfonic acid [2-(3,4-dimethoxy-phenyl)-ethyl]-methyl-amide

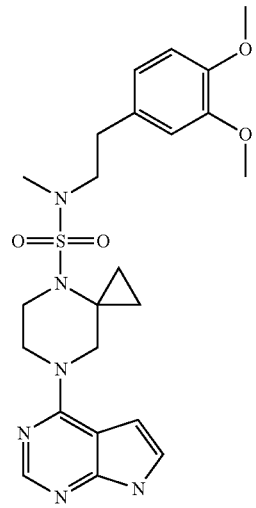 [SMILES: COc1ccc(CCN(C)S(=O)(=O)N2CCN(c3ncnc4[nH]ccc34)CC23CC3)cc1OC]

1H NMR (300 MHz, DMSO) δ 11.71 (s, 1H), 8.13 (s, 1H), 7.19 (s, 1H), 6.86 (dd, J=8.1, 5.0 Hz, 2H), 6.74 (d, J=8.1 Hz, 1H), 6.57 (d, J=2.9 Hz, 1H), 4.03-3.97 (m, 2H), 3.82 (s, 2H), 3.74 (s, 3H), 3.72 (s, 3H), 3.47-3.40 (m, 2H), 3.17 (d, J=5.2 Hz, 2H), 2.76 (t, J=7.5 Hz, 2H), 2.71 (s, 3H), 0.94 (s, 2H), 0.84 (d, J=4.8 Hz, 2H).

Example 52

7-(7H-Pyrrolo[2,3-d]pyrimidin-4-yl)-4,7-diaza-spiro[2.5]octane-4-sulfonic acid benzyl-methyl-amide

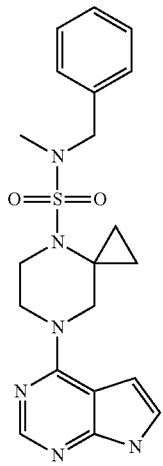 [SMILES: CN(Cc1ccccc1)S(=O)(=O)N1CCN(c2ncnc3[nH]ccc23)CC12CC2]

1H NMR (300 MHz, DMSO) δ 11.73 (s, 1H), 7.46-7.24 (m, 6H), 7.20 (d, J=3.6 Hz, 1H), 6.61 (d, J=3.6 Hz, 1H), 4.27 (s, 2H), 4.10-4.04 (m, 2H), 3.87 (s, 2H), 3.63-3.53 (m, 2H), 2.60 (s, 3H), 1.08-1.00 (m, 2H), 0.93-0.86 (m, 2H).

Example 45

7-(7H-Pyrrolo[2,3-d]pyrimidin-4-yl)-4,7-diaza-spiro[2.5]octane-4-sulfonic acid dimethylamide

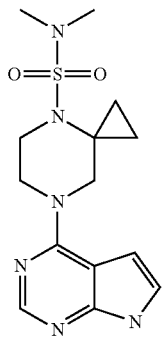 [SMILES: CN(C)S(=O)(=O)N1CCN(c2ncnc3[nH]ccc23)CC12CC2]

1H NMR (300 MHz, DMSO) δ 11.72 (s, 1H), 8.13 (s, 1H), 7.19 (dd, J=3.4, 2.5 Hz, 1H), 6.59 (dd, J=3.5, 1.8 Hz, 1H), 4.08-3.99 (m, 2H), 3.83 (s, 2H), 3.59-3.52 (m, 2H), 2.68 (s, 6H), 1.01 (t, J=6.0 Hz, 2H), 0.87 (t, J=6.1 Hz, 2H).

Example 50

7-(7H-Pyrrolo[2,3-d]pyrimidin-4-yl)-4,7-diaza-spiro[2.5]octane-4-sulfonic acid isopropylamide

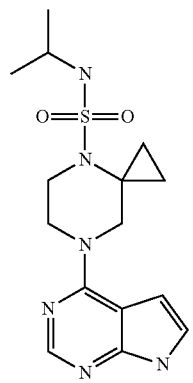 [SMILES: CC(C)NS(=O)(=O)N1CCN(c2ncnc3[nH]ccc23)CC12CC2]

1H NMR (300 MHz, DMSO) δ 11.71 (s, 1H), 8.13 (s, 1H), 7.18 (d, J=3.6 Hz, 1H), 6.59 (d, J=3.6 Hz, 1H), 4.05 (dd, J=7.5, 2.8 Hz, 2H), 3.83 (s, 2H), 3.54 (dd, J=5.7, 4.6 Hz, 2H), 1.09-1.00 (m, 8H), 0.83 (q, J=5.2 Hz, 2H).

Example 9

7-(7H-Pyrrolo[2,3-d]pyrimidin-4-yl)-4,7-diaza-spiro[2.5]octane-4-sulfonic acid phenethyl-(3-phenyl-propyl)-amide

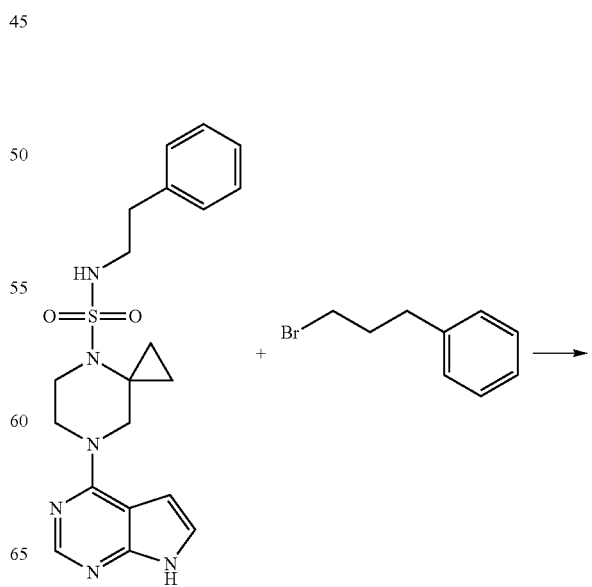

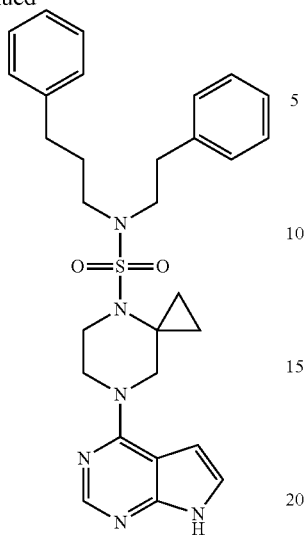

7-(7H-Pyrrolo[2,3-d]pyrimidin-4-yl)-4,7-diaza-spiro[2.5]octane-4-sulfonic acid phenethyl-amide (intermediate 5) (0.05 mmol) was dissolved in dry DMF (0.5 mL) and added Cs$_2$CO$_3$ (0.05 mmol) and (3-bromo-propyl)-benzene (0.05 mmol). Stirred at rt for 2 h and then filtered through a syringe filter (0.45 μm). The pure compounds were obtained by standard preparative HPLC purification of the reaction mixture.

1H NMR (300 MHz, DMSO) δ 11.71 (s, 1H), 8.12 (s, 1H), 7.37-7.25 (m, 4H), 7.25-7.12 (m, 7H), 6.57 (dd, J=3.5, 1.8 Hz, 1H), 4.01 (dd, J=5.2, 4.2 Hz, 2H), 3.80 (s, 2H), 3.40-3.33 (m, 4H), 3.22-3.04 (m, 2H), 2.86-2.72 (m, 2H), 2.55 (t, J=7.7 Hz, 2H), 1.82 (qd, J=8.2, 3.5 Hz, 2H), 1.03-0.71 (m, 4H).

Example 53

7-(7H-Pyrrolo[2,3-d]pyrimidin-4-yl)-4,7-diaza-spiro[2.5]octane-4-sulfonic acid (2-hydroxy-ethyl)-amide

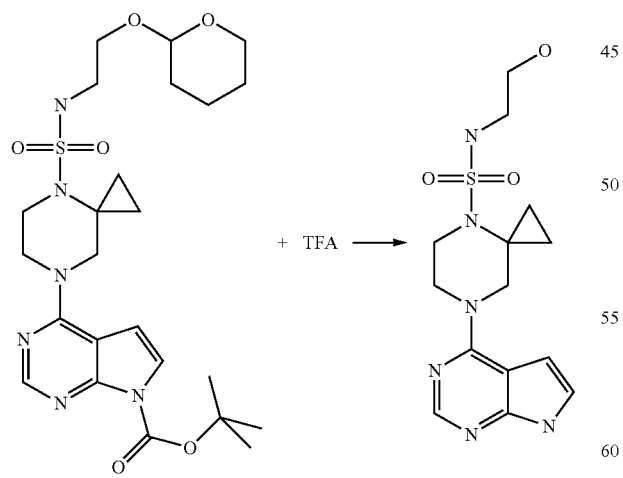

4-{4-[2-(Tetrahydro-pyran-2-yloxy)-ethylsulfamoyl]-4,7-diaza-spiro[2.5]oct-7-yl}-pyrrolo[2,3-d]pyrimidine-7-carboxylic acid tert-butyl ester (intermediate 16) was treated with TFA (1 mL) at rt for 1 h. The crude reaction mixture was concentrated in vacuo and redissolved in DMSO (0.5 mL). The pure compound was obtained by standard preparative HPLC purification of the reaction mixture.

LC-MS (MSX13841): 1.63 min, ES (+), m/z: 353.141

Example 54

7-(7H-Pyrrolo[2,3-d]pyrimidin-4-yl)-4,7-diaza-spiro[2.5]octane-4-sulfonic acid bis-(2-hydroxy-ethyl)-amide

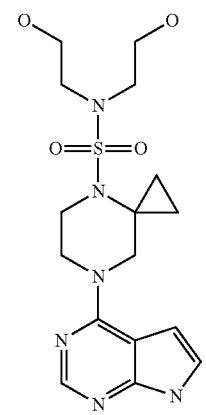 [SMILES: O=S(=O)(N(CCO)CCO)N1CCN(c2ncnc3[nH]ccc23)CC12CC2]

4-(4-{Bis-[2-(tetrahydro-pyran-2-yloxy)-ethyl]-sulfamoyl}-4,7-diaza-spiro[2.5]oct-7-yl)-pyrrolo[2,3-d]pyrimidine-7-carboxylic acid tert-butyl ester (intermediate 17) was treated with a mixture of TFA (0.5 mL), H$_2$O (0.2 mL) and THF (0.2 mL) at 40° C. for 1 h. The crude reaction mixture was neutralised using sat. NaHCO$_3$ and then extracted with EtOAc (3×10 mL). The combined organic phases were dried (Na$_2$SO$_4$), filtered and concentrated in vacuo. The pure compound was obtained by standard preparative HPLC purification of the reaction mixture.

1H NMR (300 MHz, DMSO) δ 11.71 (s, 1H), 8.13 (s, 1H), 7.18 (dd, J=3.4, 2.5 Hz, 1H), 6.59 (dd, J=3.5, 1.6 Hz, 1H), 4.11-3.99 (m, 2H), 3.84 (s, 2H), 3.52 (m, 6H), 3.20 (t, J=6.3 Hz, 4H), 1.03 (t, J=5.8 Hz, 2H), 0.85 (q, J=5.2 Hz, 2H).

Example 55

7-(7H-Pyrrolo[2,3-d]pyrimidin-4-yl)-4,7-diaza-spiro[2.5]octane-4-sulfonic acid (3-cyano-propyl)-amide

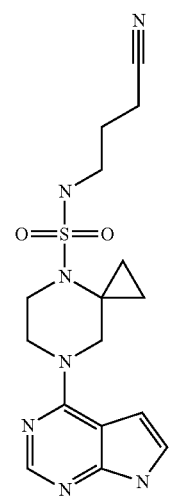 [SMILES: N#CCCCNS(=O)(=O)N1CCN(c2ncnc3[nH]ccc23)CC12CC2]

4-[4-(3-Cyano-propylsulfamoyl)-4,7-diaza-spiro[2.5]oct-7-yl]-pyrrolo[2,3-d]pyrimidine-7-carboxylic acid tert-butyl ester (intermediate 18) was dissolved in THF (1 mL), added TFA (0.5 mL) and then stirred at rt for 2 h.

The crude reaction mixture was concentrated in vacuo and redissolved in MeOH (0.5 mL). The pure compound was obtained by standard preparative HPLC purification of the reaction mixture.

1H NMR (300 MHz, DMSO) δ 12.10 (s, 1H), 8.25 (s, 1H), 7.51 (t, J=5.8 Hz, 1H), 7.30 (dd, J=3.3, 2.6 Hz, 1H), 6.74 (dd, J=3.5, 1.5 Hz, 1H), 4.13-4.05 (m, 2H), 3.88 (s, 2H), 3.62-3.54 (m, 2H), 2.84 (dd, J=12.7, 6.8 Hz, 2H), 2.57-2.51 (m, 2H), 1.72 (p, J=7.0 Hz, 2H), 1.04 (t, J=6.0 Hz, 2H), 0.94-0.83 (m, 2H).

Example 56

7-(7H-Pyrrolo[2,3-d]pyrimidin-4-yl)-4,7-diaza-spiro[2.5]octane-4-sulfonic acid bis-(3-cyano-propyl)-amide Example 57

7-(7H-Pyrrolo[2,3-d]pyrimidin-4-yl)-4,7-diaza-spiro[2.5]octane-4-sulfonic acid (3-cyano-propyl)-(3-phenyl-propyl)-amide

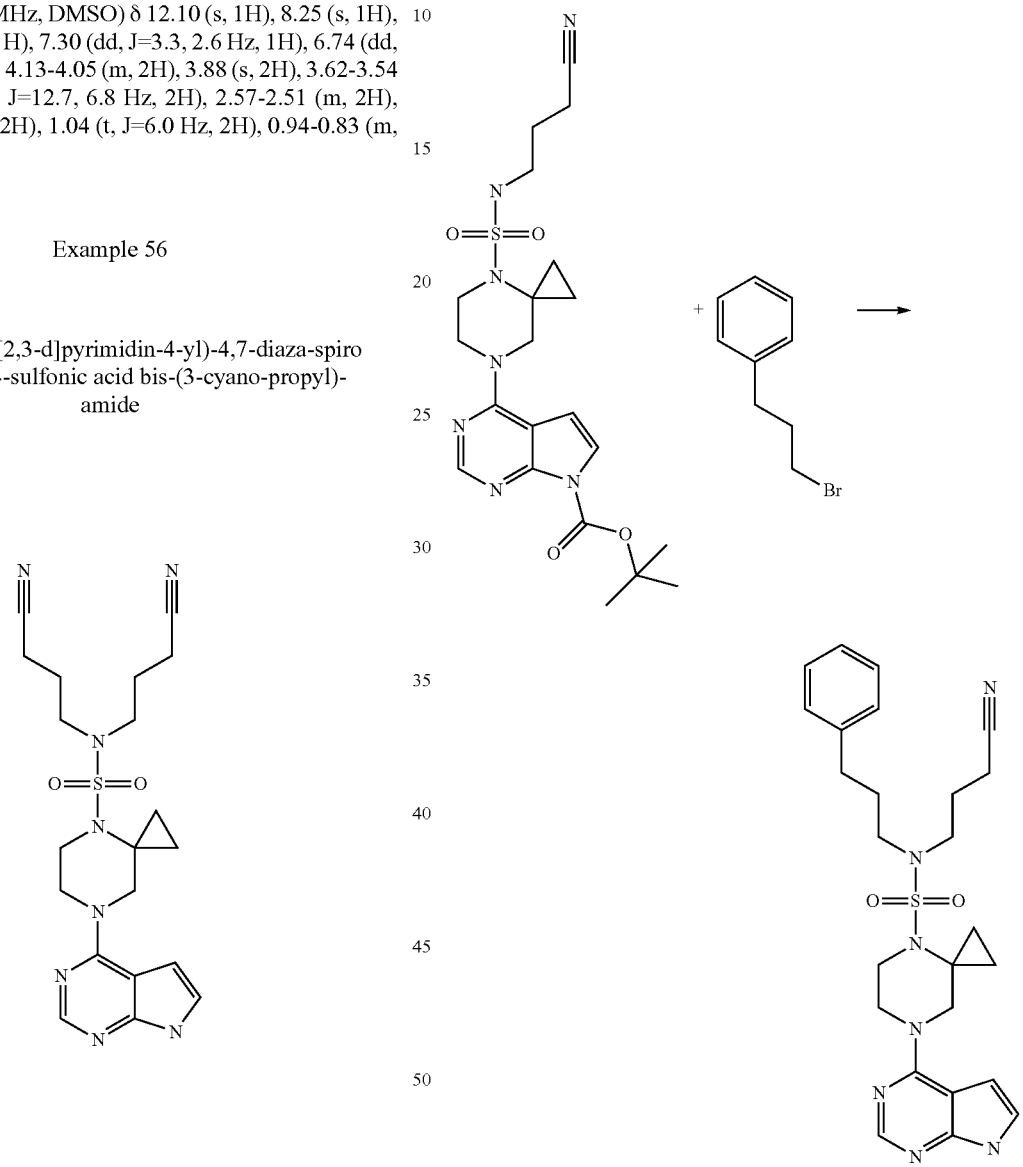

4-{4-[Bis-(3-cyano-propyl)-sulfamoyl]-4,7-diaza-spiro[2.5]oct-7-yl}-pyrrolo[2,3-d]pyrimidine-7-carboxylic acid tert-butyl ester (intermediate 19) was dissolved in THF (1 mL), added TFA (0.5 mL) and then stirred at rt for 2 h. The crude reaction mixture was concentrated in vacuo and redissolved in MeOH (0.5 mL). The pure compound was obtained by standard preparative HPLC purification of the reaction mixture.

1H NMR (300 MHz, DMSO) δ 11.96 (s, 1H), 8.21 (s, 1H), 7.37-7.08 (m, 1H), 6.68 (dd, J=3.5, 1.6 Hz, 1H), 4.14-4.06 (m, 2H), 3.86 (s, 2H), 3.59-3.46 (m, 6H), 3.26-3.08 (m, 4H), 1.90-1.70 (m, 4H), 1.05 (dd, J=6.7, 4.2 Hz, 2H), 0.91 (t, J=6.2 Hz, 2H).

4-[4-(3-Cyano-propylsulfamoyl)-4,7-diaza-spiro[2.5]oct-7-yl]-pyrrolo[2,3-d]pyrimidine-7-carboxylic acid tert-butyl ester (intermediate 18) was dissolved in CH₃CN (0.4 mL), added Cs₂CO₃ and (3-bromo-propyl)-benzene. Stirred at for 16 h and then added additional (3-bromo-propyl)-benzene (2 equivalents) before being stirred at rt for 3 days. The crude reaction mixture was filtered through a syringe filter (0.45 μm) and purified by standard preparative HPLC purification. The residual oil was dissolved in THF (1 mL), added TFA (0.5 mL) and then stirred at rt for 2 h. The crude reaction mixture was concentrated in vacuo and redissolved in MeOH (0.5 mL). The pure compound was obtained by standard preparative HPLC purification of the reaction mixture.

1H NMR (300 MHz, DMSO) δ 11.79 (s, 1H), 8.15 (s, 1H), 7.36-7.10 (m, 6H), 6.61 (dd, J=3.5, 1.7 Hz, 1H), 4.10-4.02 (m, 2H), 3.82 (s, 2H), 3.51-3.44 (m, 2H), 3.17 (dd, J=8.0, 6.9 Hz, 2H), 3.14-3.07 (m, 2H), 2.56 (t, J=7.6 Hz, 2H), 1.89-1.70 (m, 4H), 1.02-0.78 (m, 4H).

LC-MS (MSX13112): 2.30 min, ES (+), m/z: 494.219

Example 58

7-(7H-Pyrrolo[2,3-d]pyrimidin-4-yl)-4,7-diaza-spiro[2.5]octane-4-sulfonic acid methyl-phenethyl-amide

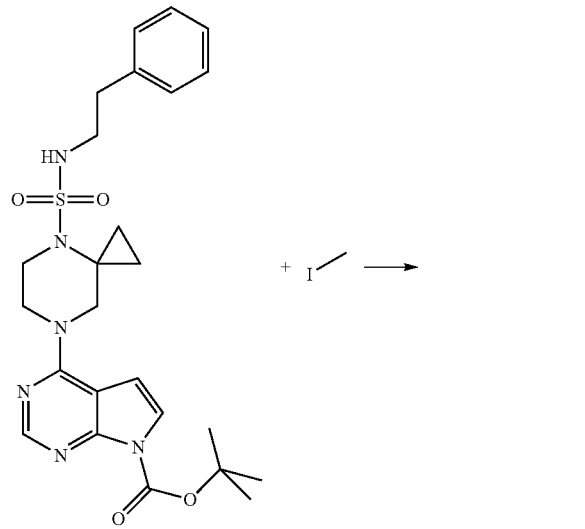

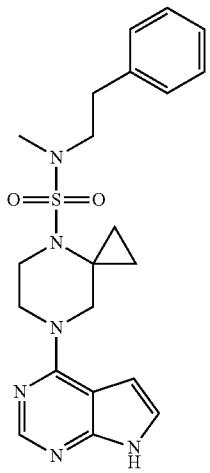

4-(4-Phenethylsulfamoyl-4,7-diaza-spiro[2.5]oct-7-yl)-pyrrolo[2,3-d]pyrimidine-7-carboxylic acid tert-butyl ester (intermediate 6) (0.78 mmol) was dissolved in dry DMF (5 mL) and added K$_2$CO$_3$ (1.56 mmol) and iodomethane (1.17 mmol). Stirred at rt for 3 h and then added H$_2$O (20 mL). Extracted with EtOAc (3×20 mL) and the combined organic phases were concentrated in vacuo. Purified by flash chromatography on silica using EtOAc in heptane as eluent. The obtained compound was treated with TFA (2 mL) at rt for 1.5 h. The crude reaction mixture was added sat. Na$_2$CO$_3$ to pH=7 and the extracted with EtOAc (3×10 mL). The combined organic phases was washes with brine (10 mL), dried (Na$_2$SO$_4$), filtered and concentrated in vacuo. The pure compound was obtained by flash chromatography on silica using EtOAc in heptane as eluent.

1H NMR (600 MHz, DMSO) δ 11.73 (s, 1H), 8.13 (s, 1H), 7.31 (t, J=7.5 Hz, 2H), 7.28-7.15 (m, 4H), 6.58 (d, J=3.6 Hz, 1H), 4.00 (s, 2H), 3.81 (s, 2H), 3.43-3.40 (m, 2H), 3.32-3.26 (m, 2H), 2.87-2.79 (m, 2H), 2.72 (s, 3H), 0.93 (t, J=5.7 Hz, 2H), 0.86-0.79 (m, 2H).

Example 94

N-isopropyl-N-methyl-5-(7H-pyrrolo[2,3-d]pyrimidin-4-yl)-5,8-diazaspiro[2.5]octane-8-sulfonamide

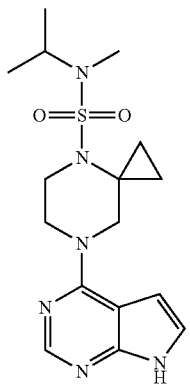 [SMILES: CC(C)N(C)S(=O)(=O)N1CCN(c2ncnc3[nH]ccc23)CC12CC2]

Prepared in a similar manner as example 1, using intermediate 32, instead of intermediate 6.

1H NMR (300 MHz, DMSO) δ 11.71 (s, 1H), 8.13 (s, 1H), 7.18 (dd, J=3.5, 2.3 Hz, 1H), 6.59 (dd, J=3.7, 1.7 Hz, 1H), 4.11-3.98 (m, 2H), 3.94-3.77 (m, 3H), 3.51 (dd, J=6.2, 4.0 Hz, 2H), 2.58 (s, 3H), 1.08 (d, J=6.7 Hz, 6H), 1.04-0.79 (m, 4H).

LC-MS: 2.05 min, ES (+), m/z: 365.160

Using this procedure the following compounds were obtained:

Example 95

N-ethyl-N-isopropyl-5-(7H-pyrrolo[2,3-d]pyrimidin-4-yl)-5,8-diazaspiro[2.5]octane-8-sulfonamide

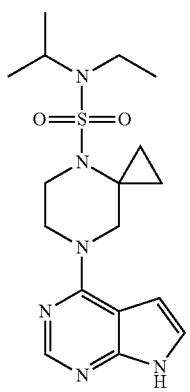 [SMILES: CCN(C(C)C)S(=O)(=O)N1CCN(c2ncnc3[nH]ccc23)CC12CC2]

1H NMR (300 MHz, DMSO) δ 11.76 (s, 1H), 8.14 (s, 1H), 7.20 (dd, J=3.6, 2.3 Hz, 1H), 6.61 (dd, J=3.5, 1.8 Hz, 1H), 4.06 (t, J=5.1 Hz, 2H), 3.84 (s, 2H), 3.73 (p, J=6.7 Hz, 1H), 3.53-3.45 (m, 2H), 3.14 (q, J=7.0 Hz, 2H), 1.23-1.06 (m, 9H), 1.04-0.80 (m, 4H).

LC-MS: 2.13 min, ES (+), m/z: 379.178

Example 96

N-(cyanomethyl)-N-isopropyl-5-(7H-pyrrolo[2,3-d]pyrimidin-4-yl)-5,8-diazaspiro[2.5]octane-8-sulfonamide

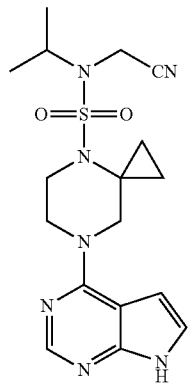 [SMILES: CC(C)N(CC#N)S(=O)(=O)N1CCN(c2ncnc3[nH]ccc23)CC12CC2]

1H NMR (300 MHz, DMSO) δ 11.73 (s, 1H), 8.14 (s, 1H), 7.20 (dd, J=3.6, 2.3 Hz, 1H), 6.60 (dd, J=3.5, 1.8 Hz, 1H), 4.29 (s, 2H), 4.06 (t, J=5.1 Hz, 2H), 3.86 (d, J=15.7 Hz, 3H), 3.54 (t, J=5.0 Hz, 2H), 1.17 (d, J=6.7 Hz, 6H), 1.12-0.82 (m, 4H).

LC-MS: 2.00 min, ES (+), m/z: 390.165

Example 97

N-(2-hydroxyethyl)-N-isopropyl-5-(7H-pyrrolo[2,3-d]pyrimidin-4-yl)-5,8-diazaspiro[2.5]octane-8-sulfonamide

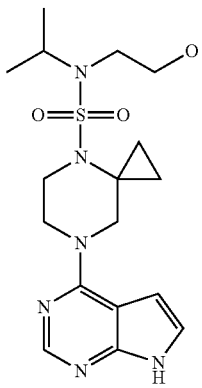 [SMILES: CC(C)N(CCO)S(=O)(=O)N1CCN(c2ncnc3[nH]ccc23)CC12CC2]

1H NMR (300 MHz, DMSO) δ 11.71 (s, 1H), 8.13 (s, 1H), 7.18 (dd, J=3.5, 2.3 Hz, 1H), 6.59 (dd, J=3.6, 1.7 Hz, 1H), 4.72 (br, 1H), 4.05 (t, J=5.1 Hz, 2H), 3.83 (s, 2H), 3.71 (p, J=6.6 Hz, 1H), 3.55-3.43 (m, 4H), 3.09 (t, J=7.2 Hz, 2H), 1.10 (d, J=6.7 Hz, 6H), 1.05-0.80 (m, 4H).

LC-MS: 1.83 min, ES (+), m/z: 395.183

Example 98

N-cyclobutyl-N-methyl-5-(7H-pyrrolo[2,3-d]pyrimidin-4-yl)-5,8-diazaspiro[2.5]octane-8-sulfonamide

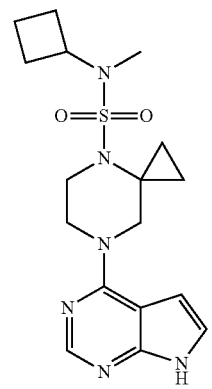 [SMILES: CN(C1CCC1)S(=O)(=O)N1CCN(c2ncnc3[nH]ccc23)CC12CC2]

Prepared in a similar manner as example 1, using intermediate 31, instead of intermediate 6.

1H NMR (300 MHz, DMSO) δ 11.71 (s, 1H), 8.13 (s, 1H), 7.19 (dd, J=3.6, 2.1 Hz, 1H), 6.59 (dd, J=3.8, 1.5 Hz, 1H), 4.18-3.97 (m, 3H), 3.82 (s, 2H), 3.50 (dd, J=6.5, 3.8 Hz, 2H), 2.67 (s, 3H), 2.24-2.06 (m, 2H), 2.06-1.90 (m, 2H), 1.65-1.45 (m, 2H), 1.02-0.78 (m, 4H).

LC-MS: 2.11 min, ES (+), m/z: 377.179

Using this procedure the following compounds were obtained:

Example 99

N-cyclobutyl-N-ethyl-5-(7H-pyrrolo[2,3-d]pyrimidin-4-yl)-5,8-diazaspiro[2.5]octane-8-sulfonamide

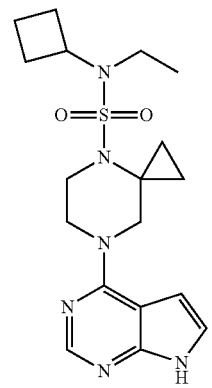 [SMILES: CCN(C1CCC1)S(=O)(=O)N1CCN(c2ncnc3[nH]ccc23)CC12CC2]

1H NMR (300 MHz, DMSO) δ 11.71 (s, 1H), 8.13 (s, 1H), 7.18 (dd, J=3.6, 2.3 Hz, 1H), 6.59 (dd, J=3.7, 1.8 Hz, 1H), 4.09-3.88 (m, 3H), 3.84 (s, 2H), 3.49 (dd, J=6.3, 4.0 Hz, 2H), 3.23 (q, J=7.1 Hz, 2H), 2.21-1.95 (m, 4H), 1.55 (m, 2H), 1.10 (t, J=7.0 Hz, 3H), 1.06-0.80 (m, 4H).

LC-MS: 2.20 min, ES (+), m/z: 391.189

Example 100

N-(cyanomethyl)-N-cyclobutyl-5-(7H-pyrrolo[2,3-d]pyrimidin-4-yl)-5,8-diazaspiro[2.5]octane-8-sulfonamide

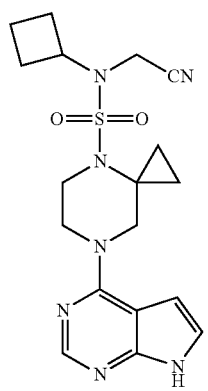

1H NMR (300 MHz, DMSO) δ 11.73 (s, 1H), 8.14 (s, 1H), 7.20 (dd, J=3.5, 2.3 Hz, 1H), 6.60 (dd, J=3.5, 1.8 Hz, 1H), 4.37 (s, 2H), 4.17-4.00 (m, 3H), 3.83 (s, 2H), 3.55 (d, J=5.1 Hz, 2H), 2.32-2.13 (m, 2H), 2.07 (m, 2H), 1.68-1.48 (m, 2H), 1.12-0.84 (m, 4H).

LC-MS: 2.07 min, ES (+), m/z: 402.169

Example 101

N-cyclobutyl-N-(2-hydroxyethyl)-5-(7H-pyrrolo[2,3-d]pyrimidin-4-yl)-5,8-diazaspiro[2.5]octane-8-sulfonamide

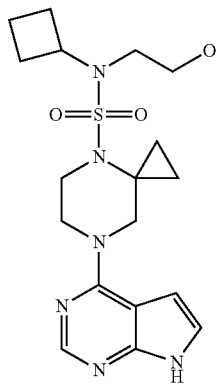 [SMILES: O=S(=O)(N(CCO)C1CCC1)N1CCN(c2ncnc3[nH]ccc23)CC12CC2]

1H NMR (300 MHz, DMSO) δ 11.71 (s, 1H), 8.13 (s, 1H), 7.18 (dd, J=3.6, 2.3 Hz, 1H), 6.59 (dd, J=3.7, 1.8 Hz, 1H), 4.77 (s, 1H), 4.09-3.89 (m, 3H), 3.83 (s, 2H), 3.54-3.40 (m, 4H), 3.20 (t, J=7.0 Hz, 2H), 2.22-1.93 (m, 4H), 1.66-1.42 (m, 2H), 1.04-0.80 (m, 4H).

LC-MS: 1.88 min, ES (+), m/z: 407.161

Example 102

N-(3-cyanopropyl)-N-cyclobutyl-5-(7H-pyrrolo[2,3-d]pyrimidin-4-yl)-5,8-diazaspiro[2.5]octane-8-sulfonamide

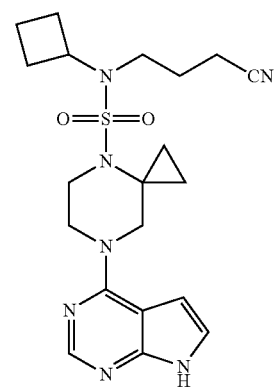 [SMILES: N#CCCCN(C1CCC1)S(=O)(=O)N1CCN(c2ncnc3[nH]ccc23)CC12CC2]

1H NMR (300 MHz, DMSO) δ 11.73 (s, 1H), 8.13 (s, 1H), 7.19 (dd, J=3.6, 2.2 Hz, 1H), 6.59 (dd, J=3.5, 1.7 Hz, 1H), 4.10-3.89 (m, 3H), 3.84 (s, 2H), 3.49 (dd, J=6.4, 3.9 Hz, 2H), 3.33-3.17 (m, 2H), 2.54 (m, 2H), 2.21-1.86 (m, 4H), 1.78 (m, 2H), 1.56 (m, 2H), 1.05-0.81 (m, 4H).

LC-MS: 2.09 min, ES (+), m/z: 430.194

Example 103

N-cyclobutyl-N-(2-methoxyethyl)-5-(7H-pyrrolo[2,3-d]pyrimidin-4-yl)-5,8-diazaspiro[2.5]octane-8-sulfonamide

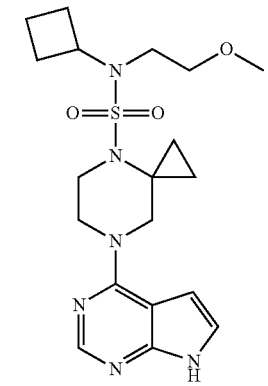 [SMILES: COCCN(C1CCC1)S(=O)(=O)N1CCN(c2ncnc3[nH]ccc23)CC12CC2]

1H NMR (300 MHz, DMSO) δ 11.71 (s, 1H), 8.13 (s, 1H), 7.19 (dd, J=3.6, 2.3 Hz, 1H), 6.59 (dd, J=3.5, 1.8 Hz, 1H), 4.09-3.87 (m, 3H), 3.84 (s, 2H), 3.55-3.23 (m, 9H), 2.22-1.93 (m, 4H), 1.66-1.39 (m, 2H), 1.05-0.80 (m, 4H).

LC-MS: 2.13 min, ES (+), m/z: 421.200

Example 104

N-cyclobutyl-N-(2-imidazol-1-ylethyl)-5-(7H-pyrrolo[2,3-d]pyrimidin-4-yl)-5,8-diazaspiro[2.5]octane-8-sulfonamide

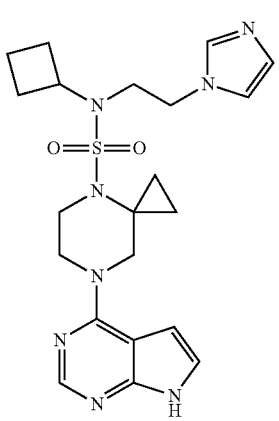 [SMILES: O=S(=O)(N(CCn1ccnc1)C1CCC1)N1CCN(c2ncnc3[nH]ccc23)CC12CC2]

LC-MS: 1.71 min, ES (+), m/z: 457.217

Example 105

N-cyclobutyl-N-[3-(dimethylamino)propyl]-5-(7H-pyrrolo[2,3-d]pyrimidin-4-yl)-5,8-diazaspiro[2.5]octane-8-sulfonamide

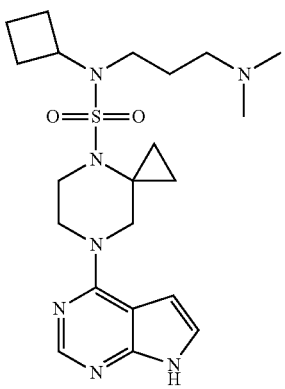 [SMILES: CN(C)CCCN(C1CCC1)S(=O)(=O)N1CCN(c2ncnc3[nH]ccc23)CC12CC2]

LC-MS: 1.73 min, ES (+), m/z: 448.247

Example 106

N-cyclobutyl-N-(2-morpholinoethyl)-5-(7H-pyrrolo[2,3-d]pyrimidin-4-yl)-5,8-diazaspiro[2.5]octane-8-sulfonamide

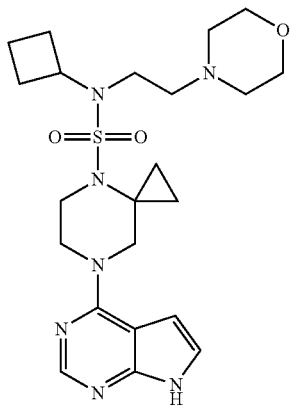 [SMILES: O=S(=O)(N(CCN1CCOCC1)C1CCC1)N1CCN(c2ncnc3[nH]ccc23)CC12CC2]

LC-MS: 1.73 min, ES (+), m/z: 476.236

Example 107

N-(1-cyanoethyl)-N-cyclobutyl-5-(7H-pyrrolo[2,3-d]pyrimidin-4-yl)-5,8-diazaspiro[2.5]octane-8-sulfonamide

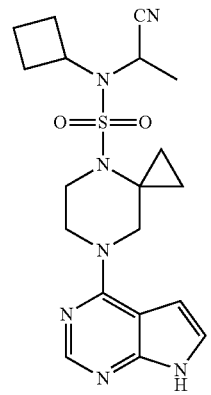 [SMILES: CC(C#N)N(C1CCC1)S(=O)(=O)N1CCN(c2ncnc3[nH]ccc23)CC12CC2]

1H NMR (300 MHz, DMSO) δ 11.74 (s, 1H), 8.14 (s, 1H), 7.24-7.16 (m, 1H), 6.61 (dd, J=3.7, 1.7 Hz, 1H), 4.90 (q, J=7.0 Hz, 1H), 4.15-3.89 (m, 3H), 3.85 (s, 2H), 3.58 (t, J=5.1 Hz, 2H), 2.33 (h, J=10.2 Hz, 2H), 2.21-2.03 (m, 2H), 1.73-1.44 (m, 5H), 1.19-0.79 (m, 4H).
LC-MS: 2.15 min, ES (+), m/z: 416.183

Example 108

N-(cyanomethyl)-N-(2-hydroxyethyl)-5-(7H-pyrrolo[2,3-d]pyrimidin-4-yl)-5,8-diazaspiro[2.5]octane-8-sulfonamide

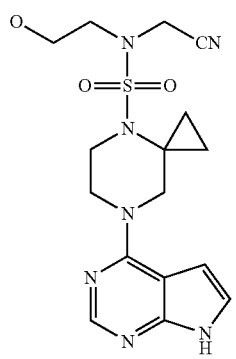 [SMILES: N#CCN(CCO)S(=O)(=O)N1CCN(c2ncnc3[nH]ccc23)CC12CC2]

Prepared in a similar manner as example 1, using intermediate 16, instead of intermediate 6.

LC-MS: 1.72 min, ES (+), m/z: 392.153

Example 109

N-(2-hydroxyethyl)-N-methyl-5-(7H-pyrrolo[2,3-d]pyrimidin-4-yl)-5,8-diazaspiro[2.5]octane-8-sulfonamide

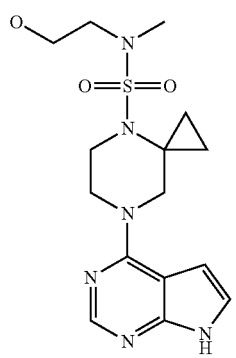 [SMILES: CN(CCO)S(=O)(=O)N1CCN(c2ncnc3[nH]ccc23)CC12CC2]

LC-MS: 1.68 min, ES (+), m/z: 367.154

Example 110

N-(3-cyanopropyl)-N-(2-hydroxyethyl)-5-(7H-pyrrolo[2,3-d]pyrimidin-4-yl)-5,8-diazaspiro[2.5]octane-8-sulfonamide

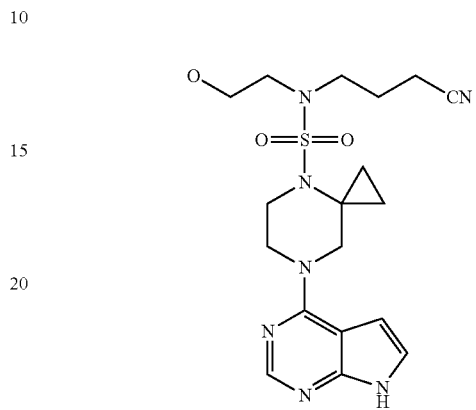

1H NMR (300 MHz, DMSO) δ 12.00 (s, 1H), 8.22 (s, 1H), 7.27 (t, J=3.0 Hz, 1H), 6.76-6.64 (m, 1H), 4.21-4.03 (m, 2H), 3.87 (s, 2H), 3.60-3.47 (m, 6H), 3.25-3.06 (m, 4H), 1.83 (p, J=7.3 Hz, 2H), 1.20-0.79 (m, 4H).

LC-MS: 1.73 min, ES (+), m/z: 420.180

Example 111

N-(2-hydroxyethyl)-N-(2-phenoxyethyl)-5-(7H-pyrrolo[2,3-d]pyrimidin-4-yl)-5,8-diazaspiro[2.5]octane-8-sulfonamide

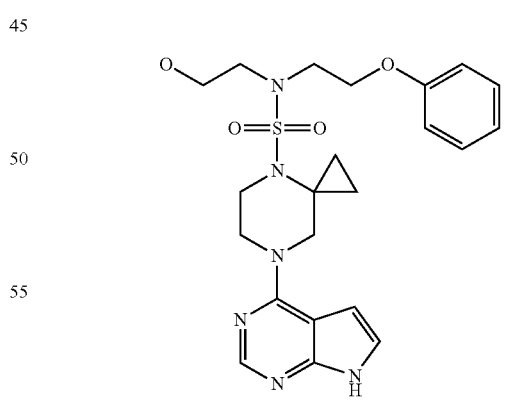

1H NMR (300 MHz, DMSO) δ 11.71 (s, 1H), 8.13 (s, 1H), 7.38-7.23 (m, 2H), 7.21-7.14 (m, 1H), 7.00-6.89 (m, 3H), 6.58 (dd, J=3.7, 1.8 Hz, 1H), 4.78 (br, 1H), 4.11 (t, J=5.8 Hz, 2H), 4.07-4.00 (m, 2H), 3.85 (s, 2H), 3.55 (t, J=5.4 Hz, 4H), 3.33-3.16 (m, 4H), 1.08-0.80 (m, 4H).

LC-MS: 2.05 min, ES (+), m/z: 473.194

Example 112

N-methyl-N-(oxetan-3-yl)-5-(7H-pyrrolo[2,3-d]pyrimidin-4-yl)-5,8-diazaspiro[2.5]octane-8-sulfonamide

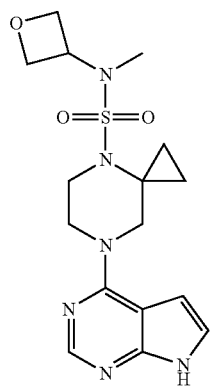

Prepared in a similar manner as example 58, using intermediate 43, instead of intermediate 6.

1H NMR (300 MHz, DMSO) δ 11.73 (s, 1H), 8.14 (s, 1H), 7.24-7.15 (m, 1H), 6.59 (dd, J=3.5, 1.8 Hz, 1H), 4.79-4.55 (m, 5H), 4.08-3.98 (m, 2H), 3.81 (s, 2H), 3.51 (dd, J=6.2, 4.0 Hz, 2H), 2.77 (s, 3H), 1.06-0.80 (m, 4H).

LC-MS: 1.80 min, ES (+), m/z: 379.144

Example 113

N-(cyanomethyl)-N-(oxetan-3-yl)-5-(7H-pyrrolo[2,3-d]pyrimidin-4-yl)-5,8-diazaspiro[2.5]octane-8-sulfonamide

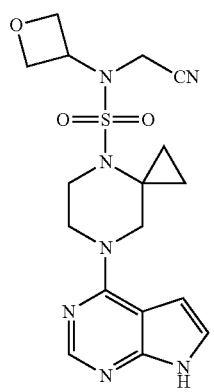 [SMILES: N#CCN(C1COC1)S(=O)(=O)N1CCN(c2ncnc3[nH]ccc23)CC12CC2]

Prepared in a similar manner as example 1, using intermediate 43, instead of intermediate 6.

1H NMR (300 MHz, DMSO) δ 11.74 (s, 1H), 8.15 (s, 1H), 7.25-7.16 (m, 1H), 6.60 (dd, J=3.7, 1.8 Hz, 1H), 4.86-4.57 (m, 5H), 4.48 (s, 2H), 4.04 (dd, J=6.3, 3.8 Hz, 2H), 3.83 (s, 2H), 3.58 (dd, J=6.2, 3.9 Hz, 2H), 1.14-0.81 (m, 4H).

LC-MS: 1.84 min, ES (+), m/z: 404.151

Using this procedure the following compounds were obtained:

Example 114

N-(3-cyanopropyl)-N-(oxetan-3-yl)-5-(7H-pyrrolo[2,3-d]pyrimidin-4-yl)-5,8-diazaspiro[2.5]octane-8-sulfonamide

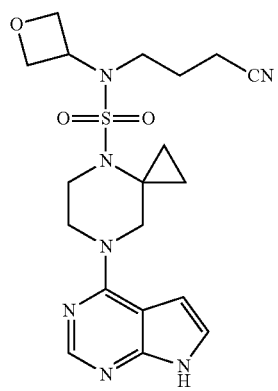 [SMILES: N#CCCCN(C1COC1)S(=O)(=O)N1CCN(c2ncnc3[nH]ccc23)CC12CC2]

1H NMR (300 MHz, DMSO) δ 11.73 (s, 1H), 8.14 (s, 1H), 7.24-7.14 (m, 1H), 6.65-6.54 (m, 1H), 4.80-4.55 (m, 4H), 4.12-4.00 (m, 2H), 3.83 (s, 2H), 3.52 (dd, J=6.2, 3.9 Hz, 2H), 3.37-3.25 (m, 3H), 2.55 (t, J=7.1 Hz, 2H), 1.84 (p, J=7.3 Hz, 2H), 1.15-0.76 (m, 4H).

LC-MS: 1.84 min, ES (+), m/z: 432.174

Example 115

N-(oxetan-3-yl)-N-(2-phenoxyethyl)-5-(7H-pyrrolo[2,3-d]pyrimidin-4-yl)-5,8-diazaspiro[2.5]octane-8-sulfonamide

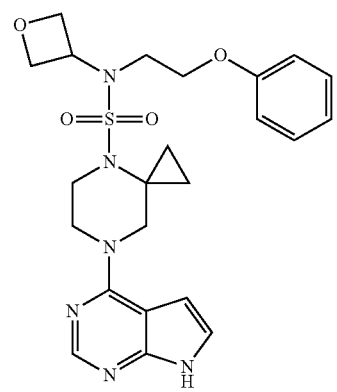 [SMILES: O=S(=O)(N(CCOc1ccccc1)C1COC1)N1CCN(c2ncnc3[nH]ccc23)CC12CC2]

1H NMR (300 MHz, DMSO) δ 11.73 (s, 1H), 8.13 (s, 1H), 7.38-7.24 (m, 2H), 7.23-7.14 (m, 1H), 7.01-6.88 (m, 3H), 6.57 (dd, J=3.6, 1.8 Hz, 1H), 4.84-4.58 (m, 5H), 4.12 (t, J=5.4 Hz, 2H), 4.04 (t, J=5.1 Hz, 2H), 3.83 (s, 2H), 3.67 (t, J=5.5 Hz, 2H), 3.59-3.50 (m, 2H), 1.07-0.79 (m, 4H).

LC-MS: 2.19 min, ES (+), m/z: 485.183

Example 116

N-(2-hydroxyethyl)-N-(oxetan-3-yl)-5-(7H-pyrrolo[2,3-d]pyrimidin-4-yl)-5,8-diazaspiro[2.5]octane-8-sulfonamide

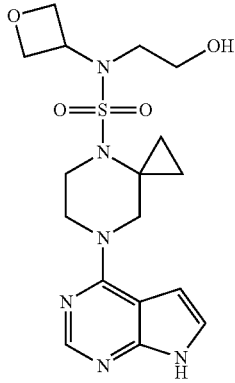 [SMILES: O=S(=O)(N(CCO)C1COC1)N1CCN(c2ncnc3[nH]ccc23)CC12CC2]

1H NMR (300 MHz, DMSO) δ 11.95 (s, 1H), 8.20 (s, 1H), 7.26 (dd, J=3.5, 2.2 Hz, 1H), 6.68 (dd, J=3.5, 1.7 Hz, 1H), 4.33-3.26 (m, 14H), 3.26-2.96 (m, 2H), 1.20-1.00 (m, 2H), 0.96-0.78 (m, 2H).

LC-MS: 1.69 min, ES (+), m/z: 409.156

Example 117

N-(1-cyanoethyl)-N-(oxetan-3-yl)-5-(7H-pyrrolo[2,3-d]pyrimidin-4-yl)-5,8-diazaspiro[2.5]octane-8-sulfonamide

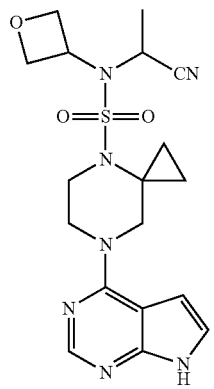 [SMILES: CC(C#N)N(C1COC1)S(=O)(=O)N1CCN(c2ncnc3[nH]ccc23)CC12CC2]

1H NMR (300 MHz, DMSO) δ 11.74 (s, 1H), 8.15 (s, 1H), 7.25-7.16 (m, 1H), 6.61 (dd, J=3.5, 1.8 Hz, 1H), 4.97-4.56 (m, 6H), 4.06 (t, J=5.3 Hz, 2H), 3.85 (s, 2H), 3.62 (t, J=5.0 Hz, 2H), 1.49 (d, J=7.1 Hz, 3H), 1.16-1.03 (m, 2H), 0.94 (d, J=6.6 Hz, 2H).

LC-MS: 1.90 min, ES (+), m/z: 418.167

Example 118

N-methyl-N-[(1-propylsulfonylpyrrolidin-3-yl)methyl]-5-(7H-pyrrolo[2,3-d]pyrimidin-4-yl)-5,8-diazaspiro[2.5]octane-8-sulfonamide

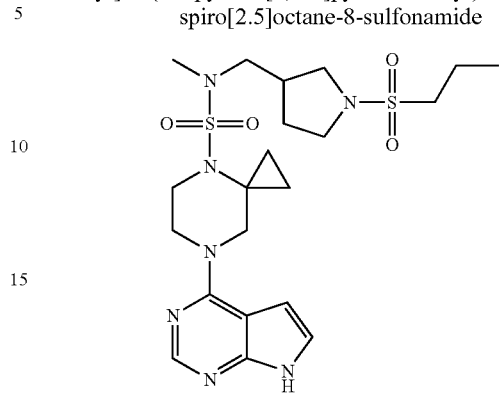

N-methyl-N-(pyrrolidin-3-ylmethyl)-5-(7H-pyrrolo[2,3-d]pyrimidin-4-yl)-5,8-diazaspiro[2.5]octane-8-sulfonamide (intermediate 25) (0.042 mmol) was dissolved in dry DMSO (0.5 mL), added DIPEA (0.25 mL) and propane-1-sulfonyl chloride (0.050 mmol) and then stirred at 40° C. for 1 h. The pure compound was obtained by standard preparative HPLC purification of the reaction mixture.

1H NMR (300 MHz, DMSO) δ 11.71 (s, 1H), 8.14 (s, 1H), 7.19 (dd, J=3.5, 2.3 Hz, 1H), 6.59 (dd, J=3.7, 1.8 Hz, 1H), 4.13-3.97 (m, 2H), 3.84 (s, 2H), 3.53 (t, J=5.0 Hz, 2H), 3.44-3.18 (m, 4H), 3.14-2.91 (m, 5H), 2.71 (s, 3H), 2.64-2.50 (m, 1H), 1.98 (m, 1H), 1.79-1.54 (m, 2H), 1.13-0.82 (m, 7H).

LC-MS: 2.04 min, ES (+), m/z: 512.207

Using this procedure the following compounds were obtained:

Example 119

N-methyl-N-[(1-methylsulfonylpyrrolidin-3-yl)methyl]-5-(7H-pyrrolo[2,3-d]pyrimidin-4-yl)-5,8-diazaspiro[2.5]octane-8-sulfonamide

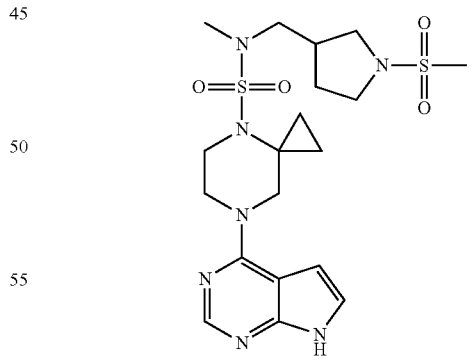

1H NMR (300 MHz, DMSO) δ 11.71 (s, 1H), 8.14 (s, 1H), 7.19 (dd, J=3.7, 2.4 Hz, 1H), 6.59 (dd, J=3.5, 1.8 Hz, 1H), 4.05 (t, J=5.3 Hz, 2H), 3.84 (s, 2H), 3.54 (t, J=5.1 Hz, 2H), 3.45-3.15 (m, 3H), 3.10 (d, J=7.5 Hz, 2H), 2.94 (dd, J=9.9, 7.0 Hz, 1H), 2.89 (s, 3H), 2.71 (s, 3H), 2.61-2.50 (m, 1H), 1.98 (dtd, J=12.1, 7.0, 4.8 Hz, 1H), 1.63 (dq, J=12.4, 7.8 Hz, 1H), 1.05-0.82 (m, 4H).

LC-MS: 1.89 min, ES (+), m/z: 484.180

Example 120

N-[[1-(2-methoxyethylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide

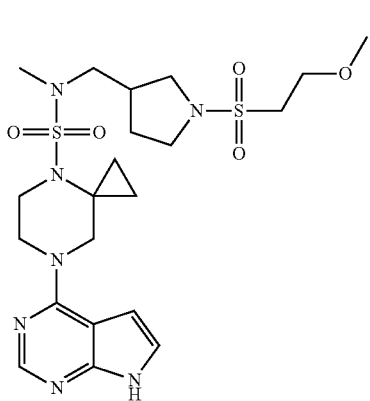 [SMILES: COCCS(=O)(=O)N1CCC(CN(C)S(=O)(=O)N2CCN(c3ncnc4[nH]ccc34)CC23CC3)C1]

1H NMR (300 MHz, DMSO) δ 11.72 (s, 1H), 8.14 (s, 1H), 7.19 (dd, J=3.5, 2.3 Hz, 1H), 6.59 (dd, J=3.7, 1.8 Hz, 1H), 4.05 (t, J=5.3 Hz, 2H), 3.84 (s, 2H), 3.66 (t, J=5.9 Hz, 2H), 3.53 (t, J=5.2 Hz, 2H), 3.43-3.18 (m, 8H), 3.10 (d, J=7.4 Hz, 2H), 2.96 (dd, J=9.6, 7.0 Hz, 1H), 2.71 (s, 3H), 2.61-2.50 (m, 1H), 1.97 (dtd, J=11.7, 6.9, 4.7 Hz, 1H), 1.62 (dq, J=12.4, 7.9 Hz, 1H), 1.05-0.82 (m, 4H).

LC-MS: 1.95 min, ES (+), m/z: 528.185

Example 121

N-[[1-(3-cyanopropylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide

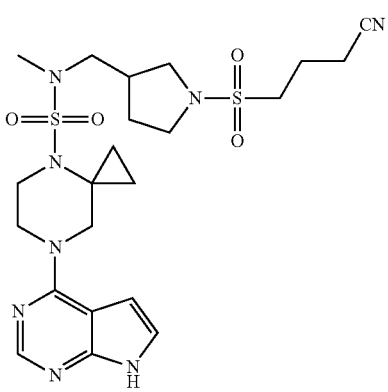 [SMILES: CN(CC1CCN(S(=O)(=O)CCCC#N)C1)S(=O)(=O)N1CCN(c2ncnc3[nH]ccc23)CC12CC2]

1H NMR (300 MHz, DMSO) δ 11.71 (s, 1H), 8.14 (s, 1H), 7.19 (dd, J=3.5, 2.3 Hz, 1H), 6.59 (dd, J=3.6, 1.8 Hz, 1H), 4.05 (t, J=5.2 Hz, 2H), 3.84 (s, 2H), 3.54 (t, J=5.1 Hz, 2H), 3.47-3.05 (m, 8H), 2.99 (dd, J=9.7, 7.0 Hz, 1H), 2.71 (s, 3H), 2.65 (t, J=7.2 Hz, 2H), 2.12-1.88 (m, 3H), 1.75-1.56 (m, 1H), 1.05-0.82 (m, 4H).

LC-MS: 1.96 min, ES (+), m/z: 537.204

Example 122

N-[[1-(cyclopropylmethylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide

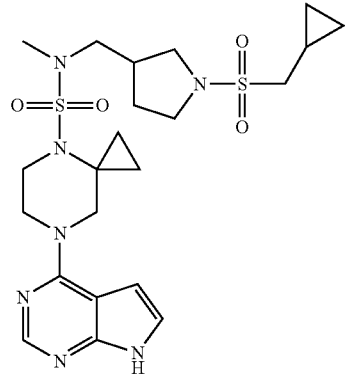 [SMILES: CN(CC1CCN(S(=O)(=O)CC2CC2)C1)S(=O)(=O)N1CCN(c2ncnc3[nH]ccc23)CC12CC2]

1H NMR (300 MHz, DMSO) δ 11.71 (s, 1H), 8.14 (s, 1H), 7.19 (dd, J=3.5, 2.4 Hz, 1H), 6.59 (dd, J=3.7, 1.7 Hz, 1H), 4.05 (t, J=5.2 Hz, 2H), 3.84 (s, 2H), 3.60-3.21 (m, 6H), 3.17-2.91 (m, 5H), 2.71 (s, 3H), 2.62-2.51 (m, 1H), 2.06-1.87 (m, 1H), 1.73-1.54 (m, 1H), 1.04-0.82 (m, 4H), 0.65-0.47 (m, 2H), 0.41-0.26 (m, 2H).

LC-MS: 2.05 min, ES (+), m/z: 524.208

Example 123

N-[[1-(3-hydroxypropanoyl)pyrrolidin-3-yl]methyl]-N-methyl-5-(7H-pyrrolo[2,3-d]pyrimidin-4-yl)-5,8-diazaspiro[2.5]octane-8-sulfonamide

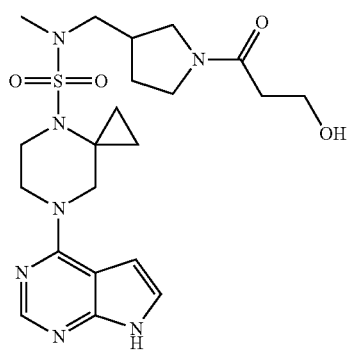

N-methyl-N-(pyrrolidin-3-ylmethyl)-5-(7H-pyrrolo[2,3-d]pyrimidin-4-yl)-5,8-diazaspiro[2.5]octane-8-sulfonamide (intermediate 25) (0.042 mmol) was dissolved in dry DMSO (0.5 mL), added DIPEA (0.25 mL), 3-hydroxypropanoic acid (0.050 mmol) and Pybrop (0.050 mmol) then stirred at 40° C. for 1 h. The pure compound was obtained by standard preparative HPLC purification of the reaction mixture.

1H NMR (300 MHz, DMSO) δ 11.75-11.68 (m, 1H), 8.13 (s, 1H), 7.19 (dd, J=3.6, 2.2 Hz, 1H), 6.59 (dd, J=3.5, 1.7 Hz, 1H), 4.48 (s, 1H), 4.05 (t, J=5.2 Hz, 2H), 3.84 (s, 2H), 3.68-3.31 (m, 7H), 3.29-2.91 (m, 4H), 2.72 (d, J=3.7 Hz, 3H), 2.49-2.30 (m, 2H), 2.07-1.82 (m, 1H), 1.61 (m, 1H), 0.94 (m, 4H).

LC-MS: 1.72 min, ES (+), m/z: 478.193

Using this procedure the following compounds were obtained:

Example 124

N-[[1-(3-hydroxybutanoyl)pyrrolidin-3-yl]methyl]-N-methyl-5-(7H-pyrrolo[2,3-d]pyrimidin-4-yl)-5,8-diazaspiro[2.5]octane-8-sulfonamide

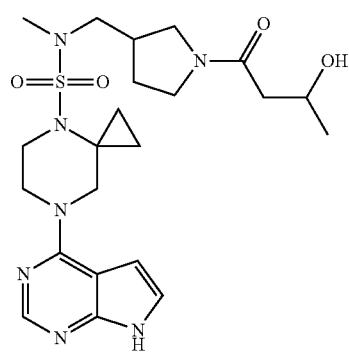 [SMILES: CC(O)CC(=O)N1CCC(CN(C)S(=O)(=O)N2CCN(c3ncnc4[nH]ccc34)CC23CC3)C1]

LC-MS: 1.76 min, ES (+), m/z: 492.209

Example 125

N-methyl-N-[(1-propanoylpyrrolidin-3-yl)methyl]-5-(7H-pyrrolo[2,3-d]pyrimidin-4-yl)-5,8-diazaspiro[2.5]octane-8-sulfonamide

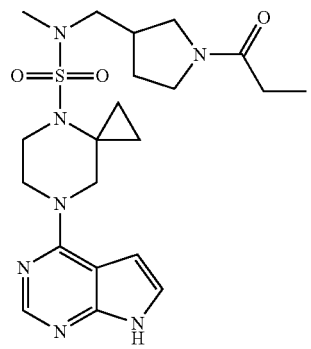 [SMILES: CCC(=O)N1CCC(CN(C)S(=O)(=O)N2CCN(c3ncnc4[nH]ccc34)CC23CC3)C1]

1H NMR (300 MHz, DMSO) δ 11.72 (s, 1H), 8.14 (s, 1H), 7.19 (dd, J=3.5, 2.3 Hz, 1H), 6.59 (dd, J=3.5, 1.8 Hz, 1H), 4.04 (d, J=5.5 Hz, 2H), 3.84 (s, 2H), 3.52 (s, 2H), 3.49-3.35 (m, 2H), 3.27-2.91 (m, 4H), 2.71 (d, J=3.4 Hz, 3H), 2.50 (m, 1H), 2.21 (q, J=7.4 Hz, 2H), 2.03-1.85 (m, 1H), 1.75-1.49 (m, 1H), 1.07-0.81 (m, 7H).

LC-MS: 1.86 min, ES (+), m/z: 462.199

Example 126

N-[[1-(3-cyanopropanoyl)pyrrolidin-3-yl]methyl]-N-methyl-5-(7H-pyrrolo[2,3-d]pyrimidin-4-yl)-5,8-diazaspiro[2.5]octane-8-sulfonamide

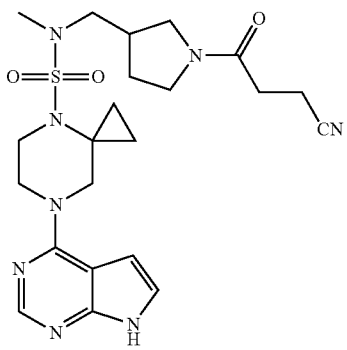 [SMILES: CN(CC1CCN(C(=O)CCC#N)C1)S(=O)(=O)N1CCN(c2ncnc3[nH]ccc23)CC12CC2]

1H NMR (300 MHz, DMSO) δ 11.79 (s, 1H), 8.16 (s, 1H), 7.21 (dd, J=3.5, 2.3 Hz, 1H), 6.66-6.58 (m, 1H), 4.06 (t, J=5.2 Hz, 2H), 3.84 (s, 2H), 3.61-3.35 (m, 5H), 3.31-2.93 (m, 4H), 2.72 (d, J=4.6 Hz, 3H), 2.61 (d, J=1.5 Hz, 3H), 2.58-2.39 (m, 1H), 2.09-1.84 (m, 1H), 1.62 (m, 1H), 1.05-0.82 (m, 4H).

LC-MS: 1.83 min, ES (+), m/z: 487.193

Example 127

N-[[1-(2,3-dihydroxypropanoyl)pyrrolidin-3-yl]methyl]-N-methyl-5-(7H-pyrrolo[2,3-d]pyrimidin-4-yl)-5,8-diazaspiro[2.5]octane-8-sulfonamide

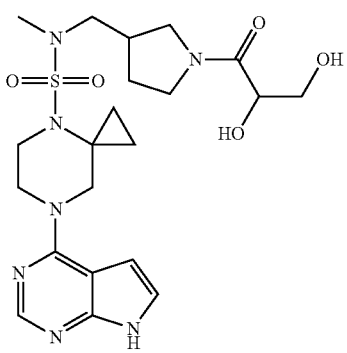 [SMILES: CN(CC1CCN(C(=O)C(O)CO)C1)S(=O)(=O)N1CCN(c2ncnc3[nH]ccc23)CC12CC2]

LC-MS: 1.68 min, ES (+), m/z: 494.213

Example 128

N-[(1-formylpyrrolidin-3-yl)methyl]-N-methyl-5-(7H-pyrrolo[2,3-d]pyrimidin-4-yl)-5,8-diazaspiro[2.5]octane-8-sulfonamide

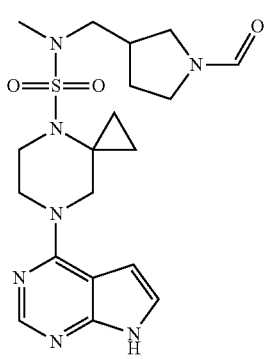 [SMILES: CN(CC1CCN(C=O)C1)S(=O)(=O)N1CCN(c2ncnc3[nH]ccc23)CC12CC2]

1H NMR (300 MHz, DMSO) δ 11.72 (s, 1H), 8.18-8.09 (m, 2H), 7.19 (dd, J=3.6, 2.1 Hz, 1H), 6.59 (dd, J=3.7, 1.6 Hz, 1H), 4.05 (dd, J=6.5, 3.8 Hz, 2H), 3.84 (s, 2H), 3.66-3.13 (m, 6H), 3.13-2.90 (m, 2H), 2.72 (d, J=1.7 Hz, 3H), 2.59-2.39 (m, 1H), 2.05-1.86 (m, 1H), 1.60 (m, 1H), 1.04-0.81 (m, 4H).

LC-MS: 1.76 min, ES (+), m/z: 434.166

Example 129

3,3,3-trifluoro-N-methyl-N-[[5-(7H-pyrrolo[2,3-d]pyrimidin-4-yl)-5,8-diazaspiro[2.5]octan-8-yl]sulfonyl]propanamide

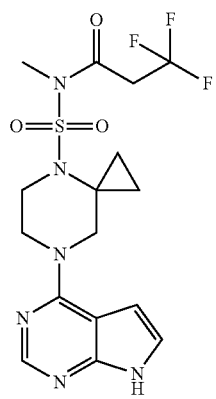 [SMILES: CN(C(=O)CC(F)(F)F)S(=O)(=O)N1CCN(c2ncnc3[nH]ccc23)CC12CC2]

3,3,3-trifluoropropanoic acid (0.24 mmol) was dissolved in dry DCM (0.5 mL) in a 4 mL vial, added oxalyl chloride (0.24 mmol) and a catalytic amount of DMF. Stirred at rt for 1 h and added to a mixture of intermediate 4 (0.05 mmol) and Et$_3$N (0.47 mmol) in dry DCM (0.5 mL). Stirred at rt for 16 h. Reaction mixture filtered through a syringe filter, added TFA (1 mL) and stirred at rt for 15 min. Reaction mixture added H$_2$O (5 mL) and extracted with DCM (3×5 mL). The organic phase was dried (Na$_2$SO$_4$), filtered, concentrated in vacuo and redissolved in DMSO (1 mL). The pure compound was obtained by standard preparative HPLC purification.

1H NMR (300 MHz, DMSO) δ 12.23 (s, 1H), 8.29 (s, 1H), 7.34 (dd, J=3.5, 2.2 Hz, 1H), 6.77 (dd, J=3.6, 1.7 Hz, 1H), 4.11 (dd, J=6.4, 4.0 Hz, 2H), 3.88 (s, 2H), 3.76 (dd, J=6.5, 3.9 Hz, 2H), 3.24 (s, 3H), 3.10 (m, 2H), 1.10-0.93 (m, 4H).

LC-MS: 2.11 min, ES (+), m/z: 433.117

Using this procedure the following compounds were obtained:

Example 130

4,4-difluoro-N-methyl-N-[[5-(7H-pyrrolo[2,3-d]pyrimidin-4-yl)-5,8-diazaspiro[2.5]octan-8-yl]sulfonyl]cyclohexanecarboxamide

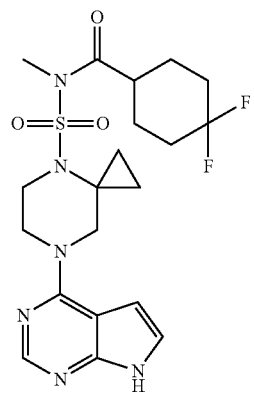 [SMILES: CN(C(=O)C1CCC(F)(F)CC1)S(=O)(=O)N1CCN(c2ncnc3[nH]ccc23)CC12CC2]

LC-MS: 2.21 min, ES (+), m/z: 469.184

Example 131

4,4,4-trifluoro-N-methyl-N-[[5-(7H-pyrrolo[2,3-d]pyrimidin-4-yl)-5,8-diazaspiro[2.5]octan-8-yl]sulfonyl]butanamide

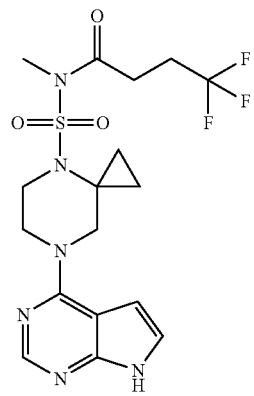 [SMILES: CN(C(=O)CCC(F)(F)F)S(=O)(=O)N1CCN(c2ncnc3[nH]ccc23)CC12CC2]

1H NMR (300 MHz, DMSO) δ 11.76 (s, 1H), 8.14 (d, J=5.5 Hz, 1H), 7.20 (q, J=3.0 Hz, 1H), 6.66-6.55 (m, 1H), 4.07 (dd, J=6.4, 3.9 Hz, 2H), 3.84 (s, 2H), 3.70 (t, J=5.2 Hz, 2H), 3.22 (s, 3H), 2.90 (t, J=7.4 Hz, 2H), 2.62-2.39 (m, 2H), 1.06-0.88 (m, 4H).

LC-MS: 2.17 min, ES (+), m/z: 447.139

Example 135

N-methyl-1,1-dioxo-N-[[5-(7H-pyrrolo[2,3-d]pyrimidin-4-yl)-5,8-diazaspiro[2.5]octan-8-yl]sulfonyl]thiolane-3-carboxamide

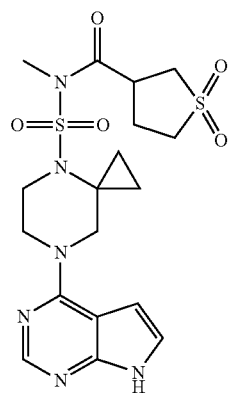 [SMILES: CN(C(=O)C1CCS(=O)(=O)C1)S(=O)(=O)N1CCN(c2ncnc3[nH]ccc23)CC12CC2]

1H NMR (300 MHz, DMSO) δ 11.76 (s, 1H), 8.15 (s, 1H), 7.21 (dd, J=3.6, 2.3 Hz, 1H), 6.61 (dd, J=3.7, 1.8 Hz, 1H), 4.14-4.00 (m, 2H), 3.90 (dd, J=8.7, 6.7 Hz, 1H), 3.83 (s, 2H), 3.77-3.63 (m, 2H), 3.44-3.29 (m, 2H), 3.25 (s, 3H), 3.23-3.04 (m, 2H), 2.50-2.30 (m, 1H), 2.08 (m, 1H), 1.10-0.92 (m, 4H).

LC-MS: 1.87 min, ES (+), m/z: 469.134

Example 136

2-(1,1-dioxothian-4-yl)-N-methyl-N-[[5-(7H-pyrrolo[2,3-d]pyrimidin-4-yl)-5,8-diazaspiro[2.5]octan-8-yl]sulfonyl]acetamide

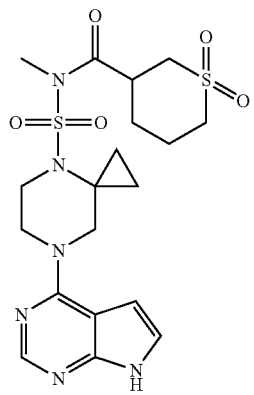

LC-MS: 1.88 min, ES (+), m/z: 497.164

Example 137

3-(1,1-dioxothiolan-3-yl)-N-methyl-N-[[5-(7H-pyrrolo[2,3-d]pyrimidin-4-yl)-5,8-diazaspiro[2.5]octan-8-yl]sulfonyl]propanamide

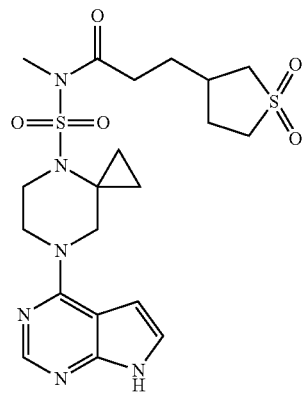 [SMILES: CN(C(=O)CCC1CCS(=O)(=O)C1)S(=O)(=O)N1CCN(c2ncnc3[nH]ccc23)CC12CC2]

1H NMR (300 MHz, DMSO) δ 11.76 (s, 1H), 8.14 (s, 1H), 7.21 (dd, J=3.6, 2.3 Hz, 1H), 6.61 (dd, J=3.5, 1.8 Hz, 1H), 4.06 (t, J=5.2 Hz, 2H), 3.83 (s, 2H), 3.71 (t, J=5.0 Hz, 2H), 3.31-3.10 (m, 5H), 3.10-2.93 (m, 1H), 2.78-2.57 (m, 3H), 2.39-2.16 (m, 2H), 1.80-1.57 (m, 3H), 1.04-0.88 (m, 4H).

LC-MS: 1.89 min, ES (+), m/z: 497.162

Example 138

2-(1,1-dioxothiolan-3-yl)-N-methyl-N-[[5-(7H-pyrrolo[2,3-d]pyrimidin-4-yl)-5,8-diazaspiro[2.5]octan-8-yl]sulfonyl]acetamide

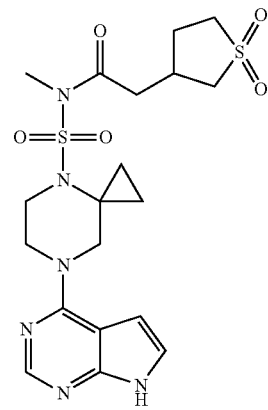 [SMILES: CN(C(=O)CC1CCS(=O)(=O)C1)S(=O)(=O)N1CCN(c2ncnc3[nH]ccc23)CC12CC2]

LC-MS: 1.87 min, ES (+), m/z: 483.148

Example 139

N-methyl-1,1-dioxo-N-[[5-(7H-pyrrolo[2,3-d]pyrimidin-4-yl)-5,8-diazaspiro[2.5]octan-8-yl]sulfonyl]thiane-4-carboxamide

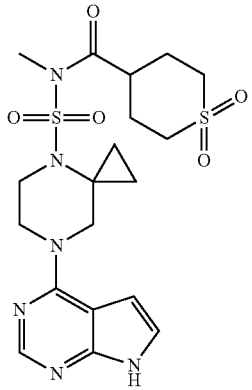

LC-MS: 1.90 min, ES (+), m/z: 483.150

Example 140

N-methyl-1,1-dioxo-N-[[5-(7H-pyrrolo[2,3-d]pyrimidin-4-yl)-5,8-diazaspiro[2.5]octan-8-yl]sulfonyl]thiane-3-carboxamide

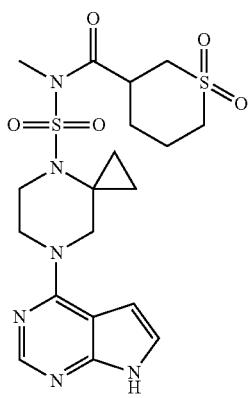 [SMILES: CN(C(=O)C1CCCS(=O)(=O)C1)S(=O)(=O)N1CCN(c2ncnc3[nH]ccc23)CC12CC2]

LC-MS: 1.91 min, ES (+), m/z: 483.148

Example 132

N-methyl-N-[[5-(7H-pyrrolo[2,3-d]pyrimidin-4-yl)-5,8-diazaspiro[2.5]octan-8-yl]sulfonyl]cyclopentanecarboxamide

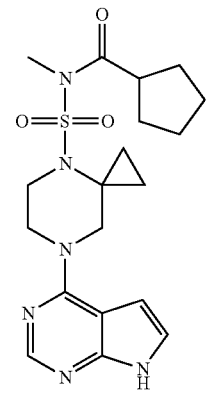 [SMILES: CN(C(=O)C1CCCC1)S(=O)(=O)N1CCN(c2ncnc3[nH]ccc23)CC12CC2]

Intermediate 4 (0.071 mmol) was dissolved in dry DCM (1 mL) and added commercial available cyclopentanecarbonyl chloride (0.085 mmol) and Et$_3$N (0.21 mmol). Stirred at rt for 1 h and then at 40° C. for 1.5 h. More 1,1-dioxothiolane-3-carbonyl chloride was added (2×0.107 mmol) with 1 h in between each portion. After being stirred at 40° C. for 1 h the reaction mixture was concentrated in vacuo, added 2,2,2-trifluoroethanol (1 mL) and stirred at 60° C. for 16 h. The pure compound was obtained by standard preparative HPLC purification of the reaction mixture.

1H NMR (300 MHz, DMSO) δ 11.74 (s, 1H), 8.14 (s, 1H), 7.20 (dd, J=3.5, 2.3 Hz, 1H), 6.61 (dd, J=3.7, 1.8 Hz, 1H), 4.11-3.99 (m, 2H), 3.83 (s, 2H), 3.70 (dd, J=6.5, 3.9 Hz, 2H), 3.23 (s, 3H), 1.89-1.67 (m, 3H), 1.58 (m, 6H), 0.97 (s, 4H).

LC-MS: 2.19 min, ES (+), m/z: 419.186

Using this procedure the following compounds were obtained:

Example 133

2-cyclopentyl-N-methyl-N-[[5-(7H-pyrrolo[2,3-d]pyrimidin-4-yl)-5,8-diazaspiro[2.5]octan-8-yl]sulfonyl]acetamide

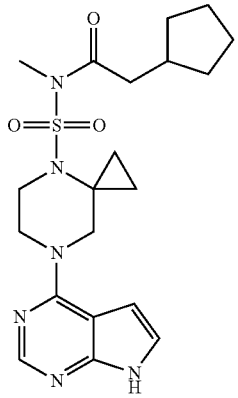

1H NMR (300 MHz, DMSO) δ 11.74 (s, 1H), 8.14 (s, 1H), 7.20 (dd, J=3.6, 2.3 Hz, 1H), 6.61 (dd, J=3.7, 1.8 Hz, 1H), 4.06 (dd, J=6.4, 3.9 Hz, 2H), 3.83 (s, 2H), 3.74-3.64 (m, 2H), 3.19 (s, 3H), 2.60 (d, J=7.0 Hz, 2H), 2.25-2.07 (m, 1H), 1.83-1.65 (m, 2H), 1.64-1.37 (m, 4H), 1.15-0.80 (m, 6H).

LC-MS: 2.33 min, ES (+), m/z: 433.199

Example 134

3-cyclopentyl-N-methyl-N-[[5-(7H-pyrrolo[2,3-d]pyrimidin-4-yl)-5,8-diazaspiro[2.5]octan-8-yl]sulfonyl]propanamide

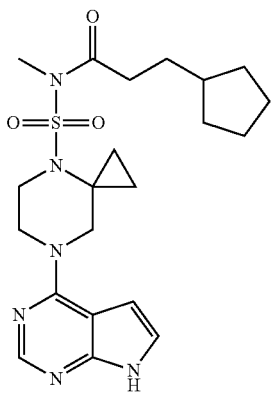 [SMILES: CN(C(=O)CCC1CCCC1)S(=O)(=O)N1CCN(c2ncnc3[nH]ccc23)CC12CC2]

1H NMR (300 MHz, DMSO) δ 11.74 (s, 1H), 8.14 (s, 1H), 7.20 (dd, J=3.6, 2.4 Hz, 1H), 6.61 (dd, J=3.5, 1.8 Hz, 1H), 4.06 (dd, J=6.4, 3.8 Hz, 2H), 3.84 (s, 2H), 3.70 (dd, J=6.4, 3.9 Hz, 2H), 3.19 (s, 3H), 2.58 (t, J=7.5 Hz, 2H), 1.83-1.36 (m, 8H), 1.17-0.80 (m, 7H).

LC-MS: 2.43 min, ES (+), m/z: 477.208

Example 141

N-cyclopropyl-N-methyl-5-(7H-pyrrolo[2,3-d]pyrimidin-4-yl)-5,8-diazaspiro[2.5]octane-8-sulfonamide

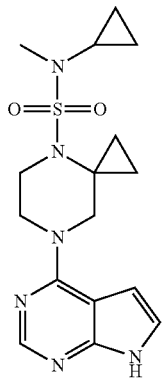 [SMILES: CN(C1CC1)S(=O)(=O)N1CCN(c2ncnc3[nH]ccc23)CC12CC2]

Sulfuryl chloride (1.44 mmol) was dissolved in dry DCM (3 mL), cooled to 0° C. and added a mixture of N-methylcyclopropanamine (0.48 mmol) and Et₃N (1.44 mmol) in dry DCM (1 mL). The reaction mixture was allowed to warm up freely to rt, stirred for 16 h. The reaction mixture was concentrated in vacuo and triturated with Et₂O (2×1 mL). Et₂O removed in vacuo and the obtained pale oil was dissolved in dry DCM (1 mL) and added to a solution of 4-(4,7-diaza-spiro[2.5]oct-7-yl)-7H-pyrrolo[2,3-d]pyrimidine (0.48 mmol) (intermediate 21) in a mixture of DMSO:DIPEA (2:1, 3 mL). The reaction mixture was stirred at 40° C. for 16 h. The pure compound was obtained by standard preparative HPLC purification of the reaction mixture.

1H NMR (300 MHz, DMSO) δ 11.72 (s, 1H), 8.13 (s, 1H), 7.19 (dd, J=3.6, 2.3 Hz, 1H), 6.59 (dd, J=3.6, 1.8 Hz, 1H), 4.05 (dd, J=6.4, 3.7 Hz, 2H), 3.83 (s, 2H), 3.55 (dd, J=6.2, 4.0 Hz, 2H), 2.70 (d, J=1.2 Hz, 3H), 2.31-2.19 (m, 1H), 1.05-0.83 (m, 4H), 0.73-0.56 (m, 4H).

LC-MS: 2.02 min, ES (+), m/z: 363.162

Using this procedure the following compounds were obtained:

Example 142

N-(2-cyanoethyl)-5-(7H-pyrrolo[2,3-d]pyrimidin-4-yl)-N-(tetrahydrofuran-2-ylmethyl)-5,8-diazaspiro[2.5]octane-8-sulfonamide

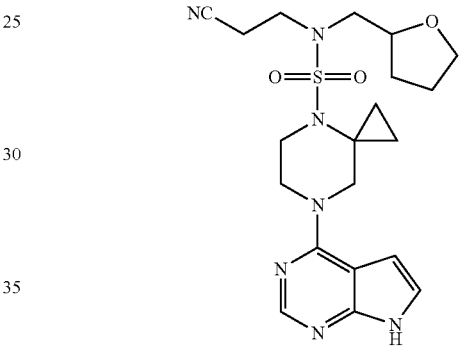

LC-MS: 1.98 min, ES (+), m/z: 446.191

Example 143

N-(1-methylbutyl)-5-(7H-pyrrolo[2,3-d]pyrimidin-4-yl)-5,8-diazaspiro[2.5]octane-8-sulfonamide

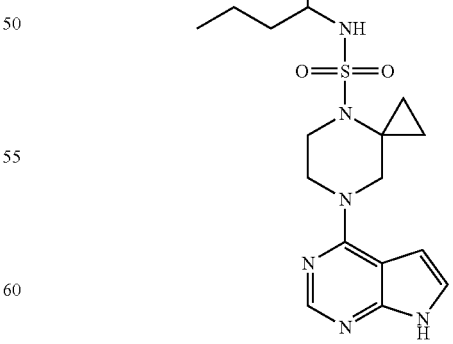

4-(4-Sulfamoyl-4,7-diaza-spiro[2.5]oct-7-yl)-pyrrolo[2,3-d]pyrimidine-7-carboxylic acid tert-butyl ester (intermediate 2) (0.049 mmol) was dissolved in dry DMF (1 mL) and added Cs₂CO₃ (0.147 mmol) and 2-bromopentane (0.074 mmol). Stirred at 60° C. for 16 h and then filtered through a syringe filter. The obtained filtrate was added 2,2,2-trifluoroethanol (1 mL) and heated to 100° C. for 1 h. The pure compound was obtained by standard preparative HPLC purification of the reaction mixture.

1H NMR (300 MHz, DMSO) δ 11.70 (s, 1H), 8.13 (s, 1H), 7.18 (dd, J=5.6, 2.2 Hz, 1H), 6.59 (dd, J=3.7, 1.8 Hz, 1H), 4.12-3.95 (m, 2H), 3.82 (d, J=1.9 Hz, 2H), 3.52 (d, J=4.4 Hz, 2H), 1.52-1.16 (m, 5H), 1.08-0.76 (m, 10H).

LC-MS: 2.13 min, ES (+), m/z: 379.187

Using this procedure the following compounds were obtained:

Example 144

N-cyclopentyl-5-(7H-pyrrolo[2,3-d]pyrimidin-4-yl)-5,8-diazaspiro[2.5]octane-8-sulfonamide

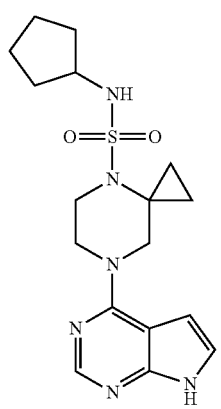

1H NMR (300 MHz, DMSO) δ 11.70 (s, 1H), 8.13 (s, 1H), 7.35 (d, J=6.9 Hz, 1H), 7.29-7.11 (m, 1H), 6.59 (dd, J=3.7, 1.8 Hz, 1H), 4.05 (t, J=5.1 Hz, 2H), 3.84 (s, 2H), 3.61-3.46 (m, 2H), 1.73 (dd, J=7.3, 4.3 Hz, 2H), 1.67-1.51 (m, 2H), 1.51-1.38 (m, 4H), 1.11-0.74 (m, 4H).

LC-MS: 2.05 min, ES (+), m/z: 377.171

Example 145

N,N-bis(cyanomethyl)-5-(7H-pyrrolo[2,3-d]pyrimidin-4-yl)-5,8-diazaspiro[2.5]octane-8-sulfonamide

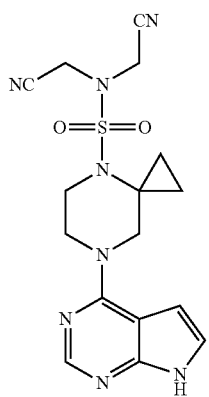 [SMILES: N#CCN(CC#N)S(=O)(=O)N1CCN(c2ncnc3[nH]ccc23)CC12CC2]

1H NMR (300 MHz, DMSO) δ 11.75 (s, 1H), 8.15 (s, 1H), 7.29-7.11 (m, 1H), 6.69-6.49 (m, 1H), 4.46 (s, 4H), 4.06 (t, J=5.1 Hz, 2H), 3.84 (s, 2H), 3.62 (d, J=5.4 Hz, 2H), 1.14-0.88 (m, 4H).

LC-MS: 1.88 min, ES (+), m/z: 387.136

Example 146

N,N-dibenzyl-5-(7H-pyrrolo[2,3-d]pyrimidin-4-yl)-5,8-diazaspiro[2.5]octane-8-sulfonamide

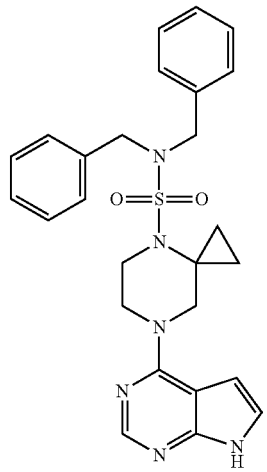 [SMILES: O=S(=O)(N(Cc1ccccc1)Cc1ccccc1)N1CCN(c2ncnc3[nH]ccc23)CC12CC2]

1H NMR (300 MHz, DMSO) δ 11.73 (s, 1H), 8.14 (s, 1H), 7.39-7.15 (m, 11H), 6.59 (d, J=3.4 Hz, 1H), 4.27 (s, 4H), 4.08 (t, J=4.9 Hz, 2H), 3.85 (s, 2H), 3.51-3.45 (m, 2H), 0.85 (d, J=9.8 Hz, 4H).

LC-MS: 2.50 min, ES (+), m/z: 489.176

Example 147

N-benzyl-5-(7H-pyrrolo[2,3-d]pyrimidin-4-yl)-5,8-diazaspiro[2.5]octane-8-sulfonamide

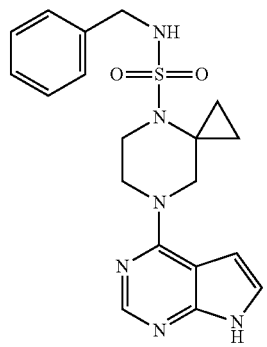 [SMILES: O=S(=O)(NCc1ccccc1)N1CCN(c2ncnc3[nH]ccc23)CC12CC2]

1H NMR (300 MHz, DMSO) δ 11.69 (s, 1H), 8.12 (s, 1H), 7.89 (t, J=6.0 Hz, 1H), 7.38-7.21 (m, 5H), 7.20-7.13 (m, 1H), 6.58 (d, J=3.9 Hz, 1H), 4.04 (t, J=5.2 Hz, 2H), 3.98 (d, J=4.7 Hz, 2H), 3.82 (s, 2H), 0.98-0.70 (m, 4H).

LC-MS: 2.06 min, ES (+), m/z: 399.134

Example 148

N-[(4,4-difluorocyclohexyl)methyl]-5-(7H-pyrrolo[2,3-d]pyrimidin-4-yl)-5,8-diazaspiro[2.5]octane-8-sulfonamide

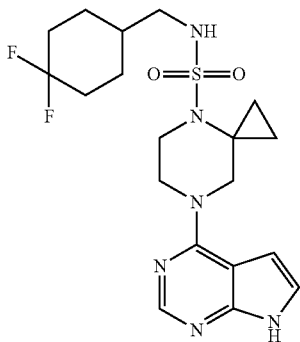 [SMILES: O=S(=O)(NCC1CCC(F)(F)CC1)N1CCN(c2ncnc3[nH]ccc23)CC12CC2]

Example 149

N-[(4,4-difluorocyclohexyl)methyl]-N-ethyl-5-(7H-pyrrolo[2,3-d]pyrimidin-4-yl)-5,8-diazaspiro[2.5]octane-8-sulfonamide

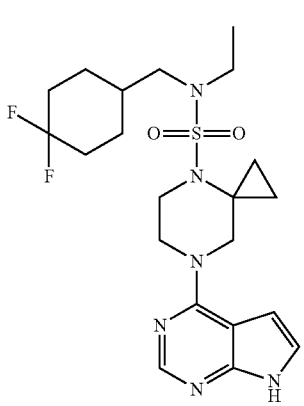 [SMILES: CCN(CC1CCC(F)(F)CC1)S(=O)(=O)N1CCN(c2ncnc3[nH]ccc23)CC12CC2]

Example 150

N,N-bis[(4,4-difluorocyclohexyl)methyl]-5-(7H-pyrrolo[2,3-d]pyrimidin-4-yl)-5,8-diazaspiro[2.5]octane-8-sulfonamide

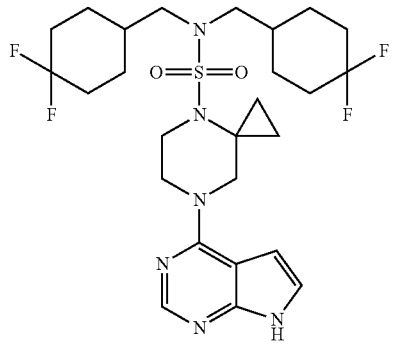 [SMILES: O=S(=O)(N(CC1CCC(F)(F)CC1)CC1CCC(F)(F)CC1)N1CCN(c2ncnc3[nH]ccc23)CC12CC2]

4-(4-Sulfamoyl-4,7-diaza-spiro[2.5]oct-7-yl)-pyrrolo[2,3-d]pyrimidine-7-carboxylic acid tert-butyl ester (intermediate 2) (0.049 mmol) was dissolved in dry DMF (1 mL) and added Cs$_2$CO$_3$ (0.147 mmol) and 4-(bromomethyl)-1,1-difluoro-cyclohexane (0.044 mmol) and stirred at 45° C. for 16 h. The obtained reaction mixture was added bromoethane (0.098 mmol) and stirred at 45° C. for 2 h before being filtered through a syringe filter. The obtained filtrate was added 2,2,2-trifluoroethanol (1 mL) and heated to 100° C. for 1 h. The pure compounds were obtained by standard preparative HPLC purification of the reaction mixture.

Example 148

1H NMR (300 MHz, DMSO) δ 11.71 (s, 1H), 8.13 (s, 1H), 7.43 (t, J=6.0 Hz, 1H), 7.18 (dd, J=3.5, 2.3 Hz, 1H), 6.59 (dd, J=3.5, 1.8 Hz, 1H), 4.05 (t, J=5.0 Hz, 2H), 3.84 (s, 2H), 3.55 (t, J=5.2 Hz, 2H), 2.66 (t, J=6.4 Hz, 2H), 2.07-1.91 (m, 2H), 1.84-1.64 (m, 3H), 1.29-1.07 (m, 4H), 1.06-0.78 (m, 4H).

LC-MS: 2.12 min, ES (+), m/z: 441.187

Example 149

LC-MS: 2.31 min, ES (+), m/z: 469.220

Example 150

1H NMR (300 MHz, DMSO) δ 11.72 (s, 1H), 8.49 (s, 1H), 7.23-7.12 (m, 1H), 6.59 (dd, J=3.7, 1.8 Hz, 1H), 4.11-4.02 (m, 2H), 3.82 (s, 2H), 3.49-3.44 (m, 2H), 2.99 (d, J=6.8 Hz, 4H), 2.10-1.66 (m, 14H), 1.35-1.07 (m, 4H), 1.00-0.79 (m, 4H).

LC-MS: 2.49 min, ES (+), m/z: 537.260

Example 151

N-[[1-(3-hydroxypropanoyl)-4-piperidyl]methyl]-N-methyl-5-(7H-pyrrolo[2,3-d]pyrimidin-4-yl)-5,8-diazaspiro[2.5]octane-8-sulfonamide

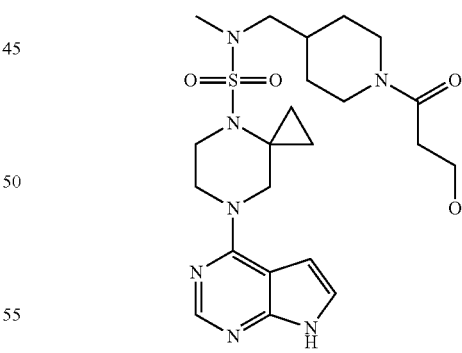

Prepared in a similar manner as example 123, using intermediate 26, instead of intermediate 25.

1H NMR (300 MHz, DMSO) δ 11.72 (s, 1H), 8.13 (s, 1H), 7.19 (dd, J=3.6, 2.4 Hz, 1H), 6.59 (dd, J=3.7, 1.8 Hz, 1H), 4.56-4.32 (m, 2H), 4.04 (d, J=5.2 Hz, 2H), 3.94-3.78 (m, 3H), 3.61 (t, J=6.6 Hz, 2H), 3.52 (t, J=5.0 Hz, 2H), 3.05-2.89 (m, 3H), 2.69 (s, 3H), 2.49-2.40 (m, 3H), 1.90-1.75 (m, 1H), 1.66 (t, J=14.1 Hz, 2H), 1.16-0.83 (m, 6H).

LC-MS: 1.76 min, ES (+), m/z: 492.218

Using this procedure the following compounds were obtained:

Example 152

N-[[1-(3-cyanopropanoyl)-4-piperidyl]methyl]-N-methyl-5-(7H-pyrrolo[2,3-d]pyrimidin-4-yl)-5,8-diazaspiro[2.5]octane-8-sulfonamide

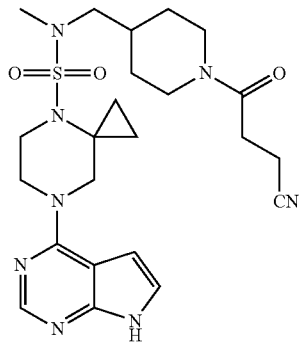 [SMILES: CN(CC1CCN(C(=O)CCC#N)CC1)S(=O)(=O)N1CCN(c2ncnc3[nH]ccc23)CC12CC2]

1H NMR (300 MHz, DMSO) δ 11.71 (s, 1H), 8.13 (s, 1H), 7.19 (dd, J=3.6, 2.3 Hz, 1H), 6.59 (dd, J=3.5, 1.8 Hz, 1H), 4.36 (d, J=13.0 Hz, 1H), 4.04 (t, J=5.1 Hz, 2H), 3.91-3.75 (m, 3H), 3.52 (t, J=5.1 Hz, 2H), 3.04-2.88 (m, 3H), 2.77-2.64 (m, 5H), 2.59 (dd, J=7.1, 5.3 Hz, 3H), 1.84 (ddd, J=11.1, 7.6, 3.9 Hz, 1H), 1.66 (s, 2H), 1.18-0.77 (m, 6H).

LC-MS: 1.89 min, ES (+), m/z: 501.212

Example 153

N-[[1-(3-cyanopropanoyl)-3-piperidyl]methyl]-N-methyl-5-(7H-pyrrolo[2,3-d]pyrimidin-4-yl)-5,8-diazaspiro[2.5]octane-8-sulfonamide

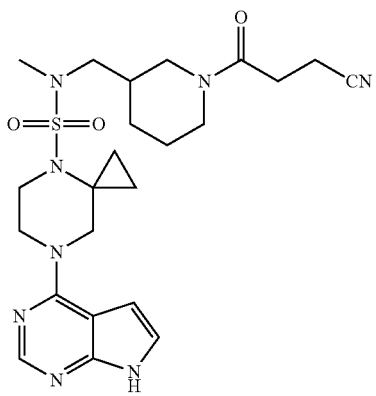 [SMILES: CN(CC1CCCN(C(=O)CCC#N)C1)S(=O)(=O)N1CCN(c2ncnc3[nH]ccc23)CC12CC2]

Prepared in a similar manner as example 123, using intermediate 27, instead of intermediate 25.

LC-MS: 1.92 min, ES (+), m/z: 501.215

Using this procedure the following compounds were obtained:

Example 154

N-[[1-(3-hydroxypropanoyl)-3-piperidyl]methyl]-N-methyl-5-(7H-pyrrolo[2,3-d]pyrimidin-4-yl)-5,8-diazaspiro[2.5]octane-8-sulfonamide

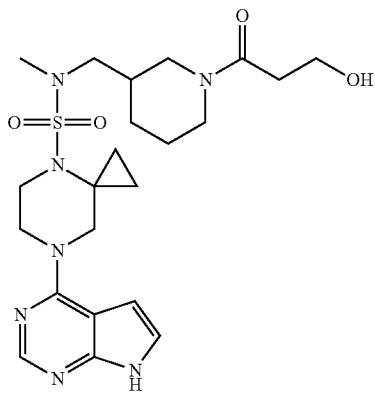 [SMILES: CN(CC1CCCN(C(=O)CCO)C1)S(=O)(=O)N1CCN(c2ncnc3[nH]ccc23)CC12CC2]

1H NMR (300 MHz, DMF) δ 11.95 (s, 1H), 8.34 (s, 1H), 7.40 (dd, J=3.6, 2.4 Hz, 1H), 6.81 (dd, J=3.6, 1.8 Hz, 1H), 4.46 (d, J=13.1 Hz, 1H), 4.25 (t, J=5.3 Hz, 2H), 4.04 (m, 3H), 3.88-3.78 (m, 2H), 3.73 (t, J=5.0 Hz, 2H), 3.28-3.07 (m, 3H), 3.03-2.79 (m, 5H), 2.63-2.50 (m, 2H), 2.09-1.76 (m, 3H), 1.66-1.31 (m, 2H), 1.30-1.03 (m, 4H).

LC-MS: 1.79 min, ES (+), m/z: 492.242

Example 155

N-[[(2S)-4,4-difluoro-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide

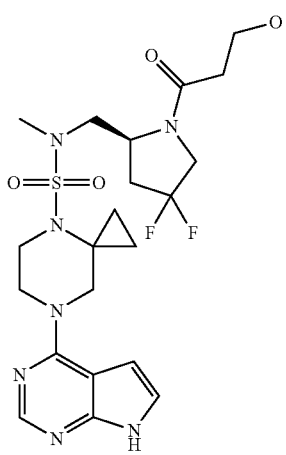

Prepared in a similar manner as example 123, using intermediate 28, instead of intermediate 25.

1H NMR (300 MHz, DMSO) δ 11.72 (s, 1H), 8.13 (s, 1H), 7.19 (dd, J=3.7, 2.4 Hz, 1H), 6.59 (dd, J=3.7, 1.8 Hz, 1H), 4.53 (t, J=5.3 Hz, 1H), 4.47-4.28 (m, 1H), 4.00 (dd, J=24.5, 9.9 Hz, 4H), 3.83 (d, J=3.5 Hz, 2H), 3.64 (p, J=5.6 Hz, 2H), 3.52 (m, 2H), 3.20 (d, J=5.8 Hz, 2H), 2.77 (d, J=7.1 Hz, 3H), 2.40 (q, J=6.6 Hz, 3H), 1.08-0.81 (m, 4H).

LC-MS: 1.82 min, ES (+), m/z: 514.208

Using this procedure the following compounds were obtained:

Example 156

N-[[(2S)-1-(3-cyanopropanoyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide

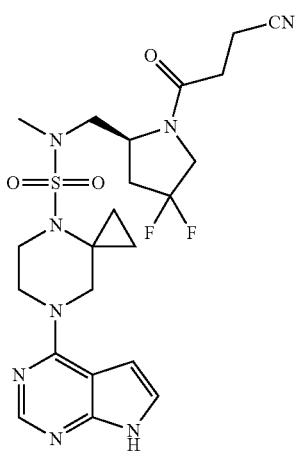 [SMILES: CN(C[C@@H]1CC(F)(F)CN1C(=O)CCC#N)S(=O)(=O)N1CCN(c2ncnc3[nH]ccc23)CC12CC2]

1H NMR (300 MHz, DMSO) δ 11.71 (s, 1H), 8.13 (d, J=1.4 Hz, 1H), 7.19 (dd, J=3.5, 2.3 Hz, 1H), 6.59 (dd, J=3.5, 1.8 Hz, 1H), 4.57-4.36 (m, 1H), 4.14-3.91 (m, 4H), 3.83 (d, J=3.9 Hz, 2H), 3.52 (t, J=5.3 Hz, 2H), 3.23-3.09 (m, 3H), 2.78 (d, J=4.2 Hz, 3H), 2.69-2.58 (m, 4H), 2.47-2.30 (m, 1H), 1.07-0.82 (m, 4H).

LC-MS: 1.96 min, ES (+), m/z: 523.202

Example 157

N-[[(2S)-4,4-difluoro-1-formyl-pyrrolidin-2-yl]methyl]-N-methyl-5-(7H-pyrrolo[2,3-d]pyrimidin-4-yl)-5,8-diazaspiro[2.5]octane-8-sulfonamide

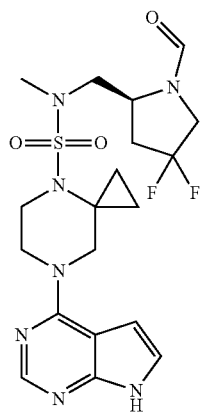

1H NMR (300 MHz, DMSO) δ 11.72 (s, 1H), 8.13 (s, 1H), 7.19 (dd, J=3.6, 2.4 Hz, 1H), 6.59 (dd, J=3.7, 1.8 Hz, 1H), 4.49-4.35 (m, 1H), 4.04 (d, J=5.5 Hz, 2H), 3.97 (d, J=13.5 Hz, 1H), 3.83 (d, J=1.9 Hz, 2H), 3.57-3.48 (m, 2H), 3.23-3.10 (m, 2H), 2.76 (d, J=3.0 Hz, 3H), 1.08-0.78 (m, 4H).

LC-MS: 1.85 min, ES (+), m/z: 470.180

Example 158

N-methyl-N-[(1-methylsulfonyl-4-piperidyl)methyl]-5-(7H-pyrrolo[2,3-d]pyrimidin-4-yl)-5,8-diazaspiro[2.5]octane-8-sulfonamide

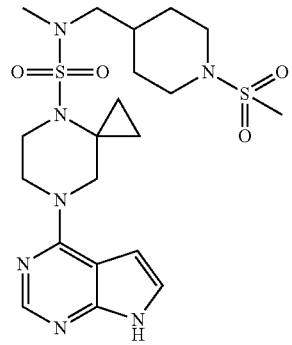 [SMILES: CN(CC1CCN(S(C)(=O)=O)CC1)S(=O)(=O)N1CCN(c2ncnc3[nH]ccc23)CC12CC2]

Prepared in a similar manner as example 118, using intermediate 26, instead of intermediate 25.

1H NMR (300 MHz, DMSO) δ 11.71 (s, 1H), 8.13 (s, 1H), 7.19 (dd, J=3.7, 2.3 Hz, 1H), 6.59 (dd, J=3.7, 1.8 Hz, 1H), 4.05 (t, J=5.1 Hz, 2H), 3.84 (s, 2H), 3.62-3.48 (m, 4H), 2.98 (d, J=6.6 Hz, 2H), 2.84 (s, 3H), 2.78-2.63 (m, 5H), 1.83-1.63 (m, 3H), 1.26-1.08 (m, 2H), 1.06-0.83 (m, 4H).

LC-MS: 1.94 min, ES (+), m/z: 498.191

Using this procedure the following compounds were obtained:

Example 159

N-[[1-(3-cyanopropylsulfonyl)-4-piperidyl]methyl]-N-methyl-5-(7H-pyrrolo[2,3-d]pyrimidin-4-yl)-5,8-diazaspiro[2.5]octane-8-sulfonamide

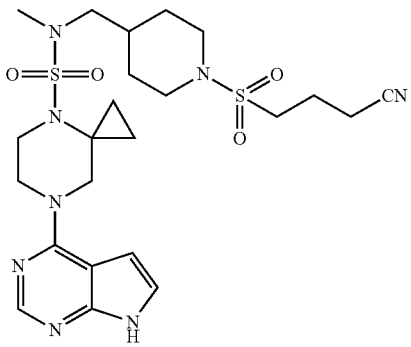 [SMILES: CN(CC1CCN(S(=O)(=O)CCCC#N)CC1)S(=O)(=O)N1CCN(c2ncnc3[nH]ccc23)CC12CC2]

1H NMR (300 MHz, DMSO) δ 11.71 (s, 1H), 8.13 (s, 1H), 7.19 (dd, J=3.6, 2.4 Hz, 1H), 6.59 (dd, J=3.7, 1.7 Hz, 1H), 4.04 (d, J=5.4 Hz, 2H), 3.84 (s, 2H), 3.61 (d, J=12.4 Hz, 2H), 3.53 (dd, J=6.3, 3.7 Hz, 2H), 3.16-3.04 (m, 2H), 2.98 (d, J=6.7 Hz, 2H), 2.81 (td, J=12.2, 2.3 Hz, 2H), 2.69 (s, 3H), 2.65 (t, J=7.3 Hz, 2H), 2.09-1.88 (m, 2H), 1.73 (d, J=11.7 Hz, 3H), 1.27-1.03 (m, 2H), 1.03-0.79 (m, 4H).

LC-MS: 2.01 min, ES (+), m/z: 551.213

Example 160

N-methyl-N-[(1-methylsulfonyl-3-piperidyl)methyl]-5-(7H-pyrrolo[2,3-d]pyrimidin-4-yl)-5,8-diazaspiro[2.5]octane-8-sulfonamide

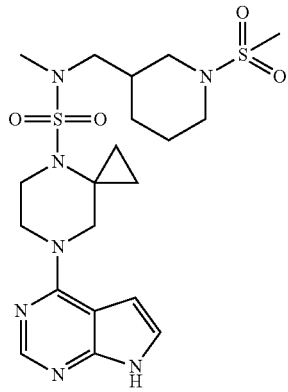 [SMILES: CN(CC1CCCN(S(C)(=O)=O)C1)S(=O)(=O)N1CCN(c2ncnc3[nH]ccc23)CC12CC2]

Prepared in a similar manner as example 118, using intermediate 27, instead of intermediate 25.

1H NMR (300 MHz, DMSO) δ 11.71 (s, 1H), 8.14 (s, 1H), 7.19 (dd, J=3.6, 2.3 Hz, 1H), 6.59 (dd, J=3.7, 1.8 Hz, 1H), 4.09-3.96 (m, 2H), 3.84 (s, 2H), 3.53 (t, J=5.3 Hz, 2H), 3.49-3.35 (m, 2H), 3.00 (d, J=7.2 Hz, 2H), 2.83 (s, 3H), 2.80-2.60 (m, 4H), 2.50-2.46 (m, 1H), 1.95-1.83 (m, 1H), 1.83-1.61 (m, 2H), 1.58-1.41 (m, 1H), 1.09 (dd, J=11.3, 9.0 Hz, 1H), 1.02-0.81 (m, 4H).

LC-MS: 1.97 min, ES (+), m/z: 498.184

Using this procedure the following compounds were obtained:

Example 161

N-[[1-(3-cyanopropylsulfonyl)-3-piperidyl]methyl]-N-methyl-5-(7H-pyrrolo[2,3-d]pyrimidin-4-yl)-5,8-diazaspiro[2.5]octane-8-sulfonamide

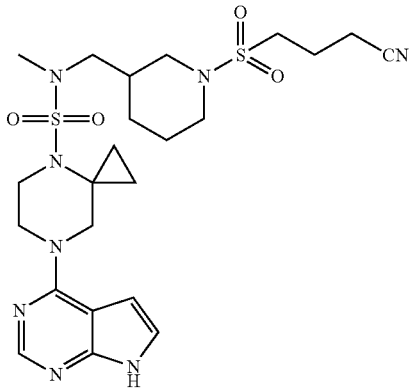 [SMILES: CN(CC1CCCN(S(=O)(=O)CCCC#N)C1)S(=O)(=O)N1CCN(c2ncnc3[nH]ccc23)CC12CC2]

1H NMR (300 MHz, DMSO) δ 11.71 (s, 1H), 8.14 (s, 1H), 7.19 (dd, J=3.6, 2.3 Hz, 1H), 6.59 (dd, J=3.7, 1.8 Hz, 1H), 4.05 (s, 1H), 3.84 (s, 2H), 3.62-3.42 (m, 5H), 3.14-3.05 (m, 2H), 2.99 (d, J=7.2 Hz, 2H), 2.89-2.77 (m, 1H), 2.69 (s, 3H), 2.65 (t, J=7.4 Hz, 2H), 2.61-2.53 (m, 1H), 1.98 (p, J=7.3 Hz, 2H), 1.91-1.80 (m, 1H), 1.78-1.64 (m, 2H), 1.57-1.35 (m, 1H), 1.22-1.04 (m, 1H), 1.04-0.75 (m, 4H).

LC-MS: 2.04 min, ES (+), m/z: 551.215

Example 162

N-[[(2S)-4,4-difluoro-1-methylsulfonyl-pyrrolidin-2-yl]methyl]-N-methyl-5-(7H-pyrrolo[2,3-d]pyrimidin-4-yl)-5,8-diazaspiro[2.5]octane-8-sulfonamide

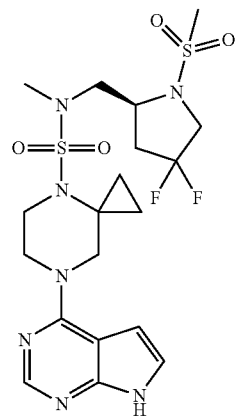 [SMILES: CN(C[C@@H]1CC(F)(F)CN1S(C)(=O)=O)S(=O)(=O)N1CCN(c2ncnc3[nH]ccc23)CC12CC2]

Prepared in a similar manner as example 118, using intermediate 28, instead of intermediate 25.

1H NMR (300 MHz, DMSO) δ 11.71 (s, 1H), 8.14 (s, 1H), 7.19 (dd, J=3.6, 2.3 Hz, 1H), 6.59 (dd, J=3.7, 1.8 Hz, 1H), 4.27-4.13 (m, 1H), 4.10-4.00 (m, 2H), 3.99-3.63 (m, 4H), 3.53 (t, J=5.1 Hz, 2H), 3.29 (d, J=7.5 Hz, 2H), 3.06 (s, 3H), 2.77 (s, 3H), 2.74-2.56 (m, 1H), 2.46-2.33 (m, 1H), 1.06-0.82 (m, 4H).

LC-MS: 2.02 min, ES (+), m/z: 520.162

Using this procedure the following compounds were obtained:

Example 163

N-[[(2S)-1-(3-cyanopropylsulfonyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide

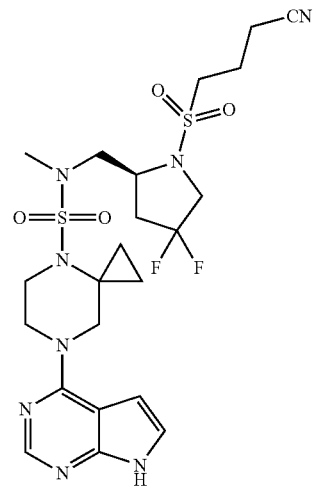 [SMILES: CN(C[C@@H]1CC(F)(F)CN1S(=O)(=O)CCCC#N)S(=O)(=O)N1CCN(c2ncnc3[nH]ccc23)CC12CC2]

1H NMR (300 MHz, DMSO) δ 11.71 (s, 1H), 8.14 (s, 1H), 7.19 (dd, J=3.6, 2.4 Hz, 1H), 6.59 (dd, J=3.5, 1.8 Hz, 1H), 4.34-4.18 (m, 1H), 4.12-4.01 (m, 2H), 4.01-3.64 (m, 4H), 3.54 (t, J=5.1 Hz, 2H), 3.37-3.21 (m, 4H), 2.76 (s, 3H), 2.65 (t, J=7.3 Hz, 2H), 2.51-2.32 (m, 1H), 2.10-1.92 (m, 2H), 1.04-0.82 (m, 4H).

LC-MS: 2.07 min, ES (+), m/z: 573.185

Example 164

N-[[(2S)-1-(cyclopropylmethylsulfonyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide

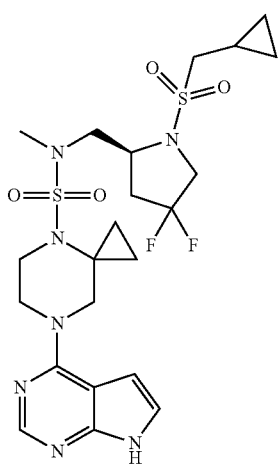 [SMILES: CN(C[C@@H]1CC(F)(F)CN1S(=O)(=O)CC1CC1)S(=O)(=O)N1CCN(c2ncnc3[nH]ccc23)CC12CC2]

LC-MS: 2.19 min, ES (+), m/z: 560.193

Example 165

N-[(1,1-dioxothiolan-3-yl)methyl]-N-methyl-5-(7H-pyrrolo[2,3-d]pyrimidin-4-yl)-5,8-diazaspiro[2.5]octane-8-sulfonamide

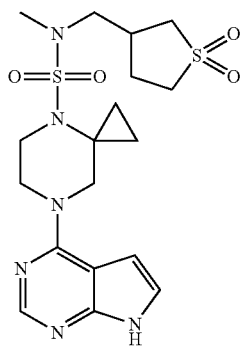 [SMILES: CN(CC1CCS(=O)(=O)C1)S(=O)(=O)N1CCN(c2ncnc3[nH]ccc23)CC12CC2]

Prepared in a similar manner as example 143, using intermediate 42, instead of intermediate 2.

1H NMR (300 MHz, DMSO) δ 11.79 (s, 1H), 8.16 (s, 1H), 7.25-7.14 (m, 1H), 6.62 (dd, J=3.7, 1.8 Hz, 1H), 4.06 (t, J=5.2 Hz, 2H), 3.84 (s, 2H), 3.54 (t, J=5.2 Hz, 2H), 3.26-3.00 (m, 6H), 2.91-2.74 (m, 1H), 2.72 (s, 3H), 2.30-2.13 (m, 1H), 1.89-1.69 (m, 1H), 1.04-0.84 (m, 4H).

LC-MS: 1.81 min, ES (+), m/z: 455.197

Example 166

N-(cyanomethyl)-N-[(1,1-dioxothiolan-3-yl)methyl]-5-(7H-pyrrolo[2,3-d]pyrimidin-4-yl)-5,8-diazaspiro[2.5]octane-8-sulfonamide

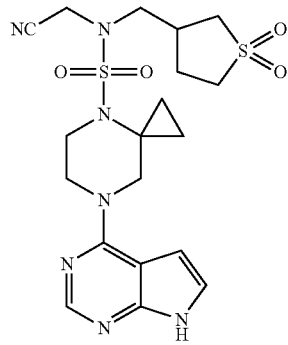 [SMILES: N#CCN(CC1CCS(=O)(=O)C1)S(=O)(=O)N1CCN(c2ncnc3[nH]ccc23)CC12CC2]

1H NMR (300 MHz, DMSO) δ 12.30 (s, 1H), 8.31 (s, 1H), 7.39-7.32 (m, 1H), 6.80 (dd, J=3.7, 1.8 Hz, 1H), 4.39 (s, 2H), 4.13 (d, J=5.5 Hz, 2H), 3.90 (s, 2H), 3.60 (t, J=5.2 Hz, 2H), 3.32 (dd, J=7.1, 1.8 Hz, 2H), 3.28-3.15 (m, 2H), 3.15-3.01 (m, 1H), 2.92-2.70 (m, 2H), 2.30-2.18 (m, 1H), 1.82 (m, J=13.1, 9.1 Hz, 1H), 1.17-0.92 (m, 4H).

LC-MS: 1.84 min, ES (+), m/z: 480.133

Example 167

N-[(1,1-dioxothiolan-3-yl)methyl]-N-(2-hydroxyethyl)-5-(7H-pyrrolo[2,3-d]pyrimidin-4-yl)-5,8-diazaspiro[2.5]octane-8-sulfonamide

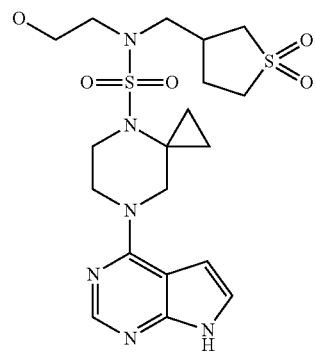 [SMILES: O=S1(=O)CCC(CN(CCO)S(=O)(=O)N2CCN(c3ncnc4[nH]ccc34)CC23CC3)C1]

1H NMR (300 MHz, DMSO) δ 12.22 (s, 1H), 8.28 (s, 1H), 7.36-7.28 (m, 1H), 6.77 (dd, J=3.6, 1.7 Hz, 1H), 4.11 (t, J=5.1 Hz, 2H), 3.89 (s, 2H), 3.60-3.48 (m, 4H), 3.33-3.00 (m, 8H), 2.87-2.64 (m, 2H), 2.36-2.11 (m, 1H), 1.93-1.67 (m, 1H), 1.11-0.83 (m, 4H).

LC-MS: 1.70 min, ES (+), m/z: 485.163

Example 178

N-[1-(2-hydroxyacetyl)azetidin-3-yl]-N-methyl-5-(7H-pyrrolo[2,3-d]pyrimidin-4-yl)-5,8-diazaspiro[2.5]octane-8-sulfonamide

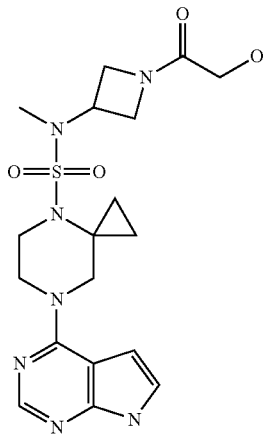 [SMILES: CN(C1CN(C(=O)CO)C1)S(=O)(=O)N1CCN(c2ncnc3[nH]ccc23)CC12CC2]

Prepared in a similar manner as example 123, using intermediate 50, instead of intermediate 25.

1H NMR (300 MHz, DMSO) δ 11.74 (b, 1H), 8.14 (s, 1H), 7.19 (d, J=3.5 Hz, 1H), 6.59 (d, J=3.6 Hz, 1H), 4.87 (b, 1H), 4.61-4.46 (m, 1H), 4.31 (q, J=7.9, 6.2 Hz, 2H), 4.02 (dt, J=11.9, 5.4 Hz, 4H), 3.90 (s, 2H), 3.81 (s, 2H), 3.51 (dd, J=6.2, 3.8 Hz, 2H), 2.77 (s, 3H), 1.08-0.82 (m, 4H).

LC-MS: 1.66 min, ES (+), m/z: 436.176

Using this procedure the following compounds were obtained:

Example 179

N-[1-(3-hydroxypropanoyl)azetidin-3-yl]-N-methyl-5-(7H-pyrrolo[2,3-d]pyrimidin-4-yl)-5,8-diazaspiro[2.5]octane-8-sulfonamide

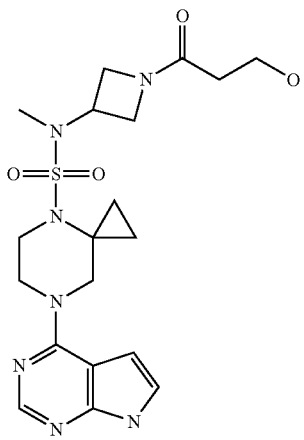 [SMILES: CN(C1CN(C(=O)CCO)C1)S(=O)(=O)N1CCN(c2ncnc3[nH]ccc23)CC12CC2]

1H NMR (300 MHz, DMSO) δ 11.72 (s, 1H), 8.14 (s, 1H), 7.19 (dd, J=3.6, 1.7 Hz, 1H), 6.59 (d, J=3.5 Hz, 1H), 4.62-4.44 (m, 2H), 4.33-4.19 (m, 2H), 4.10-4.01 (m, 2H), 4.01-3.88 (m, 2H), 3.82 (s, 2H), 3.64-3.55 (m, 2H), 3.51 (t, J=5.0 Hz, 2H), 2.77 (s, 3H), 2.20 (td, J=6.5, 3.4 Hz, 2H), 1.09-0.80 (m, 4H).

LC-MS: 1.66 min, ES (+), m/z: 450.193

Example 180

N-methyl-N-(1-methylsulfonylazetidin-3-yl)-5-(7H-pyrrolo[2,3-d]pyrimidin-4-yl)-5,8-diazaspiro[2.5]octane-8-sulfonamide

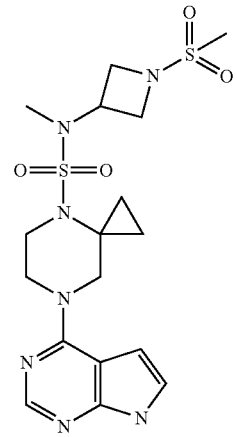 [SMILES: CN(C1CN(S(C)(=O)=O)C1)S(=O)(=O)N1CCN(c2ncnc3[nH]ccc23)CC12CC2]

Prepared in a similar manner as example 118, using intermediate 50, instead of intermediate 25.

1H NMR (300 MHz, DMSO) δ 11.72 (s, 1H), 8.14 (s, 1H), 7.19 (dd, J=3.7, 1.8 Hz, 1H), 6.58 (d, J=3.4 Hz, 1H), 4.57-4.41 (m, 1H), 4.12-3.92 (m, 6H), 3.81 (s, 2H), 3.52 (t, J=5.0 Hz, 2H), 3.28 (s, 1H), 3.06 (s, 3H), 2.78 (s, 3H), 1.07-0.83 (m, 4H).

LC-MS: 1.85 min, ES (+), m/z: 456.149

Example 181

N-methyl-N-[[(2R)-1-methylsulfonylpyrrolidin-2-yl]methyl]-5-(7H-pyrrolo[2,3-d]pyrimidin-4-yl)-5,8-diazaspiro[2.5]octane-8-sulfonamide

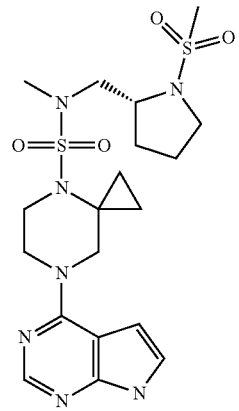

Prepared in a similar manner as example 118, using intermediate 51, instead of intermediate 25.

1H NMR (300 MHz, DMSO) δ 11.68 (b, 1H), 8.14 (s, 1H), 7.19 (d, J=3.6 Hz, 1H), 6.59 (d, J=3.6 Hz, 1H), 4.12-3.99 (m, 2H), 3.91-3.74 (m, 3H), 3.53 (t, J=5.1 Hz, 2H), 3.31-3.04 (m, 4H), 2.93 (s, 3H), 2.74 (s, 3H), 1.87 (m, 4H), 1.08-0.80 (m, 4H).

LC-MS: 1.91 min, ES (+), m/z: 484.178

Using this procedure the following compounds were obtained:

Example 182

N-[[(2R)-1-(3-cyanopropylsulfonyl)pyrrolidin-2-yl]methyl]-N-methyl-5-(7H-pyrrolo[2,3-d]pyrimidin-4-yl)-5,8-diazaspiro[2.5]octane-8-sulfonamide

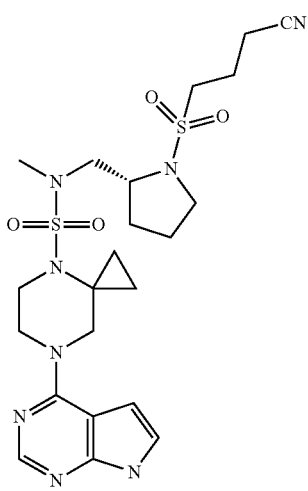 [SMILES: CN(C[C@H]1CCCN1S(=O)(=O)CCCC#N)S(=O)(=O)N1CCN(c2ncnc3[nH]ccc23)CC12CC2]

1H NMR (300 MHz, DMSO) δ 11.73 (b, 1H), 8.14 (s, 1H), 7.19 (d, J=3.6 Hz, 1H), 6.59 (d, J=3.6 Hz, 1H), 4.14-3.99 (m, 2H), 3.99-3.86 (m, 1H), 3.83 (d, J=2.3 Hz, 2H), 3.53 (t, J=5.1 Hz, 2H), 3.31-3.04 (m, 6H), 2.74 (s, 3H), 2.65 (t, J=7.2 Hz, 2H), 2.11-1.81 (m, 6H), 1.08-0.81 (m, 4H).
LC-MS: 1.98 min, ES (+), m/z: 537.205

Example 185

N-[[(2R)-1-(2-hydroxyacetyl)pyrrolidin-2-yl]methyl]-N-methyl-5-(7H-pyrrolo[2,3-d]pyrimidin-4-yl)-5,8-diazaspiro[2.5]octane-8-sulfonamide

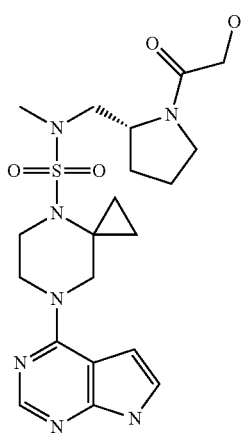 [SMILES: CN(C[C@H]1CCCN1C(=O)CO)S(=O)(=O)N1CCN(c2ncnc3[nH]ccc23)CC12CC2]

Prepared in a similar manner as example 123, using intermediate 51, instead of intermediate 25.
1H NMR (300 MHz, DMSO) δ 11.92 (s, 1H), 8.19 (s, 1H), 7.25 (dd, J=3.7, 2.3 Hz, 1H), 6.67 (dd, J=3.5, 1.7 Hz, 1H), 4.14 (s, 1H), 4.11-4.02 (m, 2H), 3.98 (d, J=1.8 Hz, 2H), 3.85 (s, 2H), 3.54 (t, J=5.1 Hz, 2H), 3.42-3.24 (m, 3H), 3.23-3.00 (m, 2H), 2.76 (s, 3H), 1.85 (td, J=11.6, 5.2 Hz, 4H), 1.08-0.81 (m, 4H).
LC-MS: 1.76 min, ES (+), m/z: 464.205

Using this procedure the following compounds were obtained:

Example 186

N-[[(2R)-1-(2,3-dihydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide

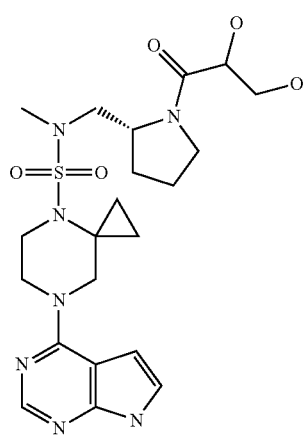 [SMILES: CN(C[C@H]1CCCN1C(=O)C(O)CO)S(=O)(=O)N1CCN(c2ncnc3[nH]ccc23)CC12CC2]

LC-MS: 1.70 min, ES (+), m/z: 494.218

Example 187

N-[[(2R)-1-(3-cyanopropanoyl)pyrrolidin-2-yl]methyl]-N-methyl-5-(7H-pyrrolo[2,3-d]pyrimidin-4-yl)-5,8-diazaspiro[2.5]octane-8-sulfonamide

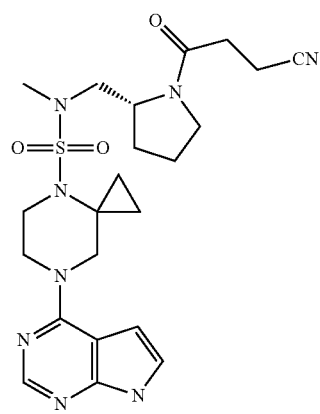 [SMILES: CN(C[C@H]1CCCN1C(=O)CCC#N)S(=O)(=O)N1CCN(c2ncnc3[nH]ccc23)CC12CC2]

1H NMR (300 MHz, DMSO) δ 11.71 (s, 1H), 8.13 (d, J=1.3 Hz, 1H), 7.19 (dd, J=3.4, 2.3 Hz, 1H), 6.59 (dd, J=3.5, 1.8 Hz, 1H), 4.15 (d, J=6.5 Hz, 1H), 4.04 (q, J=4.3 Hz, 2H), 3.87-3.75 (m, 2H), 3.58-3.34 (m, 4H), 3.17-3.05 (m, 2H), 2.85-2.69 (m, 3H), 2.68-2.56 (m, 3H), 1.99-1.74 (m, 4H), 1.04-0.80 (m, 4H).
LC-MS: 1.88 min, ES (+), m/z: 487.227

Example 188

N-[[(2R)-1-formylpyrrolidin-2-yl]methyl]-N-methyl-5-(7H-pyrrolo[2,3-d]pyrimidin-4-yl)-5,8-diazaspiro[2.5]octane-8-sulfonamide

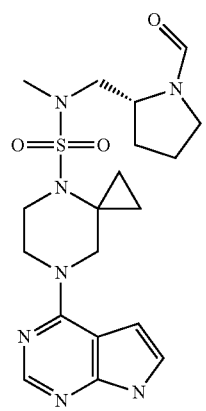 [SMILES: CN(C[C@H]1CCCN1C=O)S(=O)(=O)N1CCN(c2ncnc3[nH]ccc23)CC12CC2]

1H NMR (300 MHz, DMSO) δ 11.86 (s, 1H), 8.29-8.06 (m, 2H), 7.23 (dd, J=3.6, 1.9 Hz, 1H), 6.65 (d, J=3.4 Hz, 1H), 4.08 (dt, J=10.2, 5.8 Hz, 3H), 3.84 (s, 2H), 3.53 (t, J=5.2 Hz, 2H), 3.38 (d, J=11.5 Hz, 2H), 3.09 (d, J=7.6 Hz, 2H), 2.75 (s, 3H), 2.08-1.64 (m, 4H), 1.07-0.78 (m, 4H).

LC-MS: 1.76 min, ES (+), m/z: 434.197

Example 189

N-[[(2R)-1-(2-cyanoacetyl)pyrrolidin-2-yl]methyl]-N-methyl-5-(7H-pyrrolo[2,3-d]pyrimidin-4-yl)-5,8-diazaspiro[2.5]octane-8-sulfonamide

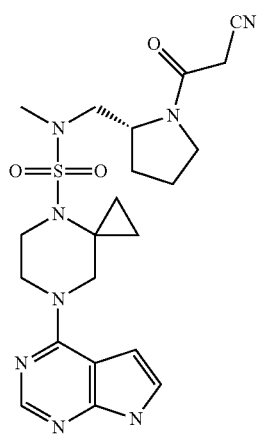 [SMILES: CN(C[C@H]1CCCN1C(=O)CC#N)S(=O)(=O)N1CCN(c2ncnc3[nH]ccc23)CC12CC2]

1H NMR (300 MHz, DMSO) δ 11.74 (s, 1H), 8.14 (s, 1H), 7.20 (dd, J=3.5, 2.3 Hz, 1H), 6.60 (dd, J=3.7, 1.7 Hz, 1H), 4.19-4.00 (m, 3H), 3.91 (d, J=4.0 Hz, 2H), 3.86-3.81 (m, 2H), 3.58-3.37 (m, 4H), 3.18-3.05 (m, 2H), 2.75 (s, 3H), 1.97-1.77 (m, 4H), 1.06-0.79 (m, 4H). LC-MS: 1.85 min, ES (+), m/z: 473.209

Example 190

N-[[(2R)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide

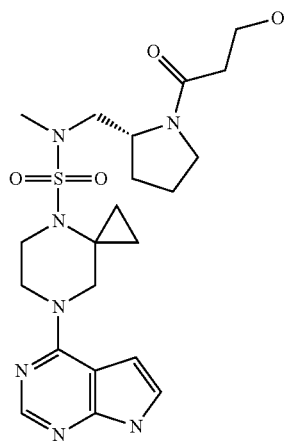

LC-MS: 1.75 min, ES (+), m/z: 478.221

Example 191

N-[[(2S)-1-formylpyrrolidin-2-yl]methyl]-N-methyl-5-(7H-pyrrolo[2,3-d]pyrimidin-4-yl)-5,8-diazaspiro[2.5]octane-8-sulfonamide

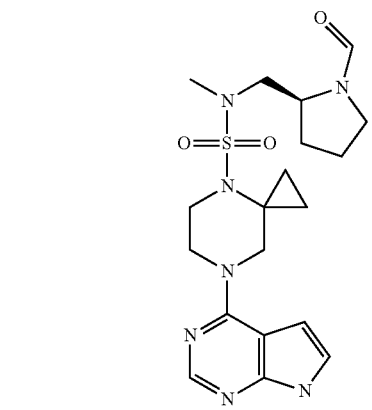 [SMILES: CN(C[C@@H]1CCCN1C=O)S(=O)(=O)N1CCN(c2ncnc3[nH]ccc23)CC12CC2]

Prepared in a similar manner as example 123, using intermediate 52, instead of intermediate 25.

1H NMR (300 MHz, DMSO) δ 11.71 (s, 1H), 8.25-8.07 (m, 2H), 7.19 (dd, J=3.5, 1.8 Hz, 1H), 6.62-6.55 (m, 1H), 4.17-3.99 (m, 3H), 3.83 (s, 2H), 3.52 (t, J=5.1 Hz, 2H), 3.11 (d, J=7.1 Hz, 2H), 2.74 (s, 3H), 2.00-1.69 (m, 4H), 1.01-0.78 (m, 4H).

LC-MS: 1.76 min, ES (+), m/z: 434.197

Using this procedure the following compounds were obtained:

Example 192

N-[[(2S)-1-(2-hydroxyacetyl)pyrrolidin-2-yl]methyl]-N-methyl-5-(7H-pyrrolo[2,3-d]pyrimidin-4-yl)-5,8-diazaspiro[2.5]octane-8-sulfonamide

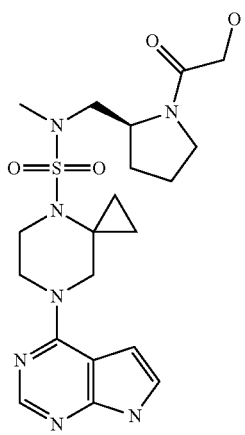 [SMILES: CN(C[C@@H]1CCCN1C(=O)CO)S(=O)(=O)N1CCN(c2ncnc3[nH]ccc23)CC12CC2]

LC-MS: 1.76 min, ES (+), m/z: 464.189

Example 193

N-[[(2S)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide

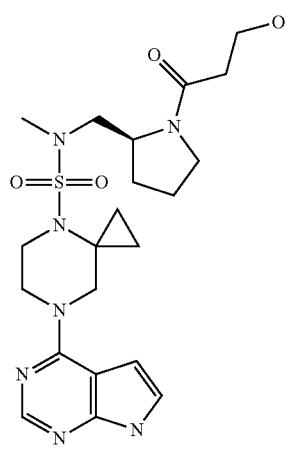 [SMILES: CN(C[C@@H]1CCCN1C(=O)CCO)S(=O)(=O)N1CCN(c2ncnc3[nH]ccc23)CC12CC2]

LC-MS: 1.75 min, ES (+), m/z: 478.223

Example 194

N-methyl-N-[[(2S)-1-methylsulfonylpyrrolidin-2-yl]methyl]-5-(7H-pyrrolo[2,3-d]pyrimidin-4-yl)-5,8-diazaspiro[2.5]octane-8-sulfonamide

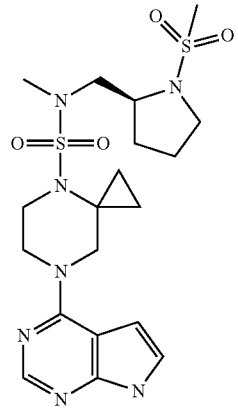 [SMILES: CN(C[C@@H]1CCCN1S(C)(=O)=O)S(=O)(=O)N1CCN(c2ncnc3[nH]ccc23)CC12CC2]

Prepared in a similar manner as example 118, using intermediate 52, instead of intermediate 25.

1H NMR (300 MHz, DMSO) δ 11.72 (s, 1H), 8.14 (s, 1H), 7.19 (dd, J=3.6, 2.3 Hz, 1H), 6.59 (dd, J=3.5, 1.7 Hz, 1H), 4.05 (d, J=4.6 Hz, 2H), 3.83 (d, J=2.7 Hz, 3H), 3.53 (t, J=5.2 Hz, 2H), 3.26 (s, 2H), 3.18-3.03 (m, 2H), 2.93 (s, 3H), 2.74 (s, 3H), 1.96-1.77 (m, 4H), 1.12-0.83 (m, 4H).

LC-MS: 1.91 min, ES (+), m/z: 484.182

Example 168

N-[(1,1-dioxothian-4-yl)methyl]-N-methyl-5-(7H-pyrrolo[2,3-d]pyrimidin-4-yl)-5,8-diazaspiro[2.5]octane-8-sulfonamide

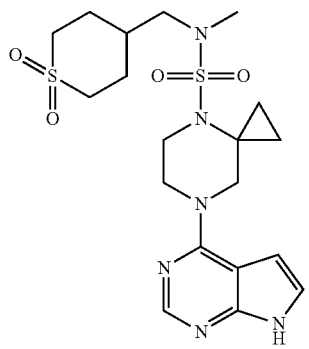 [SMILES: CN(CC1CCS(=O)(=O)CC1)S(=O)(=O)N1CCN(c2ncnc3[nH]ccc23)CC12CC2]

Prepared in a similar manner as example 143, using intermediate 44, instead of intermediate 2.

1H NMR (300 MHz, DMSO) δ 11.72 (s, 1H), 8.13 (s, 1H), 7.19 (dd, J=3.6, 2.3 Hz, 1H), 6.59 (dd, J=3.5, 1.8 Hz, 1H), 4.05 (t, J=5.2 Hz, 2H), 3.83 (s, 2H), 3.53 (t, J=5.2 Hz, 2H), 3.19-2.96 (m, 6H), 2.69 (s, 3H), 2.06-1.84 (m, 3H), 1.69-1.47 (m, 2H), 1.06-0.74 (m, 4H).

LC-MS: 1.81 min, ES (+), m/z: 469.170

Example 169

N-(cyanomethyl)-N-[(1,1-dioxothian-4-yl)methyl]-5-(7H-pyrrolo[2,3-d]pyrimidin-4-yl)-5,8-diazaspiro[2.5]octane-8-sulfonamide

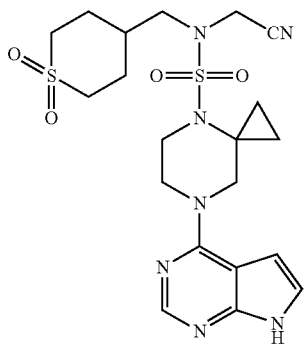 [SMILES: N#CCN(CC1CCS(=O)(=O)CC1)S(=O)(=O)N1CCN(c2ncnc3[nH]ccc23)CC12CC2]

1H NMR (300 MHz, DMSO) δ 11.74 (s, 1H), 8.15 (s, 1H), 7.20 (dd, J=3.5, 2.3 Hz, 1H), 6.59 (dd, J=3.5, 1.8 Hz, 1H), 4.33 (s, 2H), 4.07 (t, J=5.1 Hz, 2H), 3.83 (s, 2H), 3.54 (s, 2H), 3.15 (d, J=6.9 Hz, 2H), 3.13-3.03 (m, 4H), 2.06-1.89 (m, 3H), 1.70-1.53 (m, 2H), 1.10-0.87 (m, 4H).

LC-MS: 1.84 min, ES (+), m/z: 494.166

Example 170

N-[(1,1-dioxothian-4-yl)methyl]-N-(2-hydroxyethyl)-5-(7H-pyrrolo[2,3-d]pyrimidin-4-yl)-5,8-diazaspiro[2.5]octane-8-sulfonamide

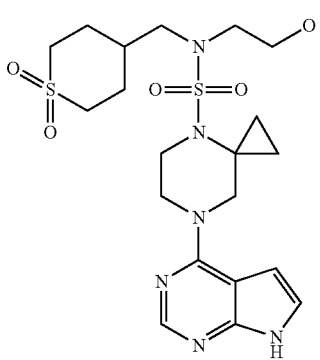 [SMILES: O=S1(=O)CCC(CN(CCO)S(=O)(=O)N2CCN(c3ncnc4[nH]ccc34)CC23CC3)CC1]

LC-MS: 1.70 min, ES (+), m/z: 499.176

Example 171

N-(2-cyanoethyl)-N-(cyanomethyl)-5-(7H-pyrrolo[2,3-d]pyrimidin-4-yl)-5,8-diazaspiro[2.5]octane-8-sulfonamide

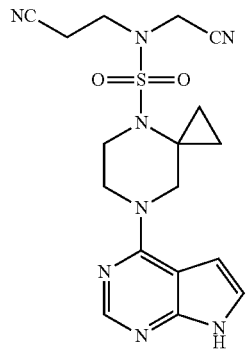

Prepared in a similar manner as example 143, using intermediate 45, instead of intermediate 2.

1H NMR (300 MHz, DMSO) δ 11.74 (s, 1H), 8.15 (s, 1H), 7.20 (dd, J=3.6, 2.4 Hz, 1H), 6.60 (dd, J=3.5, 1.8 Hz, 1H), 4.40 (s, 2H), 4.07 (t, J=5.1 Hz, 2H), 3.84 (s, 2H), 3.59 (t, J=5.3 Hz, 2H), 3.47 (t, J=6.6 Hz, 2H), 2.86 (t, J=6.4 Hz, 2H), 1.20-0.81 (m, 4H).

LC-MS: 1.85 min, ES (+), m/z: 401.147

Example 172

N-[(1,1-dioxothiolan-3-yl)methyl]-N-[[5-(7H-pyrrolo[2,3-d]pyrimidin-4-yl)-5,8-diazaspiro[2.5]octan-8-yl]sulfonyl]acetamide

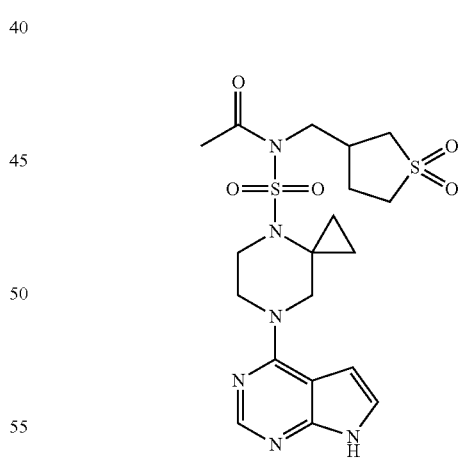

Prepared in a similar manner as example 132, using intermediate 42, instead of intermediate 4.

1H NMR (300 MHz, DMSO) δ 11.75 (s, 1H), 8.15 (s, 1H), 7.24-7.18 (m, 1H), 6.61 (dd, J=3.7, 1.8 Hz, 1H), 4.15-4.00 (m, 2H), 3.90-3.80 (m, 4H), 3.75-3.66 (m, 2H), 3.27-3.16 (m, 2H), 3.15-2.99 (m, 1H), 2.87 (dd, J=12.9, 10.1 Hz, 1H), 2.78-2.63 (m, 1H), 2.32 (s, 3H), 2.29-2.12 (m, 1H), 1.96-1.75 (m, 1H), 1.04-0.90 (m, 4H).

LC-MS: 1.87 min, ES (+), m/z: 483.147

Example 173

N-[(1,1-dioxothian-4-yl)methyl]-N-[[5-(7H-pyrrolo[2,3-d]pyrimidin-4-yl)-5,8-diazaspiro[2.5]octan-8-yl]sulfonyl]acetamide

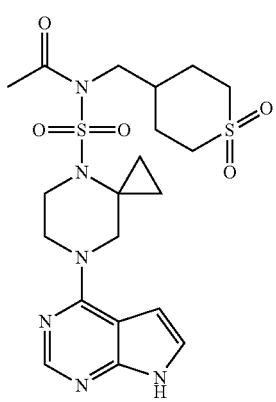 [SMILES: CC(=O)N(CC1CCS(=O)(=O)CC1)S(=O)(=O)N1CCN(c2ncnc3[nH]ccc23)CC12CC2]

Prepared in a similar manner as example 132, using intermediate 44, instead of intermediate 4.

1H NMR (300 MHz, DMSO) δ 11.75 (s, 1H), 8.15 (s, 1H), 7.36-7.09 (m, 1H), 6.61 (dd, J=3.7, 1.8 Hz, 1H), 4.07 (s, 2H), 3.87 (s, 2H), 3.75-3.65 (m, 4H), 3.20-2.97 (m, 4H), 2.30 (s, 3H), 1.97 (d, J=13.3 Hz, 3H), 1.74-1.53 (m, 2H), 1.04-0.86 (m, 4H).

LC-MS: 1.86 min, ES (+), m/z: 497.163

Example 174

N-benzyloxy-N-methyl-5-(7H-pyrrolo[2,3-d]pyrimidin-4-yl)-5,8-diazaspiro[2.5]octane-8-sulfonamide

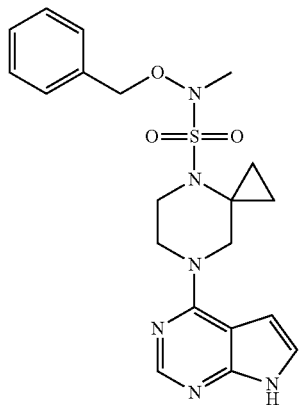 [SMILES: CN(OCc1ccccc1)S(=O)(=O)N1CCN(c2ncnc3[nH]ccc23)CC12CC2]

Prepared in a similar manner as example 58, using intermediate 46, instead of intermediate 6.

1H NMR (300 MHz, DMSO) δ 11.74 (s, 1H), 8.14 (s, 1H), 7.38 (d, J=2.4 Hz, 5H), 7.20 (dd, J=3.6, 2.3 Hz, 1H), 6.60 (dd, J=3.5, 1.8 Hz, 1H), 4.84 (s, 2H), 4.05 (t, J=5.0 Hz, 2H), 3.85 (s, 2H), 3.66 (t, J=5.0 Hz, 2H), 2.75 (s, 3H), 1.14-1.05 (m, 2H), 0.94-0.83 (m, 2H).

Example 175

N-[[(2S)-1-benzylpyrrolidin-2-yl]methyl]-5-(7H-pyrrolo[2,3-d]pyrimidin-4-yl)-5,8-diazaspiro[2.5]octane-8-sulfonamide

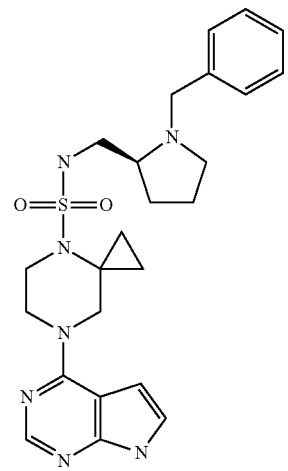 [SMILES: O=S(=O)(NC[C@@H]1CCCN1Cc1ccccc1)N1CCN(c2ncnc3[nH]ccc23)CC12CC2]

tert-butyl 4-[8-[[[(2S)-1-benzylpyrrolidin-2-yl]methyl-tert-butoxycarbonyl-sulfamoyl]-5,8-diazaspiro[2.5]octan-5-yl]pyrrolo[2,3-d]pyrimidine-7-carboxylate (Intermediate 48) (0.57 mmol) was dissolved in DCM (10 mL) and added TFA (1 mL). The reaction mixture was stirred at rt for 16 h, then added NaHCO$_3$ (15 mL) and extracted with EtOAc (2×25 mL). The combined organic phases were dried over Na$_2$SO$_4$, filtered and concentrated in vacuo. The product was purified by flash chromatography on silica using EtOAc and MeOH in heptane as eluent.

1H NMR (300 MHz, DMSO) δ 11.70 (s, 1H), 8.13 (s, 1H), 7.37-7.13 (m, 7H), 6.59 (dd, J=3.5, 1.5 Hz, 1H), 4.04 (t, J=5.2 Hz, 2H), 3.89 (d, J=13.1 Hz, 1H), 3.82 (s, 2H), 3.52 (t, J=5.2 Hz, 2H), 2.92-2.81 (m, 1H), 2.81-2.70 (m, 1H), 2.69-2.54 (m, 2H), 2.21-2.08 (m, 1H), 1.93-1.79 (m, 1H), 1.73-1.48 (m, 3H), 1.03-0.75 (m, 4H).

LC-MS: 1.75 min, ES (+), m/z: 482.232

Example 176

N-[[5-(7H-pyrrolo[2,3-d]pyrimidin-4-yl)-5,8-diazaspiro[2.5]octan-8-yl]sulfonyl]formamide

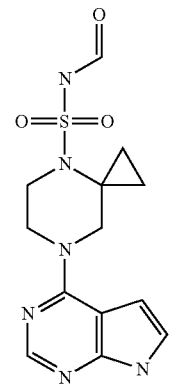

Formic acid (0.24 mmol) was dissolved in dry THF (0.5 mL), added di(imidazol-1-yl)methanone (0.29 mmol) and then stirred at 50° C. for 30 min. before being cooled to rt and added 4-(4-Sulfamoyl-4,7-diaza-spiro[2.5]oct-7-yl)-pyrrolo[2,3-d]pyrimidine-7-carboxylic acid tert-butyl ester (Intermediate 2) (0.24 mmol) and DBU (0.29 mmol). The reaction mixture was stirred at rt for 16 h. The pure compounds were obtained by standard preparative HPLC purification of the reaction mixture.

1H NMR (300 MHz, DMSO) δ 12.69 (s, 1H), 11.72 (s, 1H), 8.56 (s, 1H), 7.19 (dd, J=3.7, 2.3 Hz, 1H), 6.59 (dd, J=3.6, 1.8 Hz, 1H), 4.05 (t, J=5.2 Hz, 2H), 3.82 (s, 2H), 3.66 (dd, J=6.7, 3.8 Hz, 2H), 1.17-1.03 (m, 2H), 0.87 (b, 2H).

LC-MS: 1.64 min, ES (+), m/z: 337.110

Example 195

N-[(4-methoxyphenyl)methyl]-5-(7H-pyrrolo[2,3-d]pyrimidin-4-yl)-5,8-diazaspiro[2.5]octane-8-sulfonamide

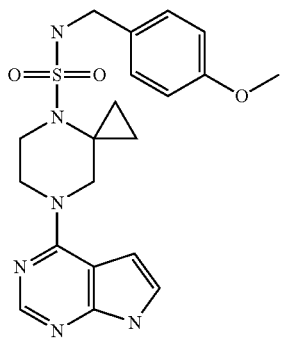 [SMILES: COc1ccc(CNS(=O)(=O)N2CCN(c3ncnc4[nH]ccc34)CC23CC3)cc1]

(NZ)—N-[(4-methoxyphenyl)methylene]-5-(7H-pyrrolo[2,3-d]pyrimidin-4-yl)-5,8-diazaspiro[2.5]octane-8-sulfonamide (intermediate 49) was dissolved in MeOH, added NaBH$_4$ (1 eq) and stirred at rt for 2 h. The pure compound was obtained by standard preparative HPLC purification of the reaction mixture.

1H NMR (300 MHz, DMSO) δ 11.72 (s, 1H), 8.12 (s, 1H), 7.81 (m, 1H), 7.21 (d, 2H), 7.18 (m, 1H), 6.88 (d, 2H), 6.58 (m, 1H), 4.03 (m, 2H), 3.91 (m, 2H), 3.82 (s, 2H), 3.72 (s, 3H), 3.48 (m, 2H), 0.94 (m, 2H), 0.80 (m, 2H).

LC-MS: 2.06 min, ES (+), m/z: 429.173

Example 196 tert-butyl N-(3-methylsulfonylpropyl)-N-[[5-(7H-pyrrolo[2,3-d]pyrimidin-4-yl)-5,8-diazaspiro[2.5]octan-8-yl]sulfonyl]carbamate

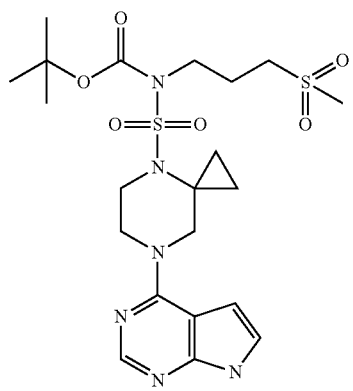 [SMILES: CC(C)(C)OC(=O)N(CCCS(C)(=O)=O)S(=O)(=O)N1CCN(c2ncnc3[nH]ccc23)CC12CC2]

Tert-butyl N—[[5-(7H-pyrrolo[2,3-d]pyrimidin-4-yl)-5,8-diazaspiro[2.5]octan-8-yl]sulfonyl]carbamate (Intermediate 53)(0.12 mmol) was dissolved in dry THF (1 mL) and added 3-methylsulfonylpropan-1-ol (0.13 mmol) and triphenylphosphine (0.15 mmol). The reaction mixture was cooled to 0° C. and slowly added isopropyl (NZ)—N-isopropoxycarbonyliminocarbamate (0.15 mmol). The reaction mixture was allowed to warm up freely to rt and stirred at rt for 16 h. The crude mixture was treated with water (50 mL) and extracted with EtOAc (3×50 mL). The combined organic phases were washed with H$_2$O (2×50 mL), brine (2×50 mL), dried over Na$_2$SO$_4$, filtered and concentrated in vacuo. The product was purified by flash chromatography on silica using EtOAc in heptane as eluent.

1H NMR (300 MHz, DMSO) δ 11.73 (s, 1H), 8.14 (s, 1H), 7.20 (dd, J=3.5, 2.3 Hz, 1H), 6.61 (dd, J=3.4, 1.8 Hz, 1H), 4.06 (dd, J=6.6, 3.7 Hz, 2H), 3.88-3.66 (m, 6H), 3.19-3.09 (m, 2H), 3.00 (s, 3H), 2.01 (p, J=8.8, 8.4 Hz, 2H), 1.42 (s, 9H), 1.04-0.91 (m, 4H).

JAK Kinase Assays:

Human baculovirus-expressed JAK1, 2, 3 and TYK2 were purchased from Carna Biosciences, Inc. All four purified enzymes contain only the catalytic domain. JAK1 (aa 850-1154) and TYK2 (aa 871-1187) are expressed with an N-terminally fused GST-tag, and JAK2 and JAK3 with an N-terminally fused His-tag.

Inhibition of phosphorylation of a synthetic peptide was measured in an HTRF-based assay using the TK substrate-Biotin from the Cisbio HTRFKinEASE TK kit. First, 2 µl of TK solution (TK substrate-biotin in kinase buffer [1× enzymatic buffer from HTRFKinEASE TK kit, 1 mM DTT]) is added to a plate containing 1 µl prediluted compound (final assay concentration DMSO: 0.75%). Then, 5 µl kinase-ATP mix (prepared in kinase buffer) is added to the wells and the plates are incubated at RT for 20-30 min. For all four kinases a concentration of ATP that corresponded to the Km for ATP was used. The final concentrations of buffers, substrate, kinase and ATP were: JAK1: 50 mM Hepes buffer pH 7.0, 0.01% BSA, 10 mM MgCl$_2$, 1 mM DTT, 7 µM ATP, 50 nM SEB, 1 µM TK Substrate-Biotin and 5 ng JAK1; JAK2: 50 mM Hepes buffer pH 7.0, 0.01% BSA, 5 mM MgCl$_2$, 1 mM DTT, 4 µM ATP, 1 µM TK Substrate-Biotin and 0.1 ng JAK2; JAK3: 50 mM Hepes buffer pH 7.0, 0.01% BSA, 5 mM MgCl$_2$, 1 mM DTT, 2 µM ATP, 1 µM TK Substrate-Biotin and 0.3 ng JAK3; TYK2: 50 mM Hepes buffer pH 7.0, 0.01% BSA, 5 mM MgCl$_2$, 1 mM DTT, 13 µM ATP, 50 nM SEB, 1 µM TK Substrate-Biotin and 0.8 ng TYK2. Thereafter, the kinase reaction is stopped by adding 4 µl detection mix (final concentrations: 50 mM Hepes buffer pH 7.0, 0.01% BSA, 0.8 M KF, 20 mM EDTA, 42 nM Streptavidin-XL665 and 1:400 STK Ab Cryptate) and the plates are incubated overnight in the dark. The HTRF signal is read using an Envision plate reader.

In Table 1 selected JAK kinase inhibitory activities are listed with the following indicators: I: EC$_{50}$<100 nM, II: 100 nM≤EC$_{50}$≤500 nM and III: EC$_{50}$>500 nM TABLE 1
| Example number | Structure | JAK1 | JAK2 | JAK3 | TYK2 |
|---|---|---|---|---|---|
| Int 1 | 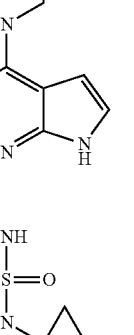 | I | I | I | II |
| Int 3 | 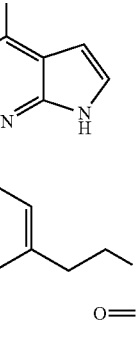 | I | I | I | II |
| Int 5 | 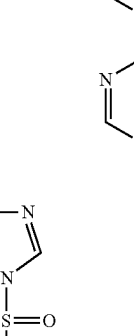 | I | I | II | III |
| Int 15 | 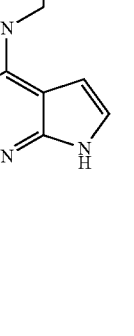 | II | I | III | III |

TABLE 1-continued
| Example number | Structure | JAK1 | JAK2 | JAK3 | TYK2 |
|---|---|---|---|---|---|
| Int 25 | 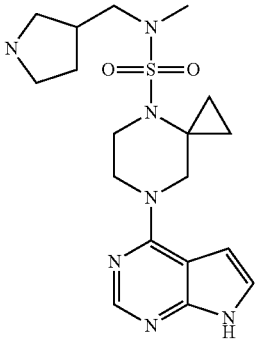 [SMILES: CN(CC1CCNC1)S(=O)(=O)N1CCN(c2ncnc3[nH]ccc23)CC12CC2] | I | I | II | III |
| Int 26 | 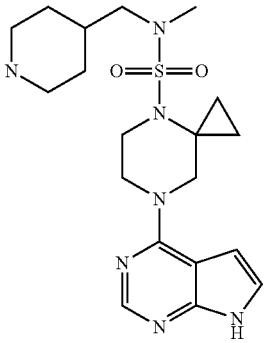 | I | I | II | III |
| Int 27 | 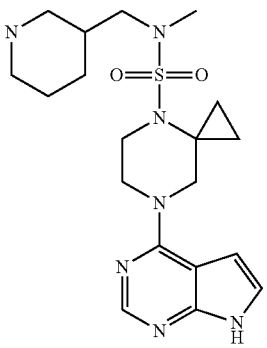 | II | II | III | III |
| Int 28 | 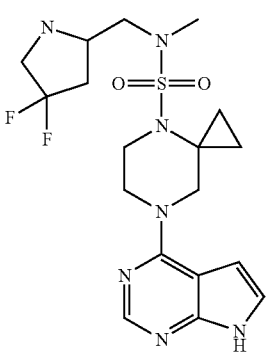 [SMILES: CN(CC1CC(F)(F)CN1)S(=O)(=O)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| Int 30 | 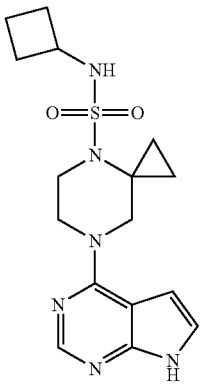 | I | I | II | III |
| Int 37 | 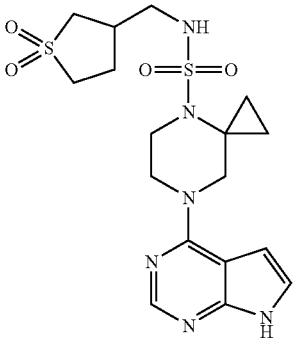 [SMILES: O=S1(=O)CCC(CNS(=O)(=O)N2CCN(c3ncnc4[nH]ccc34)CC23CC3)C1] | I | I | I | III |
| Int 38 | 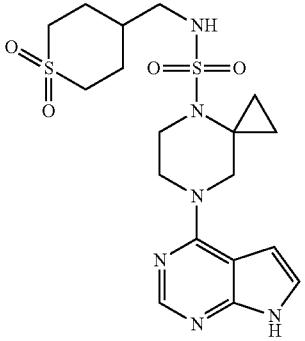 [SMILES: O=S1(=O)CCC(CNS(=O)(=O)N2CCN(c3ncnc4[nH]ccc34)CC23CC3)CC1] | I | I | I | III |
| Int 40 | 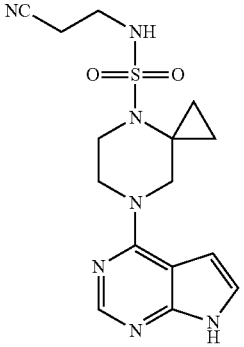 [SMILES: N#CCCNS(=O)(=O)N1CCN(c2ncnc3[nH]ccc23)CC12CC2] | I | I | I | III |

TABLE 1-continued
| Example number | Structure | JAK1 | JAK2 | JAK3 | TYK2 |
|---|---|---|---|---|---|
| Int 41 | 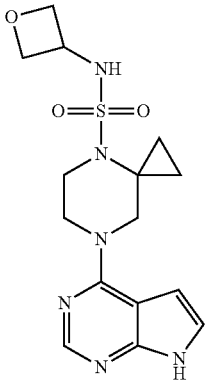 [SMILES: O=S(=O)(NC1COC1)N1CCN(c2ncnc3[nH]ccc23)CC12CC2] | I | I | I | II |
| Int 46 | 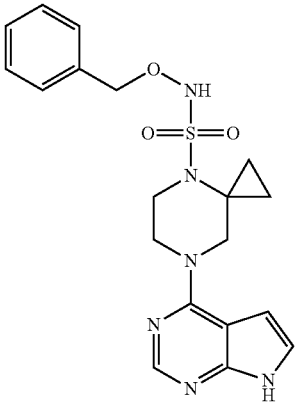 [SMILES: O=S(=O)(NOCc1ccccc1)N1CCN(c2ncnc3[nH]ccc23)CC12CC2] | I | I | II | II |
| Int 49 | 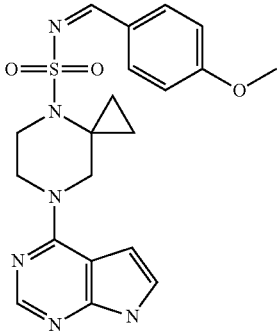 [SMILES: COc1ccc(/C=N\S(=O)(=O)N2CCN(c3ncnc4[nH]ccc34)CC23CC3)cc1] | I | I | I | II |
| Int 50 | 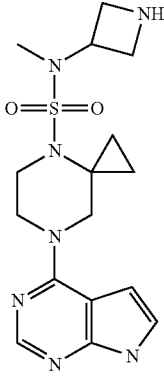 [SMILES: CN(C1CNC1)S(=O)(=O)N1CCN(c2ncnc3[nH]ccc23)CC12CC2] | I | I | II | III |

TABLE 1-continued

| Example number | Structure | JAK1 | JAK2 | JAK3 | TYK2 |
|---|---|---|---|---|---|
| Int 51 | 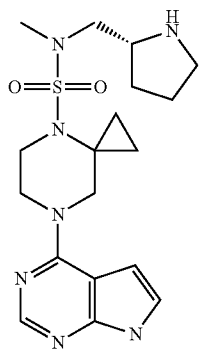 [SMILES: CN(C[C@H]1CCCN1)S(=O)(=O)N1CCN(c2ncnc3[nH]ccc23)CC12CC2] | II | II | III | III |
| Int 52 | 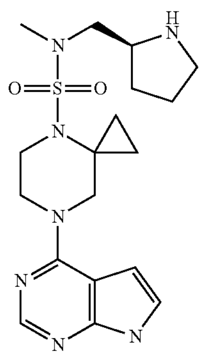 [SMILES: CN(C[C@@H]1CCCN1)S(=O)(=O)N1CCN(c2ncnc3[nH]ccc23)CC12CC2] | I | I | II | III |
| Int 53 | 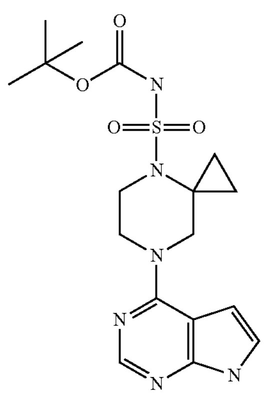 [SMILES: CC(C)(C)OC(=O)NS(=O)(=O)N1CCN(c2ncnc3[nH]ccc23)CC12CC2] | I | I | I | III |
| 1 | 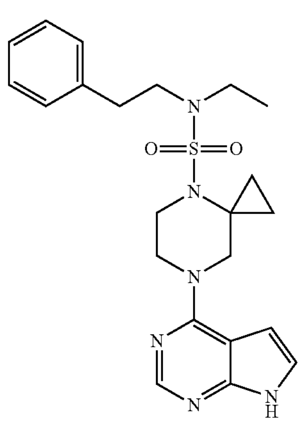 [SMILES: CCN(CCc1ccccc1)S(=O)(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 2 | 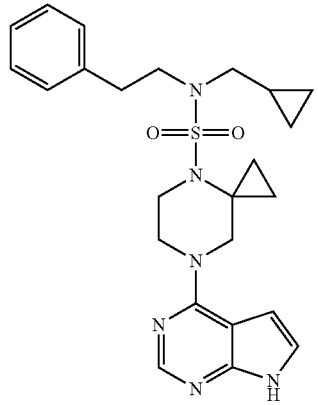 [SMILES: O=S(=O)(N(CCc1ccccc1)CC1CC1)N1CCN(c2ncnc3[nH]ccc23)CC12CC2] | I | I | II | III |
| 3 | 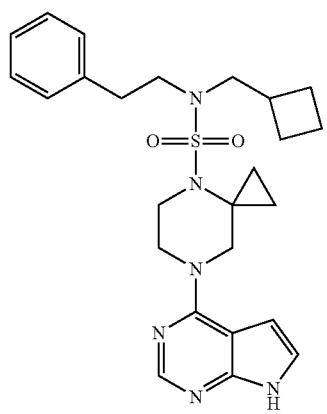 [SMILES: O=S(=O)(N(CCc1ccccc1)CC1CCC1)N1CCN(c2ncnc3[nH]ccc23)CC12CC2] | II | I | II | III |
| 4 | 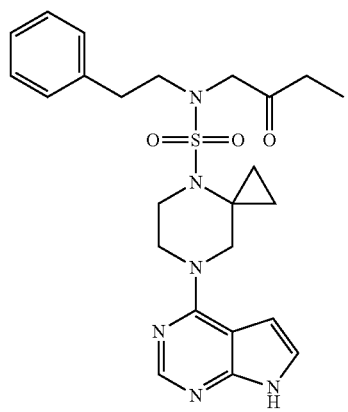 [SMILES: CCC(=O)CN(CCc1ccccc1)S(=O)(=O)N1CCN(c2ncnc3[nH]ccc23)CC12CC2] | I | I | II | III |

TABLE 1-continued
| Example number | Structure | JAK1 | JAK2 | JAK3 | TYK2 |
|---|---|---|---|---|---|
| 5 | 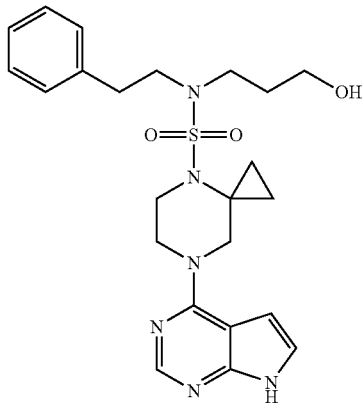 [SMILES: O=S(=O)(N(CCCO)CCc1ccccc1)N1CCN(c2ncnc3[nH]ccc23)CC12CC2] | I | I | I | II |
| 6 | 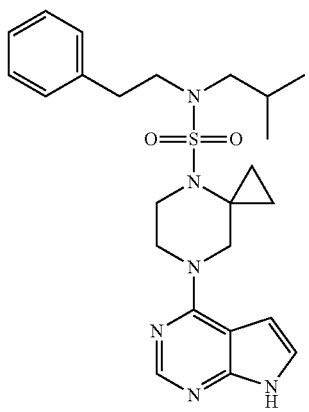 [SMILES: CC(C)CN(CCc1ccccc1)S(=O)(=O)N1CCN(c2ncnc3[nH]ccc23)CC12CC2] | II | I | II | III |
| 7 | 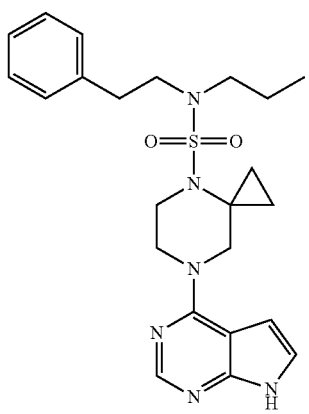 [SMILES: CCCN(CCc1ccccc1)S(=O)(=O)N1CCN(c2ncnc3[nH]ccc23)CC12CC2] | I | I | II | III |

TABLE 1-continued

| Example number | Structure | JAK1 | JAK2 | JAK3 | TYK2 |
|---|---|---|---|---|---|
| 8 | 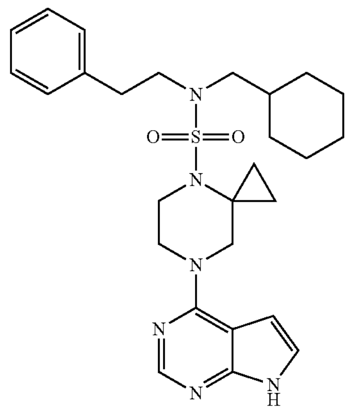 [SMILES: O=S(=O)(N(CCc1ccccc1)CC1CCCCC1)N1CCN(c2ncnc3[nH]ccc23)CC12CC2] | III | III | III | III |
| 9 | 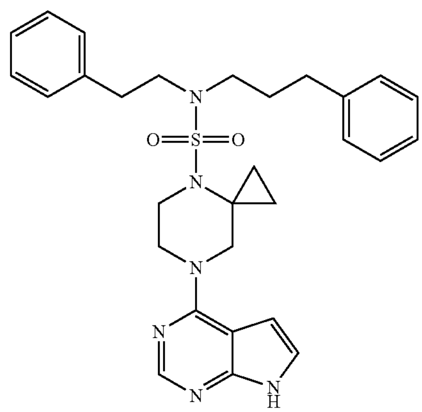 [SMILES: O=S(=O)(N(CCCc1ccccc1)CCc1ccccc1)N1CCN(c2ncnc3[nH]ccc23)CC12CC2] | III | II | III | III |
| 10 | 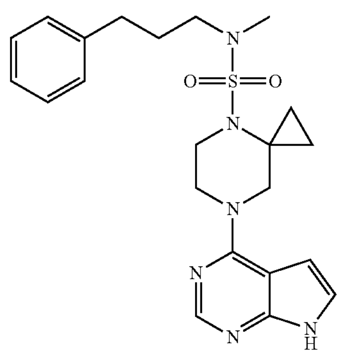 [SMILES: CN(CCCc1ccccc1)S(=O)(=O)N1CCN(c2ncnc3[nH]ccc23)CC12CC2] | I | I | II | III |
| 11 | 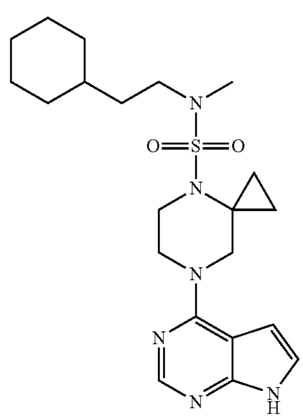 [SMILES: CN(CCC1CCCCC1)S(=O)(=O)N1CCN(c2ncnc3[nH]ccc23)CC12CC2] | I | I | II | III |

TABLE 1-continued

| Example number | Structure | JAK1 | JAK2 | JAK3 | TYK2 |
|---|---|---|---|---|---|
| 12 | 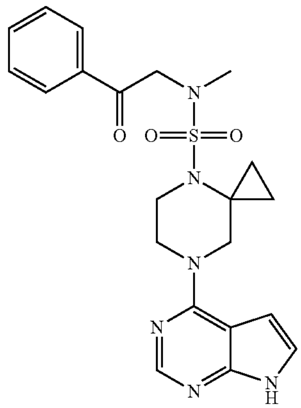 [SMILES: CN(CC(=O)c1ccccc1)S(=O)(=O)N1CCN(c2ncnc3[nH]ccc23)CC12CC2] | I | I | II | III |
| 13 | 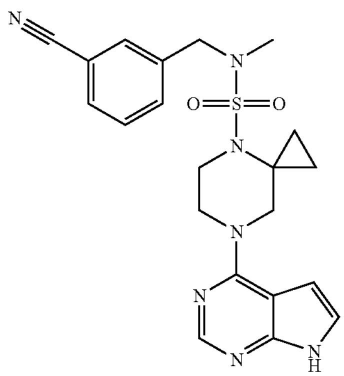 [SMILES: CN(Cc1cccc(C#N)c1)S(=O)(=O)N1CCN(c2ncnc3[nH]ccc23)CC12CC2] | I | I | I | II |
| 14 | 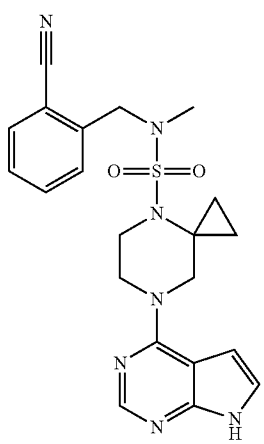 [SMILES: CN(Cc1ccccc1C#N)S(=O)(=O)N1CCN(c2ncnc3[nH]ccc23)CC12CC2] | I | I | II | I |
| 15 | 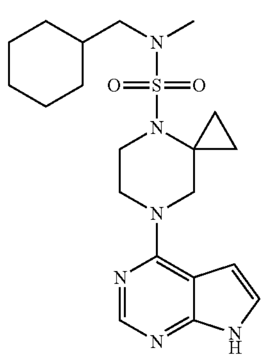 [SMILES: CN(CC1CCCCC1)S(=O)(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 16 | 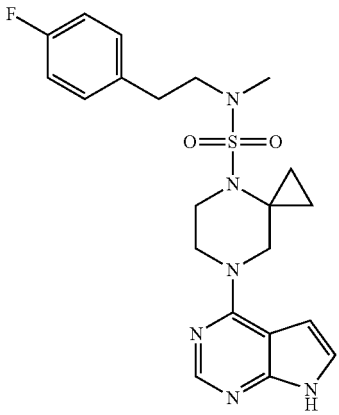 [SMILES: CN(CCc1ccc(F)cc1)S(=O)(=O)N1CCN(c2ncnc3[nH]ccc23)CC12CC2] | I | I | I | II |
| 17 | 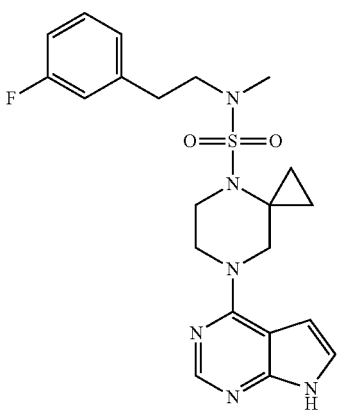 [SMILES: CN(CCc1cccc(F)c1)S(=O)(=O)N1CCN(c2ncnc3[nH]ccc23)CC12CC2] | I | I | I | I |
| 18 | 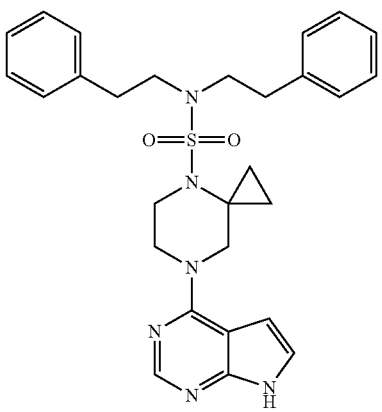 [SMILES: O=S(=O)(N(CCc1ccccc1)CCc1ccccc1)N1CCN(c2ncnc3[nH]ccc23)CC12CC2] | II | II | III | III |

TABLE 1-continued
| Example number | Structure | JAK1 | JAK2 | JAK3 | TYK2 |
|---|---|---|---|---|---|
| 19 | 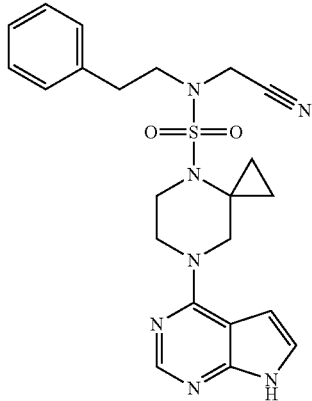 [SMILES: N#CCN(CCc1ccccc1)S(=O)(=O)N1CCN(c2ncnc3[nH]ccc23)CC12CC2] | I | I | I | I |
| 20 | 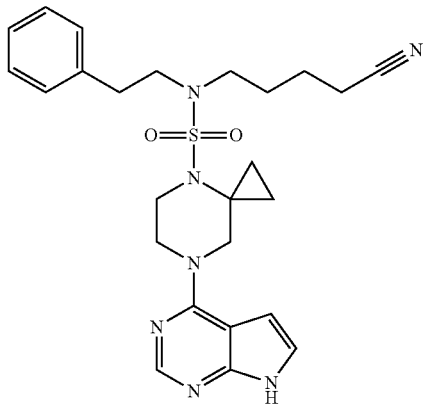 [SMILES: N#CCCCCN(CCc1ccccc1)S(=O)(=O)N1CCN(c2ncnc3[nH]ccc23)CC12CC2] | I | I | I | |
| 21 | 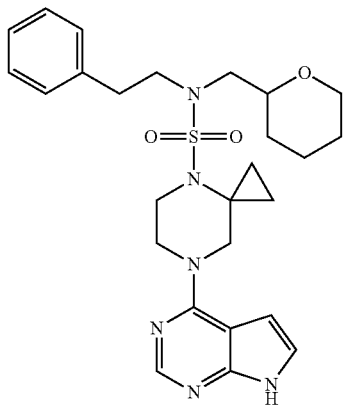 [SMILES: O=S(=O)(N(CCc1ccccc1)CC1CCCCO1)N1CCN(c2ncnc3[nH]ccc23)CC12CC2] | I | I | II | III |

TABLE 1-continued
| Example number | Structure | JAK1 | JAK2 | JAK3 | TYK2 |
|---|---|---|---|---|---|
| 22 | 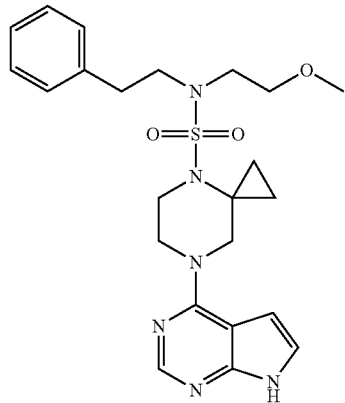 [SMILES: COCCN(CCc1ccccc1)S(=O)(=O)N1CCN(c2ncnc3[nH]ccc23)CC12CC2] | I | I | I | II |
| 23 | 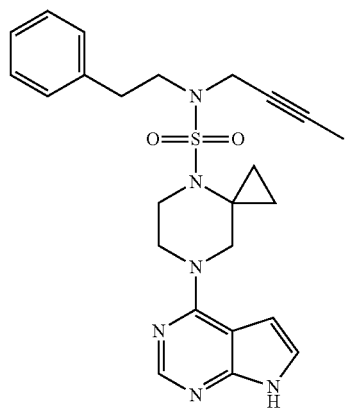 [SMILES: CC#CCN(CCc1ccccc1)S(=O)(=O)N1CCN(c2ncnc3[nH]ccc23)CC12CC2] | I | I | II | III |
| 24 | 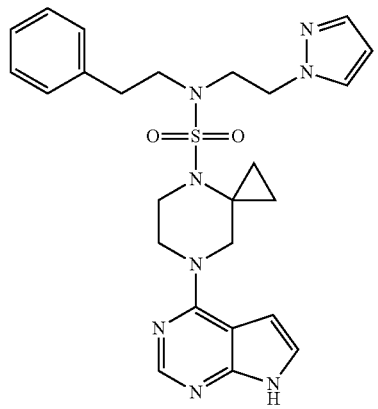 [SMILES: O=S(=O)(N(CCc1ccccc1)CCn1cccn1)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 25 | 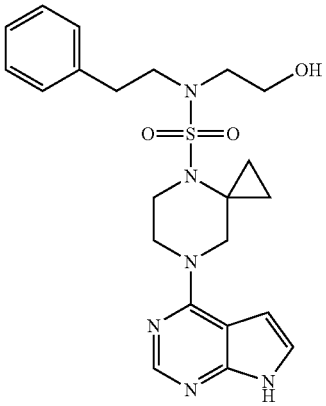 [SMILES: O=S(=O)(N(CCO)CCc1ccccc1)N1CCN(c2ncnc3[nH]ccc23)CC12CC2] | I | I | I | I |
| 26 | 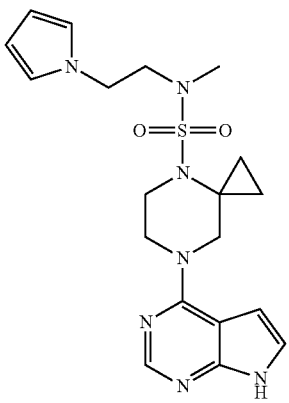 | I | I | I | I |
| 27 | 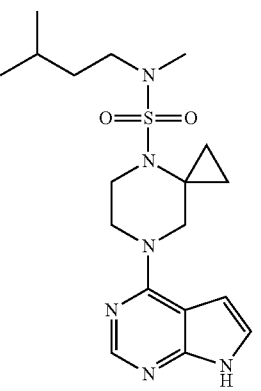 [SMILES: CC(C)CCN(C)S(=O)(=O)N1CCN(c2ncnc3[nH]ccc23)CC12CC2] | I | I | I | II |
| 28 | 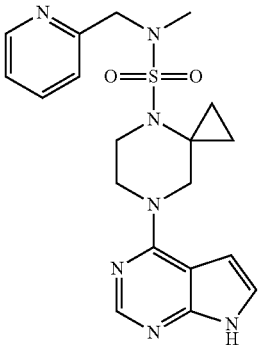 [SMILES: CN(Cc1ccccn1)S(=O)(=O)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 29 | 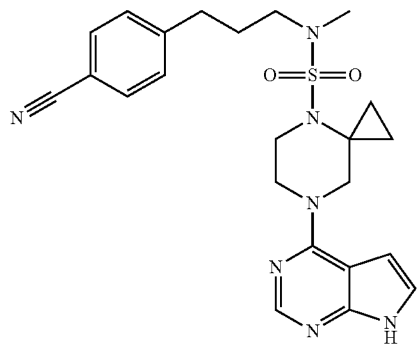 [SMILES: CN(CCCc1ccc(C#N)cc1)S(=O)(=O)N1CCN(c2ncnc3[nH]ccc23)CC12CC2] | I | I | II | III |
| 30 | 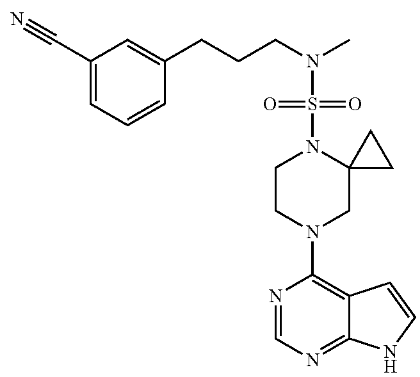 [SMILES: CN(CCCc1cccc(C#N)c1)S(=O)(=O)N1CCN(c2ncnc3[nH]ccc23)CC12CC2] | I | I | II | III |
| 31 | 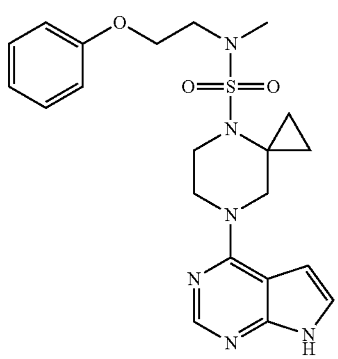 [SMILES: CN(CCOc1ccccc1)S(=O)(=O)N1CCN(c2ncnc3[nH]ccc23)CC12CC2] | I | I | II | II |
| 32 | 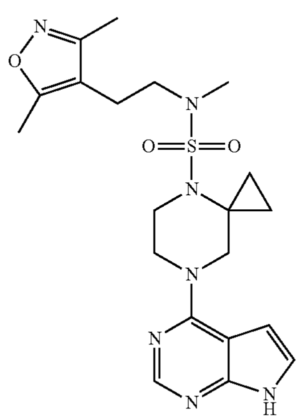 [SMILES: Cc1noc(C)c1CCN(C)S(=O)(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 33 | 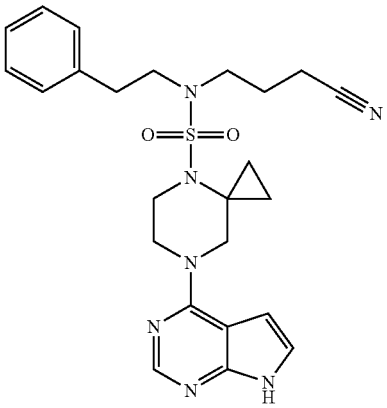 [SMILES: N#CCCCN(CCc1ccccc1)S(=O)(=O)N1CCN(c2ncnc3[nH]ccc23)CC12CC2] | I | I | I | |
| 34 | 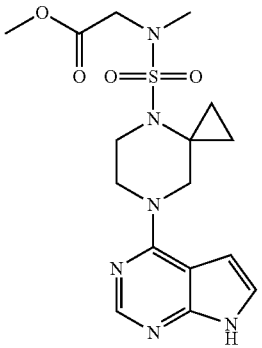 [SMILES: COC(=O)CN(C)S(=O)(=O)N1CCN(c2ncnc3[nH]ccc23)CC12CC2] | I | I | I | II |
| 35 | 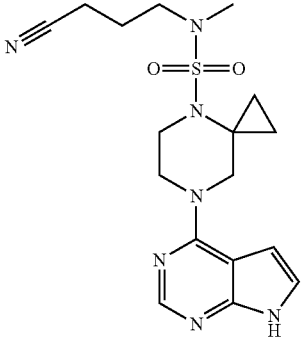 [SMILES: CN(CCCC#N)S(=O)(=O)N1CCN(c2ncnc3[nH]ccc23)CC12CC2] | I | I | I | I |
| 36 | 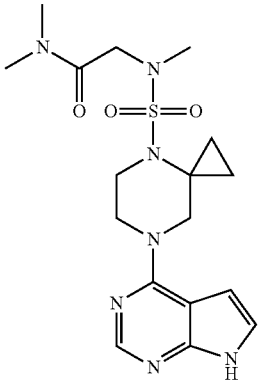 [SMILES: CN(C)C(=O)CN(C)S(=O)(=O)N1CCN(c2ncnc3[nH]ccc23)CC12CC2] | I | I | II | II |

TABLE 1-continued
| Example number | Structure | JAK1 | JAK2 | JAK3 | TYK2 |
|---|---|---|---|---|---|
| 37 | 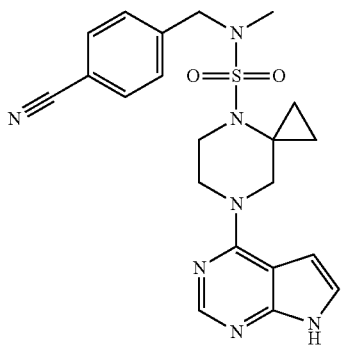 [SMILES: CN(Cc1ccc(C#N)cc1)S(=O)(=O)N1CCN(c2ncnc3[nH]ccc23)CC12CC2] | I | I | I | II |
| 38 | 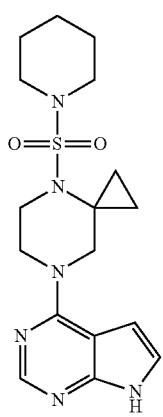 [SMILES: O=S(=O)(N1CCCCC1)N1CCN(c2ncnc3[nH]ccc23)CC12CC2] | II | I | II | II |
| 39 | 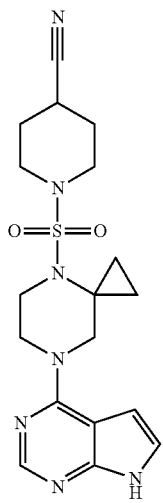 [SMILES: N#CC1CCN(S(=O)(=O)N2CCN(c3ncnc4[nH]ccc34)CC23CC3)CC1] | I | I | II | III |

TABLE 1-continued

| Example number | Structure | JAK1 | JAK2 | JAK3 | TYK2 |
|---|---|---|---|---|---|
| 40 | 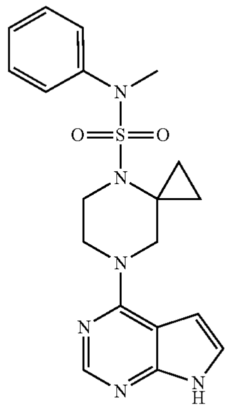 [SMILES: CN(c1ccccc1)S(=O)(=O)N1CCN(c2ncnc3[nH]ccc23)CC12CC2] | I | I | II | II |
| 41 | 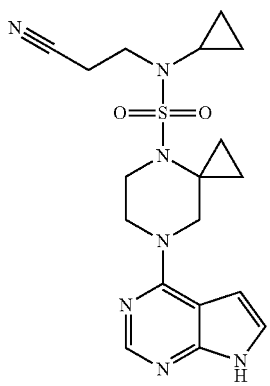 [SMILES: N#CCCN(C1CC1)S(=O)(=O)N1CCN(c2ncnc3[nH]ccc23)CC12CC2] | I | I | I | |
| 42 | 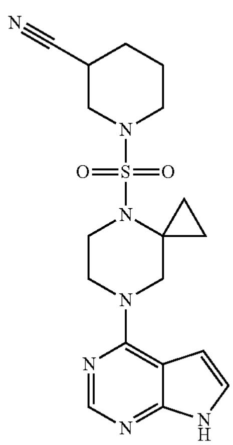 [SMILES: N#CC1CCCN(S(=O)(=O)N2CCN(c3ncnc4[nH]ccc34)CC23CC3)C1] | I | I | II | III |
| 45 | 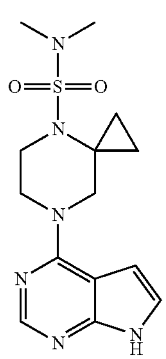 [SMILES: CN(C)S(=O)(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 46 | 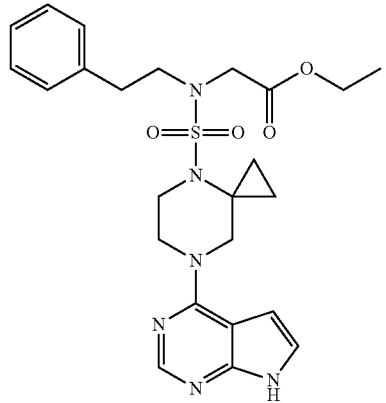 [SMILES: CCOC(=O)CN(CCc1ccccc1)S(=O)(=O)N1CCN(c2ncnc3[nH]ccc23)CC12CC2] | I | I | II | III |
| 47 | 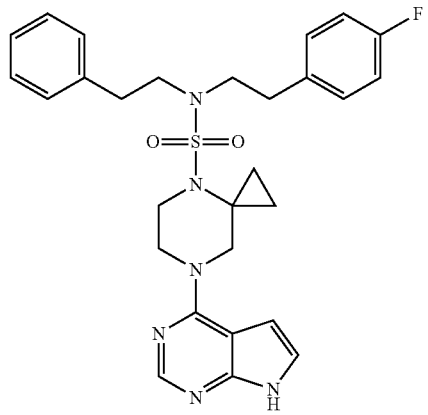 [SMILES: O=S(=O)(N(CCc1ccccc1)CCc1ccc(F)cc1)N1CCN(c2ncnc3[nH]ccc23)CC12CC2] | II | II | III | III |
| 48 | 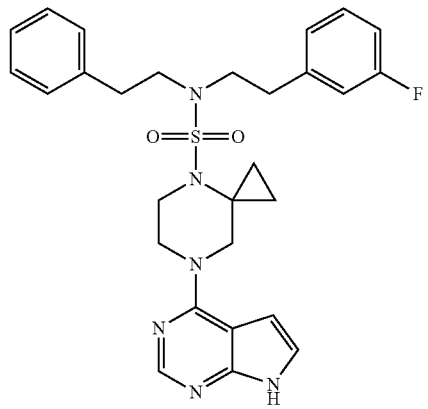 [SMILES: O=S(=O)(N(CCc1ccccc1)CCc1cccc(F)c1)N1CCN(c2ncnc3[nH]ccc23)CC12CC2] | II | II | III | III |

TABLE 1-continued
| Example number | Structure | JAK1 | JAK2 | JAK3 | TYK2 |
|---|---|---|---|---|---|
| 49 | 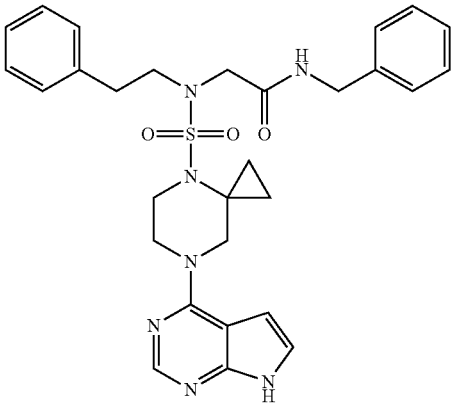 [SMILES: O=C(CN(CCc1ccccc1)S(=O)(=O)N1CCN(c2ncnc3[nH]ccc23)CC12CC2)NCc1ccccc1] | I | I | II | III |
| 50 | 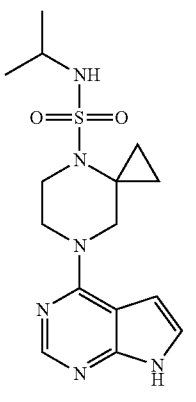 [SMILES: CC(C)NS(=O)(=O)N1CCN(c2ncnc3[nH]ccc23)CC12CC2] | II | I | II | II |
| 51 | 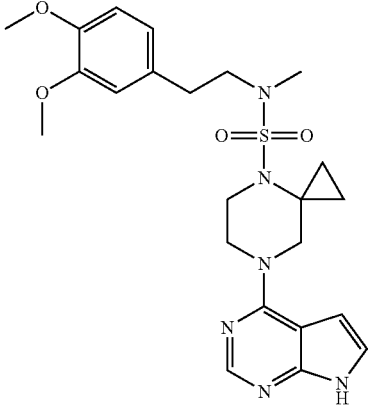 [SMILES: COc1ccc(CCN(C)S(=O)(=O)N2CCN(c3ncnc4[nH]ccc34)CC23CC3)cc1OC] | I | I | I | II |
| 52 | 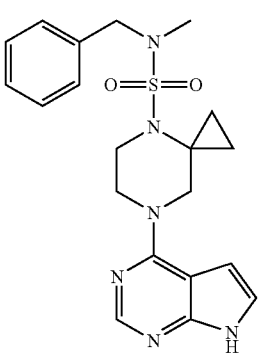 [SMILES: CN(Cc1ccccc1)S(=O)(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 53 | 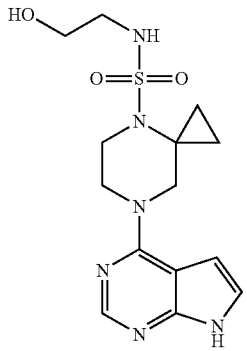 [SMILES: O=S(=O)(NCCO)N1CCN(c2ncnc3[nH]ccc23)CC12CC2] | I | I | I | |
| 54 | 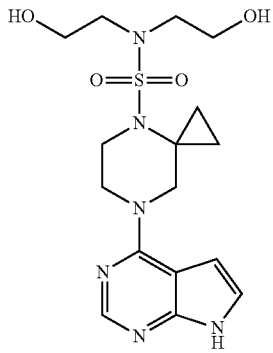 [SMILES: O=S(=O)(N(CCO)CCO)N1CCN(c2ncnc3[nH]ccc23)CC12CC2] | I | I | I | II |
| 55 | 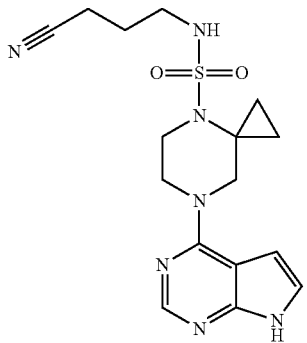 [SMILES: N#CCCCNS(=O)(=O)N1CCN(c2ncnc3[nH]ccc23)CC12CC2] | I | I | I | II |
| 56 | 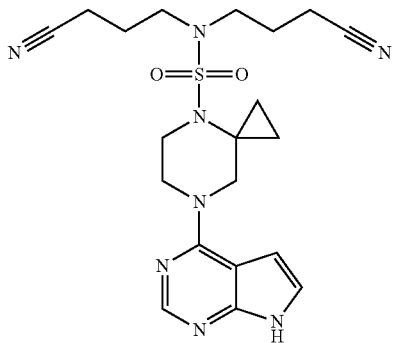 [SMILES: N#CCCCN(CCCC#N)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 57 | 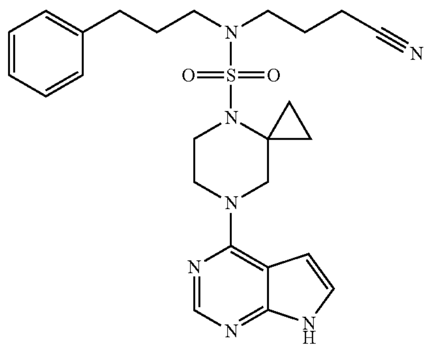 [SMILES: N#CCCCN(CCCc1ccccc1)S(=O)(=O)N1CCN(c2ncnc3[nH]ccc23)CC12CC2] | I | I | I | III |
| 58 | 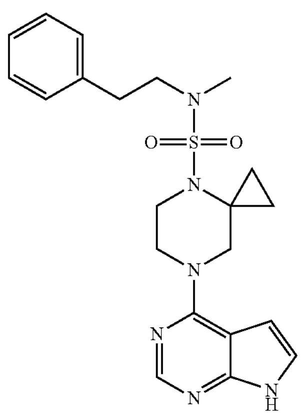 [SMILES: CN(CCc1ccccc1)S(=O)(=O)N1CCN(c2ncnc3[nH]ccc23)CC12CC2] | I | I | I | II |
| 59 | 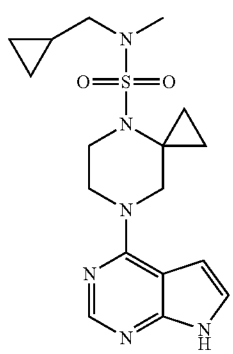 [SMILES: CN(CC1CC1)S(=O)(=O)N1CCN(c2ncnc3[nH]ccc23)CC12CC2] | I | I | I | I |
| 60 | 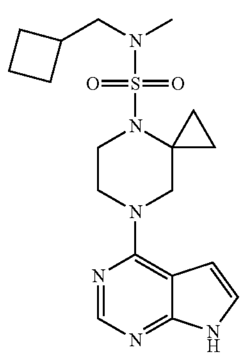 [SMILES: CN(CC1CCC1)S(=O)(=O)N1CCN(c2ncnc3[nH]ccc23)CC12CC2] | I | I | I | I |

TABLE 1-continued

| Example number | Structure | JAK1 | JAK2 | JAK3 | TYK2 |
|---|---|---|---|---|---|
| 61 | 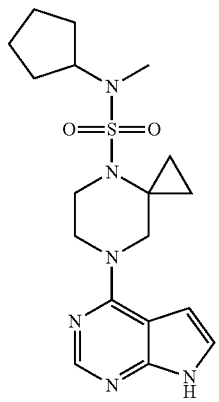 [SMILES: CN(C1CCCC1)S(=O)(=O)N1CCN(c2ncnc3[nH]ccc23)CC12CC2] | I | I | I | II |
| 62 | 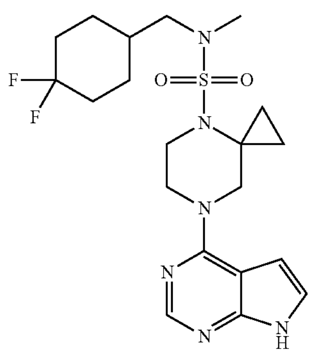 [SMILES: CN(CC1CCC(F)(F)CC1)S(=O)(=O)N1CCN(c2ncnc3[nH]ccc23)CC12CC2] | I | I | I | I |
| 63 | 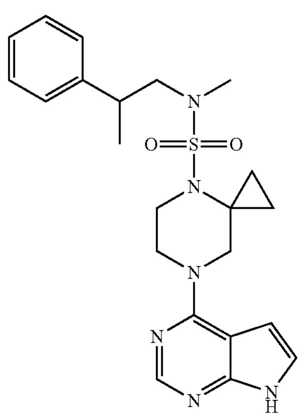 [SMILES: CC(CN(C)S(=O)(=O)N1CCN(c2ncnc3[nH]ccc23)CC12CC2)c1ccccc1] | I | I | I | II |
| 64 | 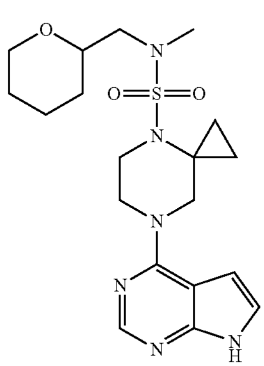 [SMILES: CN(CC1CCCCO1)S(=O)(=O)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 65 | 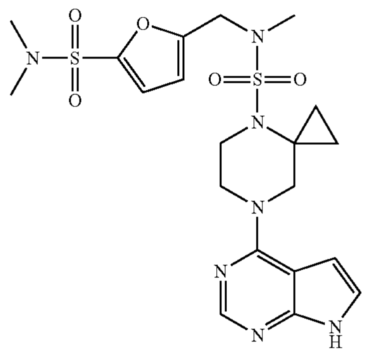 [SMILES: CN(C)S(=O)(=O)c1ccc(CN(C)S(=O)(=O)N2CCN(c3ncnc4[nH]ccc34)CC23CC3)o1] | I | I | II | II |
| 66 | 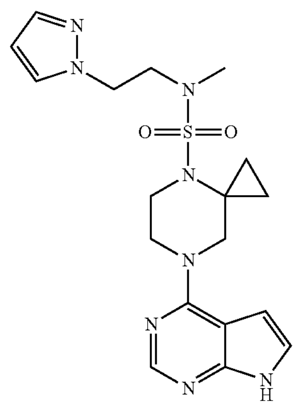 [SMILES: CN(CCn1cccn1)S(=O)(=O)N1CCN(c2ncnc3[nH]ccc23)CC12CC2] | I | I | I | II |
| 67 | 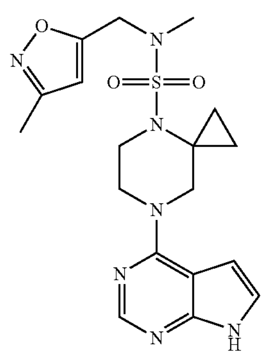 [SMILES: Cc1cc(CN(C)S(=O)(=O)N2CCN(c3ncnc4[nH]ccc34)CC23CC3)on1] | I | I | I | II |
| 68 | 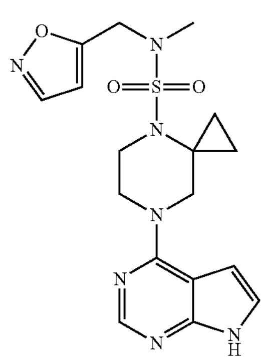 [SMILES: CN(Cc1ccno1)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 69 | 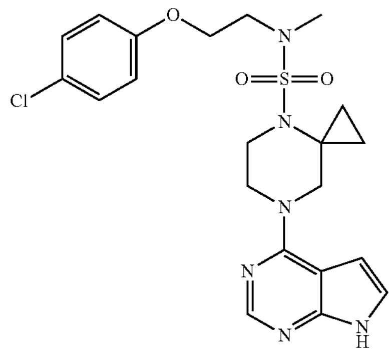 [SMILES: CN(CCOc1ccc(Cl)cc1)S(=O)(=O)N1CCN(c2ncnc3[nH]ccc23)CC12CC2] | I | I | II | III |
| 70 | 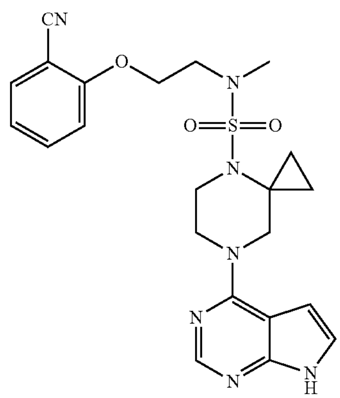 [SMILES: CN(CCOc1ccccc1C#N)S(=O)(=O)N1CCN(c2ncnc3[nH]ccc23)CC12CC2] | I | I | II | III |
| 71 | 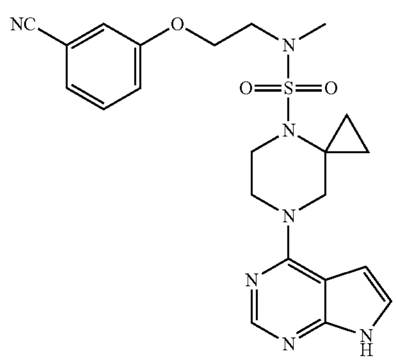 [SMILES: CN(CCOc1cccc(C#N)c1)S(=O)(=O)N1CCN(c2ncnc3[nH]ccc23)CC12CC2] | I | I | II | III |
| 72 | 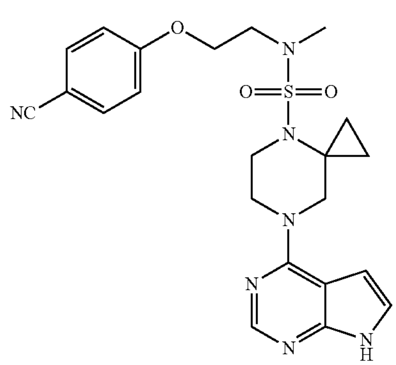 [SMILES: CN(CCOc1ccc(C#N)cc1)S(=O)(=O)N1CCN(c2ncnc3[nH]ccc23)CC12CC2] | I | I | II | III |

TABLE 1-continued

| Example number | Structure | JAK1 | JAK2 | JAK3 | TYK2 |
|---|---|---|---|---|---|
| 73 | 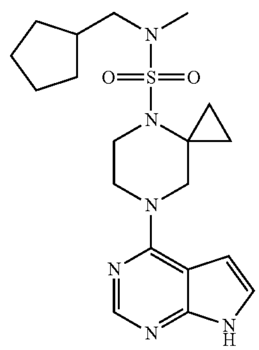 [SMILES: CN(CC1CCCC1)S(=O)(=O)N1CCN(c2ncnc3[nH]ccc23)CC12CC2] | I | I | I | I |
| 74 | 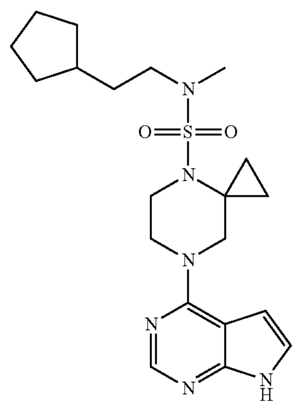 [SMILES: CN(CCC1CCCC1)S(=O)(=O)N1CCN(c2ncnc3[nH]ccc23)CC12CC2] | I | I | II | II |
| 75 | 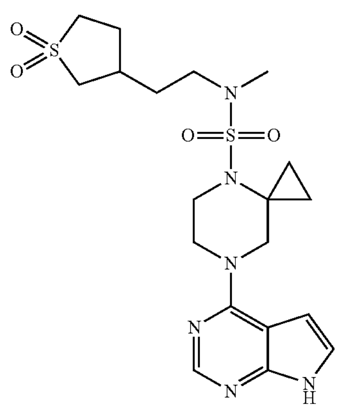 [SMILES: CN(CCC1CCS(=O)(=O)C1)S(=O)(=O)N1CCN(c2ncnc3[nH]ccc23)CC12CC2] | I | I | I | II |
| 76 | 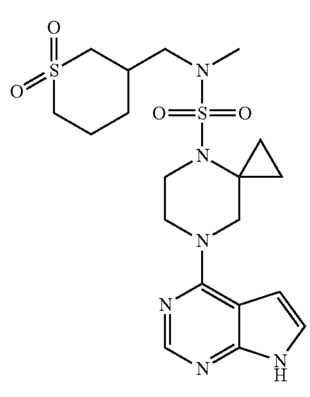 [SMILES: CN(CC1CCCS(=O)(=O)C1)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 77 | 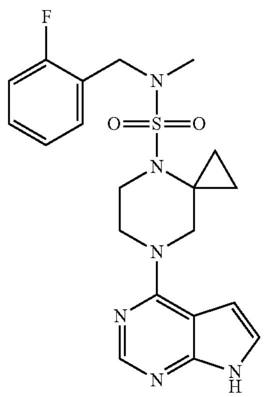 [SMILES: CN(Cc1ccccc1F)S(=O)(=O)N1CCN(c2ncnc3[nH]ccc23)CC12CC2] | I | I | II | II |
| 78 | 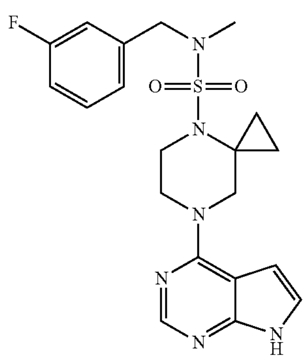 [SMILES: CN(Cc1cccc(F)c1)S(=O)(=O)N1CCN(c2ncnc3[nH]ccc23)CC12CC2] | I | I | I | II |
| 79 | 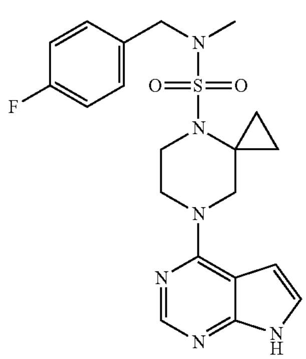 [SMILES: CN(Cc1ccc(F)cc1)S(=O)(=O)N1CCN(c2ncnc3[nH]ccc23)CC12CC2] | I | I | I | II |
| 80 | 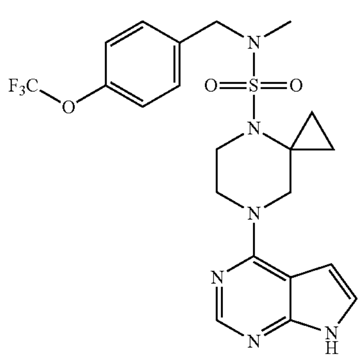 [SMILES: CN(Cc1ccc(OC(F)(F)F)cc1)S(=O)(=O)N1CCN(c2ncnc3[nH]ccc23)CC12CC2] | II | II | III | III |

TABLE 1-continued
| Example number | Structure | JAK1 | JAK2 | JAK3 | TYK2 |
|---|---|---|---|---|---|
| 81 | 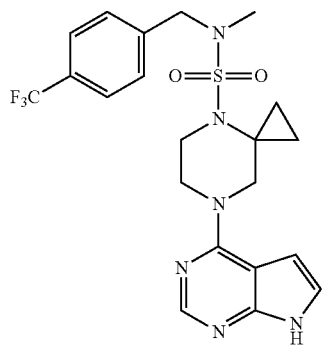 [SMILES: CN(Cc1ccc(C(F)(F)F)cc1)S(=O)(=O)N1CCN(c2ncnc3[nH]ccc23)CC12CC2] | I | I | | III |
| 82 | 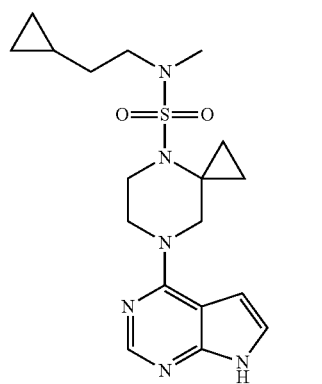 [SMILES: CN(CCC1CC1)S(=O)(=O)N1CCN(c2ncnc3[nH]ccc23)CC12CC2] | I | I | I | I |
| 83 | 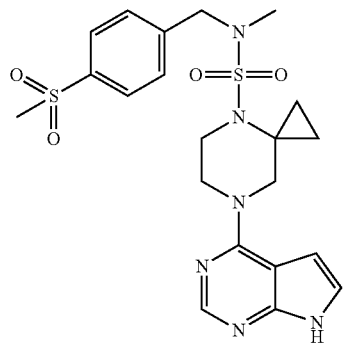 [SMILES: CN(Cc1ccc(S(C)(=O)=O)cc1)S(=O)(=O)N1CCN(c2ncnc3[nH]ccc23)CC12CC2] | I | I | I | I |
| 84 | 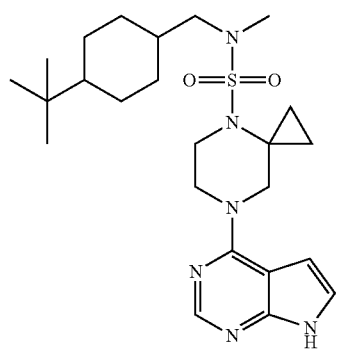 [SMILES: CN(CC1CCC(C(C)(C)C)CC1)S(=O)(=O)N1CCN(c2ncnc3[nH]ccc23)CC12CC2] | III | III | III | III |

TABLE 1-continued
| Example number | Structure | JAK1 | JAK2 | JAK3 | TYK2 |
|---|---|---|---|---|---|
| 85 | 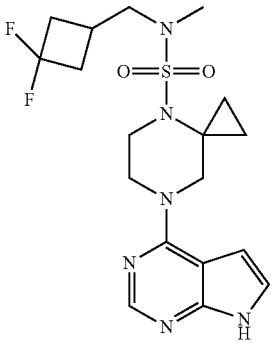 [SMILES: CN(CC1CC(F)(F)C1)S(=O)(=O)N1CCN(c2ncnc3[nH]ccc23)CC12CC2] | I | I | I | I |
| 86 | 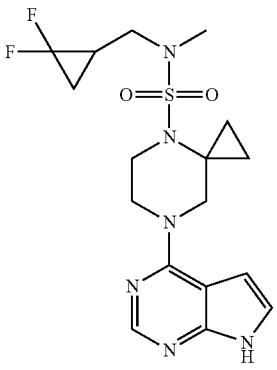 [SMILES: CN(CC1CC1(F)F)S(=O)(=O)N1CCN(c2ncnc3[nH]ccc23)CC12CC2] | I | I | I | I |
| 87 | 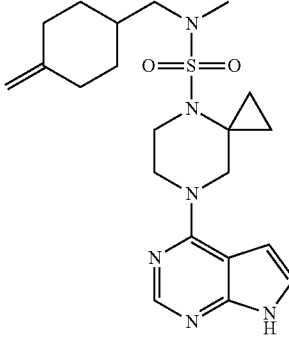 | I | I | I | II |
| 88 | 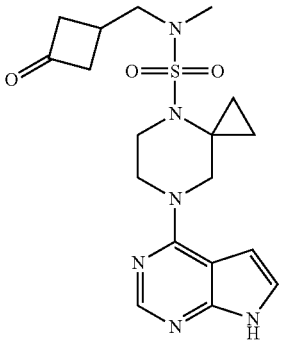 [SMILES: CN(CC1CC(=O)C1)S(=O)(=O)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 89 | 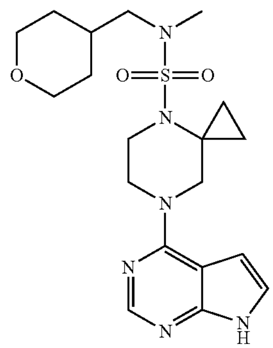 | I | I | II | II |
| 90 | 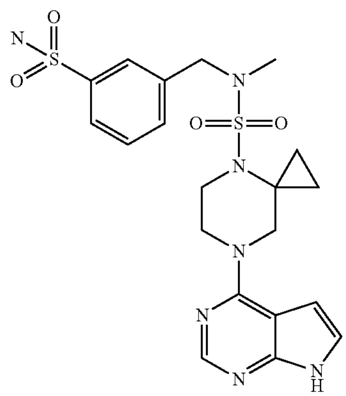 [SMILES: CN(Cc1cccc(S(N)(=O)=O)c1)S(=O)(=O)N1CCN(c2ncnc3[nH]ccc23)CC12CC2] | I | I | I | I |
| 91 | 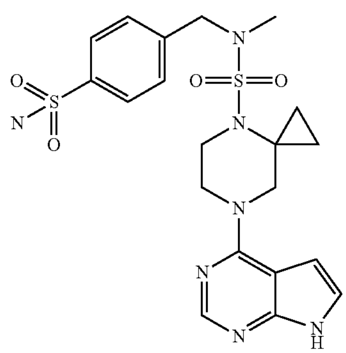 | I | I | I | I |
| 92 | 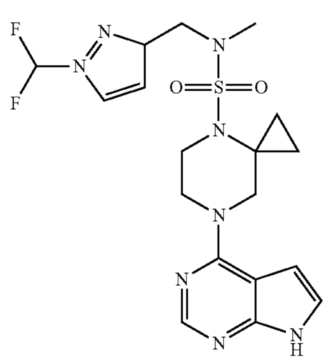 | I | I | I | II |

TABLE 1-continued

| Example number | Structure | JAK1 | JAK2 | JAK3 | TYK2 |
|---|---|---|---|---|---|
| 93 | 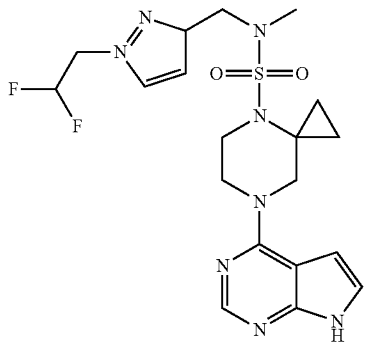 | I | I | II | II |
| 94 | 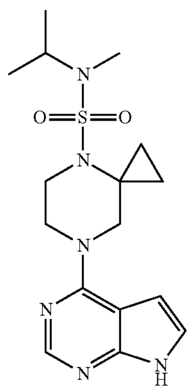 [SMILES: CC(C)N(C)S(=O)(=O)N1CCN(c2ncnc3[nH]ccc23)CC12CC2] | I | I | II | III |
| 95 | 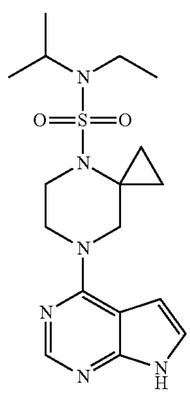 [SMILES: CCN(C(C)C)S(=O)(=O)N1CCN(c2ncnc3[nH]ccc23)CC12CC2] | II | I | II | III |
| 96 | 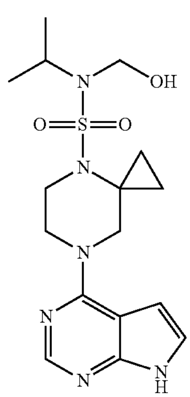 | I | I | II | III |

TABLE 1-continued
| Example number | Structure | JAK1 | JAK2 | JAK3 | TYK2 |
|---|---|---|---|---|---|
| 97 | 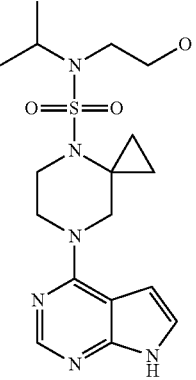 [SMILES: CC(C)N(CCO)S(=O)(=O)N1CCN(c2ncnc3[nH]ccc23)CC12CC2] | I | I | II | III |
| 98 | 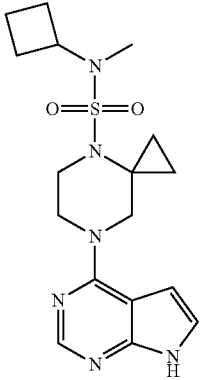 | I | I | II | II |
| 99 | 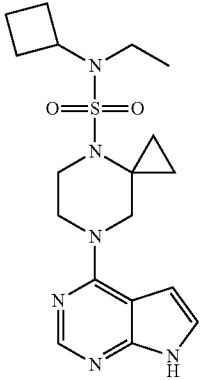 | I | I | II | I |
| 100 | 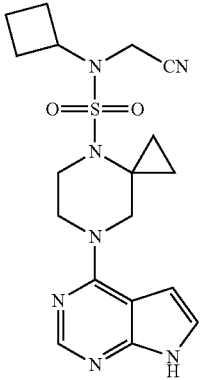 | I | I | I | I |

TABLE 1-continued
| Example number | Structure | JAK1 | JAK2 | JAK3 | TYK2 |
|---|---|---|---|---|---|
| 101 | 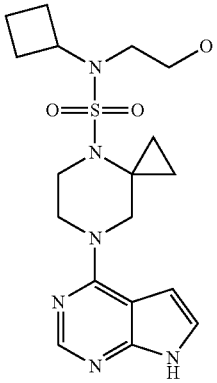 [SMILES: O=S(=O)(N(CCO)C1CCC1)N1CCN(c2ncnc3[nH]ccc23)CC12CC2] | I | I | I | I |
| 102 | 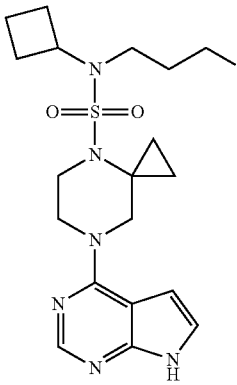 | I | I | I | II |
| 103 | 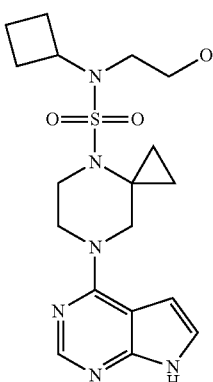 | I | I | II | II |
| 104 | 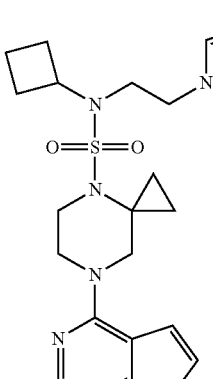 | I | I | II | II |

TABLE 1-continued
| Example number | Structure | JAK1 | JAK2 | JAK3 | TYK2 |
|---|---|---|---|---|---|
| 105 | 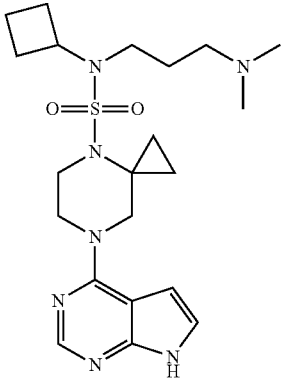 [SMILES: CN(C)CCCN(C1CCC1)S(=O)(=O)N1CCN(c2ncnc3[nH]ccc23)CC12CC2] | II | I | III | III |
| 106 | 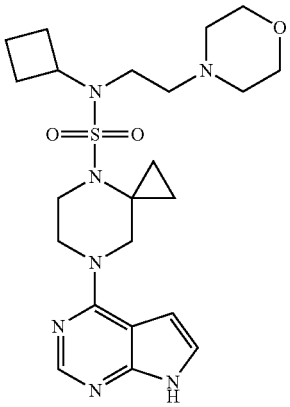 [SMILES: O=S(=O)(N(CCN1CCOCC1)C1CCC1)N1CCN(c2ncnc3[nH]ccc23)CC12CC2] | I | I | II | III |
| 107 | 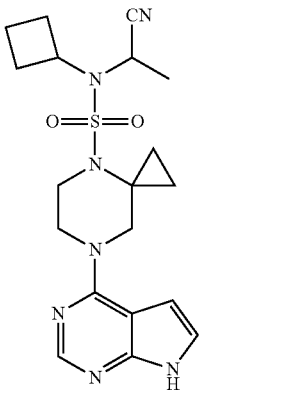 [SMILES: CC(C#N)N(C1CCC1)S(=O)(=O)N1CCN(c2ncnc3[nH]ccc23)CC12CC2] | I | I | I | II |
| 108 | 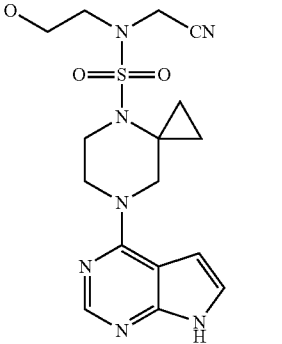 [SMILES: N#CCN(CCO)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 109 | 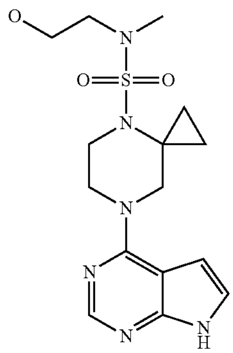 [SMILES: CN(CCO)S(=O)(=O)N1CCN(c2ncnc3[nH]ccc23)CC12CC2] | I | I | II | II |
| 110 | 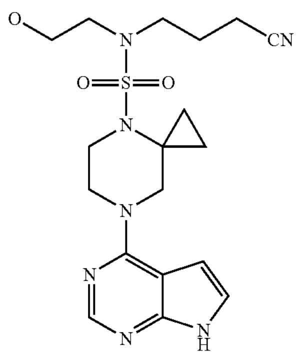 [SMILES: N#CCCCN(CCO)S(=O)(=O)N1CCN(c2ncnc3[nH]ccc23)CC12CC2] | I | I | I | II |
| 111 | 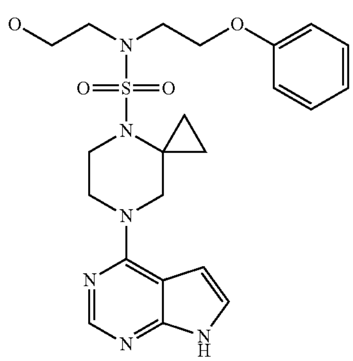 [SMILES: O=S(=O)(N(CCO)CCOc1ccccc1)N1CCN(c2ncnc3[nH]ccc23)CC12CC2] | II | I | II | III |
| 112 | 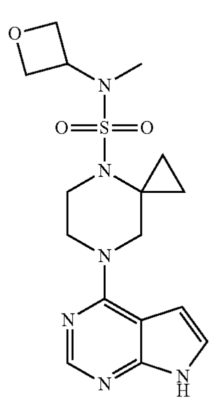 [SMILES: CN(C1COC1)S(=O)(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 113 | 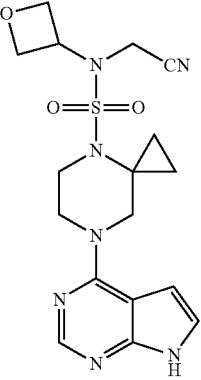 [SMILES: N#CCN(C1COC1)S(=O)(=O)N1CCN(c2ncnc3[nH]ccc23)CC12CC2] | I | I | I | I |
| 114 | 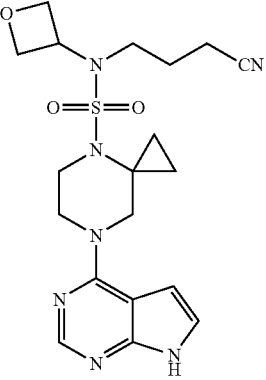 [SMILES: N#CCCCN(C1COC1)S(=O)(=O)N1CCN(c2ncnc3[nH]ccc23)CC12CC2] | I | I | I | I |
| 115 | 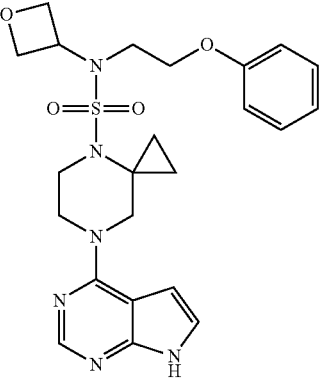 [SMILES: O=S(=O)(N(CCOc1ccccc1)C1COC1)N1CCN(c2ncnc3[nH]ccc23)CC12CC2] | I | I | I | II |
| 116 | 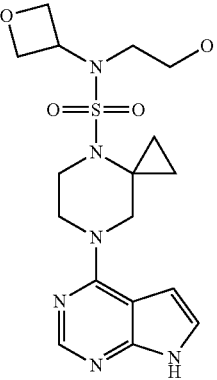 [SMILES: O=S(=O)(N(CCO)C1COC1)N1CCN(c2ncnc3[nH]ccc23)CC12CC2] | I | I | II | III |

TABLE 1-continued
| Example number | Structure | JAK1 | JAK2 | JAK3 | TYK2 |
|---|---|---|---|---|---|
| 117 | 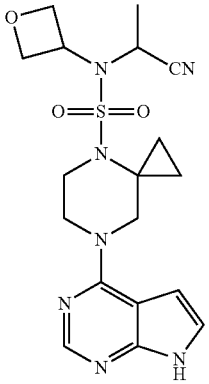 [SMILES: CC(C#N)N(C1COC1)S(=O)(=O)N1CCN(c2ncnc3[nH]ccc23)CC12CC2] | I | I | I | II |
| 118 | 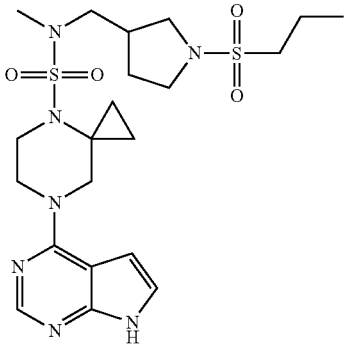 [SMILES: CCCS(=O)(=O)N1CCC(CN(C)S(=O)(=O)N2CCN(c3ncnc4[nH]ccc34)CC23CC3)C1] | I | I | I | II |
| 119 | 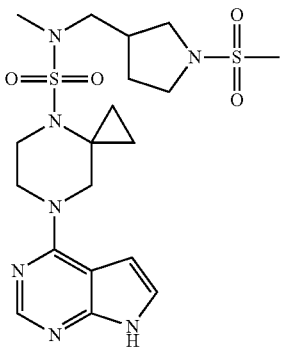 [SMILES: CN(CC1CCN(S(C)(=O)=O)C1)S(=O)(=O)N1CCN(c2ncnc3[nH]ccc23)CC12CC2] | I | I | I | II |
| 120 | 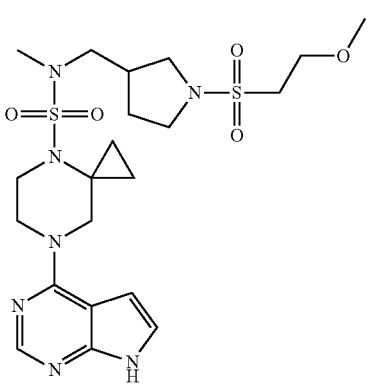 [SMILES: COCCS(=O)(=O)N1CCC(CN(C)S(=O)(=O)N2CCN(c3ncnc4[nH]ccc34)CC23CC3)C1] | I | I | I | II |

TABLE 1-continued
| Example number | Structure | JAK1 | JAK2 | JAK3 | TYK2 |
|---|---|---|---|---|---|
| 121 | 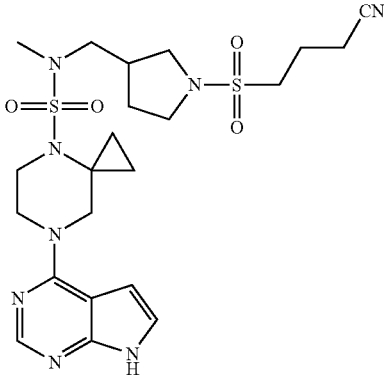 [SMILES: CN(CC1CCN(S(=O)(=O)CCCC#N)C1)S(=O)(=O)N1CCN(c2ncnc3[nH]ccc23)CC12CC2] | I | I | I | II |
| 122 | 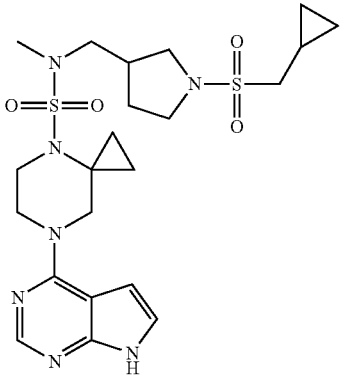 [SMILES: CN(CC1CCN(S(=O)(=O)CC2CC2)C1)S(=O)(=O)N1CCN(c2ncnc3[nH]ccc23)CC12CC2] | I | I | I | II |
| 123 | 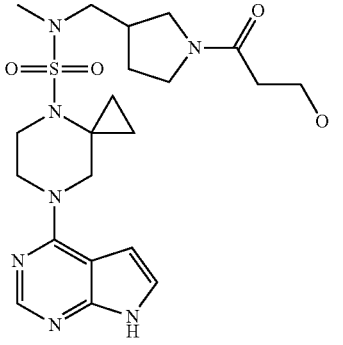 [SMILES: CN(CC1CCN(C(=O)CCO)C1)S(=O)(=O)N1CCN(c2ncnc3[nH]ccc23)CC12CC2] | I | I | II | III |
| 124 | 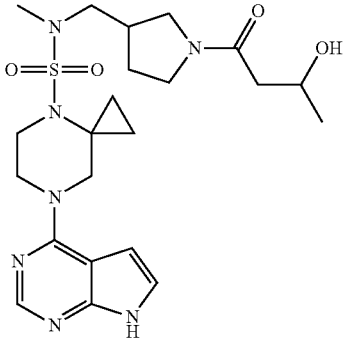 [SMILES: CC(O)CC(=O)N1CCC(CN(C)S(=O)(=O)N2CCN(c3ncnc4[nH]ccc34)CC23CC3)C1] | I | I | II | III |

TABLE 1-continued

| Example number | Structure | JAK1 | JAK2 | JAK3 | TYK2 |
|---|---|---|---|---|---|
| 125 | 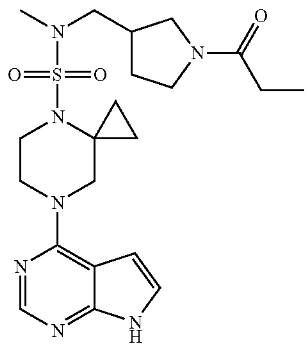 [SMILES: CCC(=O)N1CCC(CN(C)S(=O)(=O)N2CCN(c3ncnc4[nH]ccc34)CC23CC3)C1] | I | I | II | III |
| 126 | 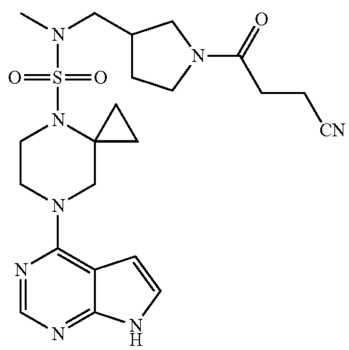 | I | I | II | III |
| 127 | 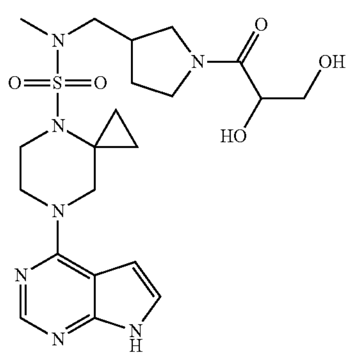 [SMILES: CN(CC1CCN(C(=O)C(O)CO)C1)S(=O)(=O)N1CCN(c2ncnc3[nH]ccc23)CC12CC2] | I | I | II | III |
| 128 | 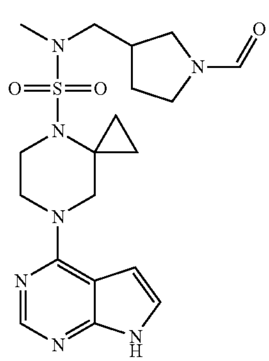 [SMILES: CN(CC1CCN(C=O)C1)S(=O)(=O)N1CCN(c2ncnc3[nH]ccc23)CC12CC2] | I | I | I | III |

TABLE 1-continued
| Example number | Structure | JAK1 | JAK2 | JAK3 | TYK2 |
|---|---|---|---|---|---|
| 129 | 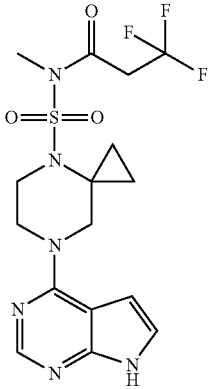 [SMILES: CN(C(=O)CC(F)(F)F)S(=O)(=O)N1CCN(c2ncnc3[nH]ccc23)CC12CC2] | I | I | II | II |
| 130 | 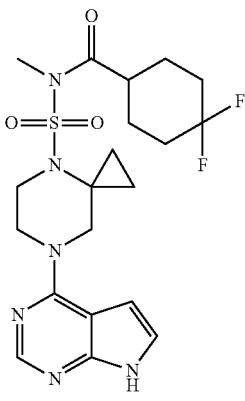 [SMILES: CN(C(=O)C1CCC(F)(F)CC1)S(=O)(=O)N1CCN(c2ncnc3[nH]ccc23)CC12CC2] | I | I | I | II |
| 131 | 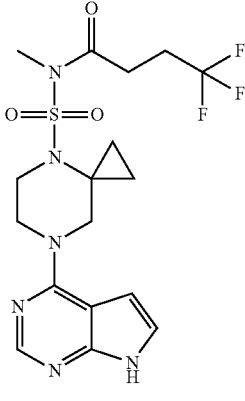 [SMILES: CN(C(=O)CCC(F)(F)F)S(=O)(=O)N1CCN(c2ncnc3[nH]ccc23)CC12CC2] | I | I | II | I |
| 132 | 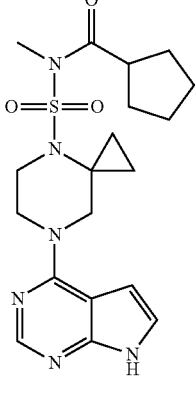 | I | I | II | II |

TABLE 1-continued

| Example number | Structure | JAK1 | JAK2 | JAK3 | TYK2 |
|---|---|---|---|---|---|
| 133 | 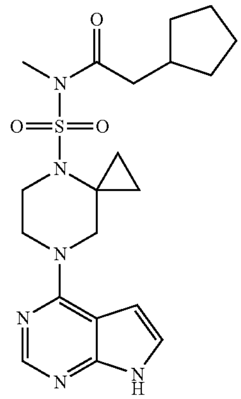 [SMILES: CN(C(=O)CC1CCCC1)S(=O)(=O)N1CCN(c2ncnc3[nH]ccc23)CC12CC2] | I | I | II | II |
| 134 | 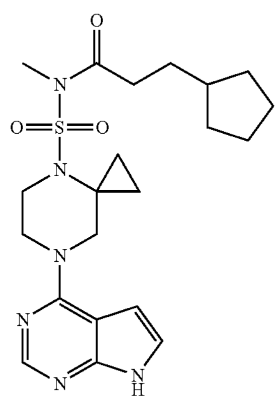 [SMILES: CN(C(=O)CCC1CCCC1)S(=O)(=O)N1CCN(c2ncnc3[nH]ccc23)CC12CC2] | I | II | III | III |
| 135 | 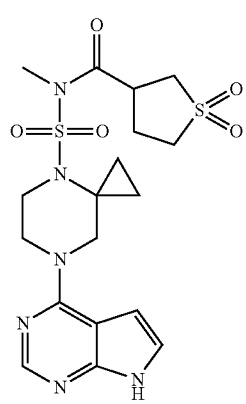 [SMILES: CN(C(=O)C1CCS(=O)(=O)C1)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 136 | 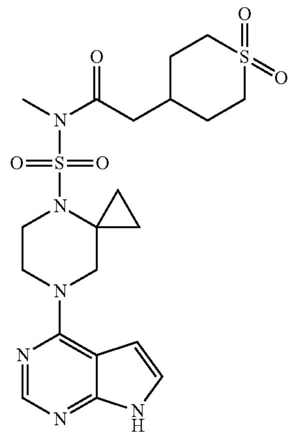 [SMILES: CN(C(=O)CC1CCS(=O)(=O)CC1)S(=O)(=O)N1CCN(c2ncnc3[nH]ccc23)CC12CC2] | I | I | II | III |
| 137 | 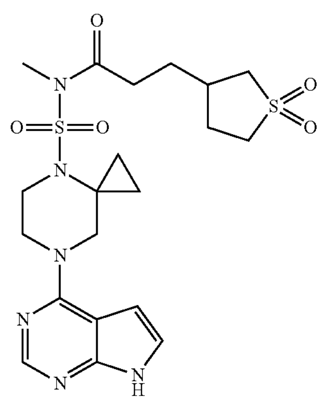 [SMILES: CN(C(=O)CCC1CCS(=O)(=O)C1)S(=O)(=O)N1CCN(c2ncnc3[nH]ccc23)CC12CC2] | I | I | II | III |
| 138 | 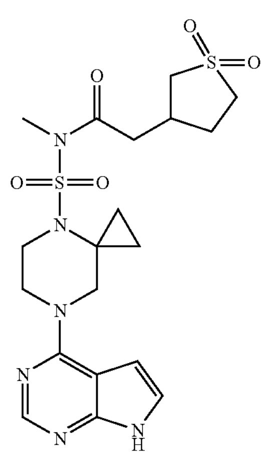 [SMILES: CN(C(=O)CC1CCS(=O)(=O)C1)S(=O)(=O)N1CCN(c2ncnc3[nH]ccc23)CC12CC2] | I | I | II | III |

TABLE 1-continued

| Example number | Structure | JAK1 | JAK2 | JAK3 | TYK2 |
|---|---|---|---|---|---|
| 139 | 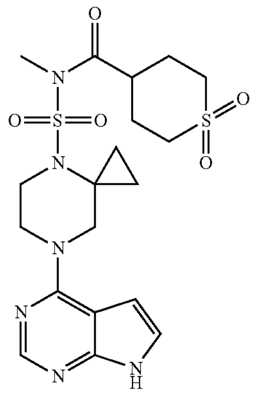 [SMILES: CN(C(=O)C1CCS(=O)(=O)CC1)S(=O)(=O)N1CCN(c2ncnc3[nH]ccc23)CC12CC2] | I | I | I | I |
| 140 | 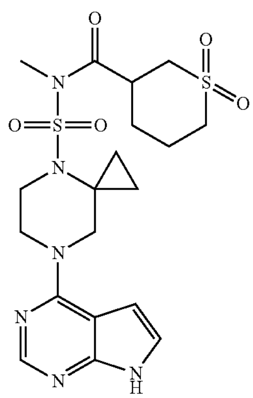 [SMILES: CN(C(=O)C1CCCS(=O)(=O)C1)S(=O)(=O)N1CCN(c2ncnc3[nH]ccc23)CC12CC2] | I | I | II | III |
| 141 | 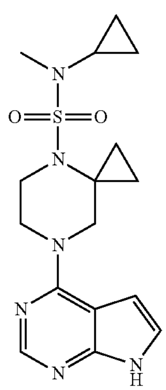 [SMILES: CN(C1CC1)S(=O)(=O)N1CCN(c2ncnc3[nH]ccc23)CC12CC2] | I | I | II | II |
| 142 | 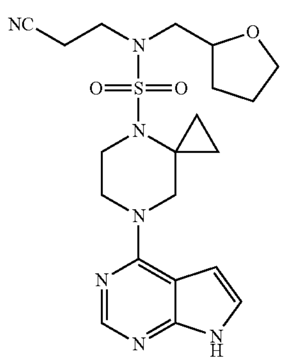 [SMILES: N#CCCN(CC1CCCO1)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 143 | 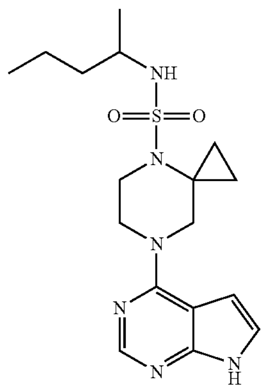 [SMILES: CCCC(C)NS(=O)(=O)N1CCN(c2ncnc3[nH]ccc23)CC12CC2] | I | I | II | III |
| 144 | 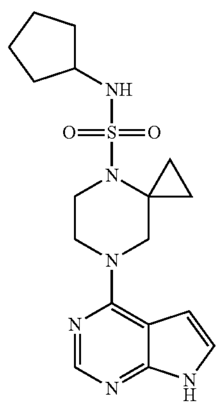 [SMILES: O=S(=O)(NC1CCCC1)N1CCN(c2ncnc3[nH]ccc23)CC12CC2] | I | I | II | II |
| 145 | 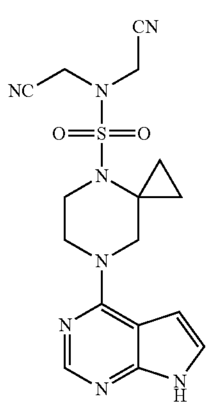 [SMILES: N#CCN(CC#N)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 146 | 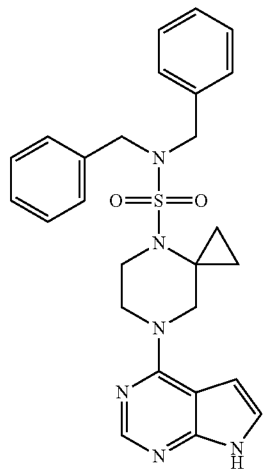 [SMILES: O=S(=O)(N(Cc1ccccc1)Cc1ccccc1)N1CCN(c2ncnc3[nH]ccc23)CC12CC2] | II | II | III | III |
| 147 | 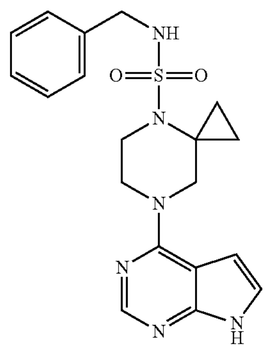 [SMILES: O=S(=O)(NCc1ccccc1)N1CCN(c2ncnc3[nH]ccc23)CC12CC2] | I | I | II | II |
| 148 | 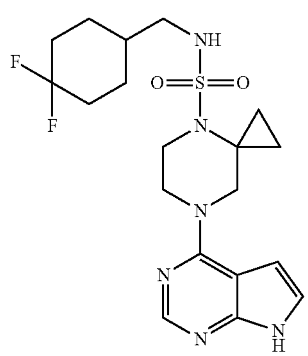 [SMILES: O=S(=O)(NCC1CCC(F)(F)CC1)N1CCN(c2ncnc3[nH]ccc23)CC12CC2] | I | I | I | II |
| 149 | 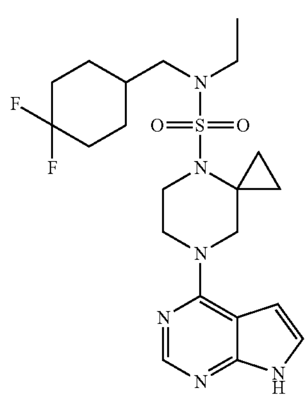 [SMILES: CCN(CC1CCC(F)(F)CC1)S(=O)(=O)N1CCN(c2ncnc3[nH]ccc23)CC12CC2] | I | I | I | III |

TABLE 1-continued
| Example number | Structure | JAK1 | JAK2 | JAK3 | TYK2 |
|---|---|---|---|---|---|
| 150 | 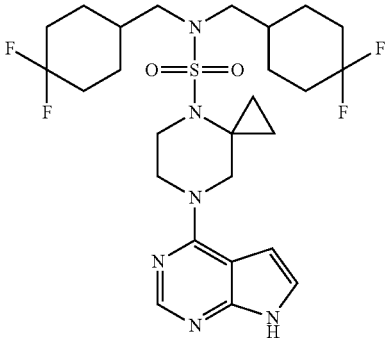 [SMILES: O=S(=O)(N(CC1CCC(F)(F)CC1)CC1CCC(F)(F)CC1)N1CCN(c2ncnc3[nH]ccc23)CC12CC2] | II | I | II | III |
| 151 | 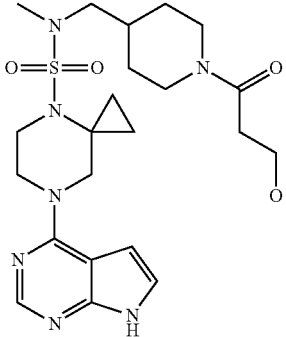 [SMILES: CN(CC1CCN(C(=O)CCO)CC1)S(=O)(=O)N1CCN(c2ncnc3[nH]ccc23)CC12CC2] | I | I | II | II |
| 152 | 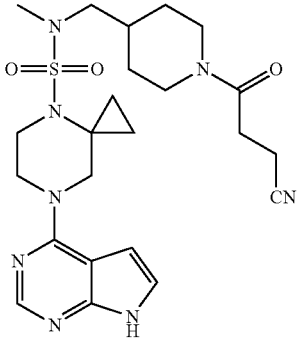 [SMILES: CN(CC1CCN(C(=O)CCC#N)CC1)S(=O)(=O)N1CCN(c2ncnc3[nH]ccc23)CC12CC2] | I | I | II | III |
| 153 | 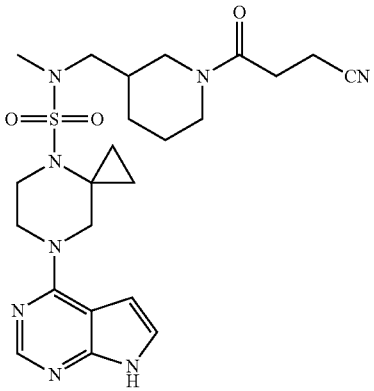 | I | I | II | III |

TABLE 1-continued
| Example number | Structure | JAK1 | JAK2 | JAK3 | TYK2 |
|---|---|---|---|---|---|
| 154 | 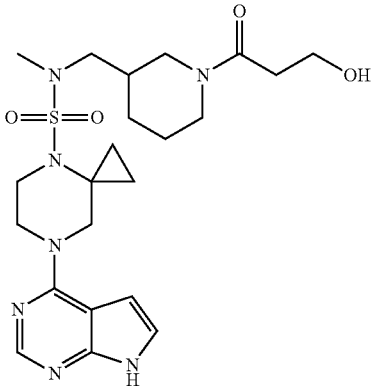 [SMILES: CN(CC1CCCN(C(=O)CCO)C1)S(=O)(=O)N1CCN(c2ncnc3[nH]ccc23)CC12CC2] | I | I | I | II |
| 155 | 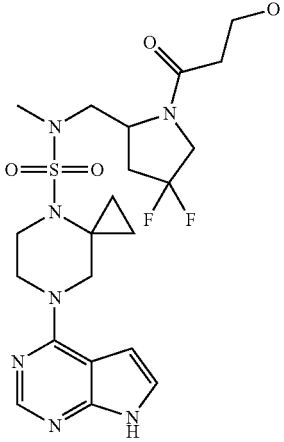 [SMILES: CN(CC1CC(F)(F)CN1C(=O)CCO)S(=O)(=O)N1CCN(c2ncnc3[nH]ccc23)CC12CC2] | I | I | I | I |
| 156 | 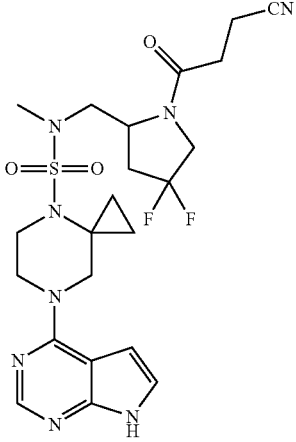 [SMILES: CN(CC1CC(F)(F)CN1C(=O)CCC#N)S(=O)(=O)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 157 | 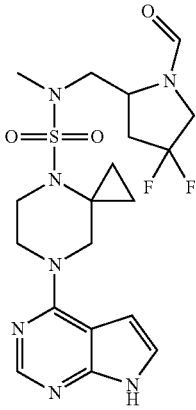 [SMILES: CN(CC1CC(F)(F)CN1C=O)S(=O)(=O)N1CCN(c2ncnc3[nH]ccc23)CC12CC2] | I | I | I | I |
| 158 | 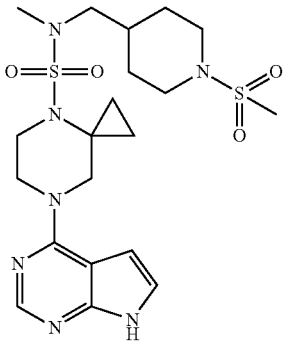 [SMILES: CN(CC1CCN(S(C)(=O)=O)CC1)S(=O)(=O)N1CCN(c2ncnc3[nH]ccc23)CC12CC2] | I | I | I | II |
| 159 | 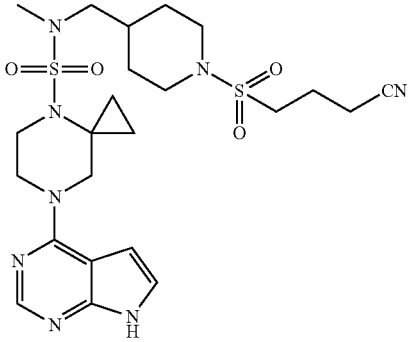 [SMILES: CN(CC1CCN(S(=O)(=O)CCCC#N)CC1)S(=O)(=O)N1CCN(c2ncnc3[nH]ccc23)CC12CC2] | I | I | I | II |
| 160 | 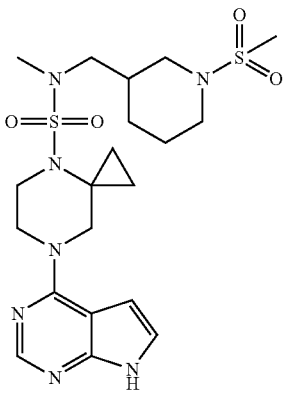 [SMILES: CN(CC1CCCN(S(C)(=O)=O)C1)S(=O)(=O)N1CCN(c2ncnc3[nH]ccc23)CC12CC2] | I | I | I | II |

TABLE 1-continued
| Example number | Structure | JAK1 | JAK2 | JAK3 | TYK2 |
|---|---|---|---|---|---|
| 161 | 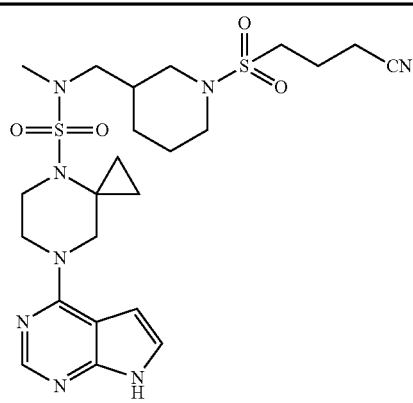 | I | I | II | III |
| 162 | 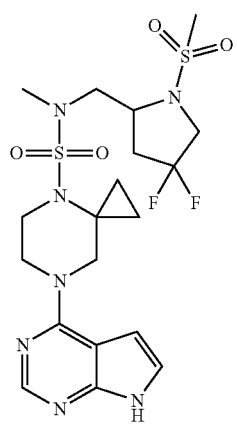 [SMILES: CN(CC1CC(F)(F)CN1S(C)(=O)=O)S(=O)(=O)N1CCN(c2ncnc3[nH]ccc23)CC12CC2] | I | I | I | I |
| 163 | 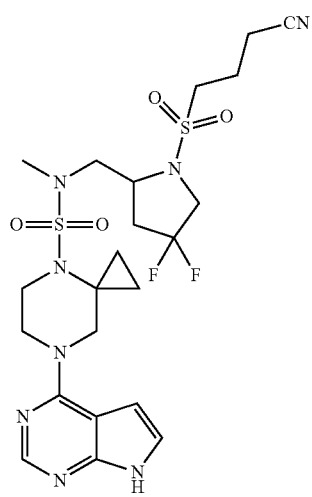 [SMILES: CN(CC1CC(F)(F)CN1S(=O)(=O)CCCC#N)S(=O)(=O)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 164 | 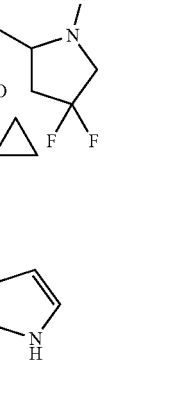 | I | I | I | I |
| 165 | 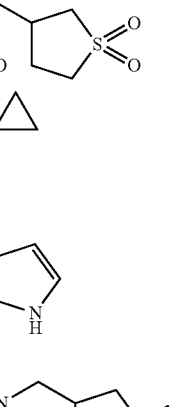 | I | I | I | II |
| 166 | 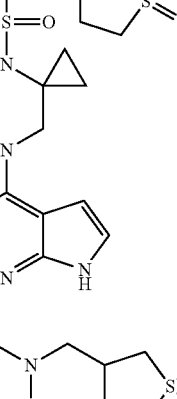 | I | I | I | I |
| 167 | 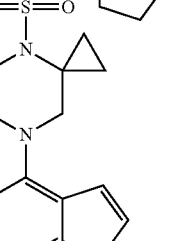 | I | I | I | II |

TABLE 1-continued

| Example number | Structure | JAK1 | JAK2 | JAK3 | TYK2 |
|---|---|---|---|---|---|
| 168 | 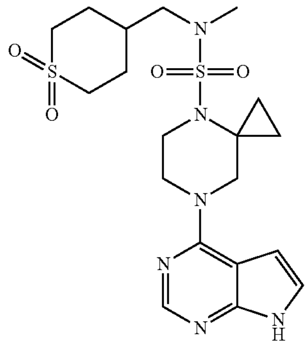 [SMILES: CN(CC1CCS(=O)(=O)CC1)S(=O)(=O)N1CCN(c2ncnc3[nH]ccc23)CC12CC2] | I | I | I | I |
| 169 | 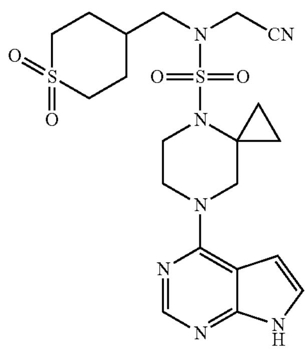 [SMILES: N#CCN(CC1CCS(=O)(=O)CC1)S(=O)(=O)N1CCN(c2ncnc3[nH]ccc23)CC12CC2] | I | I | I | I |
| 170 | 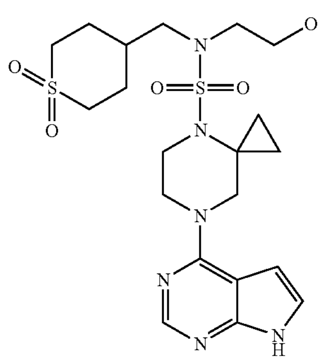 [SMILES: O=S1(=O)CCC(CN(CCO)S(=O)(=O)N2CCN(c3ncnc4[nH]ccc34)CC23CC3)CC1] | I | I | I | I |
| 171 | 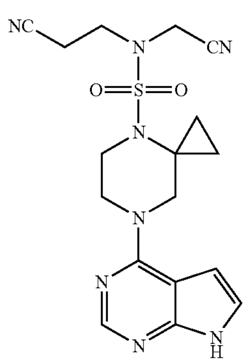 [SMILES: N#CCCN(CC#N)S(=O)(=O)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 172 | 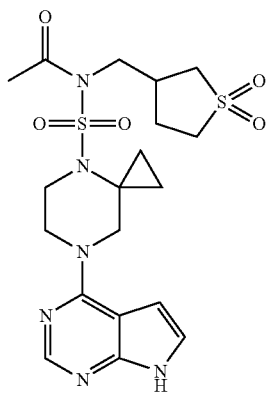 [SMILES: CC(=O)N(CC1CCS(=O)(=O)C1)S(=O)(=O)N1CCN(c2ncnc3[nH]ccc23)CC12CC2] | I | I | I | II |
| 173 | 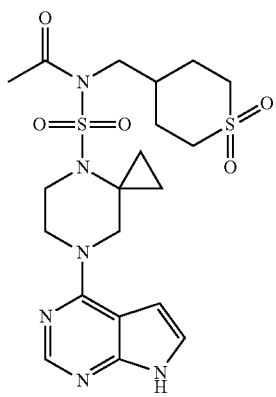 [SMILES: CC(=O)N(CC1CCS(=O)(=O)CC1)S(=O)(=O)N1CCN(c2ncnc3[nH]ccc23)CC12CC2] | I | I | I | II |
| 174 | 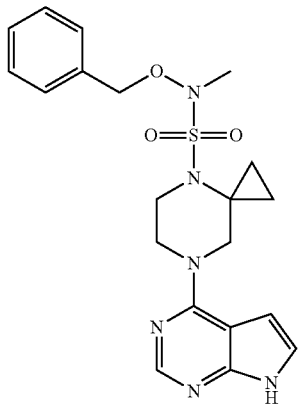 [SMILES: CN(OCc1ccccc1)S(=O)(=O)N1CCN(c2ncnc3[nH]ccc23)CC12CC2] | I | I | II | II |

TABLE 1-continued
| Example number | Structure | JAK1 | JAK2 | JAK3 | TYK2 |
|---|---|---|---|---|---|
| 175 | 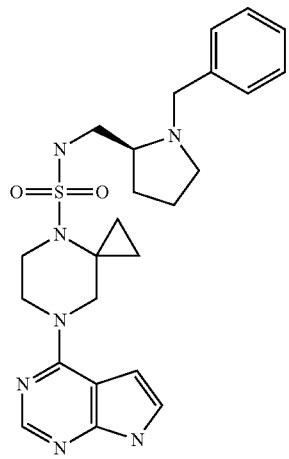 [SMILES: O=S(=O)(NC[C@@H]1CCCN1Cc1ccccc1)N1CCN(c2ncnc3[nH]ccc23)CC12CC2] | I | I | II | II |
| 176 | 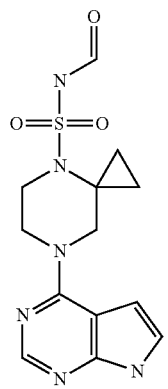 [SMILES: O=CNS(=O)(=O)N1CCN(c2ncnc3[nH]ccc23)CC12CC2] | I | I | II | III |
| 177 | 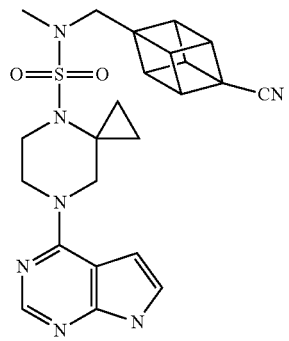 [SMILES: CN(CC12C3C4C1C1C2C3C41C#N)S(=O)(=O)N1CCN(c2ncnc3[nH]ccc23)CC12CC2] | I | I | I | I |

TABLE 1-continued

| Example number | Structure | JAK1 | JAK2 | JAK3 | TYK2 |
|---|---|---|---|---|---|
| 178 | 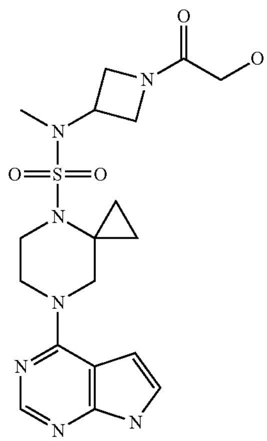 [SMILES: CN(C1CN(C(=O)CO)C1)S(=O)(=O)N1CCN(c2ncnc3[nH]ccc23)CC12CC2] | I | I | I | II |
| 179 | 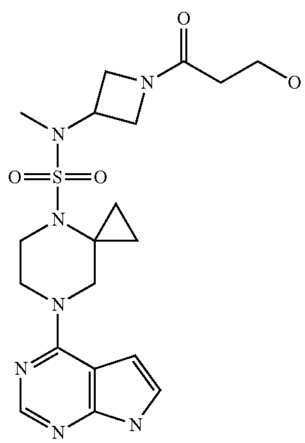 [SMILES: CN(C1CN(C(=O)CCO)C1)S(=O)(=O)N1CCN(c2ncnc3[nH]ccc23)CC12CC2] | I | I | II | II |
| 180 | 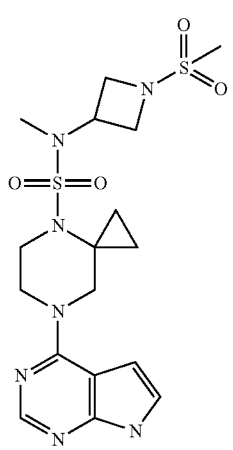 [SMILES: CN(C1CN(S(C)(=O)=O)C1)S(=O)(=O)N1CCN(c2ncnc3[nH]ccc23)CC12CC2] | I | I | I | I |

TABLE 1-continued

| Example number | Structure | JAK1 | JAK2 | JAK3 | TYK2 |
|---|---|---|---|---|---|
| 181 | 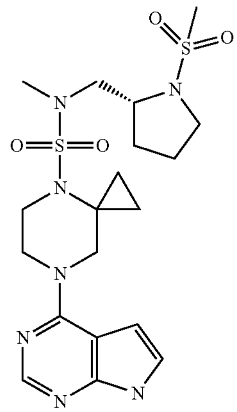 [SMILES: CN(C[C@H]1CCCN1S(C)(=O)=O)S(=O)(=O)N1CCN(c2ncnc3[nH]ccc23)CC12CC2] | I | I | I | I |
| 182 | 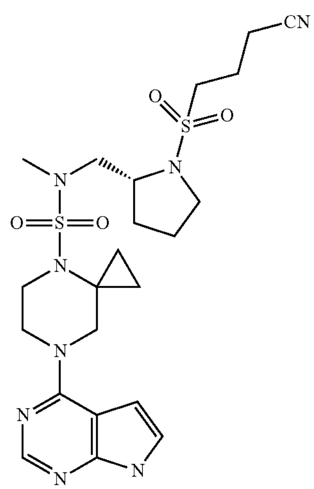 [SMILES: CN(C[C@H]1CCCN1S(=O)(=O)CCCC#N)S(=O)(=O)N1CCN(c2ncnc3[nH]ccc23)CC12CC2] | I | I | I | I |
| 183 | 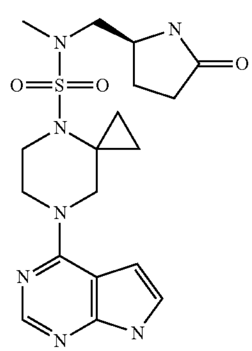 [SMILES: CN(C[C@@H]1CCC(=O)N1)S(=O)(=O)N1CCN(c2ncnc3[nH]ccc23)CC12CC2] | I | I | I | I |
| 184 | 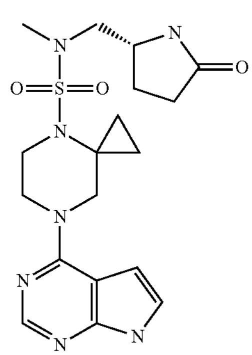 [SMILES: CN(C[C@H]1CCC(=O)N1)S(=O)(=O)N1CCN(c2ncnc3[nH]ccc23)CC12CC2] | I | I | I | I |

TABLE 1-continued
| Example number | Structure | JAK1 | JAK2 | JAK3 | TYK2 |
|---|---|---|---|---|---|
| 185 | 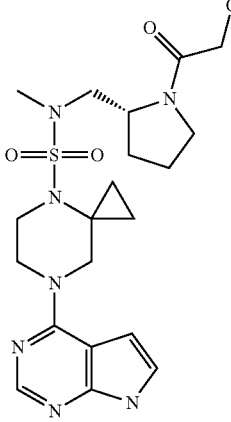 | I | I | I | I |
| 186 | 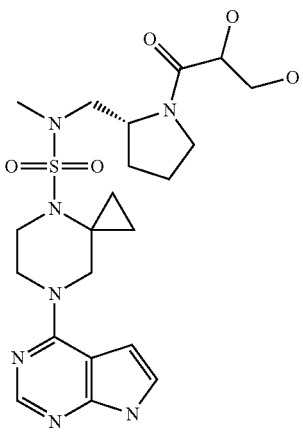 [SMILES: CN(C[C@H]1CCCN1C(=O)C(O)CO)S(=O)(=O)N1CCN(c2ncnc3[nH]ccc23)CC12CC2] | I | I | I | I |
| 187 | 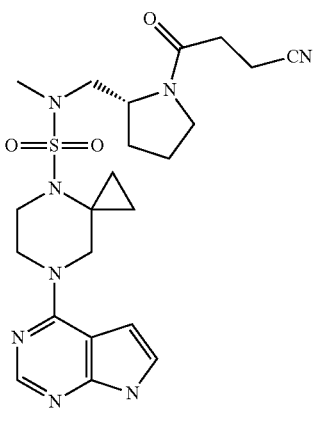 [SMILES: CN(C[C@H]1CCCN1C(=O)CCC#N)S(=O)(=O)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 188 | 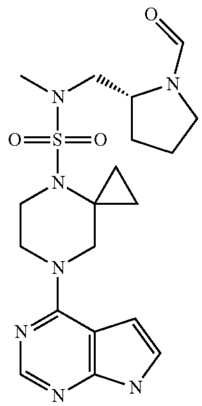 [SMILES: CN(C[C@H]1CCCN1C=O)S(=O)(=O)N1CCN(c2ncnc3[nH]ccc23)CC12CC2] | I | I | I | II |
| 189 | 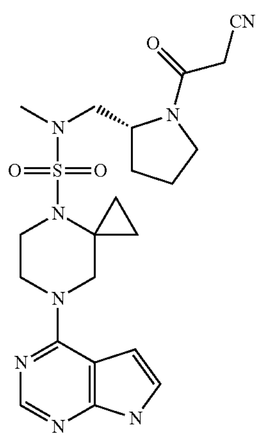 [SMILES: CN(C[C@H]1CCCN1C(=O)CC#N)S(=O)(=O)N1CCN(c2ncnc3[nH]ccc23)CC12CC2] | I | I | I | II |
| 190 | 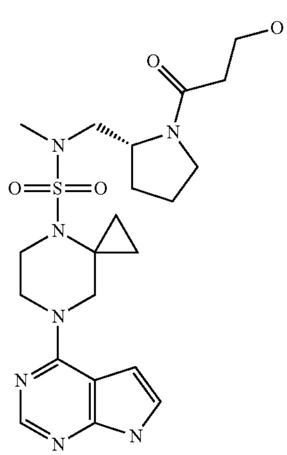 [SMILES: CN(C[C@H]1CCCN1C(=O)CCO)S(=O)(=O)N1CCN(c2ncnc3[nH]ccc23)CC12CC2] | I | I | II | II |

TABLE 1-continued

| Example number | Structure | JAK1 | JAK2 | JAK3 | TYK2 |
|---|---|---|---|---|---|
| 191 | 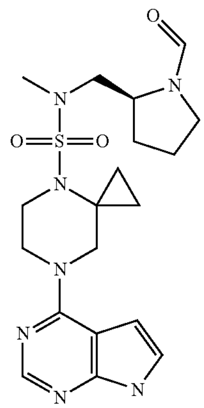 [SMILES: CN(C[C@@H]1CCCN1C=O)S(=O)(=O)N1CCN(c2ncnc3[nH]ccc23)CC12CC2] | I | I | I | II |
| 192 | 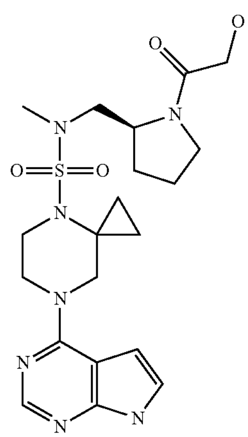 [SMILES: CN(C[C@@H]1CCCN1C(=O)CO)S(=O)(=O)N1CCN(c2ncnc3[nH]ccc23)CC12CC2] | I | I | I | I |
| 193 | 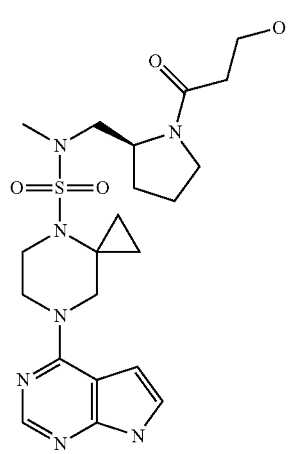 [SMILES: CN(C[C@@H]1CCCN1C(=O)CCO)S(=O)(=O)N1CCN(c2ncnc3[nH]ccc23)CC12CC2] | I | I | I | II |

TABLE 1-continued

| Example number | Structure | JAK1 | JAK2 | JAK3 | TYK2 |
|---|---|---|---|---|---|
| 194 | 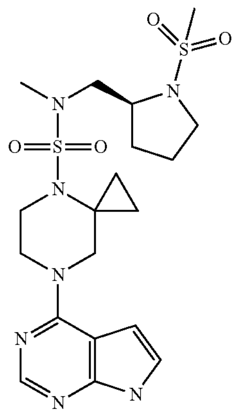 [SMILES: CN(C[C@@H]1CCCN1S(C)(=O)=O)S(=O)(=O)N1CCN(c2ncnc3[nH]ccc23)CC12CC2] | I | I | I | II |
| 195 | 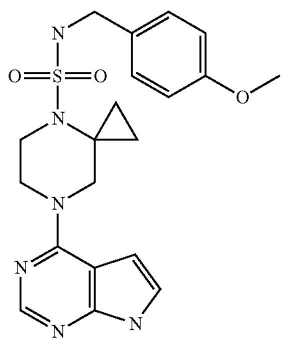 [SMILES: COc1ccc(CNS(=O)(=O)N2CCN(c3ncnc4[nH]ccc34)CC23CC3)cc1] | II | II | III | III |
| 196 | 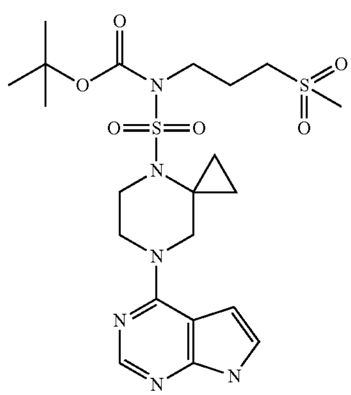 [SMILES: CC(C)(C)OC(=O)N(CCCS(C)(=O)=O)S(=O)(=O)N1CCN(c2ncnc3[nH]ccc23)CC12CC2] | II | II | III | III |

The invention claimed is:

1. A compound of general formula I

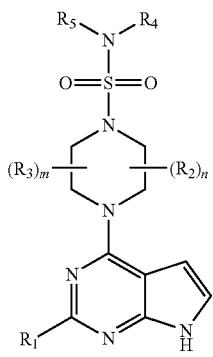

wherein m is zero;

n is 2;

$R_1$ is hydrogen;

together with the piperazinyl ring forms a diazaspiro[2.5]octyl moiety;

$R_3$ independently at each occurrence is selected from the group consisting of halogen, cyano, hydroxy, oxo, alkyl-, heteroalkyl-, cycloalkyl-, heterocyclyl-, $R_{3a}O$—, $R_{3a}S$—, $(R_{3a})_2N$—, $R_{3a}$—$C(=O)$—, $R_{3a}O$—$C(=O)$—, $(R_{3a})_2N$—$C(=O)$—, $R_{3a}$—$C(=O)N(R_{3b})$—, $R_{3a}O$—$C(=O)N(R_{3b})$—, $R_{3a}$—$C(=O)O$—, $(R_{3a})_2N$—$C(=O)O$—, $R_{3a}$—$S(=O)$—, $R_{3a}$—$S(=O)_2$—, $(R_{3a})_2N$—$S(=O)_2$— and $R_{3a}$—$S(=O)_2N(R_{3b})$—;

$R_{3a}$ and $R_{3b}$ independently at each occurrence are selected from the group consisting of hydrogen, alkyl-, heteroalkyl-, cycloalkyl- and heterocyclylor in the case where two $R_{3a}$s are attached to the same N, they may together with the N atom to which they are attached form a heterocycle;

$R_4$ and $R_5$ independently at each occurrence is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, aryloxyalkyl-, heteroarylalkyl-, heteroaryloxyalkyl-, $R_6$O-L-, $R_6$S-L-, $(R_6)_2$N-L-, $R_6$—C(=O)-L-, $R_6$O—C(=O)-L-, $(R_6)_2$N—C(=O)-L-, $R_6$—C(=O)N($R_6$)-L-, $R_6$O—C(=O)N($R_6$)-L-, $(R_6)_2$N—C(=O)N($R_6$)-L-, $R_6$—C(=O)O-L-, $(R_6)_2$N—C(=O)O-L-, $R_6$—S(=O)$_2$-L-, $(R_6)_2$N—S(=O)$_2$-L-, $R_6$—S(=O)$_2$N($R_6$)-L- and $(R_6)_2$N—S(=O)$_2$N($R_6$)-L either of which may be optionally substituted with one or more $R_7$;

or $R_4$ and $R_5$ can together with the N atom to which they are attached form a heterocyclic ring which may be optionally substituted with one or more $R_7$;

or $R_4$ and $R_5$ independently can be hydrogen;

L is independently at each occurrence selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, aryloxyalkyl-, heteroarylalkyl- and heteroaryloxyalkyl-;

or when $R_4$ or $R_5$ is selected from $R_6$O-L-, L can also be a bond;

$R_6$ independently at each occurrence is selected from the group consisting of hydrogen, alkyl-, heteroalkyl-, alkenyl-, alkynyl-, cycloalkyl-, heterocyclyl-, aryl-, arylalkyl- and heteroaryl-, cycloalkylalkyl- either of which may be optionally substituted with one or more substituents selected from the group consisting of halogen, cyano, hydroxy, trifluoromethyl, oxo, —NH$_2$, —SO$_2$NH$_2$, —SONH$_2$, —CONH$_2$ and —O(C$_1$-C$_4$);

or in the case where two $R_6$ are attached to the same N, they may together with the N atom to which they are attached form a heterocycle which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

$R_7$ independently at each occurrence is selected from the group consisting of halogen, cyano, hydroxy, trifluoromethyl, oxo, —NH$_2$, —SO$_2$NH$_2$, —SONH$_2$, —CONH$_2$ and =CH$_2$, or $R_7$ is selected from the group consisting of alkyl-, heteroalkyl-, alkenyl-, alkynyl-, cycloalkyl-, cycloalkenyl-, cycloalkynyl-, heterocyclyl-, cycloalkylalkyl-, heterocyclylalkyl, alkylcycloalkyl-, alkylheterocyclyl-, aryl-, heteroaryl-, arylalkyl-, alkoxy-, aryloxyalkyl-, heteroarylalkyl-, heteroaryloxyalkyl-, $R_8$O-L-, $R_8$S-L-, $(R_8)_2$N-L-, $R_8$—C(=O)-L-, $R_8$O—C(=O)-L-, $(R_8)_2$N—C(=O)-L-, $R_8$—C(=O)N($R_8$)-L-, $R_8$O—C(=O)N($R_8$)-L-, $(R_8)_2$N—C(=O)N($R_8$)-L-, $R_8$—C(=O)O-L-, $(R_8)_2$N—C(=O)O-L-, $R_8$—S(=O)$_2$-L-, $(R_8)_2$N—S(=O)$_2$-L-, $R_8$—S(=O)$_2$N($R_8$)-L- and $(R_8)_2$N—S(=O)$_2$N($R_8$)-L either of which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

$R_8$ independently at each occurrence is selected from the group consisting of hydrogen, alkyl-, heteroalkyl-, alkenyl-, alkynyl-, cycloalkyl-, heterocyclyl-, cyclolalkylalkyl-, heterocyclylalkyl-, aryl-, arylalkyl-, heteroaryl-, and heteroarylalkyl- either of which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

or in the case where two $R_8$ are attached to the same N, they may together with the N atom to which they are attached form a heterocycle which may be optionally substituted with one or more substituents selected from the group consisting of halogen, cyano, hydroxy, trifluoromethyl, oxo, —NH$_2$, —SO$_2$NH$_2$, —SONH$_2$ and —CONH$_2$;

and pharmaceutically acceptable salts, prodrugs, hydrates, or solvates thereof;

with the proviso that when n is 2, and $R_4$ is methyl, $R_5$ is not selected from the group consisting of cyanoethyl or cyclohexyl;

and with the proviso that when n is 2, and $R_5$ is methyl, $R_4$ is not selected from the group consisting of cyanoethyl or cyclohexyl;

and with the proviso that when and n is 2, and $R_4$ is ethyl, $R_5$ is not ethyl.

2. The compound according to claim 1, wherein one of $R_4$ and $R_5$ is selected from the group consisting of (C$_1$-C$_2$)alkyl-, heteroalkyl-, (C$_2$-C$_4$)alkenyl-, (C$_2$-C$_4$)alkynyl-, (C$_3$-C$_8$)cycloalkyl-, cycloalkenyl-, cycloalkynyl-, heterocyclyl-, cycloalkyl(C$_1$-C$_4$)alkyl-, heterocyclyl(C$_1$-C$_4$)alkyl, (C$_1$-C$_4$)alkyl(C$_3$-C$_8$)cycloalkyl-, (C$_1$-C$_4$)alkylheterocyclyl-, aryl-, heteroaryl-, aryl(C$_1$-C$_4$)alkyl-, aryloxy(C$_1$-C$_4$)alkyl-, heteroaryl(C$_1$-C$_4$)alkyl-, heteroaryloxy(C$_1$-C$_4$)alkyl-, $R_6$O-L-, $R_6$S-L-, $(R_6)_2$N-L-, $R_6$—C(=O)-L-, $R_6$O—C(=O)-L-, $(R_6)_2$N—C(=O)-L-, $R_6$—C(=O)N($R_6$)-L-, $R_6$O—C(=O)N($R_6$)-L-, $(R_6)_2$N—C(=O)N($R_6$)-L-, $R_6$—C(=O)O-L-, $(R_6)_2$N—C(=O)O-L-, $R_6$—S(=O)$_2$-L-, $(R_6)_2$N—S(=O)$_2$-L-, $R_6$—S(=O)$_2$N($R_6$)-L- and $(R_6)_2$N—S(=O)$_2$N($R_6$)-L either of which may be optionally substituted with one or more $R_7$; and wherein the other $R_4$ or $R_5$ is selected from the group consisting of (C$_3$-C$_5$)alkyl-, heteroalkyl-, (C$_2$-C$_4$)alkenyl-, (C$_2$-C$_4$)alkynyl-, (C$_3$-C$_5$)cycloalkyl-, cycloalkenyl-, cycloalkynyl-, heterocyclyl-, cycloalkyl(C$_1$-C$_4$)alkyl-, heterocyclyl(C$_1$-C$_4$)alkyl, (C$_1$-C$_4$)alkyl(C$_3$-C$_8$)cycloalkyl-, (C$_1$-C$_4$)alkylheterocyclyl-, aryl-, heteroaryl-, aryl(C$_1$-C$_4$)alkyl-, aryloxy(C$_1$-C$_4$)alkyl-, heteroaryl(C$_1$-C$_4$)alkyl-, heteroaryloxy(C$_1$-C$_4$)alkyl-, $R_6$O-L-, $R_6$S-L-, $(R_6)_2$N-L-, $R_6$—C(=O)-L-, $R_6$O—C(=O)-L-, $(R_6)_2$N—C(=O)-L-, $R_6$—C(=O)N($R_6$)-L-, $R_6$O—C(=O)N($R_6$)-L-, $(R_6)_2$N—C(=O)N($R_6$)-L-, $R_6$—C(=O)O-L-, $(R_6)_2$N—C(=O)O-L-, $R_6$—S(=O)$_2$-L-, $(R_6)_2$N—S(=O)$_2$-L-, $R_6$—S(=O)$_2$N($R_6$)-L- and $(R_6)_2$N—S(=O)$_2$N($R_6$)-L either of which may be optionally substituted with one or more $R_7$;

or $R_4$ and $R_5$ can together with the N atom to which they are attached form a heterocyclic ring which may be optionally substituted with one or more $R_7$;

or $R_4$ and $R_5$ independently can be hydrogen.

3. The compound according to claim 1 wherein formula I has the following structure:

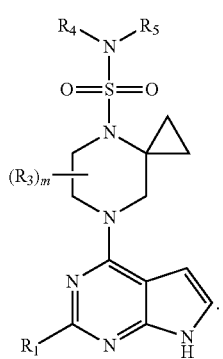

4. The compound according to claim 1 wherein $R_3$ independently at each occurrence is selected from the group consisting of cyano, hydroxy, oxo, $(C_1-C_4)$alkyl-, heteroalkyl-, and $R_{3a}O$—.

5. The compound according to claim 1 wherein $R_4$ and $R_5$ independently at each occurrence is selected from the group consisting of $(C_1-C_5)$alkyl-, heteroalkyl-, $(C_3-C_8)$cycloalkyl-, heterocyclyl-, $(C_3-C_8)$cycloalkyl$(C_1-C_4)$alkyl-, heterocyclyl$(C_1-C_4)$alkyl, $(C_1-C_4)$alkyl$(C_3-C_8)$cycloalkyl-, $(C_1-C_4)$alkylheterocyclyl-, aryl-, heteroaryl-, aryl$(C_1-C_4)$alkyl-, aryloxy$(C_1-C_4)$alkyl-, heteroaryl$(C_1-C_4)$alkyl-, heteroaryloxy$(C_1-C_4)$alkyl-, $R_6$O-L-, $R_6$S-L-, $(R_6)_2$N-L-, $R_6$O—C(=O)-L-, $(R_6)_2$N—C(=O)-L-, $R_6$—C(=O)N($R_6$)-L-, $R_6$O—C(=O)N($R_6$)-L-, $(R_6)_2$N—C(=O)N($R_6$)-L-, $R_6$—C(=O)O-L-, $(R_6)_2$N—C(=O)O-L-, $R_6$—S(=O)$_2$-L-, $(R_6)_2$N—S(=O)$_2$-L-, $R_6$—S(=O)$_2$N($R_6$)-L- and $(R_6)_2$N—S(=O)$_2$N($R_6$)-L either of which may be optionally substituted with one or more $R_7$.

6. The compound according to claim 1 wherein at least one of $R_4$ and $R_5$ is selected from the group consisting of heteroalkyl-, heterocyclyl$(C_1-C_4)$alkyl-, aryl$(C_1-C_4)$alkyl- and heteroaryl$(C_1-C_4)$alkyl-, wherein said heteroalkyl-, heterocyclyl$(C_1-C_4)$alkyl-, aryl$(C_1-C_4)$alkyl- and heteroaryl$(C_1-C_4)$alkyl- is substituted with one or more $R_7$.

7. The compound according to claim 6 wherein at least one of $R_4$ and $R_5$ is benzyl.

8. The compound according to claim 1 wherein at least one of $R_4$ and $R_5$ is selected from the group consisting of $R_6$O-L-, $R_6$S-L-, $(R_6)_2$N-L-, $R_6$—C(=O)-L-, $R_6$O—C(=O)-L-, $(R_6)_2$N—C(=O)-L-, $R_6$—C(=O)N($R_6$)-L-, $R_6$O—C(=O)N($R_6$)-L-, $(R_6)_2$N—C(=O)N($R_6$)-L-, $R_6$—C(=O)O-L-, $(R_6)_2$N—C(=O)O-L-, $R_6$—S(=O)$_2$-L-, $(R_6)_2$N—S(=O)$_2$-L-, $R_6$—S(=O)$_2$N($R_6$)-L- and $(R_6)_2$N—S(=O)$_2$N($R_6$)-L-, either of which may be optionally substituted with one or more $R_7$; wherein L independently at each occurrence is selected from the group consisting of heterocyclyl-, heterocyclyl$(C_1-C_4)$alkyl, $(C_1-C_4)$alkylheterocyclyl-, aryl$(C_1-C_4)$alkyl- and heteroaryl$(C_1-C_4)$alkyl-.

9. The compound according to claim 1 wherein one of $R_4$ and $R_5$ is selected from the group consisting of dioxothiolanylmethyl, dioxothiolanylethyl, dioxothianylmethyl and dioxothianylethyl.

10. The compound according to claim 9 wherein one of $R_4$ and $R_5$ is dioxothiolanylmethyl.

11. The compound according to claim 9 wherein one of $R_4$ and $R_5$ is dioxothianylmethyl.

12. The compound according to claim 8 wherein at least one of $R_4$ and $R_5$ is selected from $R_6$—C(=O)-L-, $R_6$—S(=O)$_2$-L- or $(R_6)_2$N—S(=O)$_2$-L-, which may be optionally substituted with one or more $R_7$; wherein L is selected from the group consisting of heterocyclyl-, heterocyclyl$(C_1-C_4)$alkyl, $(C_1-C_4)$alkylheterocyclyl-, aryl$(C_1-C_4)$alkyl- and heteroaryl$(C_1-C_4)$alkyl-.

13. The compound according to claim 12 wherein L is selected from the group consisting of piperidinylmethyl, pyrrolidinylmethyl, benzyl and azetidinyl; and wherein $R_6$ is selected from the group consisting of hydrogen, methyl, ethyl, propyl, cyclopropylmethyl, hydroxymethyl, hydroxyethyl, cyanoethyl, cyanopropyl.

14. The compound according to claim 12 wherein $R_6$—C(=O)-L-, $R_6$—S(=O)$_2$-L- and $(R_6)_2$N—S(=O)$_2$-L- is substituted with at least two fluoro.

15. The compound according to claim 1 wherein one of $R_4$ and $R_5$ is selected from the group consisting of heterocyclyl $(C_1-C_4)$alkyl and $(C_3-C_6)$cycloalkyl$(C_1-C_4)$alkyl wherein said heterocyclyl$(C_1-C_4)$alkyl and $(C_3-C_6)$cycloalkyl$(C_1-C_4)$alkyl is substituted with two or more $R_7$'s; wherein at least two $R_7$'s are fluoro.

16. The compound according to claim 15 wherein one of $R_4$ and $R_5$ is selected from the group consisting of cyclopropylmethyl, cyclobutylmethyl, cyclohexylmethyl and pyrrolidinylmethyl.

17. The compound according to claim 1 wherein $R_4$ and $R_5$ together with the N atom to which they are attached form a heterocyclic ring which may be optionally substituted with one or more $R_7$.

18. The compound according to claim 1 wherein $R_4$ is hydrogen.

19. The compound according to claim 1 wherein $R_5$ is hydrogen.

20. The compound according to claim 1 wherein $R_4$ is methyl.

21. The compound according to claim 1 wherein $R_5$ is methyl.

22. The compound according to claim 1 wherein L is independently at each occurrence selected from the group consisting of $(C_1-C_4)$alkyl-, heteroalkyl-, $(C_3-C_8)$cycloalkyl-, heterocyclyl-, $(C_3-C_8)$cycloalkyl$(C_1-C_4)$alkyl-, heterocyclyl $(C_1-C_4)$alkyl, alkyl$(C_3-C_8)$cycloalkyl-, $(C_1-C_4)$alkylheterocyclyl-, aryl$(C_1-C_4)$alkyl- and heteroaryl$(C_1-C_4)$alkyl-.

23. The compound according to claim 1,
wherein $R_4$ and $R_5$ independently are selected from the group consisting of hydrogen, methyl, ethyl, propyl, butyl, isopropyl, isobutyl, isoamyl, pentyl, benzyl, butynyl, cyclopropyl, cyclobutyl, cyclopentyl, oxetanyl, phenyl, phenylpropyl, phenethyl, pyridylmethyl, cyclopropylmethyl, cyclopropylethyl, cyclobutylmethyl, cyclopentylmethyl, cyclopentylethyl, cyclopentylpropyl, cyclohexylmethyl, cyclohexylethyl, cubanylmethyl, tetrahydrofuranylmethyl, tetrahydropyranylmethyl, morpholinylethyl, dioxothiolanylmethyl, dioxothiolanylethyl, dioxothianyl, dioxothianylmethyl, dioxothianylethyl, azetidinyl, pyrrolidinylmethyl, piperidinylmethyl, pyrazolylmethyl, pyrazolylethyl, pyrrolylethyl, isoxazolylmethyl, isoxazolylethyl, imidazolylethyl, $R_6$O—C(=O)-L-, $R_6$—C(=O)N($R_6$)-L-, $R_6$O-L-, $(R_6)_2$N—C(=O)-L-, $(R_6)_2$N-L-, $(R_6)_2$N—S(=O)$_2$-L-, $R_6$—S(=O)$_2$-L-, $R_6$—C(=O)-L-, either of which may be optionally substituted with one or more $R_7$;
wherein L is selected from the group consisting of methyl, ethyl, propyl, furanylmethyl, benzyl, azetidinyl, pyrrolidinylmethyl, piperidinylmethyl; and
wherein $R_6$ is independently selected from the group consisting of hydrogen, methyl, ethyl, propyl, isobutyl, tert-butyl, phenyl, benzyl, trifluoromethyl, cyclopropylmethyl, either of which $R_6$ may be optionally substituted with one or more substituents selected from the group consisting of halogen, cyano, hydroxy, trifluoromethyl, oxo, —$NH_2$, —$SO_2NH_2$, —$SONH_2$ and —$CONH_2$, —$O(C_1$-$C_4)$.

24. The compound according to claim 1 wherein $R_7$ independently at each occurrence is selected from the group consisting of fluoro, chloro, cyano, hydroxy, trifluoromethyl, oxo, —$NH_2$, —$SO_2NH_2$, —$SONH_2$, —$CONH_2$, and =$CH_2$.

25. The compound according to claim 1 wherein $R_7$ is selected from the group consisting of ($C_1$-$C_4$)alkyl-, heteroalkyl-, ($C_2$-$C_4$)alkynyl-, ($C_3$-$C_8$)cycloalkyl-, heterocyclyl-, ($C_3$-$C_8$)cycloalkyl($C_1$-$C_4$)alkyl-, heterocyclyl($C_1$-$C_4$)alkyl, ($C_1$-$C_4$)alkyl($C_3$-$C_8$)cycloalkyl-, ($C_1$-$C_4$)alkylheterocyclyl-, aryl($C_1$-$C_4$)alkyl-, $R_8$O—, $R_8$S—, ($R_8$)$_2$N—, $R_8$O—C(=O)—, ($R_8$)$_2$N—C(=O)—, $R_8$—C(=O)N($R_8$)—, $R_8$O—C(=O)N($R_8$)—, ($R_8$)$_2$N—C(=O)N($R_8$)—, $R_8$—C(=O)O—, ($R_8$)$_2$N—C(=O)O—, $R_8$—S(=O)$_2$—, ($R_8$)$_2$N—S(=O)$_2$—, $R_8$—S(=O)$_2$N($R_8$)— and ($R_8$)$_2$N—S(=O)$_2$N($R_8$)— either of which may be optionally substituted with one or more substituents selected from the group consisting of halogen, cyano, hydroxy, trifluoromethyl, oxo, —$NH_2$, —$SO_2NH_2$, —$SONH_2$ and —$CONH_2$.

26. The compound according to claim 25 wherein $R_7$ is selected from the group consisting of methyl, tert-butyl, phenyl, cyclopropyl, cyclobutyl, cyclopentyl, cyclohexyl, tetrahydrofuranyl, tetrahydropyranyl, morpholinyl, dioxothiolanyl, dioxothianyl, pyrrolidinyl, piperidinyl, pyrazolyl, pyrrolyl, pyridyl, imidazolyl, benzyl, $R_8$O—C(=O)—, $R_8$O—, ($R_8$)$_2$N—C(=O)— and ($R_8$)$_2$N—, either of which may be optionally substituted with one or more substituents selected from the group consisting of fluoro, chloro, cyano, hydroxy, trifluoromethyl and oxo;
and wherein $R_8$ is selected from the group consisting of methyl, ethyl and phenyl.

27. The compound according to claim 1 wherein $R_8$ independently at each occurrence is selected from the group consisting of hydrogen, ($C_1$-$C_4$)alkyl-, heteroalkyl-, ($C_3$-$C_6$)cycloalkyl-, heterocyclyl-, ($C_3$-$C_6$)cyclolalkyl($C_1$-$C_4$)alkyl-, heterocyclyl($C_1$-$C_4$)alkyl-, aryl-, aryl($C_1$-$C_4$)alkyl-, heteroaryl-, and heteroaryl($C_1$-$C_4$)alkyl- either of which may be optionally substituted with one or more substituents selected from the group consisting of halogen, cyano, hydroxy, trifluoromethyl, oxo, —$NH_2$, —$SO_2NH_2$, —$SONH_2$ and —$CONH_2$.

28. The compound according to claim 1 which is selected from the group consisting of
7-(7H-Pyrrolo[2,3-d]pyrimidin-4-yl)-4,7-diaza-spiro[2.5]octane-4-sulfonic acid amide,
7-(7H-Pyrrolo[2,3-d]pyrimidin-4-yl)-4,7-diaza-spiro[2.5]octane-4-sulfonic acid methylamide,
7-(7H-Pyrrolo[2,3-d]pyrimidin-4-yl)-4,7-diaza-spiro[2.5]octane-4-sulfonic acid phenethyl-amide,
4-[4-(Imidazole-1-sulfonyl)-4,7-diaza-spiro[2.5]oct-7-yl]-7H-pyrrolo[2,3-d]pyrimidine,
N-methyl-N-(pyrrolidin-3-ylmethyl)-5-(7H-pyrrolo[2,3-d]pyrimidin-4-yl)-5,8-diazaspiro[2.5]octane-8-sulfonamide,
N-methyl-N-(4-piperidylmethyl)-5-(7H-pyrrolo[2,3-d]pyrimidin-4-yl)-5,8-diazaspiro[2.5]octane-8-sulfonamide as formoc acid salt,
N-methyl-N-(3-piperidylmethyl)-5-(7H-pyrrolo[2,3-d]pyrimidin-4-yl)-5,8-diazaspiro[2.5]octane-8-sulfonamide as formic acid salt,
N-[[(2S)-4,4-difluoropyrrolidin-2-yl]methyl]-N-methyl-5-(7H-pyrrolo[2,3-d]pyrimidin-4-yl)-5,8-diazaspiro[2.5]octane-8-sulfonamide as formic acid salt,
N-cyclobutyl-5-(7H-pyrrolo[2,3-d]pyrimidin-4-yl)-5,8-diazaspiro[2.5]octane-8-sulfonamide,
N-[(1,1-dioxothiolan-3-yl)methyl]-5-(7H-pyrrolo[2,3-d]pyrimidin-4-yl)-5,8-diazaspiro[2.5]octane-8-sulfonamide,
N-[(1,1-dioxothian-4-yl)methyl]-5-(7H-pyrrolo[2,3-d]pyrimidin-4-yl)-5,8-diazaspiro[2.5]octane-8-sulfonamide,
N-(2-cyanoethyl)-5-(7H-pyrrolo[2,3-d]pyrimidin-4-yl)-5,8-diazaspiro[2.5]octane-8-sulfonamide,
N-(oxetan-3-yl)-5-(7H-pyrrolo[2,3-d]pyrimidin-4-yl)-5,8-diazaspiro[2.5]octane-8-sulfonamide,
N-benzyloxy-5-(7H-pyrrolo[2,3-d]pyrimidin-4-yl)-5,8-diazaspiro[2.5]octane-8-sulfonamide,
(NZ)—N-[(4-methoxyphenyl)methylene]-5-(7H-pyrrolo[2,3-d]pyrimidin-4-yl)-5,8-diazaspiro[2.5]octane-8-sulfonamide,
N-(azetidin-3-yl)-N-methyl-5-(7H-pyrrolo[2,3-d]pyrimidin-4-yl)-5,8-diazaspiro[2.5]octane-8-sulfonamide,
N-methyl-N-[[(2R)-pyrrolidin-2-yl]methyl]-5-(7H-pyrrolo[2,3-d]pyrimidin-4-yl)-5,8-diazaspiro[2.5]octane-8-sulfonamide,
N-methyl-N-[[(2S)-pyrrolidin-2-yl]methyl]-5-(7H-pyrrolo[2,3-d]pyrimidin-4-yl)-5,8-diazaspiro[2.5]octane-8-sulfonamide as formic acid salt,
tert-butyl N-[[5-(7H-pyrrolo[2,3-d]pyrimidin-4-yl)-5,8-diazaspiro[2.5]octan-8-yl]sulfonyl]carbamate,
4-{4-[Phenethyl-(3-phenyl-propyl)-sulfamoyl]-4,7-diazaspiro[2.5]oct-7-yl}-pyrrolo[2,3-d]pyrimidine-7-carboxylic acid tert-butyl ester,
7-(7H-Pyrrolo[2,3-d]pyrimidin-4-yl)-4,7-diaza-spiro[2.5]octane-4-sulfonic acid cyclopropylmethyl-phenethyl-amide,
7-(7H-Pyrrolo[2,3-d]pyrimidin-4-yl)-4,7-diaza-spiro[2.5]octane-4-sulfonic acid cyclobutylmethyl-phenethyl-amide,
7-(7H-Pyrrolo[2,3-d]pyrimidin-4-yl)-4,7-diaza-spiro[2.5]octane-4-sulfonic acid (2-oxo-butyl)-phenethyl-amide,
7-(7H-Pyrrolo[2,3-d]pyrimidin-4-yl)-4,7-diaza-spiro[2.5]octane-4-sulfonic acid (3-hydroxy-propyl)-phenethyl-amide,
7-(7H-Pyrrolo[2,3-d]pyrimidin-4-yl)-4,7-diaza-spiro[2.5]octane-4-sulfonic acid isobutyl-phenethyl-amide,
7-(7H-Pyrrolo[2,3-d]pyrimidin-4-yl)-4,7-diaza-spiro[2.5]octane-4-sulfonic acid phenethyl-propyl-amide,
7-(7H-Pyrrolo[2,3-d]pyrimidin-4-yl)-4,7-diaza-spiro[2.5]octane-4-sulfonic acid cyclohexylmethyl-phenethyl-amide,
7-(7H-Pyrrolo[2,3-d]pyrimidin-4-yl)-4,7-diaza-spiro[2.5]octane-4-sulfonic acid diphenethylamide,
7-(7H-Pyrrolo[2,3-d]pyrimidin-4-yl)-4,7-diaza-spiro[2.5]octane-4-sulfonic acid cyanomethyl-phenethyl-amide,
7-(7H-Pyrrolo[2,3-d]pyrimidin-4-yl)-4,7-diaza-spiro[2.5]octane-4-sulfonic acid (4-cyano-butyl)-phenethyl-amide,
7-(7H-Pyrrolo[2,3-d]pyrimidin-4-yl)-4,7-diaza-spiro[2.5]octane-4-sulfonic acid phenethyl-(tetrahydro-pyran-2-ylmethyl)-amide,
7-(7H-Pyrrolo[2,3-d]pyrimidin-4-yl)-4,7-diaza-spiro[2.5]octane-4-sulfonic acid (2-methoxy-ethyl)-phenethyl-amide,
7-(7H-Pyrrolo[2,3-d]pyrimidin-4-yl)-4,7-diaza-spiro[2.5]octane-4-sulfonic acid but-2-ynyl-phenethyl-amide,
7-(7H-Pyrrolo[2,3-d]pyrimidin-4-yl)-4,7-diaza-spiro[2.5]octane-4-sulfonic acid phenethyl-(2-pyrazol-1-yl-ethyl)-amide,
7-(7H-Pyrrolo[2,3-d]pyrimidin-4-yl)-4,7-diaza-spiro[2.5]octane-4-sulfonic acid (2-hydroxy-ethyl)-phenethyl-amide, {Phenethyl-[7-(7H-pyrrolo[2,3-d]pyrimidin-4-yl)-4,7-diaza-spiro[2.5]octane-4-sulfonyl]-amino}-acetic acid ethyl ester,
7-(7H-Pyrrolo[2,3-d]pyrimidin-4-yl)-4,7-diaza-spiro[2.5]octane-4-sulfonic acid [2-(4-fluoro-phenyl)-ethyl]-phenethyl-amide,
7-(7H-Pyrrolo[2,3-d]pyrimidin-4-yl)-4,7-diaza-spiro[2.5]octane-4-sulfonic acid [2-(3-fluoro-phenyl)-ethyl]-phenethyl-amide,
N-Benzyl-2-{phenethyl-[7-(7H-pyrrolo[2,3-d]pyrimidin-4-yl)-4,7-diaza-spiro[2.5]octane-4-sulfonyl]-amino}-acetamide,
7-(7H-Pyrrolo[2,3-d]pyrimidin-4-yl)-4,7-diaza-spiro[2.5]octane-4-sulfonic acid methyl-(3-phenyl-propyl)-amide,
7-(7H-Pyrrolo[2,3-d]pyrimidin-4-yl)-4,7-diaza-spiro[2.5]octane-4-sulfonic acid (2-cyclohexyl-ethyl)-methyl-amide,
7-(7H-Pyrrolo[2,3-d]pyrimidin-4-yl)-4,7-diaza-spiro[2.5]octane-4-sulfonic acid methyl-(2-oxo-2-phenyl-ethyl)-amide,
7-(7H-Pyrrolo[2,3-d]pyrimidin-4-yl)-4,7-diaza-spiro[2.5]octane-4-sulfonic acid (3-cyano-benzyl)-methyl-amide,
7-(7H-Pyrrolo[2,3-d]pyrimidin-4-yl)-4,7-diaza-spiro[2.5]octane-4-sulfonic acid (2-cyano-benzyl)-methyl-amide,
7-(7H-Pyrrolo[2,3-d]pyrimidin-4-yl)-4,7-diaza-spiro[2.5]octane-4-sulfonic acid cyclohexylmethyl-methyl-amide,
7-(7H-Pyrrolo[2,3-d]pyrimidin-4-yl)-4,7-diaza-spiro[2.5]octane-4-sulfonic acid [2-(4-fluoro-phenyl)-ethyl]-methyl-amide,
7-(7H-Pyrrolo[2,3-d]pyrimidin-4-yl)-4,7-diaza-spiro[2.5]octane-4-sulfonic acid [2-(3-fluoro-phenyl)-ethyl]-methyl-amide,
7-(7H-Pyrrolo[2,3-d]pyrimidin-4-yl)-4,7-diaza-spiro[2.5]octane-4-sulfonic acid methyl-(2-pyrrol-1-yl-ethyl)-amide,
7-(7H-Pyrrolo[2,3-d]pyrimidin-4-yl)-4,7-diaza-spiro[2.5]octane-4-sulfonic acid methyl-(3-methyl-butyl)-amide,
7-(7H-Pyrrolo[2,3-d]pyrimidin-4-yl)-4,7-diaza-spiro[2.5]octane-4-sulfonic acid methyl-pyridin-2-ylmethyl-amide,
7-(7H-Pyrrolo[2,3-d]pyrimidin-4-yl)-4,7-diaza-spiro[2.5]octane-4-sulfonic acid [3-(4-cyano-phenyl)-propyl]-methyl-amide,
7-(7H-Pyrrolo[2,3-d]pyrimidin-4-yl)-4,7-diaza-spiro[2.5]octane-4-sulfonic acid [3-(3-cyano-phenyl)-propyl]-methyl-amide,
7-(7H-Pyrrolo[2,3-d]pyrimidin-4-yl)-4,7-diaza-spiro[2.5]octane-4-sulfonic acid methyl-(2-phenoxy-ethyl)-amide,
7-(7H-Pyrrolo[2,3-d]pyrimidin-4-yl)-4,7-diaza-spiro[2.5]octane-4-sulfonic acid [2-(3,5-dimethyl-isoxazol-4-yl)-ethyl]-methyl-amide,
7-(7H-Pyrrolo[2,3-d]pyrimidin-4-yl)-4,7-diaza-spiro[2.5]octane-4-sulfonic acid (3-cyano-propyl)-phenethyl-amide,
{Methyl-[7-(7H-pyrrolo[2,3-d]pyrimidin-4-yl)-4,7-diaza-spiro[2.5]octane-4-sulfonyl]-amino}-acetic acid methyl ester,
7-(7H-Pyrrolo[2,3-d]pyrimidin-4-yl)-4,7-diaza-spiro[2.5]octane-4-sulfonic acid (3-cyano-propyl)-methyl-amide,
N,N-Dimethyl-2-{methyl-[7-(7H-pyrrolo[2,3-d]pyrimidin-4-yl)-4,7-diaza-spiro[2.5]octane-4-sulfonyl]-amino}-acetamide,
N-(cyclopropylmethyl)-N-methyl-5-(7H-pyrrolo[2,3-d]pyrimidin-4-yl)-5,8-diazaspiro[2.5]octane-8-sulfonamide,
N-(cyclobutylmethyl)-N-methyl-5-(7H-pyrrolo[2,3-d]pyrimidin-4-yl)-5,8-diazaspiro[2.5]octane-8-sulfonamide,
N-cyclopentyl-N-methyl-5-(7H-pyrrolo[2,3-d]pyrimidin-4-yl)-5,8-diazaspiro[2.5]octane-8-sulfonamide,
N-[(4,4-difluorocyclohexyl)methyl]-N-methyl-5-(7H-pyrrolo[2,3-d]pyrimidin-4-yl)-5,8-diazaspiro[2.5]octane-8-sulfonamide,
N-methyl-N-(2-phenylpropyl)-5-(7H-pyrrolo[2,3-d]pyrimidin-4-yl)-5,8-diazaspiro[2.5]octane-8-sulfonamide,
N-methyl-5-(7H-pyrrolo[2,3-d]pyrimidin-4-yl)-N-(tetrahydropyran-2-ylmethyl)-5,8-diazaspiro[2.5]octane-8-sulfonamide,
N-[[5-(dimethylsulfamoyl)-2-furyl]methyl]-N-methyl-5-(7H-pyrrolo[2,3-d]pyrimidin-4-yl)-5,8-diazaspiro[2.5]octane-8-sulfonamide,
N-methyl-N-(2-pyrazol-1-ylethyl)-5-(7H-pyrrolo[2,3-d]pyrimidin-4-yl)-5,8-diazaspiro[2.5]octane-8-sulfonamide,
N-methyl-N-[(3-methylisoxazol-5-yl)methyl]-5-(7H-pyrrolo[2,3-d]pyrimidin-4-yl)-5,8-diazaspiro[2.5]octane-8-sulfonamide,
N-(isoxazol-5-ylmethyl)-N-methyl-5-(7H-pyrrolo[2,3-d]pyrimidin-4-yl)-5,8-diazaspiro[2.5]octane-8-sulfonamide,
N-[2-(4-chlorophenoxy)ethyl]-N-methyl-5-(7H-pyrrolo[2,3-d]pyrimidin-4-yl)-5,8-diazaspiro[2.5]octane-8-sulfonamide,
N-[2-(2-cyanophenoxy)ethyl]-N-methyl-5-(7H-pyrrolo[2,3-d]pyrimidin-4-yl)-5,8-diazaspiro[2.5]octane-8-sulfonamide,
N-[2-(3-cyanophenoxy)ethyl]-N-methyl-5-(7H-pyrrolo[2,3-d]pyrimidin-4-yl)-5,8-diazaspiro[2.5]octane-8-sulfonamide,
N-[2-(4-cyanophenoxy)ethyl]-N-methyl-5-(7H-pyrrolo[2,3-d]pyrimidin-4-yl)-5,8-diazaspiro[2.5]octane-8-sulfonamide,
N-(cyclopentylmethyl)-N-methyl-5-(7H-pyrrolo[2,3-d]pyrimidin-4-yl)-5,8-diazaspiro[2.5]octane-8-sulfonamide,
N-(2-cyclopentylethyl)-N-methyl-5-(7H-pyrrolo[2,3-d]pyrimidin-4-yl)-5,8-diazaspiro[2.5]octane-8-sulfonamide,
N-[2-(1,1-dioxothiolan-3-yl)ethyl]-N-methyl-5-(7H-pyrrolo[2,3-d]pyrimidin-4-yl)-5,8-diazaspiro[2.5]octane-8-sulfonamide,
N-[(1,1-dioxothian-3-yl)methyl]-N-methyl-5-(7H-pyrrolo[2,3-d]pyrimidin-4-yl)-5,8-diazaspiro[2.5]octane-8-sulfonamide,
N-[(2-fluorophenyl)methyl]-N-methyl-5-(7H-pyrrolo[2,3-d]pyrimidin-4-yl)-5,8-diazaspiro[2.5]octane-8-sulfonamide,
N-[(3-fluorophenyl)methyl]-N-methyl-5-(7H-pyrrolo[2,3-d]pyrimidin-4-yl)-5,8-diazaspiro[2.5]octane-8-sulfonamide,
N-[(4-fluorophenyl)methyl]-N-methyl-5-(7H-pyrrolo[2,3-d]pyrimidin-4-yl)-5,8-diazaspiro[2.5]octane-8-sulfonamide,
N-methyl-5-(7H-pyrrolo[2,3-d]pyrimidin-4-yl)-N-[[4-(trifluoromethoxy)phenyl]methyl]-5,8-diazaspiro[2.5]octane-8-sulfonamide,
N-methyl-5-(7H-pyrrolo[2,3-d]pyrimidin-4-yl)-N-[[4-(trifluoromethyl)phenyl]methyl]-5,8-diazaspiro[2.5]octane-8-sulfonamide, N-(2-cyclopropylethyl)-N-methyl-5-(7H-pyrrolo[2,3-d]pyrimidin-4-yl)-5,8-diazaspiro[2.5]octane-8-sulfonamide,
N-methyl-N-[(4-methylsulfonylphenyl)methyl]-5-(7H-pyrrolo[2,3-d]pyrimidin-4-yl)-5,8-diazaspiro[2.5]octane-8-sulfonamide,
N-[(4-tert-butylcyclohexyl)methyl]-N-methyl-5-(7H-pyrrolo[2,3-d]pyrimidin-4-yl)-5,8-diazaspiro[2.5]octane-8-sulfonamide,
N-[(3,3-difluorocyclobutyl)methyl]-N-methyl-5-(7H-pyrrolo[2,3-d]pyrimidin-4-yl)-5,8-diazaspiro[2.5]octane-8-sulfonamide,
N-[(2,2-difluorocyclopropyl)methyl]-N-methyl-5-(7H-pyrrolo[2,3-d]pyrimidin-4-yl)-5,8-diazaspiro[2.5]octane-8-sulfonamide,
N-methyl-N-[(4-methylenecyclohexyl)methyl]-5-(7H-pyrrolo[2,3-d]pyrimidin-4-yl)-5,8-diazaspiro[2.5]octane-8-sulfonamide,
N-methyl-N-[(3-oxocyclobutyl)methyl]-5-(7H-pyrrolo[2,3-d]pyrimidin-4-yl)-5,8-diazaspiro[2.5]octane-8-sulfonamide,
N-methyl-5-(7H-pyrrolo[2,3-d]pyrimidin-4-yl)-N-(tetrahydropyran-4-ylmethyl)-5,8-diazaspiro[2.5]octane-8-sulfonamide,
N-methyl-5-(7H-pyrrolo[2,3-d]pyrimidin-4-yl)-N-[(3-sulfamoylphenyl)methyl]-5,8-diazaspiro[2.5]octane-8-sulfonamide,
N-methyl-5-(7H-pyrrolo[2,3-d]pyrimidin-4-yl)-N-[(4-sulfamoylphenyl)methyl]-5,8-diazaspiro[2.5]octane-8-sulfonamide,
N-[[1-(difluoromethyl)-3H-pyrazol-3-yl]methyl]-N-methyl-5-(7H-pyrrolo[2,3-d]pyrimidin-4-yl)-5,8-diazaspiro[2.5]octane-8-sulfonamide,
N-[[1-(2,2-difluoroethyl)-3H-pyrazol-3-yl]methyl]-N-methyl-5-(7H-pyrrolo[2,3-d]pyrimidin-4-yl)-5,8-diazaspiro[2.5]octane-8-sulfonamide,
7-(7H-Pyrrolo[2,3-d]pyrimidin-4-yl)-4,7-diaza-spiro[2.5]octane-4-sulfonic acid (4-cyano-benzyl)-methyl-amide,
4-[4-(Piperidine-1-sulfonyl)-4,7-diaza-spiro[2.5]oct-7-yl]-7H-pyrrolo[2,3-d]pyrimidine,
1-[7-(7H-Pyrrolo[2,3-d]pyrimidin-4-yl)-4,7-diaza-spiro[2.5]octane-4-sulfonyl]-piperidine-4-carbonitrile,
7-(7H-Pyrrolo[2,3-d]pyrimidin-4-yl)-4,7-diaza-spiro[2.5]octane-4-sulfonic acid methyl-phenyl-amide,
7-(7H-Pyrrolo[2,3-d]pyrimidin-4-yl)-4,7-diaza-spiro[2.5]octane-4-sulfonic acid (2-cyano-ethyl)-cyclopropyl-amide,
1-[7-(7H-Pyrrolo[2,3-d]pyrimidin-4-yl)-4,7-diaza-spiro[2.5]octane-4-sulfonyl]-piperidine-3-carbonitrile,
7-(7H-Pyrrolo[2,3-d]pyrimidin-4-yl)-4,7-diaza-spiro[2.5]octane-4-sulfonic acid [2-(3,4-dimethoxy-phenyl)-ethyl]-methyl-amide,
7-(7H-Pyrrolo[2,3-d]pyrimidin-4-yl)-4,7-diaza-spiro[2.5]octane-4-sulfonic acid benzyl-methyl-amide,
7-(7H-Pyrrolo[2,3-d]pyrimidin-4-yl)-4,7-diaza-spiro[2.5]octane-4-sulfonic acid dimethylamide,
7-(7H-Pyrrolo[2,3-d]pyrimidin-4-yl)-4,7-diaza-spiro[2.5]octane-4-sulfonic acid isopropylamide,
7-(7H-Pyrrolo[2,3-d]pyrimidin-4-yl)-4,7-diaza-spiro[2.5]octane-4-sulfonic acid phenethyl-(3-phenyl-propyl)-amide,
7-(7H-Pyrrolo[2,3-d]pyrimidin-4-yl)-4,7-diaza-spiro[2.5]octane-4-sulfonic acid (2-hydroxy-ethyl)-amide,
7-(7H-Pyrrolo[2,3-d]pyrimidin-4-yl)-4,7-diaza-spiro[2.5]octane-4-sulfonic acid bis-(2-hydroxy-ethyl)-amide,
7-(7H-Pyrrolo[2,3-d]pyrimidin-4-yl)-4,7-diaza-spiro[2.5]octane-4-sulfonic acid (3-cyano-propyl)-amide,
7-(7H-Pyrrolo[2,3-d]pyrimidin-4-yl)-4,7-diaza-spiro[2.5]octane-4-sulfonic acid bis-(3-cyano-propyl)-amide,
7-(7H-Pyrrolo[2,3-d]pyrimidin-4-yl)-4,7-diaza-spiro[2.5]octane-4-sulfonic acid (3-cyano-propyl)-(3-phenyl-propyl)-amide,
7-(7H-Pyrrolo[2,3-d]pyrimidin-4-yl)-4,7-diaza-spiro[2.5]octane-4-sulfonic acid methyl-phenethyl-amide,
N-isopropyl-N-methyl-5-(7H-pyrrolo[2,3-d]pyrimidin-4-yl)-5,8-diazaspiro[2.5]octane-8-sulfonamide,
N-ethyl-N-isopropyl-5-(7H-pyrrolo[2,3-d]pyrimidin-4-yl)-5,8-diazaspiro[2.5]octane-8-sulfonamide,
N-(cyanomethyl)-N-isopropyl-5-(7H-pyrrolo[2,3-d]pyrimidin-4-yl)-5,8-diazaspiro[2.5]octane-8-sulfonamide,
N-(2-hydroxyethyl)-N-isopropyl-5-(7H-pyrrolo[2,3-d]pyrimidin-4-yl)-5,8-diazaspiro[2.5]octane-8-sulfonamide,
N-cyclobutyl-N-methyl-5-(7H-pyrrolo[2,3-d]pyrimidin-4-yl)-5,8-diazaspiro[2.5]octane-8-sulfonamide,
N-cyclobutyl-N-ethyl-5-(7H-pyrrolo[2,3-d]pyrimidin-4-yl)-5,8-diazaspiro[2.5]octane-8-sulfonamide,
N-(cyanomethyl)-N-cyclobutyl-5-(7H-pyrrolo[2,3-d]pyrimidin-4-yl)-5,8-diazaspiro[2.5]octane-8-sulfonamide,
N-cyclobutyl-N-(2-hydroxyethyl)-5-(7H-pyrrolo[2,3-d]pyrimidin-4-yl)-5,8-diazaspiro[2.5]octane-8-sulfonamide,
N-(3-cyanopropyl)-N-cyclobutyl-5-(7H-pyrrolo[2,3-d]pyrimidin-4-yl)-5,8-diazaspiro[2.5]octane-8-sulfonamide,
N-cyclobutyl-N-(2-methoxyethyl)-5-(7H-pyrrolo[2,3-d]pyrimidin-4-yl)-5,8-diazaspiro[2.5]octane-8-sulfonamide,
N-cyclobutyl-N-(2-imidazol-1-ylethyl)-5-(7H-pyrrolo[2,3-d]pyrimidin-4-yl)-5,8-diazaspiro[2.5]octane-8-sulfonamide,
N-cyclobutyl-N-[3-(dimethylamino)propyl]-5-(7H-pyrrolo[2,3-d]pyrimidin-4-yl)-5,8-diazaspiro[2.5]octane-8-sulfonamide,
N-cyclobutyl-N-(2-morpholinoethyl)-5-(7H-pyrrolo[2,3-d]pyrimidin-4-yl)-5,8-diazaspiro[2.5]octane-8-sulfonamide,
N-(1-cyanoethyl)-N-cyclobutyl-5-(7H-pyrrolo[2,3-d]pyrimidin-4-yl)-5,8-diazaspiro[2.5]octane-8-sulfonamide,
N-(cyanomethyl)-N-(2-hydroxyethyl)-5-(7H-pyrrolo[2,3-d]pyrimidin-4-yl)-5,8-diazaspiro[2.5]octane-8-sulfonamide,
N-(2-hydroxyethyl)-N-methyl-5-(7H-pyrrolo[2,3-d]pyrimidin-4-yl)-5,8-diazaspiro[2.5]octane-8-sulfonamide,
N-(3-cyanopropyl)-N-(2-hydroxyethyl)-5-(7H-pyrrolo[2,3-d]pyrimidin-4-yl)-5,8-diazaspiro[2.5]octane-8-sulfonamide,
N-(2-hydroxyethyl)-N-(2-phenoxyethyl)-5-(7H-pyrrolo[2,3-d]pyrimidin-4-yl)-5,8-diazaspiro[2.5]octane-8-sulfonamide,
N-methyl-N-(oxetan-3-yl)-5-(7H-pyrrolo[2,3-d]pyrimidin-4-yl)-5,8-diazaspiro[2.5]octane-8-sulfonamide,
N-(cyanomethyl)-N-(oxetan-3-yl)-5-(7H-pyrrolo[2,3-d]pyrimidin-4-yl)-5,8-diazaspiro[2.5]octane-8-sulfonamide,
N-(3-cyanopropyl)-N-(oxetan-3-yl)-5-(7H-pyrrolo[2,3-d]pyrimidin-4-yl)-5,8-diazaspiro[2.5]octane-8-sulfonamide,
N-(oxetan-3-yl)-N-(2-phenoxyethyl)-5-(7H-pyrrolo[2,3-d]pyrimidin-4-yl)-5,8-diazaspiro[2.5]octane-8-sulfonamide, N-(2-hydroxyethyl)-N-(oxetan-3-yl)-5-(7H-pyrrolo[2,3-d]pyrimidin-4-yl)-5,8-diazaspiro[2.5]octane-8-sulfonamide, N-(1-cyanoethyl)-N-(oxetan-3-yl)-5-(7H-pyrrolo[2,3-d]pyrimidin-4-yl)-5,8-diazaspiro[2.5]octane-8-sulfonamide, N-methyl-N-[(1-propylsulfonylpyrrolidin-3-yl)methyl]-5-(7H-pyrrolo[2,3-d]pyrimidin-4-yl)-5,8-diazaspiro[2.5]octane-8-sulfonamide, N-methyl-N-[(1-methylsulfonylpyrrolidin-3-yl)methyl]-5-(7H-pyrrolo[2,3-d]pyrimidin-4-yl)-5,8-diazaspiro[2.5]octane-8-sulfonamide, N-[[1-(2-methoxyethylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide, N-[[1-(3-cyanopropylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide, N-[1-(cyclopropylmethylsulfonyl)pyrrolidin-3-yl]methyl]-N-methyl-5-(7H-pyrrolo[2,3-d]pyrimidin-4-yl)-5,8-diazaspiro[2.5]octane-8-sulfonamide, N-[[1-(3-hydroxypropanoyl)pyrrolidin-3-yl]methyl]-N-methyl-5-(7H-pyrrolo[2,3-d]pyrimidin-4-yl)-5,8-diazaspiro[2.5]octane-8-sulfonamide, N-[[1-(3-hydroxybutanoyl)pyrrolidin-3-yl]methyl]-N-methyl-5-(7H-pyrrolo[2,3-d]pyrimidin-4-yl)-5,8-diazaspiro[2.5]octane-8-sulfonamide, N-methyl-N-[(1-propanoylpyrrolidin-3-yl)methyl]-5-(7H-pyrrolo[2,3-d]pyrimidin-4-yl)-5,8-diazaspiro[2.5]octane-8-sulfonamide, N-[[1-(3-cyanopropanoyl)pyrrolidin-3-yl]methyl]-N-methyl-5-(7H-pyrrolo[2,3-d]pyrimidin-4-yl)-5,8-diazaspiro[2.5]octane-8-sulfonamide, N-[[1-(2,3-dihydroxypropanoyl)pyrrolidin-3-yl]methyl]-N-methyl-5-(7H-pyrrolo[2,3-d]pyrimidin-4-yl)-5,8-diazaspiro[2.5]octane-8-sulfonamide, N-[(1-formylpyrrolidin-3-yl)methyl]-N-methyl-5-(7H-pyrrolo[2,3-d]pyrimidin-4-yl)-5,8-diazaspiro[2.5]octane-8-sulfonamide, 3,3,3-trifluoro-N-methyl-N-[[5-(7H-pyrrolo[2,3-d]pyrimidin-4-yl)-5,8-diazaspiro[2.5]octan-8-yl]sulfonyl]propanamide, 4,4-difluoro-N-methyl-N-[[5-(7H-pyrrolo[2,3-d]pyrimidin-4-yl)-5,8-diazaspiro[2.5]octan-8-yl]sulfonyl]cyclohexanecarboxamide, 4,4,4-trifluoro-N-methyl-N-[[5-(7H-pyrrolo[2,3-d]pyrimidin-4-yl)-5,8-diazaspiro[2.5]octan-8-yl]sulfonyl]butanamide, N-methyl-1,1-dioxo-N-[[5-(7H-pyrrolo[2,3-d]pyrimidin-4-yl)-5,8-diazaspiro[2.5]octan-8-yl]sulfonyl]thiolane-3-carboxamide, 2-(1,1-dioxothian-4-yl)-N-methyl-N-[[5-(7H-pyrrolo[2,3-d]pyrimidin-4-yl)-5,8-diazaspiro[2.5]octan-8-yl]sulfonyl]acetamide, 3-(1,1-dioxothiolan-3-yl)-N-methyl-N-[[5-(7H-pyrrolo[2,3-d]pyrimidin-4-yl)-5,8-diazaspiro[2.5]octan-8-yl]sulfonyl]propanamide, 2-(1,1-dioxothiolan-3-yl)-N-methyl-N-[[5-(7H-pyrrolo[2,3-d]pyrimidin-4-yl)-5,8-diazaspiro[2.5]octan-8-yl]sulfonyl]acetamide, N-methyl-1,1-dioxo-N-[[5-(7H-pyrrolo[2,3-d]pyrimidin-4-yl)-5,8-diazaspiro[2.5]octan-8-yl]sulfonyl]thiane-4-carboxamide, N-methyl-1,1-dioxo-N-[[5-(7H-pyrrolo[2,3-d]pyrimidin-4-yl)-5,8-diazaspiro[2.5]octan-8-yl]sulfonyl]thiane-3-carboxamide, N-methyl-N-[[5-(7H-pyrrolo[2,3-d]pyrimidin-4-yl)-5,8-diazaspiro[2.5]octan-8-yl]sulfonyl]cyclopentanecarboxamide, 2-cyclopentyl-N-methyl-N-[[5-(7H-pyrrolo[2,3-d]pyrimidin-4-yl)-5,8-diazaspiro[2.5]octan-8-yl]sulfonyl]acetamide, 3-cyclopentyl-N-methyl-N-[[5-(7H-pyrrolo[2,3-d]pyrimidin-4-yl)-5,8-diazaspiro[2.5]octan-8-yl]sulfonyl]propanamide, N-cyclopropyl-N-methyl-5-(7H-pyrrolo[2,3-d]pyrimidin-4-yl)-5,8-diazaspiro[2.5]octane-8-sulfonamide, N-(2-cyanoethyl)-5-(7H-pyrrolo[2,3-d]pyrimidin-4-yl)-N-(tetrahydrofuran-2-ylmethyl)-5,8-diazaspiro[2.5]octane-8-sulfonamide, N-(1-methylbutyl)-5-(7H-pyrrolo[2,3-d]pyrimidin-4-yl)-5,8-diazaspiro[2.5]octane-8-sulfonamide, N-cyclopentyl-5-(7H-pyrrolo[2,3-d]pyrimidin-4-yl)-5,8-diazaspiro[2.5]octane-8-sulfonamide, N,N-bis(cyanomethyl)-5-(7H-pyrrolo[2,3-d]pyrimidin-4-yl)-5,8-diazaspiro[2.5]octane-8-sulfonamide, N,N-dibenzyl-5-(7H-pyrrolo[2,3-d]pyrimidin-4-yl)-5,8-diazaspiro[2.5]octane-8-sulfonamide, N-benzyl-5-(7H-pyrrolo[2,3-d]pyrimidin-4-yl)-5,8-diazaspiro[2.5]octane-8-sulfonamide, N-[(4,4-difluorocyclohexyl)methyl]-5-(7H-pyrrolo[2,3-d]pyrimidin-4-yl)-5,8-diazaspiro[2.5]octane-8-sulfonamide, N-[(4,4-difluorocyclohexyl)methyl]-N-ethyl-5-(7H-pyrrolo[2,3-d]pyrimidin-4-yl)-5,8-diazaspiro[2.5]octane-8-sulfonamide, N,N-bis[(4,4-difluorocyclohexyl)methyl]-5-(7H-pyrrolo[2,3-d]pyrimidin-4-yl)-5,8-diazaspiro[2.5]octane-8-sulfonamide, N-[[1-(3-hydroxypropanoyl)-4-piperidyl]methyl]-N-methyl-5-(7H-pyrrolo[2,3-d]pyrimidin-4-yl)-5,8-diazaspiro[2.5]octane-8-sulfonamide, N-[[1-(3-cyanopropanoyl)-4-piperidyl]methyl]-N-methyl-5-(7H-pyrrolo[2,3-d]pyrimidin-4-yl)-5,8-diazaspiro[2.5]octane-8-sulfonamide, N-[[1-(3-cyanopropanoyl)-3-piperidyl]methyl]-N-methyl-5-(7H-pyrrolo[2,3-d]pyrimidin-4-yl)-5,8-diazaspiro[2.5]octane-8-sulfonamide, N-[[1-(3-hydroxypropanoyl)-3-piperidyl]methyl]-N-methyl-5-(7H-pyrrolo[2,3-d]pyrimidin-4-yl)-5,8-diazaspiro[2.5]octane-8-sulfonamide, N-[[(2S)-4,4-difluoro-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide, N-[[(2S)-1-(3-cyanopropanoyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide, N-[[(2S)-4,4-difluoro-1-formyl-pyrrolidin-2-yl]methyl]-N-methyl-5-(7H-pyrrolo[2,3-d]pyrimidin-4-yl)-5,8-diazaspiro[2.5]octane-8-sulfonamide, N-methyl-N-[(1-methylsulfonyl-4-piperidyl)methyl]-5-(7H-pyrrolo[2,3-d]pyrimidin-4-yl)-5,8-diazaspiro[2.5]octane-8-sulfonamide, N-[[1-(3-cyanopropylsulfonyl)-4-piperidyl]methyl]-N-methyl-5-(7H-pyrrolo[2,3-d]pyrimidin-4-yl)-5,8-diazaspiro[2.5]octane-8-sulfonamide, N-methyl-N-[(1-methylsulfonyl-3-piperidyl)methyl]-5-(7H-pyrrolo[2,3-d]pyrimidin-4-yl)-5,8-diazaspiro[2.5]octane-8-sulfonamide, N-[[1-(3-cyanopropylsulfonyl)-3-piperidyl]methyl]-N-methyl-5-(7H-pyrrolo[2,3-d]pyrimidin-4-yl)-5,8-diazaspiro[2.5]octane-8-sulfonamide, N-[[(2S)-4,4-difluoro-1-methylsulfonyl-pyrrolidin-2-yl]methyl]-N-methyl-5-(7H-pyrrolo[2,3-d]pyrimidin-4-yl)-5,8-diazaspiro[2.5]octane-8-sulfonamide, N-[[(2S)-1-(3-cyanopropylsulfonyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide, N-[[(2S)-1-(cyclopropylmethylsulfonyl)-4,4-difluoro-pyrrolidin-2-yl]methyl]-N-methyl-5-(7H-pyrrolo[2,3-d]pyrimidin-4-yl)-5,8-diazaspiro[2.5]octane-8-sulfonamide, N-[(1,1-dioxothiolan-3-yl)methyl]-N-methyl-5-(7H-pyrrolo[2,3-d]pyrimidin-4-yl)-5,8-diazaspiro[2.5]octane-8-sulfonamide, N-(cyanomethyl)-N-[(1,1-dioxothiolan-3-yl)methyl]-5-(7H-pyrrolo[2,3-d]pyrimidin-4-yl)-5,8-diazaspiro[2.5]octane-8-sulfonamide, N-[(1,1-dioxothiolan-3-yl)methyl]-N-(2-hydroxyethyl)-5-(7H-pyrrolo[2,3-d]pyrimidin-4-yl)-5,8-diazaspiro[2.5]octane-8-sulfonamide, N-[(1,1-dioxothian-4-yl)methyl]-N-methyl-5-(7H-pyrrolo[2,3-d]pyrimidin-4-yl)-5,8-diazaspiro[2.5]octane-8-sulfonamide, N-(cyanomethyl)-N-[(1,1-dioxothian-4-yl)methyl]-5-(7H-pyrrolo[2,3-d]pyrimidin-4-yl)-5,8-diazaspiro[2.5]octane-8-sulfonamide, N-[(1,1-dioxothian-4-yl)methyl]-N-(2-hydroxyethyl)-5-(7H-pyrrolo[2,3-d]pyrimidin-4-yl)-5,8-diazaspiro[2.5]octane-8-sulfonamide, N-(2-cyanoethyl)-N-(cyanomethyl)-5-(7H-pyrrolo[2,3-d]pyrimidin-4-yl)-5,8-diazaspiro[2.5]octane-8-sulfonamide, N-[(1,1-dioxothiolan-3-yl)methyl]-N-[[5-(7H-pyrrolo[2,3-d]pyrimidin-4-yl)-5,8-diazaspiro[2.5]octan-8-yl]sulfonyl]acetamide, N-[(1,1-dioxothian-4-yl)methyl]-N-[[5-(7H-pyrrolo[2,3-d]pyrimidin-4-yl)-5,8-diazaspiro[2.5]octan-8-yl]sulfonyl]acetamide, N-benzyloxy-N-methyl-5-(7H-pyrrolo[2,3-d]pyrimidin-4-yl)-5,8-diazaspiro[2.5]octane-8-sulfonamide, N-[[(2S)-1-benzylpyrrolidin-2-yl]methyl]-5-(7H-pyrrolo[2,3-d]pyrimidin-4-yl)-5,8-diazaspiro[2.5]octane-8-sulfonamide, N-[[5-(7H-pyrrolo[2,3-d]pyrimidin-4-yl)-5,8-diazaspiro[2.5]octan-8-yl]sulfonyl]formamide, N-[(4-cyanocuban-1-yl)methyl]-N-methyl-5-(7H-pyrrolo[2,3-d]pyrimidin-4-yl)-5,8-diazaspiro[2.5]octane-8-sulfonamide, N-[1-(2-hydroxyacetyl)azetidin-3-yl]-N-methyl-5-(7H-pyrrolo[2,3-d]pyrimidin-4-yl)-5,8-diazaspiro[2.5]octane-8-sulfonamide, N-[1-(3-hydroxypropanoyl)azetidin-3-yl]-N-methyl-5-(7H-pyrrolo[2,3-d]pyrimidin-4-yl)-5,8-diazaspiro[2.5]octane-8-sulfonamide, N-methyl-N-(1-methylsulfonylazetidin-3-yl)-5-(7H-pyrrolo[2,3-d]pyrimidin-4-yl)-5,8-diazaspiro[2.5]octane-8-sulfonamide, N-methyl-N-[[(2R)-1-methylsulfonylpyrrolidin-2-yl]methyl]-5-(7H-pyrrolo[2,3-d]pyrimidin-4-yl)-5,8-diazaspiro[2.5]octane-8-sulfonamide, N-[[(2R)-1-(3-cyanopropylsulfonyl)pyrrolidin-2-yl]methyl]-N-methyl-5-(7H-pyrrolo[2,3-d]pyrimidin-4-yl)-5,8-diazaspiro[2.5]octane-8-sulfonamide, N-methyl-N-[[(2S)-5-oxopyrrolidin-2-yl]methyl]-5-(7H-pyrrolo[2,3-d]pyrimidin-4-yl)-5,8-diazaspiro[2.5]octane-8-sulfonamide, N-methyl-N-[[(2R)-5-oxopyrrolidin-2-yl]methyl]-5-(7H-pyrrolo[2,3-d]pyrimidin-4-yl)-5,8-diazaspiro[2.5]octane-8-sulfonamide, N-[[(2R)-1-(2-hydroxyacetyl)pyrrolidin-2-yl]methyl]-N-methyl-5-(7H-pyrrolo[2,3-d]pyrimidin-4-yl)-5,8-diazaspiro[2.5]octane-8-sulfonamide, N-[[(2R)-1-(2,3-dihydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide, N-[[(2R)-1-(3-cyanopropanoyl)pyrrolidin-2-yl]methyl]-N-methyl-5-(7H-pyrrolo[2,3-d]pyrimidin-4-yl)-5,8-diazaspiro[2.5]octane-8-sulfonamide, N-[[(2R)-1-formylpyrrolidin-2-yl]methyl]-N-methyl-5-(7H-pyrrolo[2,3-d]pyrimidin-4-yl)-5,8-diazaspiro[2.5]octane-8-sulfonamide, N-[[(2R)-1-(2-cyanoacetyl)pyrrolidin-2-yl]methyl]-N-methyl-5-(7H-pyrrolo[2,3-d]pyrimidin-4-yl)-5,8-diazaspiro[2.5]octane-8-sulfonamide, N-[[(2R)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide, N-[[(2S)-1-formylpyrrolidin-2-yl]methyl]-N-methyl-5-(7H-pyrrolo[2,3-d]pyrimidin-4-yl)-5,8-diazaspiro[2.5]octane-8-sulfonamide, N-[[(2S)-1-(2-hydroxyacetyl)pyrrolidin-2-yl]methyl]-N-methyl-5-(7H-pyrrolo[2,3-d]pyrimidin-4-yl)-5,8-diazaspiro[2.5]octane-8-sulfonamide, N-[[(2S)-1-(3-hydroxypropanoyl)pyrrolidin-2-yl]methyl]-N-methyl-5-(7H-pyrrolo[2,3-d]pyrimidin-4-yl)-5,8-diazaspiro[2.5]octane-8-sulfonamide, N-methyl-N-[[(2S)-1-methylsulfonylpyrrolidin-2-yl]methyl]-5-(7H-pyrrolo[2,3-d]pyrimidin-4-yl)-5,8-diazaspiro[2.5]octane-8-sulfonamide, N-[(4-methoxyphenyl)methyl]-5-(7H-pyrrolo[2,3-d]pyrimidin-4-yl)-5,8-diazaspiro[2.5]octane-8-sulfonamide and tert-butyl N-(3-methylsulfonylpropyl)-N-[[5-(7H-pyrrolo[2,3-d]pyrimidin-4-yl)-5,8-diazaspiro[2.5]octan-8-yl]sulfonyl]carbamate.

29. A pharmaceutical composition comprising a compound according to claim 1 or a pharmaceutically acceptable salt, hydrate, or solvate thereof together with a pharmaceutically acceptable vehicle or excipient.

* * * * *